United States Patent
Hoelder et al.

(10) Patent No.: US 9,895,364 B2
(45) Date of Patent: Feb. 20, 2018

(54) PHARMACOLOGICALLY ACTIVE COMPOUNDS

(71) Applicant: Cancer Research Technology Limited, London (GB)

(72) Inventors: Swen Hoelder, London (GB); Julian Blagg, London (GB); Kwai-Ming J. Cheung, London (GB); Butrus Atrash, London (GB); Peter Sheldrake, London (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 15/069,012

(22) Filed: Mar. 14, 2016

(65) Prior Publication Data

US 2016/0296514 A1    Oct. 13, 2016

Related U.S. Application Data

(62) Division of application No. 14/426,574, filed as application No. PCT/GB2013/052361 on Sep. 9, 2013, now Pat. No. 9,334,286.

(30) Foreign Application Priority Data

Sep. 7, 2012 (GB) .................................. 1216018.0

(51) Int. Cl.
| | |
|---|---|
| *C07D 401/14* | (2006.01) |
| *C07D 405/14* | (2006.01) |
| *C07D 413/14* | (2006.01) |
| *C07D 417/14* | (2006.01) |
| *C07D 471/04* | (2006.01) |
| *A61K 31/4725* | (2006.01) |
| *A61K 31/4747* | (2006.01) |
| *C07D 401/04* | (2006.01) |
| *C07D 401/12* | (2006.01) |
| *C07D 487/04* | (2006.01) |
| *C07D 491/107* | (2006.01) |
| *A61K 31/4375* | (2006.01) |
| *A61K 31/496* | (2006.01) |
| *A61K 31/4985* | (2006.01) |
| *A61K 31/506* | (2006.01) |
| *A61K 31/519* | (2006.01) |
| *A61K 31/5355* | (2006.01) |
| *A61K 31/541* | (2006.01) |

(52) U.S. Cl.
CPC ...... *A61K 31/4725* (2013.01); *A61K 31/4375* (2013.01); *A61K 31/4747* (2013.01); *A61K 31/496* (2013.01); *A61K 31/4985* (2013.01); *A61K 31/506* (2013.01); *A61K 31/519* (2013.01); *A61K 31/5355* (2013.01); *A61K 31/541* (2013.01); *C07D 401/04* (2013.01); *C07D 401/12* (2013.01); *C07D 401/14* (2013.01); *C07D 405/14* (2013.01); *C07D 413/14* (2013.01); *C07D 417/14* (2013.01); *C07D 471/04* (2013.01); *C07D 487/04* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 2,697,710 A | 12/1954 | Hitchings et al. | |
| 3,021,332 A | 2/1962 | Hitchings et al. | |
| 9,334,286 B2 * | 5/2016 | Hoelder | C07D 401/14 |
| 2003/0073668 A1 | 4/2003 | Booth et al. | |
| 2003/0105115 A1 | 6/2003 | Metcalf et al. | |
| 2004/0092521 A1 | 5/2004 | Altenbach et al. | |
| 2005/0256118 A1 | 11/2005 | Altenbach et al. | |
| 2005/0272728 A1 | 12/2005 | Altenbach et al. | |
| 2011/0212975 A1 | 9/2011 | Kao et al. | |
| 2011/0257196 A1 | 10/2011 | Lu et al. | |
| 2015/0031672 A1 | 1/2015 | Ren et al. | |

FOREIGN PATENT DOCUMENTS

| | | |
|---|---|---|
| JP | 2009/051827 A | 3/2009 |
| WO | WO-1996/015128 A2 | 5/1996 |

(Continued)

OTHER PUBLICATIONS

Dubey et al, Endocrinology, Sep. 2007, vol. 148, No. 9, pp. 4125-4127.*

(Continued)

*Primary Examiner* — Zinna Northington Davis
(74) *Attorney, Agent, or Firm* — David P. Halstead; Foley Hoag LLP

(57) ABSTRACT

The present invention relates to compounds of formula II

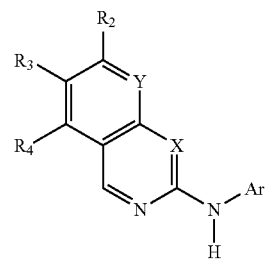

wherein X, Y, $R_2$, $R_3$, $R_4$ and Ar are all as defined herein. The compounds of the present invention are known to inhibit the spindle checkpoint function of Monospindle 1 (Mps1—also known as TTK) kinases either directly or indirectly via interaction with the Mps1 kinase itself. In particular, the present invention relates to the use of these compounds as therapeutic agents for the treatment and/or prevention of proliferative diseases, such as cancer. The present invention also relates to processes for the preparation of these compounds, and to pharmaceutical compositions comprising them.

15 Claims, No Drawings

(56) References Cited

FOREIGN PATENT DOCUMENTS

| WO | WO-2000/025780 |    | 5/2000  |
|----|----------------|----|---------|
| WO | WO-2000/068203 |    | 11/2000 |
| WO | WO-2001/019788 |    | 3/2001  |
| WO | WO-2001/055147 | A1 | 8/2001  |
| WO | WO-2001/064642 |    | 9/2001  |
| WO | WO-2001/064643 |    | 9/2001  |
| WO | WO-2002/000647 |    | 1/2002  |
| WO | WO-2002/09036  | A1 | 11/2002 |
| WO | WO-2003/007955 |    | 1/2003  |
| WO | WO-2003/051366 | A2 | 6/2003  |
| WO | WO-2003/074530 | A1 | 9/2003  |
| WO | WO-2004/007472 | A1 | 1/2004  |
| WO | WO-2004/043458 | A1 | 5/2004  |
| WO | WO-2004/065378 | A1 | 8/2004  |
| WO | WO-2004/085385 | A2 | 10/2004 |
| WO | WO-2006/001463 | A1 | 1/2006  |
| WO | WO-2007/000240 | A1 | 1/2007  |
| WO | WO-2007/011759 | A2 | 1/2007  |
| WO | WO-2007/088996 | A1 | 8/2007  |
| WO | WO-2007/088999 | A1 | 8/2007  |
| WO | WO-2007/125405 | A2 | 11/2007 |
| WO | WO-2007/140222 | A2 | 12/2007 |
| WO | WO-2008/073670 | A2 | 6/2008  |
| WO | WO-2008-079988 | A2 | 7/2008  |
| WO | WO-2008/135232 | A1 | 11/2008 |
| WO | WO-2009/010455 | A2 | 1/2009  |
| WO | WO-2009/010871 | A2 | 1/2009  |
| WO | WO-2009/026717 | A1 | 3/2009  |
| WO | WO-2009/032694 | A1 | 3/2009  |
| WO | WO-2009/076618 | A2 | 6/2009  |
| WO | WO-2009/103966 | A1 | 8/2009  |
| WO | WO-2010/007374 | A1 | 1/2010  |
| WO | WO-2010/048149 | A2 | 4/2010  |
| WO | WO-2010/080537 | A1 | 7/2010  |
| WO | WO-2010/129816 | A2 | 11/2010 |
| WO | WO-2011/015037 | A1 | 2/2011  |
| WO | WO-2011/159297 | A1 | 12/2011 |
| WO | WO-2012/013557 | A1 | 2/2012  |
| WO | WO-2012/028756 | A1 | 3/2012  |
| WO | WO-2012/064973 | A2 | 5/2012  |
| WO | WO-2012/079032 | A2 | 6/2012  |
| WO | WO-2012/080284 | A2 | 6/2012  |
| WO | WO-2012/080729 | A2 | 6/2012  |
| WO | WO-2012/088438 | A1 | 6/2012  |
| WO | WO-2012/092471 | A2 | 7/2012  |
| WO | WO-2012/101032 | A1 | 8/2012  |
| WO | WO-2012/123745 | A1 | 9/2012  |
| WO | WO-2014/037750 | A1 | 3/2014  |

OTHER PUBLICATIONS

Balog et al., "Novel fluorescent isoquinoline derivatives obtained via Buchwald-Hartwig coupling of isoquinolin-3-amines", Arkivoc., 5:109-19 (2012).
Bathini et al., "2-Aminoquinazoline inhibitors of cyclin-dependent kinases", Bioorg. Med. Chem. Lett., 15(17):3881-5 (2005).
Cabarello et al., "2D Autocorrelation, CoMFA, and CoMSIA modeling of protein tyrosine kinases' inhibition by substituted pyrido[2,3-d]pyrimidine derivatives", Bioorg. Med. Chem., 16(2):810-21 (2008).
Database PubChem Compounds [Online] Dec. 1, 2012 (Dec. 1, 2012), XP002714058, Database accession No. CID 70113665 abstract.
Database PubChem Compounds [Online] Jul. 13, 2005 (Jul. 13, 2005), XP002714054, Database accession No. CID 2000835 abstract.
Database PubChem Compounds [Online] Jul. 13, 2005 (Jul. 13, 2005), XP002714055, Database accession No. CID 2004801 abstract.
Database PubChem Compounds [Online] Jul. 13, 2005 (Jul. 13, 2005), XP002714056, Database accession No. CID 2019230 abstract.
Database PubChem Compounds [Online] Jul. 9, 2005 (Jul. 9, 2005), XP002714051, Database accession No. CID 940974 Abstract.
Database PubChem Compounds [Online] Jul. 9, 2005 (Jul. 9, 2005), XP002714052, Database accession No. CID 945107 abstract.
Database PubChem Compounds [Online] Jul. 9, 2005 (Jul. 9, 2005), XP002714053, Database accession No. CID 945815 abstract.
Database PubChem Compounds [Online] NCBI; Dec. 1, 2012 (Dec. 1, 2012), XP002714059, Database accession No. CID 69975764 abstract.
Database PubChem Compounds [Online] NCBI; Sep. 13, 2005 (Sep. 13, 2005), XP002714057. Database accession No. CID 4000352 abstract.
Database Registry [Online] Chemical Abstracts Service. Columbus, Ohio. US; Jan. 19, 2004 (Jan. 19, 2004), XP002714050, Database accession No. 639005-15-5 abstract.
Lainchbury et al., "Discovery of 3-Alkoxyamino-5-(pyridin-2-ylamino)pyrazine-2-carbonitriles as Selective, Orally Bioavailable CHK1 Inhibitors", J. Med. Chem., 55(22):10229-40 (2012).
Proisy et al., "Rapid synthesis of 3-aminoisoquinoline-5-sulfonamides using the Buchwald-Hartwig reaction", Synthesis, 4:561-6 (2009).
Ranjitkar et al., "Affinity-Based Probes Based on Type II Kinase Inhibitors", J. Am. Chem. Soc., 134(16):19017-25 (2012).
Reader et al., "Structure-Guided Evolution of Potent and Selective CHK1 Inhibitors through Scaffold Morphing," J Med Chem, 54(24): 8328-8342 (2011).
Scifinder Search Report (Aug. 20, 2012).
Thompson et al., "Synthesis and Structure—Activity Relationships of 7-Substituted 3-(2,6-Dichlorophenyl)-1,6-naphthyridin-2(1H)-ones as Selective Inhibitors of pp60", J. Med. Chem. Lett., 43(16):3134-47 (2000).
Trumpp-Kallmeyer et al., "Development of a Binding Model to Protein Tyrosine Kinases for Substituted Pyrido[2,3-d]pyrimidine Inhibitors", J. Med. Chem., 41(11):1752-63 (1998).
Walton et al., "The Preclinical Pharmacology and Therapeutic Activity of the Novel CHK1 Inhibitor SAR-020106", Mol. Cancer Ther., 9:89 (2010).
He et al., "Synthesis and SAR of novel quinazolines as potent and brain-penetrant c-jun N-terminal kinase Inhibitors", Bioorg. Med. Chem. Let., 21:1719-1723 (2011).
Aguilera et al., "c-Jun N-terminal phosphorylation antagonizes recruitment of the Mbd3/NuRD repressor complex", Nature, 469:231-235 (2011).

* cited by examiner

PHARMACOLOGICALLY ACTIVE COMPOUNDS

RELATED APPLICATIONS

This application is a Divisional Application of U.S. patent application Ser. No. 14/426,574, filed Mar. 6, 2015, which is the U.S. National Stage of International Patent Application No. PCT/GB2013/052361, filed Sep. 9, 2013, which claims the benefit of priority to Great Britain Patent Application serial number 1216018.0, filed Sep. 7, 2012, the entire contents of each of which are expressly incorporated herein by reference in their entirety.

INTRODUCTION

The present invention relates to compounds that inhibit the spindle checkpoint function of monopolar spindle 1 (Mps1—also known as TTK) kinases, either directly or indirectly via interaction with the Mps1 kinase itself. In particular, the present invention relates to compounds for use as therapeutic agents for the treatment and/or prevention of proliferative diseases, such as cancer. The present invention also relates to processes for the preparation of these compounds, and to pharmaceutical compositions comprising them.

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the targeting of surveillance mechanisms, such as those responsible for regulating the cell cycle, with anticancer agents. For example, published patent application WO 2009/103966 (CANCER RESEARCH TECHNOLOGY LIMITED) relates to the inhibition of checkpoint kinase 1 (CHK1) kinase function, with bicyclylaryl-aryl-amine compounds, in the treatment of cancer.

The main role of the cell cycle is to enable error-free DNA replication, chromosome segregation and cytokinesis. Surveillance mechanisms, the so-called checkpoint pathways, monitor passage through mitosis at several stages. One of the best characterised is the spindle assembly checkpoint that prevents anaphase onset until the appropriate tension and attachment across kinetochores is achieved (HARDWICK KG, 1998, "The spindle checkpoint", *Trends Genet* 14, 1-4). The majority of proteins involved in the checkpoint exert their functions through protein binding interactions with the involvement of only a small number of kinases (MUSACCHIO A et al, 2007, "The spindle-assembly checkpoint in space and time", *Nature Reviews, Molecular and Cell Biology*, 8, 379-393). A mitotic checkpoint complex (MCC) that contains three checkpoint proteins (Mad2, BubR1/Mad3, Bub3) and the APC/C co-factor, CDC20, concentrates at the kinetochores and acts as a spindle checkpoint effector. Other core proteins required to amplify the checkpoint signal include Mad1 and the kinases Bub1, Mps1 (also known as TTK) and Aurora-B (MUSACCHIO, referenced above).

One of the first components of the spindle assembly checkpoint signal, identified by a genetic screen in budding yeast, was dubbed Mps1 (monopolar spindle 1) for the monopolar spindles produced by Mps1 mutant cells (WEISS E, 1996, "The *Saccharomyces cerevisiae* spindle pole body duplication gene MPS1 is part of a mitotic checkpoint", *J Cell Biol* 132, 111-123), however, it still remains one of the least studied checkpoint components in higher eukaryotes. Subsequently, the Mps1 gene was shown to encode an essential dual-specificity kinase (LAUZE et al, 1995, "Yeast spindle pole body duplication gene MPS1 encodes an essential dual specificity protein kinase", *EMBO J* 14, 1655-1663 and also POCH et al, 1994, "RPK1, an essential yeast protein kinase involved in the regulation of the onset of mitosis, shows homology to mammalian dual-specificity kinases", *Mol Gen Genet* 243, 641-653) conserved from yeast to humans (MILLS et al, 1992, "Expression of TTK, a novel human protein kinase, is associated with cell proliferation", *J Biol Chem* 267, 16000-16006). Mps1 activity peaks at the $G_2/M$ transition and is enhanced upon activation of the spindle checkpoint with nocodazole (STUCKE et al, 2002, "Human Mps1 kinase is required for the spindle assembly checkpoint but not for centrosome duplication", *EMBO J* 21, 1723-1732 and also LIU et al, 2003, "Human MPS1 kinase is required for mitotic arrest induced by the loss of CENP-E from kinetochores", *Mol Biol Cell* 14, 1638-1651). The autophosphorylation of Mps1 at Thr676 in the activation loop has been identified and is essential for Mps1 function (MATTISON et al, 2007, "Mps1 activation loop autophosphorylation enhances kinase activity", *J Biol Chem* 282, 30553-30561).

Given the importance of Mps1 in spindle checkpoint activation, the development of Mps1 inhibitors would be an asset, not only as a tool to further investigate its cell cycle-related functions, but also as a form of anticancer treatment. The first generation inhibitors of Mps1 have been described. Cincreasin, caused chromosome mis-segregation and death in yeast cells (DORER et al, 2005, "A small-molecule inhibitor of Mps1 blocks the spindle-checkpoint response to a lack of tension on mitotic chromosomes", *Curr Biol* 15, 1070-1076) and SP600125, a JNK (c-Jun amino-terminal kinase) inhibitor, also disrupts spindle checkpoint function in a JNK-independent manner via the inhibition of Mps1 (SCHMIDT et al, 2005, "Ablation of the spindle assembly checkpoint by a compound targeting Mps1", *EMBO Rep* 6, 866-872). Recently, three small molecule inhibitors of Mps1 were identified (KWIATOWSKI et al, 2010, "Small-molecule kinase inhibitors provide insight into Mps1 cell cycle function", *Nat Chem Biol* 6, 359-368; HEWITT et al, 2010, "Sustained Mps1 activity is required in mitosis to recruit 0-Mad2 to the Mad1-C-Mad2 core complex", *J Cell Biol* 190, 25-34; and SANTAGUIDA et al, 2010, "Dissecting the role of MPS1 in chromosome biorientation and the spindle checkpoint through the small molecule inhibitor reversine", *J Cell Biol* 190, 73-87). Chemical inhibition of Mps1 induced premature mitotic exit, gross aneuploidy and death to human cancer cell lines (KWIATOWSKI, above). Mps1 inhibitors AZ3146 and reversine, severely impaired recruitment of Mad1, Mad2 and CENP-E to kinetochores (HEWITT, and SANTAGUIDA, above).

Dysregulation of the mitotic checkpoint is recognised as a feature of the malignant transformation process. Mitotic checkpoint dysfunction in tumors provides an opportunity for developing a therapeutic strategy using small molecules. This is based on the proposition that pharmacologic disruption of an already compromised mitotic checkpoint may selectively sensitize tumors. This observation has led to the hypothesis that inhibition of Mps1 may be of therapeutic benefit.

SUMMARY OF THE INVENTION

In one aspect, the present invention provides a compound as defined herein, or a pharmaceutically acceptable salt or solvate thereof.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a Mps1 kinase inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an Mps1 kinase inhibitory effect.

In another aspect, the present invention provides a method of inhibiting Mps1 kinase in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound, or a pharmaceutically acceptable salt or solvate thereof, as defined herein.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicycle[2.2.2]octane, bicycle[2.1.1]hexane, bicycle[1.1.1]pentane and bicyclo[2.2.1]heptyl.

The term "(1-8C)heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "fluoroalkyl" is used herein to refer to an alkyl group in which one or more hydrogen atoms have been replaced by fluorine atoms. Examples of fluoroalkyl groups include —$CHF_2$, —$CH_2CF_3$, or perfluoroalkyl groups such as —$CF_3$ or —$CF_2CF_3$.

The term "fluoroalkoxy" is used herein to refer to an alkoxy group in which one or more hydrogen atoms have been replaced by fluorine atoms. Examples of fluoroalkoxy groups include —CHF$_2$, —CH$_2$CF$_3$, or perfluoroalkoxy groups such as —CF$_3$ or —CF$_2$CF$_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO$_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;

c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species.

Examples of aryl groups include, but are not limited to, phenyl, biphenyl, naphthyl and the like. In particular embodiment, an aryl is phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds of formula II shown below:

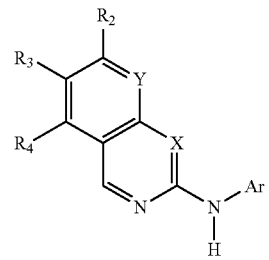

II wherein:
X is CH or N;
Y is N or C—H;
$R_2$ is selected from (1-6C)alkyl, (1-8C)heteroalkyl, aryl, aryl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, (3-8C)cycloalkyl(1-2C)alkyl, $NR_{11}R_{12}$, $OR_{13}$, $C(O)R_{13}$, $C(O)OR_{13}$, $OC(O)R_{13}$, $N(R_{14})OR_{13}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, aryl, aryl(1-2C)alkyl, heteroaryl, heteroaryl(1-2C)alkyl, heterocyclyl, heterocyclyl(1-2C)alkyl, (3-8C)cycloalkyl, or (3-8C)cycloalkyl(1-2C)alkyl, and wherein any (1-4C)alkyl, (1-4C)alkoxy, aryl, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

$R_3$ is hydrogen, (1-4C)alkyl, (3-6C)cycloalkyl, halo, $CF_3$, CN and (1-4C)alkoxy;
$R_4$ is hydrogen, (1-3C)alkyl, fluoro, chloro or $CF_3$;
Ar has the formula:

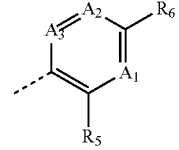

wherein:
(i) all of $A_1$, $A_2$ and $A_3$ are CH;
(ii) one of $A_1$, $A_2$ and $A_3$ is N and the others are CH; or
(iii) two of $A_1$, $A_2$ and $A_3$ are N and the other is CH;

$R_5$ is hydrogen, cyano, (1-3C)alkyl, (1-3C)fluoroalkyl, (1-3C)alkoxy, (1-3C)fluoroalkoxy, halo, (1-3C)alkanoyl, $C(O)NR_{15}R_{16}$ or $S(O)_2NR_{15}R_{16}$, and wherein $R_{15}$ and $R_{16}$ are each independently selected from H or (1-3C)alkyl, and wherein any alkyl or alkoxy moieties present within a $R_5$ substituent group are optionally further substituted by hydroxy or methoxy;

$R_6$ is halogeno, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $R_6$ is a group of the formula:

$-L^1-L^2-R_{17}$ wherein
$L^1$ is absent or a linker group of the formula $-[CR_{18}R_{19}]_n-$ in which n is an integer selected from 1, 2, 3 or 4, and $R_{18}$ and $R_{19}$ are each independently selected from hydrogen or (1-2C)alkyl;

$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{21})SO_2$, wherein $R_{20}$ and $R_{21}$ are each independently selected from hydrogen or (1-2C)alkyl; and $R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$(where $R_e$ and $R_f$ are each independently selected from hydrogen, (1-3C)alkyl, (3-6C)cycloalkyl, or (3-6C)cycloalkyl(1-2C)alkyl);

or $R_{17}$ is a group having the formula:

$-L^3-L^4-R_{24}$ wherein
$L^3$ is absent or a linker group of the formula $-[CR_{25}R_{26}]_n-$ in which n is an integer selected from 1, 2, 3 or 4, and $R_{25}$ and $R_{26}$ are each independently selected from hydrogen or (1-2C)alkyl;

$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl;

$R_{12}$ is selected from hydrogen, (1-6C)alkyl, (1-6C)alkoxy, (3-6C)cycloalkyl, (3-6C)cycloalkyl-(1-2C)alkyl, aryl, aryl-(1-2C)alkyl, heterocyclyl, heterocyclyl-(1-2C)alkyl, heteroaryl, heteroaryl-(1-2C)alkyl, and wherein $R_{12}$ is optionally further substituted by one or more substituents selected from hydroxy, fluoro, chloro, cyano, $CF_3$, $OCF_3$ (1-2C)alkyl or (1-2C)alkoxy;

$R_{13}$ is selected from hydrogen, (1-6C)alkyl, (1-6C)alkoxy, (3-6C)cycloalkyl, (3-6C)cycloalkyl-(1-2C)alkyl, aryl, aryl-(1-2C)alkyl, heteroaryl, heteroaryl-(1-2C)alkyl, and wherein $R_{13}$ is optionally further substituted by one or more substituents selected from hydroxy, fluoro, chloro, cyano, $CF_3$, $OCF_3$ (1-2C)alkyl or (1-2C)alkoxy;

$R_{11}$ and $R_{14}$ are independently selected from hydrogen, (1-6C)alkyl, (3-6C)cycloalkyl, (3-6C)cycloalkyl-(1-2C)alkyl, and wherein $R_{11}$ and $R_{14}$ are optionally further substituted by one or more substituents selected from hydroxy, fluoro, chloro, cyano, $CF_3$, $OCF_3$, (1-2C)alkyl or (1-2C)alkoxy;

subject to the proviso that:
X can only be N when Y is N; and
when X and Y are both N, $R_3$ is H or fluoro and $R_2$ is not a $NR_{11}R_{12}$ group;

or a pharmaceutically acceptable salt or solvate thereof.

In an embodiment, $R_3$ is H or fluoro when X and Y are both N, or when X is CH and Y is N.

In an embodiment, $R_3$ is H when X and Y are both N.

In an embodiment, $R_3$ is H when X and Y are both N, or when X is CH and Y is N.

In an embodiment, $R_2$ is not $NR_{11}R_{12}$ when X and Y are both N.

Particular compounds of the invention include, for example, compounds of the formula I or II, or pharmaceutically acceptable salts or solvates thereof, wherein, unless otherwise stated, each of X, Y, $R_2$, $R_3$, $R_4$, Ar, $A_1$, $A_2$, $A_3$, $R_5$, $R_6$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R^{24}$, $R^{25}$, $R^{26}$, $R^{27}$, $R_a$, $R_b$, $R_c$, $R_d$, $R_e$, $R_f$, $L^1$, $L^2$, $L^3$, and $L^4$ has any of the meanings defined hereinbefore or in any one of paragraphs (1) to (54) hereinafter:—

(1) X is CH;
(2) X and Y are both N;
(3) Y is N;
(4) Y is CH;
(5) X and Y are both CH;
(6) X is CH and Y is N;
(7) $R_2$ is selected from (1-6C)alkyl, phenyl, phenyl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, (3-8C)cycloalkyl(1-2C)alkyl, $NR_{11}R_{12}$, $OR_{13}$, $C(O)R_{13}$, $C(O)OR_{13}$, $OC(O)R_{13}$, $N(R_{14})OR_{13}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, phenyl, phenyl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, or (3-8C)cycloalkyl(1-2C)alkyl, and wherein any (1-4C)alkyl, (1-4C)alkoxy, phenyl, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

(8) $R_2$ is selected from (1-6C)alkyl, a 5 or 6 membered heteroaryl, a 3 to 6 membered heterocyclyl, a 3 to 6 membered heterocyclyl(1-2C)alkyl, (3-8C)cycloalkyl, $NR_{11}R_{12}$, $OR_{13}$, $C(O)R_{13}$, $C(O)OR_{13}$, $OC(O)R_{13}$, $N(R_{14})OR_{13}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, 5 or 6 membered heteroaryl, 5 or 6 membered heteroaryl(1-2C)alkyl, a 3 to 6 membered heterocyclyl, a 3 to 6 membered heterocyclyl(1-2C)alkyl, (3-6C)cycloalkyl, or (3-8C)cycloalkyl(1-2C)alkyl, and wherein any (1-4C)alkyl, (1-4C)alkoxy heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

(9) $R_2$ is selected from (1-6C)alkyl, a 5 or 6 membered heteroaryl, a 3 to 6 membered heterocyclyl, a 3 to 6 membered heterocyclyl(1-2C)alkyl, (3-8C)cycloalkyl, $NR_{11}R_{12}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, 5 or 6 membered heteroaryl, a 3 to 6 membered heterocyclyl, a 3 to 6 membered heterocyclyl(1-2C)alkyl, (3-6C)cycloalkyl, or (3-8C)cycloalkyl(1-2C)alkyl, and wherein any (1-4C)alkyl, (1-4C)alkoxy, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

(10) $R_2$ is selected from (1-6C)alkyl, a 5 or 6 membered heteroaryl, a 3 to 6 membered heterocyclyl, a 3 to 6 membered heterocyclyl(1-2C)alkyl, (3-8C)cycloalkyl, $NR_{11}R_{12}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, hydroxy, amino, carboxy, carbamoyl, sulphamoyl, (1-2C)alkyl, (1-2C)alkoxy, $S(O)_xCH_3$ (where x is 0, 1 or 2), methylamino or dimethylamino, 5 or 6 membered heteroaryl, a 3 to 6 membered heterocyclyl, a 3 to 6 membered heterocyclyl(1-2C)alkyl, (3-6C)cycloalkyl, or (3-8C)cycloalkyl(1-2C)alkyl, and wherein any (1-4C)alkyl, (1-4C)alkoxy, heteroaryl, heterocyclyl, or (3-8C)cycloalkyl moiety present within a substituent group on $R_2$ is optionally further substituted by fluoro, chloro, trifluoromethyl, trifluoromethoxy, cyano, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

(11) $R_2$ is selected from a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, (3-8C)cycloalkyl(1-2C)alkyl, $NR_{11}R_{12}$, $OR_{13}$, $C(O)R_{13}$, $C(O)OR_{13}$, $OC(O)R_{13}$, $N(R_{14})OR_{13}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, phenyl, phenyl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, or (3-8C)cycloalkyl(1-2C)alkyl, and wherein any (1-4C)alkyl, (1-4C)alkoxy, phenyl, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

(12) $R_2$ is a 5 or 6 membered heteroaryl which is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, 5 or 6 membered heteroaryl, 5 or 6 membered heteroaryl(1-2C)alkyl, a 3 to 6 membered heterocyclyl, a 3 to 6 membered heterocyclyl(1-2C)alkyl, (3-6C)cycloalkyl, or (3-8C)cycloalkyl(1-2C)alkyl, and wherein any (1-4C)alkyl, (1-4C)alkoxy heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)$ R$_c$, C(O)OR$_c$, OC(O)R$_c$, N(R$_d$)OR$_c$, C(O)N(R$_d$)R$_c$, N(R$_d$)C(O)R$_c$, S(O)$_y$R$_c$ (where y is 0, 1 or 2), SO$_2$N(R$_d$)R$_c$, or N(R$_d$)SO$_2$R$_c$, wherein R$_c$ and R$_d$ are each independently selected from H or (1-4C)alkyl;
or R$_2$ is C(O)N(R$_{14}$)R$_{13}$, N(R$_{14}$)C(O)R$_{13}$, wherein R$_{13}$ is (1-6C)alkyl and R$_{14}$ is hydrogen;

(13) R$_2$ is a 5 or 6 membered heteroaryl, which is optionally substituted by one or more substituent groups selected from fluoro, chloro, trifluoromethyl, trifluoromethoxy, cyano, hydroxy, amino, (1-4C)alkyl, (1-4C)alkoxy,
and wherein any (1-4C)alkyl or (1-4C)alkoxy moiety present within a substituent group on R$_2$ is optionally further substituted by fluoro, chloro, cyano, hydroxy, amino, OR$_c$, wherein R$_c$ is (1-4C)alkyl;
or R$_2$ is C(O)N(R$_{14}$)R$_{13}$, wherein R$_{13}$ is (1-4C)alkyl and R$_{14}$ is hydrogen;

(14) R$_2$ is a 5 or 6 membered heteroaryl, which is optionally substituted by one or more substituent groups selected from (1-4C)alkyl or (1-4C)alkoxy,
and wherein an (1-4C)alkyl or (1-4C)alkoxy is optionally further substituted by fluoro, chloro, cyano, hydroxy, amino, OR$_c$, wherein R$_c$ is (1-4C)alkyl;
or R$_2$ is C(O)N(R$_{14}$)R$_{13}$, wherein R$_{13}$ is methyl and R$_{14}$ is hydrogen;

(15) R$_2$ is a 5 membered heteroaryl, which is optionally substituted by one or more substituent groups selected from (1-4C)alkyl or (1-4C)alkoxy, and wherein an (1-4C)alkyl or (1-4C)alkoxy is optionally further substituted by fluoro, chloro, cyano, hydroxy, amino, OR$_c$, wherein R$_c$ is (1-4C)alkyl;

(16) R$_2$ is a pyrazolyl, which is optionally substituted by one or more substituent groups selected from (1-4C)alkyl or (1-4C)alkoxy, and wherein an (1-4C)alkyl or (1-4C)alkoxy is optionally further substituted by fluoro, chloro, cyano, hydroxy, amino, OR$_c$, wherein R$_c$ is (1-4C)alkyl;

(17) R$_3$ is hydrogen, fluoro, (1-2C)alkyl, or (3-6C)cycloalkyl;
(18) R$_3$ is hydrogen;
(19) R$_3$ is (1-2C)alkyl
(20) R$_3$ is fluoro;
(21) R$_4$ is hydrogen, (1-2C)alkyl, fluoro, chloro or CF$_3$;
(22) R$_4$ is hydrogen or methyl;
(23) R$_4$ is hydrogen;
(24) R$_4$ is methyl;
(25) Ar has the formula:

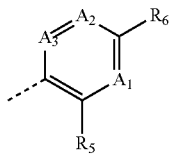

wherein:
(i) all of A$_1$, A$_2$ and A$_3$ are CH; or
(ii) A$_3$ is CH and one of A$_1$ or A$_2$ is N and the other is CH;
and R$_5$ and R$_6$ each have any one of the definitions set out herein;

(26) Ar has the formula:

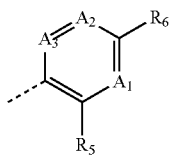

wherein:
(i) all of A$_1$, A$_2$ and A$_3$ are CH; or
(ii) A$_2$ and A$_3$ are both CH and A$_1$ is N;
and R$_5$ and R$_6$ each have any one of the definitions set out herein;

(27) Ar has the formula:

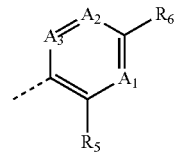

wherein:
all of A$_1$, A$_2$ and A$_3$ are CH;
and R$_5$ and R$_6$ each have any one of the definitions set out herein;

(28) R$_5$ is hydrogen, cyano, (1-3C)alkyl, (1-3C)fluoroalkyl, (1-3C)alkoxy, (1-3C)fluoroalkoxy, and halo, and wherein any alkyl or alkoxy moities present within a R$_5$ substituent group are optionally further substituted by hydroxy or methoxy;

(29) R$_5$ is hydrogen, (1-3C)alkyl, (1-3C)alkoxy, (1-3C)fluoroalkoxy and halo, and wherein any alkyl or alkoxy moities present within a R$_5$ substituent group are optionally further substituted by methoxy;

(30) R$_5$ is (1-2C)alkyl, CF$_3$, (1-2C)alkoxy, —OCF$_3$, —OCF$_2$ or Cl;
(31) R$_5$ is OCH$_3$, OCH$_2$CH$_3$ or Cl;
(32) R$_5$ is OCH$_3$;
(33) R$_5$ is Cl;
(34) R$_6$ is halogeno, trifluoromethyl, trifluoromethoxy, cyano, hydroxy, amino, carboxy, carbamoyl, sulphamoyl,
or R$_6$ is a group of the formula:

wherein
L$^1$ is absent or a linker group of the formula —[CR$_{18}$R$_{19}$]$_n$— in which n is an integer selected from 1 or 2, and R$_{18}$ and R$_{19}$ are each independently selected from hydrogen or methyl;
L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{20}$)SO$_2$, wherein R$_{20}$ and R$_{21}$ are each independently selected from hydrogen or (1-2C)alkyl; and
R$_{17}$ is (1-6C)alkyl, aryl, (3-6C)cycloalkyl, heteroaryl, or heterocyclyl,
and wherein R$_{17}$ is optionally further substituted by one or more substituent groups independently selected from oxo, halo, cyano, nitro, hydroxy, NR$_{22}$R$_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$; wherein R$_{22}$ and R$_{23}$ are each independently selected from hydrogen, (1-4C)alkyl or (3-6C)cycloalkyl or (3-6C)cycloalkyl(1-2C)alkyl; or R$_{22}$ and R$_{23}$ can be linked such that, together with the nitrogen atom to which they are attached, they form a 4-6 membered heterocyclic ring;
and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

or $R_{17}$ is a group having the formula:

-$L^3$-$L^4$-$R_{24}$ $L^3$ is absent or a linker group of the formula —$[CR_{25}R_{26}]_n$— in which n is an integer selected from 1 or 2, and $R_{25}$ and $R_{26}$ are each hydrogen;

$L^4$ is absent or is selected from O, S, SO, $SO_2$, $N(R_{27})$, C(O), C(O)O, OC(O), C(O)$N(R_{27})$, $N(R_{27})$C(O), $S(O)_2N(R_{27})$ or $N(R_{28})SO_2$, wherein $R_{27}$ and $R_{28}$ are each independently selected from hydrogen or (1-2C)alkyl; and $R_{24}$ is (1-6C)alkyl, phenyl, phenyl-(1-2C)alkyl, (3-6C)cycloalkyl, (3-6C)cycloalkyl-(1-4C)alkyl, 5 or 6-membered heteroaryl, 5 or 6-membered heteroaryl-(1-2C)alkyl, 4 to 6-membered heterocyclyl, 4 to 6-membered heterocyclyl-(1-2C)alkyl;

(35) $R_6$ is halogeno, trifluoromethyl, trifluoromethoxy, cyano, hydroxy, amino, carboxy, carbamoyl, sulphamoyl, or $R_6$ is a group of the formula:

-$L^1$-$L^2$-$R_{17}$ wherein $L^1$ is absent or a linker group of the formula —$[CR_{18}R_{19}]_n$— in which n is an integer selected from 1 or 2, and $R_{18}$ and $R_{19}$ are both hydrogen;

$L^2$ is absent or is selected from O, S, SO, $SO_2$, $N(R_{20})$, C(O), C(O)O, OC(O), CH($OR_{20}$), C(O)$N(R_{20})$, $N(R_{20})$C(O), $N(R_{20})$C(O)$N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, 5 or 6 membered monocyclic heteroaryl, 8 to 12 membered bicyclic heteroaryl, or 3 to 6 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

or $R_{17}$ is a group having the formula:

-$L^3$-$L^4$-$R_{24}$ $L^3$ is absent or —$CH_2$—;

$L^4$ is absent or selected from O, S, SO, $SO_2$, $N(R_{27})$, C(O), C(O)O, OC(O), C(O)$N(R_{27})$, $N(R_{27})$C(O), $S(O)_2N(R_{27})$ or $N(R_{28})SO_2$, wherein $R_{27}$ and $R_{28}$ are each independently selected from hydrogen or (1-2C)alkyl; and $R_{24}$ is (1-6C)alkyl;

(36) $R_6$ is a group of the formula:

-$L^1$-$L^2$-$R_{17}$ wherein $L^1$ is absent or a linker group of the formula —$[CR_{18}R_{19}]_n$— in which n is an integer selected from 1 or 2, and $R_{18}$ and $R_{19}$ are both hydrogen;

$L^2$ is absent or is selected from O, S, SO, $SO_2$, $N(R_{20})$, C(O), C(O)O, OC(O), CH($OR_{20}$), C(O)$N(R_{20})$, $N(R_{20})$C(O), $N(R_{20})$C(O)$N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, 5 or 6 membered monocyclic heteroaryl, 8 to 12 membered bicyclic heteroaryl, or 3 to 6 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

or $R_{17}$ is a group having the formula:

-$L^3$-$L^4$-$R_{24}$ $L^3$ is absent;

$L^4$ is absent or selected from O, S, SO, $SO_2$, $N(R_{27})$, C(O), C(O)O, OC(O), C(O)$N(R_{27})$, $N(R_{27})$C(O), $S(O)_2N(R_{27})$ or $N(R_{28})SO_2$, wherein $R_{27}$ and $R_{28}$ are each independently selected from hydrogen or (1-2C)alkyl; and $R_{24}$ is (1-4C)alkyl;

(37) $R_6$ is halogeno, trifluoromethyl, trifluoromethoxy, cyano, hydroxy, amino, carboxy, carbamoyl, sulphamoyl, or $R_6$ is a group of the formula:

-$L^1$-$L^2$-$R_{17}$ wherein $L^1$ is absent or a linker group of the formula —$[CR_{18}R_{19}]_n$— in which n is an integer selected from 1 or 2, and $R_{18}$ and $R_{19}$ are each independently selected from hydrogen or methyl;

$L^2$ is absent or is selected from O, S, SO, $SO_2$, $N(R_{20})$, C(O), C(O)O, OC(O), CH($OR_{20}$), C(O)$N(R_{20})$, $N(R_{20})$C(O), $N(R_{20})$C(O)$N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, heteroaryl, or heterocyclyl, and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

(38) $R_6$ is halogeno, trifluoromethyl, trifluoromethoxy, cyano, hydroxy, amino, carboxy, carbamoyl, sulphamoyl, or $R_6$ is a group of the formula:

-$L^1$-$L^2$-$R_{17}$ wherein
  $L^1$ is absent or a linker group of the formula —$[CR_{18}R_{19}]_n$— in which n is an integer selected from 1 or 2, and $R_{18}$ and $R_{19}$ are both hydrogen;
  $L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and
  $R_{17}$ is (1-6C)alkyl, aryl, (3-6C)cycloalkyl, 5 or 6 membered monocyclic heteroaryl, 8 to 12 membered bicyclic heteroaryl, or 3 to 6 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

(39) $R_6$ is a group of the formula:

-$L^1$-$L^2$-$R_{17}$ wherein
  $L^1$ is absent or a linker group of the formula —$[CR_{18}R_{19}]_n$— in which n is an integer selected from 1 or 2, and $R_{18}$ and $R_{19}$ are both hydrogen;
  $L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and
  $R_{17}$ is (1-6C)alkyl, aryl, (3-6C)cycloalkyl, 5 or 6 membered monocyclic heteroaryl, 8 to 12 membered bicyclic heteroaryl, or 3 to 6 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

(40) $R_6$ is a group of the formula:

-$L^1$-$L^2$-$R_{17}$ wherein
  $L^1$ is absent or a linker group of the formula —$[CR_{18}R_{19}]_n$— in which n is an integer selected from 1 or 2, and $R_{18}$ and $R_{19}$ are both hydrogen;
  $L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and
  $R_{17}$ is (1-6C)alkyl, aryl, (3-6C)cycloalkyl, 5 or 6 membered monocyclic heteroaryl, 8 to 12 membered bicyclic heteroaryl, or 3 to 6 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

(41) $R_6$ is a group of the formula:

-L¹-L²-R₁₇ wherein
$L^1$ is absent;
$L^2$ is absent or is selected from O, S, SO, SO₂, N($R_{20}$), C(O), C(O)O, OC(O), CH(O$R_{20}$), C(O)N($R_{20}$), N($R_{20}$)C(O), S(O)₂N($R_{20}$), or N($R_{20}$)SO₂, wherein $R_{20}$ is selected from hydrogen or (1-2C)alkyl; and
$R_{17}$ is (1-6C)alkyl, aryl, (3-6C)cycloalkyl, 5 or 6 membered heteroaryl, 8 to 12 membered bicyclic heteroaryl, or 3 to 6 membered heterocyclyl,
and wherein $R_{17}$ is optionally further substituted by one or more substituent groups independently selected from oxo, halo, cyano, hydroxy, N$R_{22}R_{23}$, (1-4C)alkoxy, (1-4C)alkyl, (1-5C)alkyl-sulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CON$R_{22}R_{23}$, and SO₂N$R_{22}R_{23}$; wherein $R_{22}$ and $R_{23}$ are each independently selected from hydrogen or (1-4C)alkyl;
and wherein when said substituent group comprises an alkyl, cycloalkyl, heterocyclyl or heteroaryl moiety then said moiety is optionally further substituted by hydroxy, fluoro, chloro, cyano, CF₃, OCF₃, (1-2C)alkyl, (1-2C)alkoxy, SO₂(1-2C)alkyl or N$R_eR_f$ (where $R_e$ and $R_f$ are each independently selected from hydrogen or (1-2C)alkyl);

(42) $R_6$ is a group of the formula:

-L¹-L²-R₁₇ wherein
$L^1$ is absent;
$L^2$ is absent or is selected from O, S, SO, SO₂, N($R_{20}$), C(O), C(O)O, OC(O), CH(O$R_{20}$), C(O)N($R_{20}$), N($R_{20}$)C(O), S(O)₂N($R_{20}$), or N($R_{20}$)SO₂, wherein $R_{20}$ is selected from hydrogen or (1-2C)alkyl; and
$R_{17}$ is (1-6C)alkyl, phenyl, (3-6C)cycloalkyl, 5 or 6 membered heteroaryl, 8 to 12 membered bicyclic heteroaryl, or 3 to 6 membered heterocyclyl,
and wherein $R_{17}$ is optionally further substituted by one or more substituent groups independently selected from oxo, halo, cyano, hydroxy, N$R_{22}R_{23}$, (1-4C)alkoxy, (1-4C)alkyl, (1-4C)alkyl-sulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CON$R_{22}R_{23}$, and SO₂N$R_{22}R_{23}$; wherein $R_{22}$ and $R_{23}$ are each independently selected from hydrogen or (1-2C)alkyl;
and wherein when said substituent group comprises an alkyl, cycloalkyl, heterocyclyl or heteroaryl moiety then said moiety is optionally further substituted by hydroxy, fluoro, chloro, cyano, CF₃, OCF₃, (1-2C)alkyl, (1-2C)alkoxy, SO₂(1-2C)alkyl or N$R_eR_f$ (where $R_e$ and $R_f$ are each independently selected from hydrogen or methyl);

(43) $R_6$ is a group of the formula:

-L¹-L²-R₁₇ wherein
$L^1$ is absent;
$L^2$ is absent, C(O) or S(O)₂N($R_{20}$), wherein $R_{20}$ is selected from hydrogen or (1-2C)alkyl; and
$R_{17}$ is:
(i) (1-6C)alkyl when $L^2$ is S(O)₂N($R_{20}$),
(ii) 5 or 6 membered heteroaryl when $L^2$ is absent, or
(iii) 3 to 6 membered nitrogen-linked heterocyclyl when $L^2$ is C(O);

and wherein $R_{17}$ is optionally further substituted by one or more substituent groups independently selected from oxo, halo, cyano, hydroxy, N$R_{22}R_{23}$, (1-4C)alkoxy, (1-4C)alkyl, (1-4C)alkyl-sulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CON$R_{22}R_{23}$, and SO₂N$R_{22}R_{23}$; wherein $R_{22}$ and $R_{23}$ are each independently selected from hydrogen or (1-2C)alkyl;
and wherein when said substituent group comprises an alkyl, cycloalkyl, heterocyclyl or heteroaryl moiety then said moiety is optionally further substituted by hydroxy, fluoro, chloro, cyano, CF₃, OCF₃, (1-2C)alkyl, (1-2C)alkoxy, SO₂(1-2C)alkyl or N$R_eR_f$ (where $R_e$ and $R_f$ are each independently selected from hydrogen or methyl);

(44) $R_{12}$ is selected from hydrogen, (1-6C)alkyl, (3-6C)cycloalkyl, (3-6C)cycloalkyl-(1-2C)alkyl, phenyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, and wherein $R_8$, $R_9$, $R_{12}$ and $R_{13}$ are optionally further substituted by one or more substituents selected from hydroxy, fluoro, chloro, cyano, CF₃, OCF₃, (1-2C)alkyl or (1-2C)alkoxy;

(45) $R_{12}$ is selected from hydrogen, (1-6C)alkyl, (3-6C)cycloalkyl, (3-6C)cycloalkyl-(1-2C)alkyl, 3 to 6 membered heterocyclyl, 3 to 6 membered heterocyclyl-(1-2C)alkyl, and wherein $R_8$, $R_9$, $R_{12}$ and $R_{13}$ are optionally further substituted by one or more substituents selected from hydroxy, fluoro, chloro, cyano, CF₃, OCF₃, methyl or methoxy;

(46) $R_{12}$ is selected from hydrogen or (1-6C)alkyl;

(47) $R_{13}$ is selected from hydrogen, (1-6C)alkyl, (3-6C)cycloalkyl, (3-6C)cycloalkyl-(1-2C)alkyl, phenyl, 5 or 6 membered heteroaryl, 5 or 6 membered heteroaryl-(1-2C)alkyl, and wherein $R_8$, $R_9$, $R_{12}$ and $R_{13}$ are optionally further substituted by one or more substituents selected from hydroxy, fluoro, chloro, cyano, CF₃, OCF₃, (1-2C)alkyl or (1-2C)alkoxy;

(48) $R_{13}$ is selected from hydrogen, (1-6C)alkyl, (3-6C)cycloalkyl, (3-6C)cycloalkyl-(1-2C)alkyl, and wherein $R_8$, $R_9$, $R_{12}$ and $R_{13}$ are optionally further substituted by one or more substituents selected from hydroxy, fluoro, chloro, cyano, CF₃, OCF₃, methyl or methoxy;

(49) $R_{13}$ is selected from hydrogen or (1-6C)alkyl;

(50) $R_{11}$ and $R_{14}$ are independently selected from hydrogen, (1-4C)alkyl, (3-6C)cycloalkyl, (3-6C)cycloalkyl-(1-2C)alkyl;

(51) $R_{11}$ and $R_{14}$ are independently selected from hydrogen or (1-4C)alkyl;

(52) $R_{11}$ and $R_{14}$ are independently selected from hydrogen or (1-2C)alkyl;

(53) $R_{11}$ and $R_{14}$ are independently selected from hydrogen or methyl;

(54) $R_{11}$ and $R_{14}$ are hydrogen.

In an embodiment, X and Y are both CH or X and Y are both N.
In an embodiment, X and Y are both CH.
In an embodiment, X and Y are both N.
In a further embodiment, X is CH and Y is N.
As stated above, in the compounds of formula II, X can only be N when Y is N. Accordingly, the compounds of formula II may have one of the structures IIa, IIb or IIc shown below:

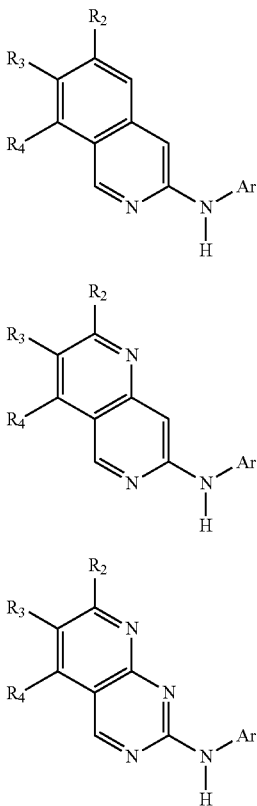

In an embodiment, the compound of the invention is a compound of formula IIa above, wherein $R_2$, $R_3$, $R_4$ and Ar each have any one of the definitions set out herein.

In an embodiment, the compound of the invention is a compound of formula IIb, wherein $R_2$, $R_3$, $R_4$ and Ar each have any one of the definitions set out herein.

In an embodiment, the compound of the invention is a compound of formula IIc, wherein $R_2$, $R_3$, $R_4$ and Ar each have any one of the definitions set out herein.

Suitably, the compounds of formula II have the structural formula IIa or IIc, especially structural formula IIa.

Suitably, $R_2$ is as defined in any one of paragraphs (7) to (16) above.

Suitably, $R_3$ is as defined in any one of paragraphs (17) to (20) above.

Suitably, $R_4$ is as defined in any one of paragraphs (21) to (24) above.

Suitably, Ar is as defined in any one of paragraphs (25) to (27) above.

Suitably, $R_5$ is as defined in any one of paragraphs (28) to (33) above.

Suitably, $R_6$ is as defined in any one of paragraphs (34) to (43) above.

Suitably, $R_{12}$ is as defined in any one of paragraphs (44) to (46) above.

Suitably, $R_{13}$ is as defined in any one of paragraphs (47) to (49) above.

Suitably, $R_{11}$ and $R_{14}$ are as defined in any one of paragraphs (50) to (54) above.

In an embodiment, the compound is a compound of formula II, IIa, IIb or IIc as defined herein wherein $R_3$ is H and $R_2$, $R_4$, and Ar each have any one of the definitions set out herein.

In an embodiment, the compound is a compound of formula II, IIa, IIb or IIc as defined herein wherein $R_4$ is H and $R_2$, $R_3$, and Ar each have any one of the definitions set out herein.

In an embodiment, the compound is a compound of formula II, IIa, IIb or IIc as defined herein wherein $R_3$ and $R_4$ are H, and $R_2$ and Ar each have any one of the definitions set out herein.

In an embodiment, the compound is a compound of formula II, IIa, IIb or IIc as defined herein wherein $A_3$ is CH and $R_2$, $R_3$, $R_4$, $R_5$, $R_6$, $A_1$ and $A_2$ each have any one of the definitions set out herein.

In an embodiment, the compound is a compound of formula II, IIa, IIb or IIc as defined herein wherein $A_3$ is CH; $R_3$ and $R_4$ are both H; and $R_2$, $R_5$, $R_6$, $A_1$ and $A_2$ each have any one of the definitions set out herein.

In an embodiment, the compound is a compound of formula II, IIa, IIb or IIc as defined herein wherein
$A_3$ is CH;
$R_3$ and $R_4$ are both H;
$R_2$ is as defined in any one of paragraphs (7) to (16) above;
$R_5$ is as defined in any one of paragraphs (28) to (33) above;
$R_6$ is as defined in any one of paragraphs (34) to (43) above;
both of $A_1$ and $A_2$ are CH or one of $A_1$ and $A_2$ is CH and the other is N.

In an embodiment, the compound is a compound of formula II, IIa, IIb or IIc as defined herein wherein
$A_3$ is CH;
$R_3$ and $R_4$ are both H;
$R_2$ is as defined in any one of paragraphs (10) to (16) above;
$R_5$ is as defined in any one of paragraphs (30) to (33) above;
$R_6$ is as defined in any one of paragraphs (36) to (43) above;
both of $A_1$ and $A_2$ are CH or one of $A_1$ and $A_2$ is CH and the other is N.

In an embodiment, the compound is a compound of formula II, IIa, IIb or IIc as defined herein wherein Ar is as defined in either paragraph (26) or (27) above, and $R_2$, $R_3$, and $R_4$ each have any one of the definitions set out herein.

In an embodiment, the compound is a compound of formula II, IIa, IIb or IIc as defined herein in which Ar has the formula:

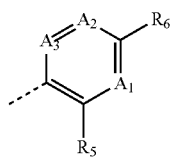

wherein:
(i) all of $A_1$, $A_2$ and $A_3$ are CH; or
(ii) $A_2$ and $A_3$ are both CH and $A_1$ is N;
$R_5$ is methoxy or chloro; and
$R_2$, $R_3$, $R_4$ and $R_6$ each have any one of the definitions set out herein.

In an embodiment, the compound is a compound of formula II, IIa, IIb or IIc as defined herein before in which Ar has the formula:

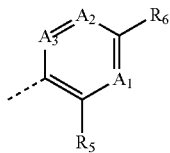

wherein:
(i) all of $A_1$, $A_2$ and $A_3$ are CH; or
(ii) $A_2$ and $A_3$ are both CH and $A_1$ is N;
$R_5$ is methoxy or chloro;
$R_3$ and $R_4$ are both hydrogen; and
$R_2$ is as defined in any one of paragraphs (7) to (16) above; and
$R_6$ is as defined in any one of paragraphs (34) to (43) above.

In an embodiment, the compound is a compound of formula IIa, IIb or IIc as defined herein before in which Ar has the formula:

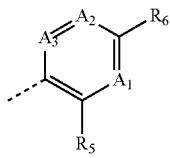

wherein:
all of $A_1$, $A_2$ and $A_3$ are CH; or
$R_5$ is methoxy or ethoxy;
$R_3$ and $R_4$ are both hydrogen; and
$R_2$ is as defined in any one of paragraphs (12) to (16) above; and
$R_6$ is as defined in any one of paragraphs (34) to (43) above.

In an embodiment, the compound is a compound of formula IIa, IIb or IIc as defined herein before in which Ar has the formula:

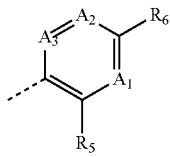

wherein:
all of $A_1$, $A_2$ and $A_3$ are CH; or
$R_5$ is methoxy or ethoxy;
$R_3$ and $R_4$ are both hydrogen; and
$R_2$ is as defined in any one of paragraphs (12) to (16) above; and
$R_6$ is as defined in any one of paragraphs (40) to (43) above.

In an embodiment, the compound is a compound of formula IIa, IIb or IIc as defined herein before in which Ar has the formula:

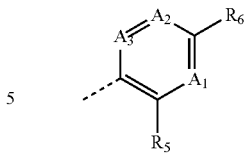

wherein:
all of $A_1$, $A_2$ and $A_3$ are CH; or
$R_5$ is methoxy or ethoxy;
$R_3$ and $R_4$ are both hydrogen; and
$R_2$ is as defined in paragraph (16) above; and
$R_6$ is as defined in paragraph (43) above.

Particular compounds of the present invention include any one of the compounds exemplified in the present application, or a pharmaceutically acceptable salt or solvate thereof, and, in particular, any one of the following:
(3-methoxy-4-((6-(1-methyl-1H-pyrazol-4-yl)isoquinolin-3-yl)amino)phenyl)(3-methoxyazetidin-1-yl)methanone;
N-(4-(1,2-dimethyl-1H-imidazol-5-yl)-2-methoxyphenyl)-6-(1-methyl-1H-pyrazol-4-yl)isoquinolin-3-amine;
N-(2-chloro-4-(1,2-dimethyl-1H-imidazol-5-yl)phenyl)-6-(1-methyl-1H-pyrazol-4-yl)isoquinolin-3-amine;
N-(2-methoxy-4-(1-methyl-1H-imidazol-5-yl)phenyl)-6-(1-methyl-1H-pyrazol-4-yl)isoquinolin-3-amine;
N-(4-(1,2-dimethyl-1H-imidazol-5-yl)-2-methoxyphenyl)-6-(1,5-dimethyl-1H-pyrazol-4-yl)isoquinolin-3-amine;
N-(4-(1,2-dimethyl-1H-imidazol-5-yl)-2-methoxyphenyl)-6-(1,3-dimethyl-1H-pyrazol-4-yl)isoquinolin-3-amine;
6-cyclopropyl-N-(4-(1,2-dimethyl-1H-imidazol-5-yl)-2-methoxyphenyl)isoquinolin-3-amine;
N-(4-(1,2-dimethyl-1H-imidazol-5-yl)-2-methoxyphenyl)-6-(pyrimidin-5-yl)isoquinolin-3-amine;
N-(4-(1,2-dimethyl-1H-imidazol-5-yl)-2-methoxyphenyl)-6-(pyridin-3-yl)isoquinolin-3-amine;
N-(4-(1,2-dimethyl-1H-imidazol-5-yl)-2-methoxyphenyl)-7-(1-methyl-1H-pyrazol-4-yl)pyrido[2,3-d]pyrimidin-2-amine;
N-(4-(1,2-dimethyl-1H-imidazol-5-yl)-2-methoxyphenyl)-6-(1-isopropyl-1H-pyrazol-4-yl)isoquinolin-3-amine;
N-(4-(1,2-dimethyl-1H-imidazol-5-yl)-2-methoxyphenyl)-6-(1-(2-methoxyethyl)-1H-pyrazol-4-yl)isoquinolin-3-amine;
N-(4-(1,2-dimethyl-1H-imidazol-5-yl)-2-methoxyphenyl)-6-(2,4-dimethylthiazol-5-yl)isoquinolin-3-amine;
tert-butyl (5-(3-((4-(1,2-dimethyl-1H-imidazol-5-yl)-2-methoxyphenyl)amino)isoquinolin-6-yl)pyridin-2-yl)(methyl)carbamate;
N-(4-(1,2-dimethyl-1H-imidazol-5-yl)-2-methoxyphenyl)-6-(6-(methylamino)pyridin-3-yl)isoquinolin-3-amine;
N-(4-(1,2-dimethyl-1H-imidazol-5-yl)-2-methoxyphenyl)-6-(6-methylpyridin-3-yl)isoquinolin-3-amine;
N-(4-(1,2-dimethyl-1H-imidazol-5-yl)-2-methoxyphenyl)-6-(1-ethyl-1H-pyrazol-4-yl)isoquinolin-3-amine;
N-(4-(1,2-dimethyl-1H-imidazol-5-yl)-2-methoxyphenyl)-6-(thiazol-5-yl)isoquinolin-3-amine;
N-(4-(1,2-dimethyl-1H-imidazol-5-yl)-2-methoxyphenyl)-6-(6-(dimethylamino)pyridin-3-yl)isoquinolin-3-amine;
N-(4-(1,2-dimethyl-1H-imidazol-5-yl)-2-methoxyphenyl)-6-(pyridin-4-yl)isoquinolin-3-amine;
N-(4-(1,2-dimethyl-1H-imidazol-5-yl)-2-methoxyphenyl)-6-(oxazol-5-yl)isoquinolin-3-amine;
6-(1,2-dimethyl-1H-imidazol-5-yl)-N-(4-(1,2-dimethyl-1H-imidazol-5-yl)-2-methoxyphenyl)isoquinolin-3-amine;

tert-butyl 4-(4-(3-((4-(1,2-dimethyl-1H-imidazol-5-yl)-2-methoxyphenyl)amino)isoquinolin-6-yl)-1H-pyrazol-1-yl)piperidine-1-carboxylate;

N-(4-(1,2-dimethyl-1H-imidazol-5-yl)-2-methoxyphenyl)-6-(1-(piperidin-4-yl)-1H-pyrazol-4-yl)isoquinolin-3-amine;

6-(1-(2,2-difluoroethyl)-1H-pyrazol-4-yl)-N-(4-(1,2-dimethyl-1H-imidazol-5-yl)-2-methoxyphenyl)isoquinolin-3-amine;

6-(1-(cyclopropylmethyl)-1H-pyrazol-4-yl)-N-(4-(1,2-dimethyl-1H-imidazol-5-yl)-2-methoxyphenyl)isoquinolin-3-amine;

N-(4-(1,2-dimethyl-1H-imidazol-5-yl)-2-methoxyphenyl)-6-(1-(((tetrahydro-2H-pyran-4-yl)methyl)-1H-pyrazol-4-yl)isoquinolin-3-amine;

N-(4-(1,2-dimethyl-1H-imidazol-5-yl)-2-methoxyphenyl)-6-(1-methyl-1H-1,2,3-triazol-5-yl)isoquinolin-3-amine;

N-(4-(1,2-dimethyl-1H-imidazol-5-yl)-2-methoxyphenyl)-6-(5-methylpyridin-3-yl)isoquinolin-3-amine;

(5-(3-methoxy-4-((6-(1-(2-methoxyethyl)-1H-pyrazol-4-yl)isoquinolin-3-yl)amino)phenyl)-1-methyl-1H-imidazol-2-yl)methanol;

6-(1-(cyclobutylmethyl)-1H-pyrazol-4-yl)-N-(4-(1,2-dimethyl-1H-imidazol-5-yl)-2-methoxyphenyl)isoquinolin-3-amine;

1-(4-(3-((4-(1,2-dimethyl-1H-imidazol-5-yl)-2-methoxyphenyl)amino)isoquinolin-6-yl)-1H-pyrazol-1-yl)-2-methylpropan-2-ol;

N-(4-(1,2-dimethyl-1H-imidazol-5-yl)-2-methoxyphenyl)-6-(1-((3-methyloxetan-3-yl)methyl)-1H-pyrazol-4-yl)isoquinolin-3-amine;

N-(2-methoxy-4-(1-(2-methoxyethyl)-2-methyl-1H-imidazol-5-yl)phenyl)-6-(1-(2-methoxyethyl)-1H-pyrazol-4-yl)isoquinolin-3-amine;

(4-(3-methoxy-4-((6-(1-(2-methoxyethyl)-1H-pyrazol-4-yl)isoquinolin-3-yl)amino)phenyl)-1-methyl-1H-pyrazol-5-yl)methanol;

N-(4-(1,2-dimethyl-1H-imidazol-5-yl)-2-methoxyphenyl)-6-(1-(oxetan-3-yl)-1H-pyrazol-4-yl)isoquinolin-3-amine;

(4-(3-((4-(1,2-dimethyl-1H-imidazol-5-yl)-2-methoxyphenyl)amino)isoquinolin-6-yl)-1-methyl-1H-pyrazol-5-yl)methanol;

1-(4-(3-((2-methoxy-4-(1-(2-methoxyethyl)-2-methyl-1H-imidazol-5-yl)phenyl)amino)isoquinolin-6-yl)-1H-pyrazol-1-yl)-2-methylpropan-2-ol;

1-(4-(3-((4-(5-(hydroxymethyl)-1-methyl-1H-pyrazol-4-yl)-2-methoxyphenyl)amino)isoquinolin-6-yl)-1H-pyrazol-1-yl)-2-methylpropan-2-ol;

N-(4-(1,2-dimethyl-1H-imidazol-5-yl)-2-methoxyphenyl)-6-(1-(oxetan-3-ylmethyl)-1H-pyrazol-4-yl)isoquinolin-3-amine;

1-(4-(3-((4-(1,2-dimethyl-1H-imidazol-5-yl)-2-methoxyphenyl)amino)isoquinolin-6-yl)-1H-pyrazol-1-yl)propan-2-ol;

N-(4-(1,2-dimethyl-1H-imidazol-5-yl)-2-methoxyphenyl)-6-(1-(tetrahydro-2H-pyran-4-yl)-1H-pyrazol-4-yl)isoquinolin-3-amine;

6-(1-((2,2-dimethyl-1,3-dioxolan-4-yl)methyl)-1H-pyrazol-4-yl)-N-(4-(1,2-dimethyl-1H-imidazol-5-yl)-2-methoxyphenyl)isoquinolin-3-amine;

3-(4-(3-((4-(1,2-dimethyl-1H-imidazol-5-yl)-2-methoxyphenyl)amino)isoquinolin-6-yl)-1H-pyrazol-1-yl)propane-1,2-diol;

1-(4-(3-((2-methoxy-4-(2-methyl-1-(piperidin-4-ylmethyl)-1H-imidazol-5-yl)phenyl)amino)isoquinolin-6-yl)-1H-pyrazol-1-yl)-2-methylpropan-2-ol;

1-(4-(3-((2-methoxy-4-(4-methyl-4H-1,2,4-triazol-3-yl)phenyl)amino)isoquinolin-6-yl)-1H-pyrazol-1-yl)-2-methylpropan-2-ol;

1-(4-(3-((2-chloro-4-(1,2-dimethyl-1H-imidazol-5-yl)phenyl)amino)isoquinolin-6-yl)-1H-pyrazol-1-yl)-2-methylpropan-2-ol;

1-((4-(3-((4-(1,2-dimethyl-1H-imidazol-5-yl)-2-methoxyphenyl)amino)isoquinolin-6-yl)-1H-pyrazol-1-yl)methyl)cyclobutanol;

N-(4-(1,2-dimethyl-1H-imidazol-5-yl)-2-methoxyphenyl)-6-(1-(2,2,2-trifluoroethyl)-1H-pyrazol-4-yl)isoquinolin-3-amine;

1-(4-(2-((4-(1,2-dimethyl-1H-imidazol-5-yl)-2-methoxyphenyl)amino)pyrido[2,3-d]pyrimidin-7-yl)-1H-pyrazol-1-yl)-2-methylpropan-2-ol;

1-(4-(3-((2-chloro-4-morpholinophenyl)amino) isoquinolin-6-yl)-1H-pyrazol-1-yl)-2-methylpropan-2-ol;

1-(4-(3-((2-methoxy-4-morpholinophenyl)amino)isoquinolin-6-yl)-1H-pyrazol-1-yl)-2-methylpropan-2-ol;

1-(4-(3-((2-methoxy-6-morpholinopyridin-3-yl)amino)isoquinolin-6-yl)-1H-pyrazol-1-yl)-2-methylpropan-2-ol;

(4-((6-(1-(2-hydroxy-2-methylpropyl)-1H-pyrazol-4-yl)isoquinolin-3-yl)amino)-3-methoxyphenyl)(3-methoxyazetidin-1-yl)methanone;

1-(4-(3-(((4-(1,2-dimethyl-1H-imidazol-5-yl)phenyl)amino)isoquinolin-6-yl)-1H-pyrazol-1-yl)-2-methylpropan-2-ol;

1-(4-(3-((2-ethoxy-4-(4-methyl-4H-1,2,4-triazol-3-yl)phenyl)amino)isoquinolin-6-yl)-1H-pyrazol-1-yl)-2-methylpropan-2-ol;

4-((6-(1-(2-hydroxy-2-methylpropyl)-1H-pyrazol-4-yl)isoquinolin-3-yl)amino)-3-methoxybenzonitrile;

1-(4-(3-((4-(1,2-dimethyl-1H-imidazol-5-yl)-3-fluoro-2-methoxyphenyl)amino)isoquinolin-6-yl)-1H-pyrazol-1-yl)-2-methylpropan-2-ol;

(S)-1-(4-(3-((4-(1,2-dimethyl-1H-imidazol-5-yl)-2-methoxyphenyl)amino)isoquinolin-6-yl)-1H-pyrazol-1-yl)propan-2-ol;

(R)-1-(4-(3-((4-(1,2-dimethyl-1H-imidazol-5-yl)-2-methoxyphenyl)amino)isoquinolin-6-yl)-1H-pyrazol-1-yl)propan-2-ol;

1-(4-(3-((2-methoxy-4-(5-(methoxymethyl)-1-methyl-1H-pyrazol-4-yl)phenyl)amino)isoquinolin-6-yl)-1H-pyrazol-1-yl)-2-methylpropan-2-ol;

1-(4-(3-((4-(1-methyl-1H-pyrazol-4-yl)phenyl)amino)isoquinolin-6-yl)-1H-pyrazol-1-yl)-2-methylpropan-2-ol;

1-(4-(3-((4-(1,5-dimethyl-1H-pyrazol-4-yl)-2-methoxyphenyl)amino)isoquinolin-6-yl)-1H-pyrazol-1-yl)-2-methylpropan-2-ol;

1-(4-(3-((4-fluoro-2-methoxyphenyl)amino)isoquinolin-6-yl)-1H-pyrazol-1-yl)-2-methylpropan-2-ol;

tert-butyl 3-(4-((6-(1-(2-hydroxy-2-methylpropyl)-1H-pyrazol-4-yl)isoquinolin-3-yl)amino)-3-methoxyphenyl)-5,6-dihydro-[1,2,4]triazolo[4,3-a]pyrazine-7(8H)-carboxylate;

1-(4-(3-((2-methoxy-4-(5,6,7,8-tetrahydro-[1,2,4]triazolo[4,3-a]pyrazin-3-yl)phenyl)amino)isoquinolin-6-yl)-1H-pyrazol-1-yl)-2-methylpropan-2-ol;

1-(4-(3-((6-(1,2-dimethyl-1H-imidazol-5-yl)-2-methoxypyridin-3-yl)amino)isoquinolin-6-yl)-1H-pyrazol-1-yl)-2-methylpropan-2-ol;

1-(4-(3-((5-(1,2-dimethyl-1H-imidazol-5-yl)-3-methoxypyridin-2-yl)amino)isoquinolin-6-yl)-1H-pyrazol-1-yl)-2-methylpropan-2-ol;

1-(4-(3-((2-chloro-4-(pyrimidin-5-yl)phenyl)amino)isoquinolin-6-yl)-1H-pyrazol-1-yl)-2-methylpropan-2-ol;

1-(4-(3-((2-chloro-4-(methylsulfonyl)phenyl)amino)isoquinolin-6-yl)-1H-pyrazol-1-yl)-2-methylpropan-2-ol;

4-((6-(1-(2-hydroxy-2-methylpropyl)-1H-pyrazol-4-yl)isoquinolin-3-yl)amino)-3-methoxy-N,N-dimethylbenzamide;

4-((6-(1-(2-hydroxy-2-methylpropyl)-1H-pyrazol-4-yl)isoquinolin-3-yl)amino)-N-(2-hydroxyethyl)-3-methoxybenzamide;

4-((6-(1-(2-hydroxy-2-methylpropyl)-1H-pyrazol-4-yl)isoquinolin-3-yl)amino)-3-methoxy-N-(2-methoxyethyl)benzamide;

1-(4-(3-((2-methoxy-4-(2-(methoxymethyl)-1-methyl-1H-imidazol-5-yl)phenyl)amino)isoquinolin-6-yl)-1H-pyrazol-1-yl)-2-methylpropan-2-ol;

1-(4-(3-((2-methoxy-4-(1-methyl-1H-1,2,4-triazol-5-yl)phenyl)amino)isoquinolin-6-yl)-1H-pyrazol-1-yl)-2-methylpropan-2-ol;

(1,1-dioxidothiomorpholino)(4-((6-(1-(2-hydroxy-2-methylpropyl)-1H-pyrazol-4-yl)isoquinolin-3-yl)amino)-3-methoxyphenyl)methanone;

N-(2-methoxy-4-(1-methyl-1H-pyrazol-4-yl)phenyl)-2-(1-methyl-1H-pyrazol-4-yl)-1,6-naphthyridin-7-amine;

1-(4-(7-((2-methoxy-4-(1-methyl-1H-pyrazol-4-yl)phenyl)amino)-1,6-naphthyridin-2-yl)-1H-pyrazol-1-yl)-2-methylpropan-2-ol;

1-(4-(7-((4-(1,2-dimethyl-1H-imidazol-5-yl)-2-methoxyphenyl)amino)-1,6-naphthyridin-2-yl)-1H-pyrazol-1-yl)-2-methylpropan-2-ol;

(4-((6-(1-(2-hydroxy-2-methylpropyl)-1H-pyrazol-4-yl)isoquinolin-3-yl)amino)-3-methoxyphenyl)(4-methylpiperazin-1-yl)methanone;

4-((6-(1-(2-hydroxy-2-methylpropyl)-1H-pyrazol-4-yl)isoquinolin-3-yl)amino)-3-methoxy-N-(1-methylpiperidin-4-yl)benzamide;

3-(4-(3-((4-(1,2-dimethyl-1H-imidazol-5-yl)-2-methoxyphenyl)amino)isoquinolin-6-yl)-1H-pyrazol-1-yl)-2-methylbutan-2-ol;

1-(5-(4-(((6-(1-(2-hydroxy-2-methylpropyl)-1H-pyrazol-4-yl)isoquinolin-3-yl)amino)-3-methoxyphenyl)-2-methyl-1H-imidazol-1-yl)-2-methylpropan-2-ol;

1-(4-(3-((2-methoxy-4-(7-methyl-5,6,7,8-tetrahydro-[1,2,4]triazolo[4,3-a]pyrazin-3-yl)phenyl)amino)isoquinolin-6-yl)-1H-pyrazol-1-yl)-2-methylpropan-2-ol;

(4-(((6-(1-(2-hydroxybutyl)-1H-pyrazol-4-yl)isoquinolin-3-yl)amino)-3-methoxyphenyl)(3-methoxyazetidin-1-yl)methanone;

(3-methoxy-4-((6-(1-(2-methoxyethyl)-1H-pyrazol-4-yl)isoquinolin-3-yl)amino)phenyl)(3-methoxyazetidin-1-yl)methanone;

(4-((6-(1-(2-hydroxy-3-methylbutyl)-1H-pyrazol-4-yl)isoquinolin-3-yl)amino)-3-methoxyphenyl)(3-methoxyazetidin-1-yl)methanone;

1-(4-(3-((2-methoxy-4-(5,6,7,8-tetrahydroimidazo[1,2-a]pyrazin-3-yl)phenyl)amino)isoquinolin-6-yl)-1H-pyrazol-1-yl)-2-methylpropan-2-ol;

(3-methoxy-4-((6-(1-(2-methoxy-2-methylpropyl)-1H-pyrazol-4-yl)isoquinolin-3-yl)amino)phenyl)(3-methoxyazetidin-1-yl)methanone;

(3-methoxy-4-((6-(1-(3,3,3-trifluoro-2-hydroxypropyl)-1H-pyrazol-4-yl)isoquinolin-3-yl)amino)phenyl)(3-methoxyazetidin-1-yl)methanone;

(4-((6-(1-(3-hydroxy-3-methylbutan-2-yl)-1H-pyrazol-4-yl)isoquinolin-3-yl)amino)-3-methoxyphenyl)(3-methoxyazetidin-1-yl)methanone;

1-(4-(7-((2-ethoxy-4-(4-methyl-4H-1,2,4-triazol-3-yl)phenyl)amino)-1,6-naphthyridin-2-yl)-1H-pyrazol-1-yl)-2-methylpropan-2-ol;

(4-((2-(1-(2-hydroxy-2-methylpropyl)-1H-pyrazol-4-yl)-1,6-naphthyridin-7-yl)amino)-3-methoxyphenyl)(3-methoxyazetidin-1-yl)methanone;

1-(4-(7-((2-methoxy-4-(4-methyl-4H-1,2,4-triazol-3-yl)phenyl)amino)-1,6-naphthyridin-2-yl)-1H-pyrazol-1-yl)-2-methylpropan-2-ol;

1-((4-(7-((4-(1,2-dimethyl-1H-imidazol-5-yl)-2-methoxyphenyl)amino)-1,6-naphthyridin-2-yl)-1H-pyrazol-1-yl)methyl)cyclobutanol;

(3-(difluoromethoxy)-4-((6-(1-(2-hydroxy-2-methylpropyl)-1H-pyrazol-4-yl)isoquinolin-3-yl)amino)phenyl)(3-methoxyazetidin-1-yl)methanone;

(3-ethoxy-4-((6-(1-(2-hydroxy-2-methylpropyl)-1H-pyrazol-4-yl)isoquinolin-3-yl)amino)phenyl)(3-methoxyazetidin-1-yl)methanone;

(3,3-difluoroazetidin-1-yl)(4-((6-(1-(2-hydroxy-2-methylpropyl)-1H-pyrazol-4-yl)isoquinolin-3-yl)amino)-3-methoxyphenyl)methanone;

1-(4-((6-(1-(2-hydroxy-2-methylpropyl)-1H-pyrazol-4-yl)isoquinolin-3-yl)amino)-3-methoxybenzoyl)piperidine-4-carbonitrile;

(4-((6-(1-(2-hydroxy-2-methylpropyl)-1H-pyrazol-4-yl)isoquinolin-3-yl)amino)-3-methoxyphenyl)(6-oxa-2-azaspiro[3.4]octan-2-yl) methanone;

1-(4-(3-((2-chloro-4-(5-methyl-1,3,4-oxadiazol-2-yl)phenyl)amino)isoquinolin-6-yl)-1H-pyrazol-1-yl)-2-methylpropan-2-ol;

(4-((6-(1-(2-hydroxy-3-methoxypropyl)-1H-pyrazol-4-yl)isoquinolin-3-yl)amino)-3-methoxyphenyl)(3-methoxyazetidin-1-yl)methanone;

(4-((6-(1-(2,3-dimethoxypropyl)-1H-pyrazol-4-yl)isoquinolin-3-yl)amino)-3-methoxyphenyl)(3-methoxyazetidin-1-yl)methanone;

4-((6-(1-(2-hydroxy-2-methylpropyl)-1H-pyrazol-4-yl)isoquinolin-3-yl)amino)-3-methoxy-N,N-dimethylbenzenesulfonamide;

(4-((6-(1-(2,3-dihydroxypropyl)-1H-pyrazol-4-yl)isoquinolin-3-yl)amino)-3-methoxyphenyl)(3-methoxyazetidin-1-yl)methanone;

(4-((6-(1-(4-hydroxytetrahydrofuran-3-yl)-1H-pyrazol-4-yl)isoquinolin-3-yl)amino)-3-methoxyphenyl)(3-methoxyazetidin-1-yl)methanone;

(4-((6-(1-(2-hydroxycyclopentyl)-1H-pyrazol-4-yl)isoquinolin-3-yl)amino)-3-methoxyphenyl)(3-methoxyazetidin-1-yl)methanone;

5-(4-((6-(1-(2-hydroxy-2-methylpropyl)-1H-pyrazol-4-yl)isoquinolin-3-yl)amino)-3-methoxyphenyl)-1-methyl-1H-imidazole-2-carbonitrile;

(4-((6-(1-(2-hydroxycyclohexyl)-1H-pyrazol-4-yl)isoquinolin-3-yl)amino)-3-methoxyphenyl)(3-methoxyazetidin-1-yl)methanone;

(4-((6-(1-(2-hydroxy-2-methylpropyl)-1H-pyrazol-4-yl)isoquinolin-3-yl)amino)-3-methoxyphenyl)(3-(methoxymethyl)azetidin-1-yl)methanone;

(4-((6-(1-((1-hydroxycyclobutyl)methyl)-1H-pyrazol-4-yl)isoquinolin-3-yl)amino)-3-methoxyphenyl)(3-methoxyazetidin-1-yl)methanone;

1-((4-(3-((2-ethoxy-4-(4-methyl-4H-1,2,4-triazol-3-yl)phenyl)amino)isoquinolin-6-yl)-1H-pyrazol-1-yl)methyl)cyclobutanol;

7-((2-methoxy-4-(1-methyl-1H-pyrazol-4-yl)phenyl)amino)-N,N-dimethyl-1,6-naphthyridine-2-carboxamide;

7-((2-methoxy-4-(1-methyl-1H-pyrazol-4-yl)phenyl)amino)-N-methyl-1,6-naphthyridine-2-carboxamide;

3-((4-(1,2-dimethyl-1H-imidazol-5-yl)-2-methoxyphenyl)amino)-N,N-dimethylisoquinoline-6-carboxamide;

3-((4-(1,2-dimethyl-1H-imidazol-5-yl)-2-methoxyphenyl) amino)-N-methylisoquinoline-6-carboxamide;

or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess Mps1 kinase inhibitory activity.

The present invention also encompasses compounds of the invention as defined herein which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and O may be in any isotopic form, including $^{16}$O and $^{18}$O; and the like.

It is also to be understood that certain compounds of the invention may exist in solvated as well as unsolvated forms such as, for example, hydrated forms. It is to be understood that the invention encompasses all such solvated forms that possess Mps1 kinase inhibitory activity.

It is also to be understood that certain compounds of the invention may exhibit polymorphism, and that the invention encompasses all such forms that possess Mps1 kinase inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

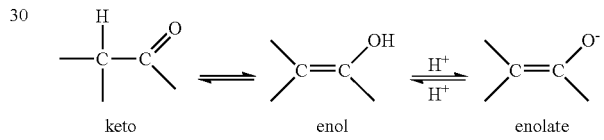

keto          enol          enolate

Compounds of the invention containing an amine function may also form N-oxides. A reference herein to a compound of the formula II that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula II as defined hereinbefore when made available by organic synthesis and when made available within the human or animal body by way of cleavage of a pro-drug thereof. Accordingly, the present invention includes those compounds of the formula II that are produced by organic synthetic means and also such compounds that are produced in the human or animal body by way of metabolism of a precursor compound, that is a compound of the formula II may be a synthetically-produced compound or a metabolically-produced compound.

A suitable pharmaceutically acceptable pro-drug of a compound of the formula II is one that is based on reasonable medical judgement as being suitable for administration to the human or animal body without undesirable pharmacological activities and without undue toxicity.

Various forms of pro-drug have been described, for example in the following documents:— a) *Methods in Enzymoloqy*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula II that possesses a carboxy group is, for example, an in vivo cleavable ester thereof. An in vivo cleavable ester of a compound of the formula II containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula II that possesses a hydroxy group is, for example, an in vivo cleavable ester or ether thereof. An in vivo cleavable ester or ether of a compound of the formula II containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula II that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_2$-4alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula II that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula II may be exerted in part by one or more metabolites that are formed within the human or animal body after administration of a compound of the formula II. As stated hereinbefore, the in vivo effects of a compound of the formula II may also be exerted by way of metabolism of a precursor compound (a pro-drug).

It shall also be appreciated that compounds of formula II may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

In a particular aspect, the present invention provides a method of synthesising a compound of the formula II, or a pharmaceutically acceptable salt or solvate thereof, the method comprising:

a) reacting a compound of formula A:

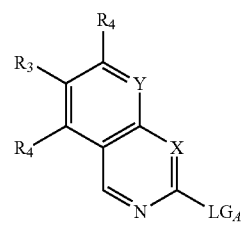

Formula A wherein X, Y, $R_2$, $R_3$ and $R_4$ each have any one of the meanings as defined hereinbefore, and $LG_A$ is a suitable leaving group;

with a compound of formula B:

Formula B wherein Ar is as defined herein; and
  b) optionally thereafter, and if necessary:
    i) removing any protecting groups present;
    ii) converting the compound formula II into another compound of formula Ii; and/or
    iii) forming a pharmaceutically acceptable salt or solvate thereof.

$LG_A$ may be any suitable leaving group. Suitably $LG_A$ is a halogen or any other suitable leaving group (e.g. trifluoromethylsulphonate etc.). Suitably $LG_A$ may be chlorine, bromine or trifluoromethylsulphonate.

Suitably the coupling reaction between compound A and compound B takes place in the presence of a suitable solvent. Any suitable solvent or solvent mixture may be used for this reaction. A person skilled in the art will know how to select suitable solvents or solvent mixtures for use in these reactions. Examples of suitable solvents include DMA, 1,4-dioxane, DMF and toluene.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 40 to 160° C. or, more suitably 120 to 160° C. (depending on the solvent utilised), for a suitable time period of, for example, 2 hours to 7 days, or more suitably 2 to 10 hours either thermally or under microwave irradiation.

Suitably the coupling reaction between compound A and compound B takes place in the presence of a catalyst, suitably a palladium-derived catalyst, such as Pd or $Pd_2(dba)_3$ or by using an acid catalysis, such as trifluoroacetic acid.

Suitably the coupling reaction between compound A and compound B takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound A and compound B takes place in the presence of a base, for example a metal carbonate, such as cesium carbonate, or metal hydrides, such as sodium hydride.

The compound of formula A can be prepared by processes known in the art, and suitably by the processes described herein with reference to the examples.

The compound of formula B can be prepared by processes known in the art, and suitably by the processes described herein with reference to the examples.

In addition to the above processes, if a suitable protecting group is present, additional deprotection conditions may be employed. Suitable protecting groups include tert-butoxycarbonate and dimethylacetal. Typical conditions comprise a suitable acid in a suitable solvent such as trifluoroacetic acid in either DCM or THF.

The racemic compound of formula 1 may be separated using suitable chiral separation chromatography to furnish the desired enantiomers.

In another aspect, the present invention provides a method of synthesising a compound of the formula II, or a pharmaceutically acceptable salt or solvate thereof, the method comprising:

a) reacting a compound of formula C:

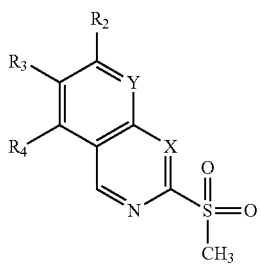

Formula C wherein X, Y, $R_2$, $R_3$ and $R_4$ each have any one of the meanings as defined hereinbefore; with a compound of formula B as defined hereinbefore, or a compound of formula D:

HC(O)HN—Ar   Formula D wherein Ar is as defined herein; and
b) optionally thereafter, and if necessary:
i) removing any protecting groups present;
ii) converting the compound formula II into another compound of formula II; and/or
iii) forming a pharmaceutically acceptable salt or solvate thereof.

Suitably the coupling reaction between compound C and compound B or D takes place in the presence of a suitable solvent. Any suitable solvent or solvent mixture may be used for this reaction. A person skilled in the art will know how to select suitable solvents or solvent mixtures for use in these reactions. Examples of suitable solvents include THF and TFE (1,2,3-trifluoroethanol).

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 30 to 170° C. or, more suitably 30 to 50° C. for compounds of formula D and 120 to 170 50° C. for compounds of formula B (depending on the solvent utilised), for a suitable time period of, for example, 2 hours to 7 days, or more suitably 2 to 10 hours either thermally or under microwave irradiation.

Suitably the coupling reaction between compound C and compounds B or D takes place in the presence of a catalyst, suitably a palladium-derived catalyst, such as Pd or $Pd_2(dba)_3$ or by using an acid catalysis, such as trifluoroacetic acid.

Suitably the coupling reaction between compound C and compounds B or D takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound C and compounds B or D takes place in the presence of a base, for example a metal carbonate, such as cesium carbonate, or metal hydrides, such as sodium hydride.

The compound of formula C can be prepared by processes known in the art, and suitably by processes described herein with reference to the examples.

The compound of formula D can be prepared by processes known in the art, and suitably by processes described herein with reference to the examples.

In another aspect, the present invention provides a method of synthesising a compound of the formula II, or a pharmaceutically acceptable salt or solvate thereof, the method comprising:

a) reacting a compound of formula E:

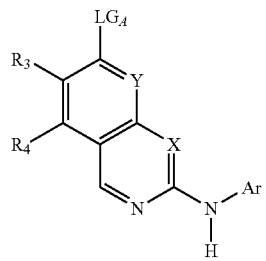

Formula E wherein X, Y, Ar, $R_3$ and $R_4$ each have any one of the meanings as defined hereinbefore, and $LG_A$ is a suitable leaving group as hereinbefore defined;
with a compound of formula F:

$H_2N$—$R_2$   Formula F or $R_2BX_2$ wherein $R_2$ is as defined herein and $BX_2$ represents boronic acids (e.g. $B(OH)_2$), tetrafluoroborates (e.g $BF_3^-$), or pinacol esters; and
b) optionally thereafter, and if necessary:
i) removing any protecting groups present;
ii) converting the compound formula II into another compound of formula II; and/or
iii) forming a pharmaceutically acceptable salt or solvate thereof.

As described above, $LG_A$ may be any suitable leaving group. Suitably $LG_A$ is a halogen or any other suitable leaving group (e.g. trifluoromethylsulphonate etc.). Suitably, $LG_A$ is chlorine, bromine or trifluoromethylsulphonate.

Suitably the coupling reaction between compound E and compound F takes place in the presence of a suitable solvent. Any suitable solvent or solvent mixture may be used for this reaction. A person skilled in the art will know how to select suitable solvents or solvent mixtures for use in these reactions. Examples of suitable solvents include DMA, 1,4-dioxane, toluene, DMF, tBuOH, or $H_2O$.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of room temperature to 160° C. or, more suitably 60 to 140° C. (depending on the solvent utilised), for a suitable time period of, for example, 2 hours to 7 days, or more suitably 2 to 10 hours either thermally or under microwave irradiation.

Suitably the coupling reaction between compound E and compound F takes place in the presence of a catalyst, suitably a palladium-derived catalyst, such as Pd or $Pd_2(dba)_3$ or by using an acid catalysis, such as trifluoroacetic acid.

Suitably the coupling reaction between compound E and compound F takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound E and compound F takes place in the presence of a base, for example a metal carbonate, such as cesium carbonate, or metal hydrides, such as sodium hydride.

The compound of formula E can be prepared by processes known in the art, suitably by processes described herein with reference to the examples.

The compound of formula F can be prepared by processes known in the art, and suitably by processes described herein with reference to the examples.

The resultant compound of formula II form the processes defined above can be isolated and purified using techniques well known in the art.

The processes defined herein may further comprise the step of subjecting the compound of formula II to a salt exchange, particularly in situations where the compound of formula II is formed as a mixture of different salt forms. The salt exchange suitably comprises immobilising the compound of formula II on a suitable solid support or resin, and eluting the compounds with an appropriate acid to yield a single salt of the compound of formula II.

In a further aspect of the invention, there is provided a compound of formula II obtainable by any one of the processes defined herein.

In a further aspect of the invention, there is provided a compound of formula II obtained by any one of the processes defined herein.

In a further aspect of the invention, there is provided a compound of formula II directly obtained by any one of the processes defined herein.

By way of example, particular synthetic schemes by which certain compounds of the invention can be prepared are shown below in Schemes 1 to 5 below:

Scheme 1:

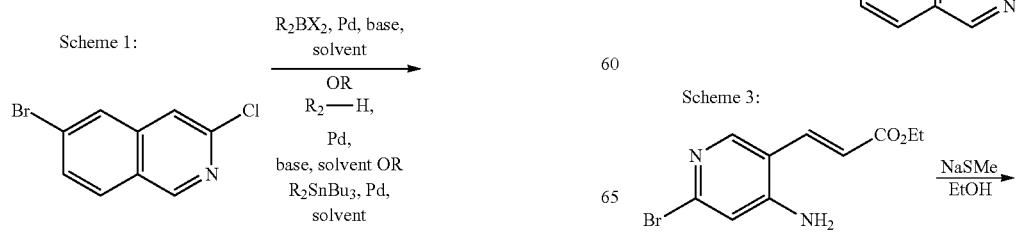

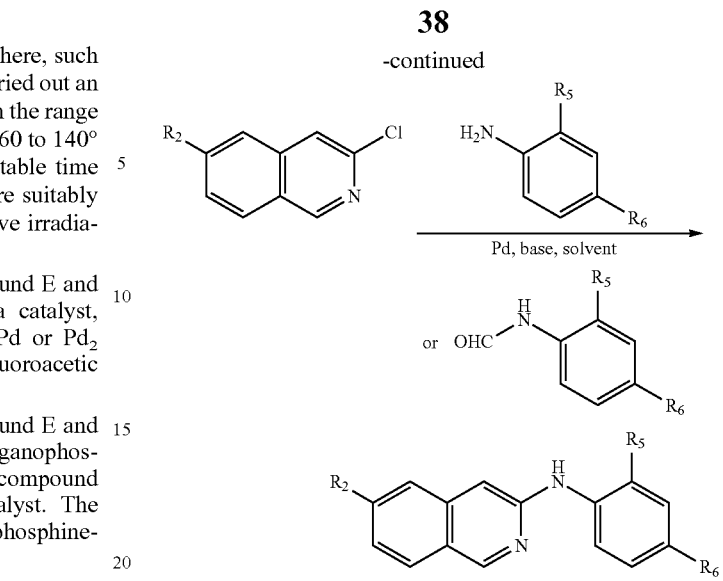

Scheme 2:

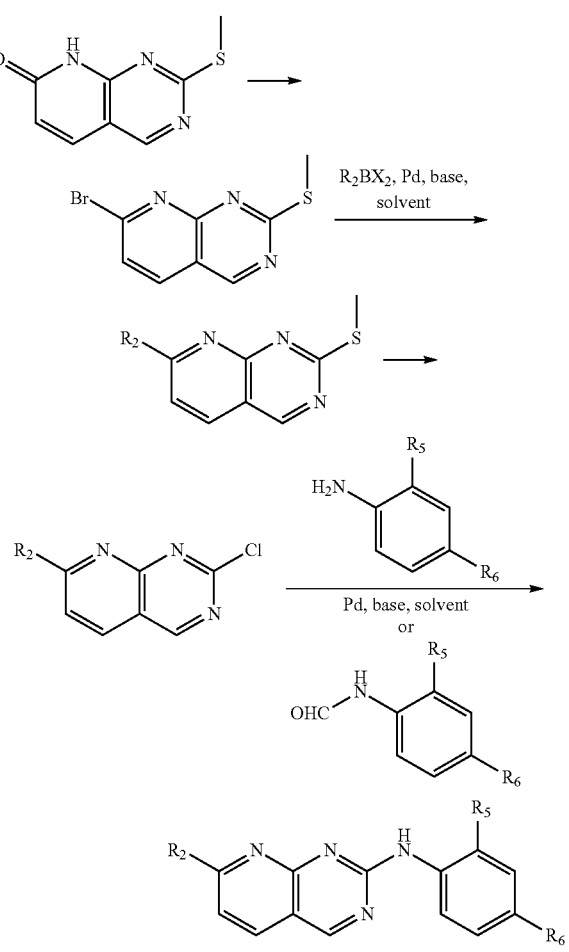

Scheme 3:

-continued

Scheme 4:

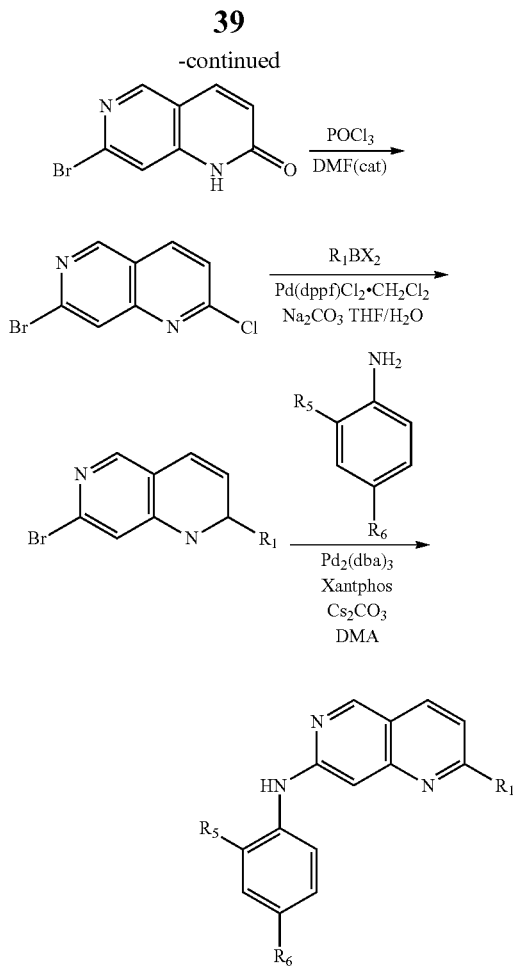
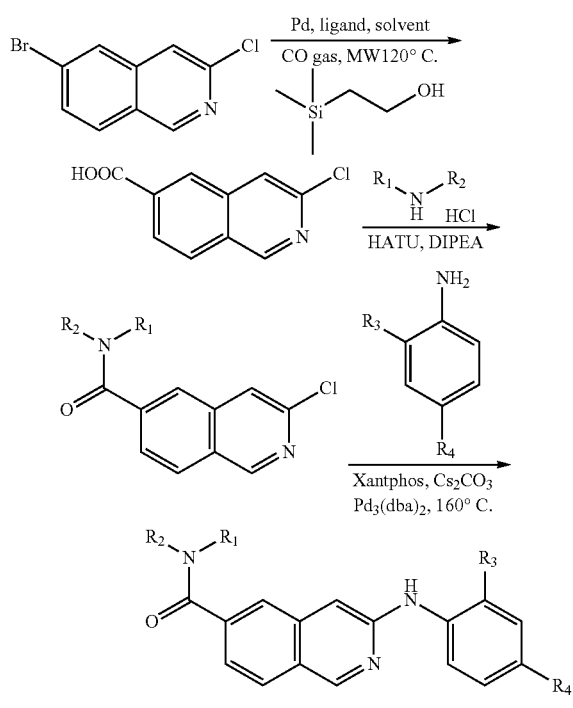

Scheme 5:

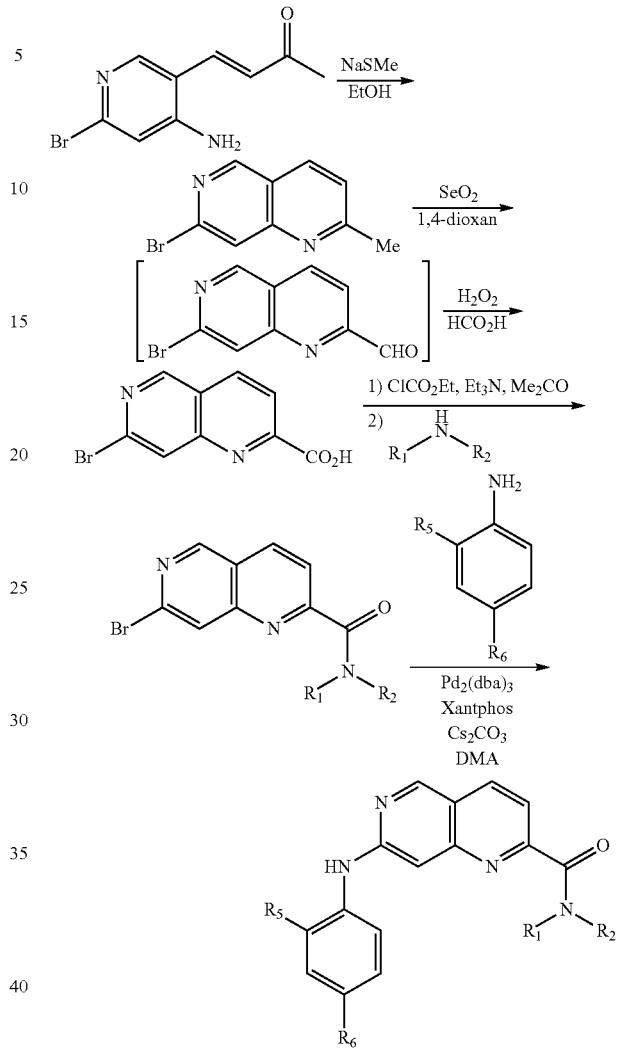

In schemes 1 to 5, $R_1$ and/or $R_2$, when present, are suitably aryl or heteroaryl, but may also be alkyl or alkenyl. BX2 represents boronic acids ($B(OH)_2$), tetrafluoroborates (e.g. $BF_3^-$), or pinacol esters, i.e.

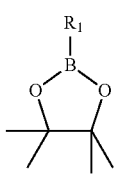

Biological Activity

The following biological assays may be used to measure the pharmacological effects of the compounds of the present invention.

Measurement of Inhibition of MPS1 Kinase

The enzyme reaction (total volume 10 μl) was carried out in black 384-well low volume plates containing full length MPS1 (12.5 nM or 3 nM), fluorescent labelled peptide [known as H236, which has the sequence: 5FAM-DHTG-FLTEYVATR-CONH$_2$](5 μM), ATP(10 μM), either DMSO (1% v/v) or the test compound (in the range 0.25 nM-100 µM in 1% DMSO) and assay buffer (50 mM HEPES (pH 7.0), 0.02% $NaN_3$, 0.01% BSA, 0.1 mM Orthovandate, 10 µM $MgCl_2$, 1 µM DTT, Roche protease inhibitor). The reaction was carried out for 60 min at room temperature and stopped by the addition of buffer (10 µl) containing 20 mM EDTA, 0.05% (v/v) Brij-35, in 0.1M HEPES-buffered saline (Free acid, Sigma, UK). The plate was read on a Caliper EZ reader II (Caliper Life Sciences).

The reader provides a Software package ('Reviewer') which converts the peak heights into % conversion by measuring both product and substrate peak and also allows selection of control well which represent 0% and 100% inhibition respectively. The % inhibition of the compounds is calculated relative to the means of selected control wells. $IC_{50}$s are determined by testing the compounds at a range of concentrations from 0.25 nM-100 µM. The % inhibitions at each concentration are then fitted to a 4 parameter logistic fit:

$$y=(a+((b-a)/(1+((c/x\char`\^d))))$$

where a=asym min, b=asym max, c=$IC_{50}$ and d=hill coefficient

In general, activity possessed by compounds of the formula II, may be demonstrated in the inhibition assay by an $IC_{50}$ value of less than 15 µM. Suitably compounds have an $IC_{50}$ value of less than 10 µM, suitably less than 1 µM, suitably less than 0.1 µM, and suitably less than 0.01 µM (i.e. less than 10 nM).

The activities of compounds of the invention in the above assay are shown in the accompanying example section.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula II will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of Formula I, or a pharmaceutically acceptable salt or solvate thereof, or a pharmaceutical composition as defined herein for use in therapy.

The compounds of the invention are capable of inhibiting Mps1 kinase activity. Thus, in another aspect, the present invention provides a method of inhibiting Mps1 kinase activity in a cell, the method comprising administering to said cell compound of formula II as defined herein, or a pharmaceutically acceptable salt or solvate thereof.

In a further aspect, the present invention provides a method of inhibiting Mps1 kinase in vitro or in vivo, said method comprising contacting a cell with an effective amount of a compound, or a pharmaceutically acceptable salt or solvate thereof, as defined herein.

In another aspect, the present invention provides a method of inhibiting Mps1 kinase activity in a human or animal subject in need of such inhibition, the method comprising administering to said subject an effective amount of a compound of formula II as defined herein, or a pharmaceutically acceptable salt or solvate thereof.

In another aspect, the present invention provides a compound of formula II as defined herein, or a pharmaceutically acceptable salt or solvate thereof for use in the treatment of disease or condition associated with Mps1 kinase activity.

In another aspect, the present invention provides the use of a compound of formula II as defined herein, or a pharmaceutically acceptable salt or solvate thereof, in the manufacture of a medicament for use in the treatment of disease or condition associated with Mps1 kinase activity.

In yet another aspect, the present invention provides a method of treating a proliferative disorder in a human or animal subject, the method comprising administering to said subject a therapeutically acceptable amount of a compound of formula II as defined herein, or a pharmaceutically acceptable salt or solvate thereof.

In yet another aspect, the present invention provides a compound of formula II as defined herein, or a pharmaceutically acceptable salt or solvate thereof, for use in the treatment of a proliferative disorder.

In yet another aspect, the present invention provides the use of a compound of formula II as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplasticgrowth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their Mps1 kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of $5\alpha$-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin $\alpha v \beta 3$ function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(ix) herein above, in association with a pharmaceutically acceptable diluent or carrier.

EXAMPLES

Commercially available starting materials, reagents and dry solvents were used as supplied. Flash column chromatography was performed using Merck silica gel 60 (0.025-0.04 mm). Column chromatography was also performed on a FlashMaster personal unit using isolute Flash silica columns or a Biotage SP1 purification system using Merck or Biotage Flash silica cartridges. Preparative TLC was performed on Analtech or Merck plates. Ion exchange chromatography was performed using acidic Isolute Flash SCX-II columns, Isolute Si-carbonate columns or basic isolute Flash $NH_2$ columns.

Where a preparative HPLC method is used, the following conditions apply:
Grad15mins20mlsLipo:
Reagents:

HPLC grade solvents, formic acid, or alternative eluent modifiers were purchased from Sigma Aldrich (Poole, UK) unless otherwise stated.
Instrumentation:

450 uL standard injections (with needle rinse) of the sample, at 10 mg/mL concentration in MeOH, were made onto a Phenomenex Gemini column (10 µm, 250×21.2 mm, C18, Phenomenex, Torrance, USA)

Chromatographic separation at room temperature was carried out using Gilson GX-281 Liquid Handler system combined with a Gilson 322 HPLC pump (Gilson, Middleton, USA) over a 15 minute gradient elution from 40:60 to 100:0 methanol:water (both modified with 0.1% formic acid) at a flow rate of 20 mL/min.

UV-Vis spectra were acquired at 254 nm on a Gilson 156 UV-Vis detector (Gilson, Middleton, USA).

Collection was triggered by UV signal, and collected using a Gilson GX-281 Liquid Handler system (Gilson, Middleton, USA).

Raw data was processed using Gilson Trilution Software.

Where an LCMS method is used, the following conditions apply:

LCT method: LC/MS analysis was also performed on a Waters Alliance 2795 Separations Module and Waters 2487 dual wavelength absorbance detector coupled to a Waters/Micromass LCt time of flight mass spectrometer with ESI source. Analytical separation was carried out at 30° C. either on a Merck Chromolith SpeedROD column (RP-18e, 50×4.6 mm) using a flow rate of 2 mL/min in a 4 minute gradient elution with detection at 254 nm or on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was as follows: 1:9 (A/B) to 9:1 (A/B) over 2.25 min, 9:1 (A/B) for 0.75 min, and then reversion back to 1:9 (A/B) over 0.3 min, finally 1:9 (A/B) for 0.2 min Where an LCMS/HRMS method is used, the following conditions apply:

Agilent ToF method: LC/MS and HRMS analysis was performed on an Agilent 1200 series HPLC and diode array detector coupled to a 6210 time of flight mass spectrometer with dual multimode APCI/ESI source.

Analytical separation was carried out at 30° C. on a Merck Purospher STAR column (RP-18e, 30×4 mm) using a flow rate of 1.5 mL/min in a 4 minute gradient elution with detection at 254 nm. The mobile phase was a mixture of methanol (solvent A) and water containing formic acid at 0.1% (solvent B). Gradient elution was as follows: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min.

The references used for HRMS analysis were: caffeine [M+H]+ 195.087652; hexakis (2,2-difluroethoxy)phosphazene [M+H]+ 622.02896; and hexakis(1H,1H,3H-tetrafluoropentoxy)phosphazene [M+H]+ 922.009798.

Routine LCMS was performed using the LCT method whereas HRMS data were recored using the Agilent ToF method.

Example 1

N-(4-(1,2-dimethyl-1H-imidazol-5-yl)-2-methoxyphenyl)-6-(1-((tetrahydro-2H-pyran-4-yl)methyl)-1H-pyrazol-4-yl)isoquinolin-3-amine

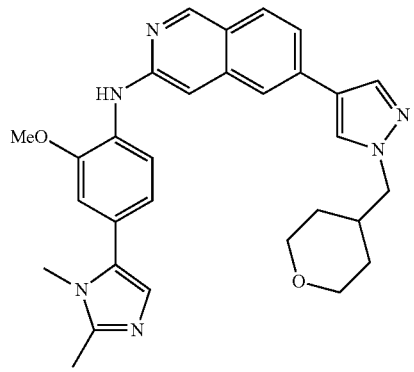 [SMILES: COc1cc(-c2cnc(C)n2C)ccc1Nc1cc2cc(-c3cnn(CC4CCOCC4)c3)ccc2cn1]

Method A

A suspension of 3-chloro-6-(1-((tetrahydro-2H-pyran-4-yl)methyl)-1H-pyrazol-4-yl)-isoquinoline (Preparation 1, 10.5 mg, 0.03 mmol), 4-(1,2-dimethyl-1H-imidazol-5-yl)-2-methoxyaniline (Preparation 74, 8.4 mg, 0.04 mmol), xantphos (11.2 mg, 0.02 mmol), $Pd_2(dba)_3$ (2.9 mg, 0.003 mmol), $Cs_2CO_3$ (83 mg, 0.26 mmol) in toluene/DMF (3/1 mL) was stirred at 160° C. under microwave irradiation for 2 hours. The reaction mixture was filtered, diluted with NaCl solution and extracted with EtOAc. The organic layer was purified by SCX-2 column eluting with 2M $NH_3$/MeOH and concentrated in vacuo. The residue was purified using Biotage silica gel column chromatography eluting with 0-12% MeOH in EtOAc to afford the title compound (4.5 mg, 28%).

$^1$H NMR (500 MHz, $CDCl_3$): δ 8.96 (d, J=1.1 Hz, 1H), 7.98-7.93 (m, 2H), 7.85 (d, J=8.4 Hz, 1H), 7.77 (t, J=1.0 Hz, 1H), 7.71 (d, J=1.5 Hz, 1H), 7.48 (dt, J=8.5, 1.5 Hz, 1H), 7.27 (s, 1H), 7.18 (s, 1H), 7.03-6.96 (m, 2H), 6.92 (d, J=1.9 Hz, 1H), 4.08 (d, J=8.0 Hz, 2H), 4.06-3.99 (m, 2H), 3.97 (s, 3H), 3.59 (s, 3H), 3.41 (td, J=11.8, 2.1 Hz, 2H), 2.52 (s, 3H), 2.30-2.20 (m, 1H), 1.62-1.53 (m, 2H), 1.50-1.38 (m, 2H).

LCMS (ESI) Rt=1.92 minutes MS m/z 509 [M+H]+

MPS1 IC50 (μM): 0.002

The following Examples were prepared according to Method A (Example 1) above using the appropriate chloroisoquinoline and 4-(1,2-dimethyl-1H-imidazol-5-yl)-2-methoxyaniline (Preparation 74) unless otherwise described. The crude reaction residues were purified as above or according to one of the following methods:

Method A: Biotage silica gel column chromatography eluting with between 0-6% MeOH/EtOAc Method B: Biotage silica gel column chromatography eluting with 0-6% MeOH/EtOAc followed by preparative HPLC.

Method C: Biotage silica gel column chromatography eluting with 0-15% MeOH/EtOAc.

Method D: Preparative HPLC followed by, where necessary elution though an SCX-2 cartridge using 2M $NH_3$/MeOH.

Method E: Biotage silica gel column chromatography eluting with 0-8% MeOH/EtOAc.

Method F: Biotage silica gel column chromatography eluting with 0-10% MeOH/EtOAc followed by preparative HPLC.

Method G: Biotage silica gel column chromatography eluting with between 50-100% EtOAc in cyclohexanes.

Method H: Biotage silica gel column chromatography eluting with EtOAc.

Method I: Elution through an SCX-2 cartridge using 50% MeOH in chloroform followed by 50% chloroform in 7N $NH_3$/MeOH, followed by silica gel column chromatography eluting with 0-10% 7N $NH_3$/MeOH in EtOAc.

Method J: Elution through an SCX-2 cartridge using 50% MeOH in chloroform followed by 50% chloroform in 7N $NH_3$/MeOH, followed by silica gel column chromatography eluting with 20% hexanes in EtOAc.

| Example No | Name/Structure | Data | MPS1 IC50 (μM) |
|---|---|---|---|
| 2 | 6-(1-(Cyclopropylmethyl)-1H-pyrazol-4-yl)-N-(4-(1,2-dimethyl-1H-imidazol-5-yl)-2-methoxyphenyl)isoquinolin-3-amine | $^1$H NMR (500 MHz, CDCl$_3$): δ 8.95 (d, J = 1.0 Hz, 1H), 7.97-7.92 (m, 2H), 7.90 (d, J = 0.8 Hz, 1H), 7.84 (d, J = 8.4 Hz, 1H), 7.72 (d, J = 1.6 Hz, 1H), 7.49 (dd, J = 8.5, 1.6 Hz, 1H), 7.26 (s, 1H), 7.17 (s, 1H), 7.00-6.95 (m, 2H), 6.92 (d, J = 1.9 Hz, 1H), 4.07 (d, J = 7.2 Hz, 2H), 3.96 (s, 3H), 3.58 (s, 3H), 2.49 (s, 3H), 1.42-1.32 (m, 1H), 0.77-0.69 (m, 2H), 0.49-0.41 (m, 2H). LCMS (ESI) Rt = 2.00 minutes, MS m/z 465 [M + H]$^+$ Using 3-chloro-6-(1-(cyclopropylmethyl)-1H-pyrazol-4-yl)isoquinoline (Preparation 4) and purification Method A. | 0.001 |
| 3 | 6-(1-(2,2-Difluoroethyl)-1H-pyrazol-4-yl)-N-(4-(1,2-dimethyl-1H-imidazol-5-yl)-2-methoxyphenyl)isoquinolin-3-amine | $^1$H NMR (500 MHz, CDCl$_3$): δ 8.99 (s, 1H), 8.04 (dd, J = 8.4, 1.3 Hz, 1H), 8.02-7.98 (m, 1H), 7.89 (m, 2H), 7.74 (d, J = 1.5 Hz, 1H), 7.51 (dt, J = 8.5, 1.5 Hz, 1H), 7.38 (s, 1H), 7.29 (d, J = 1.3 Hz, 1H), 7.17 (s, 1H), 6.99 (dd, J = 8.2, 1.9 Hz, 1H), 6.89 (d, J = 2.0 Hz, 1H), 6.33-6.01 (m, 1H), 4.57 (ddd, J = 14.7, 13.0, 4.3 Hz, 2H), 3.99 (s, 3H), 3.65 (s, 3H), 2.70 (s, 3H). LCMS (ESI) Rt = 1.87 minutes, MS m/z 475 [M + H]$^+$ Using 3-chloro-6-(1-(2,2-difluoroethyl)-1H-pyrazol-4-yl)isoquinoline (Preparation 5) and purification method B. | 0.002 |
| 4 | tert-Butyl 4-(4-(3-((4-(1,2-dimethyl-1H-imidazol-5-yl)-2-methoxyphenyl)amino)isoquinolin-6-yl)-1H-pyrazol-1-yl)piperidine-1-carboxylate | $^1$H NMR (500 MHz, CDCl$_3$): δ 8.94 (d, J = 1.0 Hz, 1H), 7.97-7.90 (m, 2H), 7.86-7.80 (m, 2H), 7.70 (d, J = 1.6 Hz, 1H), 7.46 (dd, J = 8.5, 1.6 Hz, 1H), 7.25 (s, 1H), 7.17 (s, 1H), 6.98 (dd, J = 8.5, 1.8 Hz, 1H), 6.97 (s, 1H), 6.91 (d, J = 1.8 Hz, 1H), 4.35-4.25 (m, 3H), 3.95 (s, 3H), 3.57 (s, 3H), 3.00-2.83 (m, 2H), 2.47 (s, 3H), 2.24-2.16 (m, 2H), 2.02-1.85 (m, 2H), 1.48 (s, 9H). LCMS (ESI) Rt = 2.23 minutes MS m/z 594 [M + H]$^+$ Using tert-butyl 4-(4-(3-chloroisoquinolin-6-yl)-1H-pyrazol-1-yl)piperidine-1-carboxylate (Preparation 6) at 140° C. and purification method A. | 0.110 |

| Example No | Name/Structure | Data | MPS1 IC50 (µM) |
|---|---|---|---|
| 5 | 6-(1,2-Dimethyl-1H-imidazol-5-yl)-N-(4-(1,2-dimethyl-1H-imidazol-5-yl)-2-methoxyphenyl)-isoquinolin-3-amine 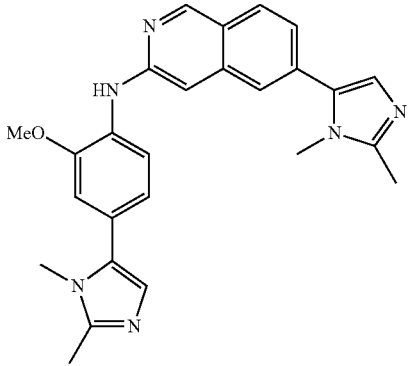 | $^1$H NMR (500 MHz, CDCl$_3$): δ 9.02 (s, 1H), 7.99-7.94 (m, 1H), 7.90 (d, J = 8.5 Hz, 1H), 7.62-7.57 (m, 1H), 7.34 (dd, J = 8.5, 1.6 Hz, 1H), 7.27 (s, 1H), 7.21 (s, 1H), 7.13 (s, 1H), 7.02-6.95 (m, 2H), 6.93 (d, J = 1.9 Hz, 1H), 3.96 (s, 3H), 3.65 (s, 3H), 3.58 (s, 3H), 2.51 (s, 3H), 2.49 (s, 3H). LCMS (ESI) Rt = 1.25 minutes MS m/z 439 [M + H]$^+$ Using 3-chloro-6-(1,2-dimethyl-1H-imidazol-5-yl)isoquinoline (Preparation 7) and purification method C. | 0.005 |
| 6 | N-(4-(1,2-dimethyl-1H-imidazol-5-yl)-2-methoxyphenyl)-6-(oxazol-5-yl)isoquinolin-3-amine 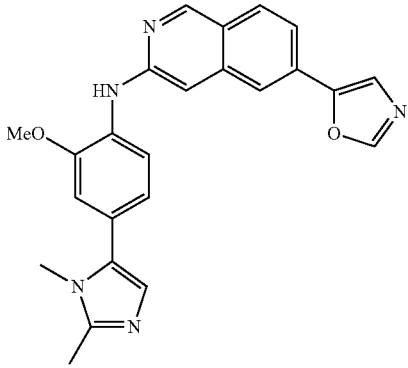 | $^1$H NMR (500 MHz, CDCl$_3$): δ 9.00 (q, J = 1.1 Hz, 1H), 8.02 (s, 1H), 7.97-7.94 (m, 1H), 7.93 (d, J = 1.5 Hz, 1H), 7.91-7.87 (m, 1H), 7.58 (dt, J = 8.3, 1.5 Hz, 1H), 7.54 (s, 1H), 7.31 (s, 1H), 7.21 (s, 1H), 7.01 (dd, J = 8.2, 1.8 Hz, 1H), 6.99 (s, 1H), 6.94 (d, J = 1.8 Hz, 1H), 3.97 (s, 3H), 3.59 (s, 3H), 2.49 (s, 3H). LCMS (ESI) Rt = 1.73 minutes MS m/z 412 [M + H]$^+$ Using 5-(3-chloroisoquinolin-6-yl)oxazole (Preparation 8). | 0.004 |
| 7 | N-(4-(1,2-dimethyl-1H-imidazol-5-yl)-2-methoxyphenyl)-6-(pyridin-4-yl)isoquinolin-3-amine 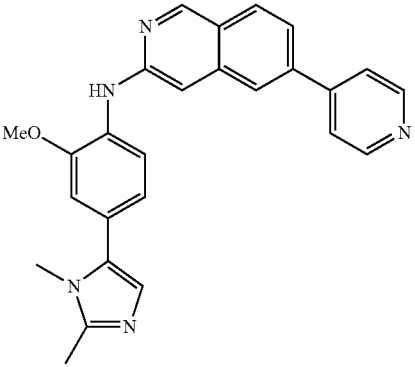 | $^1$H NMR (500 MHz, CDCl$_3$): δ 9.08 (d, J = 1.2 Hz, 1H), 8.78-8.70 (m, 2H), 7.99 (dd, J = 8.5, 2.4 Hz, 2H), 7.90 (d, J = 1.6 Hz, 1H), 7.66-7.62 (m, 2H), 7.60 (dt, J = 8.3, 1.7 Hz, 1H), 7.36 (d, J = 1.2 Hz, 1H), 7.27-7.21 (m, 1H), 7.05-6.97 (m, 2H), 6.94 (d, J = 1.8 Hz, 1H), 3.98 (s, 3H), 3.60 (s, 3H), 2.52 (s, 3H). LCMS (ESI) Rt = 1.58 minutes MS m/z 422 [M + H]$^+$ Using 3-chloro-6-(pyridin-4-yl)isoquinoline (Preparation 9). | 0.145 |

-continued

| Example No | Name/Structure | Data | MPS1 IC50 (μM) |
|---|---|---|---|
| 8 | N-(4-(1,2-dimethyl-1H-imidazol-5-yl)-2-methoxyphenyl)-6-(6-(dimethylamino)pyridin-3-yl)isoquinolin-3-amine 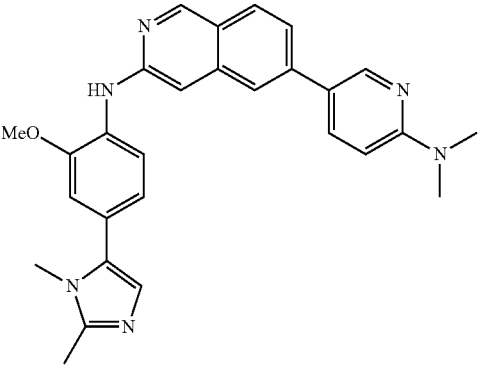 | $^1$H NMR (500 MHz, CDCl$_3$): δ 8.99 (d, J = 1.0 Hz, 1H), 8.58 (dd, J = 2.6, 0.8 Hz, 1H), 7.97 (d, J = 8.2 Hz, 1H), 7.89 (d, J = 8.5 Hz, 1H), 7.84 (dd, J = 8.9, 2.6 Hz, 1H), 7.73 (d, J = 1.7 Hz, 1H), 7.55 (dd, J = 8.5, 1.7 Hz, 1H), 7.31 (s, 1H), 7.18 (s, 1H), 7.00 (dd, J = 8.2, 1.9 Hz, 1H), 6.98 (s, 1H), 6.93 (d, J = 1.8 Hz, 1H), 6.65 (dd, J = 8.9, 0.8 Hz, 1H), 3.97 (s, 3H), 3.58 (s, 3H), 3.19 (s, 6H), 2.49 (s, 3H). LCMS (ESI) Rt = 1.55 minutes MS m/z 465 [M + H]$^+$ Using 5-(3-chloroisoquinolin-6-yl)-N,N-dimethylpyridin-2-amine (Preparation 10) and purification method C. | 0.108 |
| 9 | N-(4-(1,2-dimethyl-1H-imidazol-5-yl)-2-methoxyphenyl)-6-(thiazol-5-yl)isoquinolin-3-amine 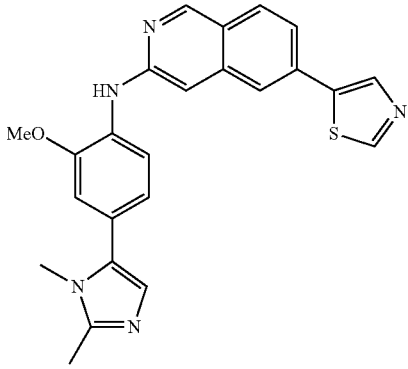 | $^1$H NMR (500 MHz, CDCl$_3$): δ 9.00 (d, J = 0.9 Hz, 1H), 8.84 (d, J = 0.7 Hz, 1H), 8.25 (d, J = 0.6 Hz, 1H), 7.94 (d, J = 8.2 Hz, 1H), 7.88 (dt, J = 8.6, 0.8 Hz, 1H), 7.83-7.76 (m, 1H), 7.55 (dd, J = 8.5, 1.7 Hz, 1H), 7.20 (s, 1H), 7.00 (dd, J = 8.2, 1.9 Hz, 1H), 6.98 (s, 1H), 6.93 (d, J = 1.9 Hz, 1H), 6.79-6.73 (m, 1H), 3.96 (s, 3H), 3.58 (s, 3H), 2.48 (s, 3H). LCMS (ESI) Rt = 1.95 minutes 428 [M + H]$^+$ Using 5-(3-chloroisoquinolin-6-yl)thiazole (Preparation 41). | 0.004 |
| 10 | N-(4-(1,2-dimethyl-1H-imidazol-5-yl)-2-methoxyphenyl)-6-(1-ethyl-1H-pyrazol-4-yl)isoquinolin-3-amine 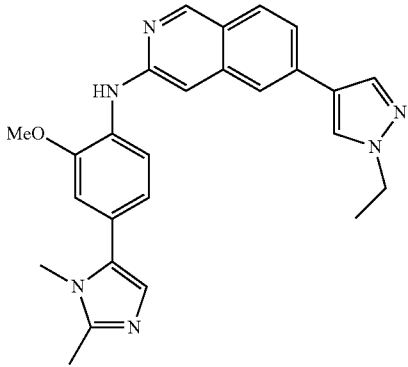 | $^1$H NMR (500 MHz, CDCl$_3$): δ 8.94 (d, J = 0.9 Hz, 1H), 7.96-7.90 (m, 2H), 7.83 (d, J = 8.5 Hz, 1H), 7.80 (d, J = 0.8 Hz, 1H), 7.72-7.67 (m, 1H), 7.47 (dd, J = 8.4, 1.6 Hz, 1H), 7.25 (d, J = 0.9 Hz, 1H), 7.16 (s, 1H), 7.02-6.95 (m, 2H), 6.92 (d, J = 1.8 Hz, 1H), 4.25 (q, J = 7.3 Hz, 2H), 3.95 (s, 3H), 3.57 (s, 3H), 2.48 (s, 3H), 1.58 (t, J = 7.2 Hz, 3H). LCMS (ESI) Rt = 1.88 minutes MS m/z 439 [M + H]$^+$ Using 3-chloro-6-(1-ethyl-1H-pyrazol-4-yl)isoquinoline (Preparation 11). | 0.007 |

-continued

| Example No | Name/Structure | Data | MPS1 IC50 (μM) |
|---|---|---|---|
| 11 | N-(4-(1,2-dimethyl-1H-imidazol-5-yl)-2-methoxyphenyl)-6-(6-methylpyridin-3-yl)isoquinolin-3-amine 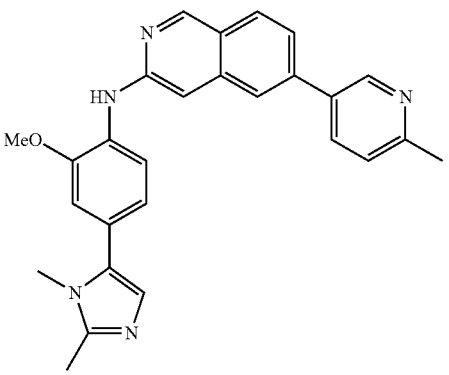 | $^1$H NMR (500 MHz, CDCl$_3$): δ 9.04 (s, 1H), 8.86 (d, J = 2.3 Hz, 1H), 7.96 (t, J = 8.2 Hz, 2H), 7.91 (dd, J = 8.0, 2.3 Hz, 1H), 7.80 (s, 1H), 7.55 (dd, J = 8.2, 2.0 Hz, 1H), 7.34 (s, 1H), 7.30 (d, J = 8.0 Hz, 1H), 7.20 (s, 1H), 7.01 (dd, J = 8.1, 1.8 Hz, 1H), 6.98 (s, 1H), 6.93 (d, J = 2.0 Hz, 1H), 3.97 (s, 3H), 3.59 (s, 3H), 2.66 (s, 3H), 2.49 (s, 3H). LCMS (ESI) Rt = 1.50 minutes MS m/z 436 [M + H]$^+$ Using 3-chloro-6-(6-methylpyridin-3-yl)isoquinoline (Preparation 12). | 0.002 |
| 12 | tert-Butyl (5-(3-((4-(1,2-dimethyl-1H-imidazol-5-yl)-2-methoxyphenyl)amino)isoquinolin-6-yl)pyridin-2-yl)(methyl)carbamate 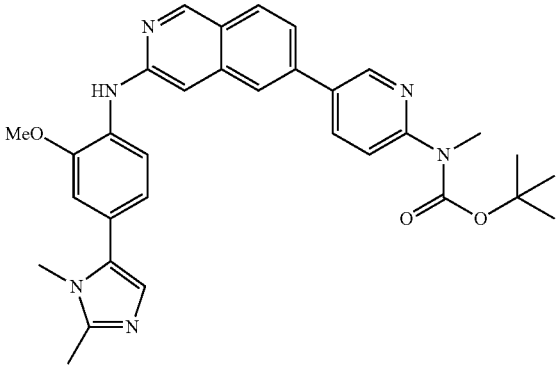 | $^1$H NMR (500 MHz, CDCl$_3$): δ 9.03 (d, J = 0.9 Hz, 1H), 8.72 (dd, J = 2.5, 0.9 Hz, 1H), 7.95 (td, J = 8.4, 5.9 Hz, 3H), 7.89-7.83 (m, 1H), 7.81-7.75 (m, 1H), 7.54 (dd, J = 8.5, 1.7 Hz, 1H), 7.32 (d, J = 1.1 Hz, 1H), 7.20 (s, 1H), 7.00 (dd, J = 8.2, 1.9 Hz, 1H), 6.97 (s, 1H), 6.92 (d, J = 1.8 Hz, 1H), 3.96 (s, 3H), 3.57 (s, 3H), 3.48 (s, 3H), 2.48 (s, 3H), 1.58 (s, 9H). LCMS (ESI) Rt = 2.38 minutes, MS m/z 551 [M + H]$^+$ Using tert-butyl (5-(3-chloroisoquinolin-6-yl)pyridin-2-yl)(methyl)carbamate (Preparation 13) and purification method D. | 0.713 |
| 13 | N-(4-(1,2-dimethyl-1H-imidazol-5-yl)-2-methoxyphenyl)-6-(2,4-dimethylthiazol-5-yl)isoquinolin-3-amine 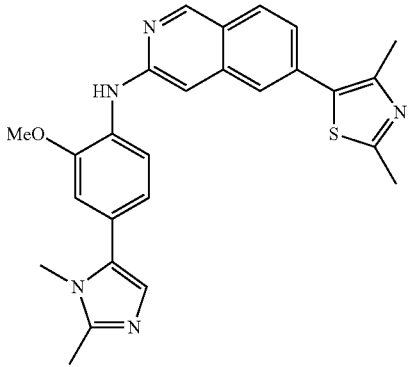 | $^1$H NMR (500 MHz, CDCl$_3$): δ 9.03 (s, 1H), 8.38 (s, broad, 1H), 8.06 (d, J = 8.3 Hz, 1H), 7.90 (d, J = 8.5 Hz, 1H), 7.66 (s, 1H), 7.50-7.36 (m, 2H), 7.19 (s, 1H), 7.00 (d, J = 8.5 Hz, 1H), 6.90 (s, 1H), 3.98 (s, 3H), 3.64 (s, 3H), 2.75 (s, 3H), 2.69 (s, 3H), 2.56 (s, 3H). LCMS (ESI) Rt = 2.20 minutes MS m/z 456 [M + H]$^+$ Using 5-(3-chloroisoquinolin-6-yl)-2,4-dimethylthiazole (Preparation 14) and purification method D. | 0.097 |

| Example No | Name/Structure | Data | MPS1 IC50 (µM) |
|---|---|---|---|
| 14 | N-(4-(1,2-dimethyl-1H-imidazol-5-yl)-2-methoxyphenyl)-6-(1-(2-methoxyethyl)-1H-pyrazol-4-yl)isoquinolin-3-amine 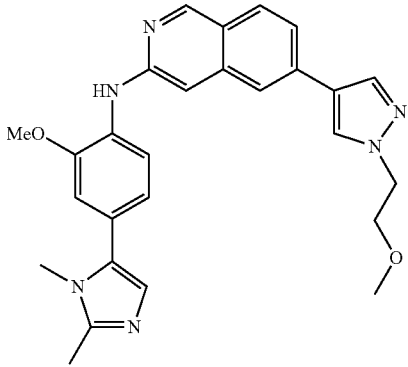 | $^1$H NMR (500 MHz, CDCl$_3$): δ 8.96 (t, J = 0.9 Hz, 1H), 8.00 (d, J = 8.2 Hz, 1H), 7.94 (d, J = 0.8 Hz, 1H), 7.89 (d, J = 0.8 Hz, 1H), 7.85 (d, J = 8.5 Hz, 1H), 7.73 (d, J = 1.5 Hz, 1H), 7.51 (dd, J = 8.5, 1.6 Hz, 1H), 7.29 (s, 1H), 7.26 (d, J = 2.0 Hz, 1H), 7.10 (s, 1H), 6.98 (dd, J = 8.2, 1.9 Hz, 1H), 6.89 (d, J = 1.9 Hz, 1H), 4.38 (t, J = 5.1 Hz, 2H), 3.97 (s, 3H), 3.82 (d, J = 5.1 Hz, 2H), 3.61 (s, 3H), 3.39 (s, 3H), 2.62 (s, 3H).<br>LCMS (ESI) Rt = 1.87 minutes MS m/z 469 [M + H]$^+$<br>Using 3-chloro-6-(1-(2-methoxyethyl)-1H-pyrazol-4-yl)isoquinoline (Preparation 15) and purification method D. | 0.020 |
| 15 | N-(4-(1,2-dimethyl-1H-imidazol-5-yl)-2-methoxyphenyl)-6-(1-isopropyl-1H-pyrazol-4-yl)isoquinolin-3-amine 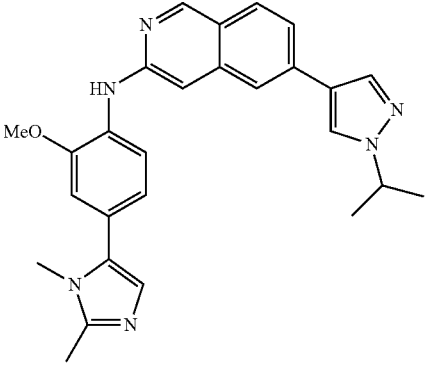 | $^1$H NMR (500 MHz, CDCl$_3$): δ 8.96 (t, J = 0.9 Hz, 1H), 8.00 (d, J = 8.2 Hz, 1H), 7.94 (d, J = 0.8 Hz, 1H), 7.85 (d, J = 8.6 Hz, 1H), 7.84 (d, J = 0.8 Hz, 1H), 7.76-7.67 (m, 1H), 7.51 (dd, J = 8.5, 1.6 Hz, 1H), 7.35 (s, 1H), 7.27 (s, 1H), 7.13 (s, 1H), 6.97 (dd, J = 8.2, 1.9 Hz, 1H), 6.89 (d, J = 1.9 Hz, 1H), 4.59 (hept, J = 6.7 Hz, 1H), 3.97 (s, 3H), 3.62 (s, 3H), 2.64 (s, 3H), 1.60 (d, J = 6.7 Hz, 6H).<br>LCMS Rt = 2.02 minutes MS m/z 453 [M + H]$^+$<br>Using 3-chloro-6-(1-isopropyl-1H-pyrazol-4-yl)isoquinoline (Preparation 16) and purification method D. | 0.003 |
| 16 | N-(4-(1,2-dimethyl-1H-imidazol-5-yl)-2-methoxyphenyl)-6-(pyridin-3-yl)isoquinolin-3-amine 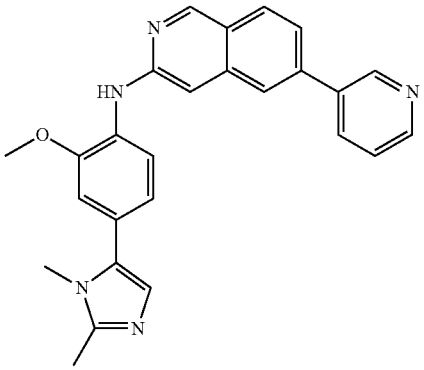 | $^1$H NMR (500 MHz, CDCl$_3$): δ 9.04 (t, J = 0.9 Hz, 1H), 8.97 (dd, J = 2.3, 0.9 Hz, 1H), 8.66 (dd, J = 4.8, 1.6 Hz, 1H), 7.99 (ddd, J = 7.9, 2.3, 1.6 Hz, 1H), 7.97-7.91 (m, 2H), 7.85-7.77 (m, 1H), 7.54 (dd, J = 8.5, 1.7 Hz, 1H), 7.43 (ddd, J = 7.9, 4.8, 0.9 Hz, 1H), 7.32 (d, J = 1.0 Hz, 1H), 7.23 (s, 1H), 7.03-6.94 (m, 2H), 6.92 (d, J = 1.8 Hz, 1H), 3.95 (s, 3H), 3.57 (s, 3H), 2.48 (s, 3H).<br>LCMS (ESI) Rt = 1.78 minutes MS m/z 422 [M + H]$^+$<br>Using of 3-chloro-6-(pyridin-3-yl)isoquinoline (Preparation 17). | 0.003 |

| Example No | Name/Structure | Data | MPS1 IC50 (μM) |
|---|---|---|---|
| 17 | N-(4-(1,2-dimethyl-1H-imidazol-5-yl)-2-methoxyphenyl)-6-(pyrimidin-5-yl)isoquinolin-3-amine | $^1$H NMR (500 MHz, CDCl$_3$): δ 9.28 (s, 1H), 9.10-9.05 (m, 3H), 8.00 (dt, J = 8.6, 0.8 Hz, 1H), 7.96 (d, J = 8.1 Hz, 1H), 7.86-7.77 (m, 1H), 7.52 (dd, J = 8.5, 1.7 Hz, 1H), 7.27-7.23 (m, 1H), 7.33 (d, J = 1.1 Hz, 1H), 7.03-6.96 (m, 2H), 6.93 (d, J = 1.9 Hz, 1H), 3.96 (s, 3H), 3.58 (s, 3H), 2.49 (s, 3H). LCMS (ESI) Rt = 1.82 minutes MS m/z 423 [M + H]$^+$ Using 3-chloro-6-(pyrimidin-5-yl)isoquinoline (Preparation 3). | 0.014 |
| 18 | 6-Cyclopropyl-N-(4-(1,2-dimethyl-1H-imidazol-5-yl)-2-methoxyphenyl)isoquinolin-3-amine | $^1$H NMR (500 MHz, CDCl$_3$): δ 8.92 (t, J = 0.8 Hz, 1H), 7.91 (d, J = 8.2 Hz, 1H), 7.73 (d, J = 8.5 Hz, 1H), 7.33-7.29 (m, 1H), 7.21-7.18 (m, 1H), 7.12 (s, 1H), 7.02 (dd, J = 8.5, 1.7 Hz, 1H), 7.00-6.94 (m, 2H), 6.91 (d, J = 1.9 Hz, 1H), 3.94 (s, 3H), 3.56 (s, 3H), 2.47 (s, 3H), 2.00-2.05 (m, 1H), 1.04-1.13 (m, 2H), 0.80-0.88 (m, 2H). LCMS (ESI) Rt = 2.05 minutes MS m/z 385 [M + H]$^+$ Using 3-chloro-6-cyclopropylisoquinoline (Preparation 2). | 0.144 |
| 19 | N-(4-(1,2-dimethyl-1H-imidazol-5-yl)-2-methoxyphenyl)-6-(1,3-dimethyl-1H-pyrazol-4-yl)isoquinolin-3-amine | $^1$H NMR (500 MHz, CDCl$_3$): δ 8.97 (d, J = 0.9 Hz, 1H), 7.96 (d, J = 8.2 Hz, 1H), 7.85 (dt, J = 8.5, 0.8 Hz, 1H), 7.62-7.59 (m, 1H), 7.58 (s, 1H), 7.39 (dd, J = 8.5, 1.6 Hz, 1H), 7.26 (d, J = 0.9 Hz, 1H), 7.20 (s, 1H), 7.01-6.95 (m, 2H), 6.91 (d, J = 1.8 Hz, 1H), 3.95 (s, 3H), 3.93 (s, 3H), 3.57 (s, 3H), 2.50 (s, 3H), 2.49 (s, 3H). LCMS (ESI) Rt = 1.93 minutes MS m/z 439 [M + H]$^+$ Using 3-chloro-6-(1,3-dimethyl-1H-pyrazol-4-yl)isoquinoline (Preparation 18). | 0.030 |

| Example No | Name/Structure | Data | MPS1 IC50 (μM) |
|---|---|---|---|
| 20 | N-(4-(1,2-dimethyl-1H-imidazol-5-yl)-2-methoxyphenyl)-6-(1,5-dimethyl-1H-pyrazol-4-yl)isoquinolin-3-amine 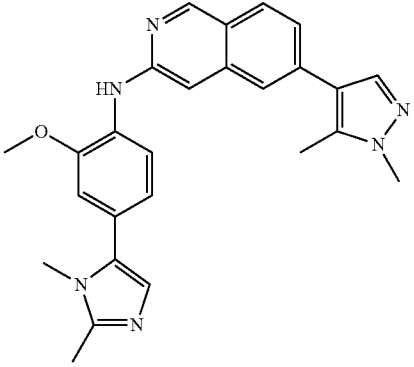 | $^1$H NMR (500 MHz, CDCl$_3$): δ 8.98 (d, J = 0.9 Hz, 1H), 7.95 (d, J = 8.2 Hz, 1H), 7.86 (dt, J = 8.6, 0.8 Hz, 1H), 7.69 (s, 1H), 7.59-7.54 (m, 1H), 7.39 (dd, J = 8.5, 1.6 Hz, 1H), 7.27 (d, J = 0.9 Hz, 1H), 7.20 (s, 1H), 7.03-6.96 (m, 2H), 6.92 (d, J = 1.8 Hz, 1H), 3.95 (s, 3H), 3.90 (s, 3H), 3.57 (s, 3H), 2.49 (s, 6H). LCMS (ESI) Rt = 1.93 minutes MS m/z 439 [M + H]$^+$ Using 3-chloro-6-(1,5-dimethyl-1H-pyrazol-4-yl)isoquinoline (Preparation 19). | 0.002 |
| 21 | N-(2-methoxy-4-(1-methyl-1H-imidazol-5-yl)phenyl)-6-(1-methyl-1H-pyrazol-4-yl)isoquinolin-3-amine 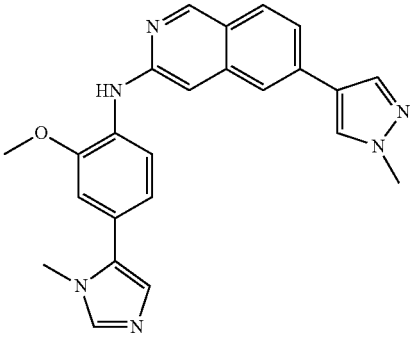 | $^1$H NMR (500 MHz, CDCl$_3$): δ 8.93 (d, J = 0.9 Hz, 1H), 7.94 (d, J = 8.2 Hz, 1H), 7.90 (d, J = 0.8 Hz, 1H), 7.82 (dt, J = 8.6, 0.8 Hz, 1H), 7.75 (d, J = 0.8 Hz, 1H), 7.71-7.65 (m, 1H), 7.55 (s, 1H), 7.45 (dd, J = 8.5, 1.6 Hz, 1H), 7.24 (d, J = 1.0 Hz, 1H), 7.19 (s, 1H), 7.11 (d, J = 1.1 Hz, 1H), 7.01 (dd, J = 8.2, 1.9 Hz, 1H), 6.93 (d, J = 1.8 Hz, 1H), 3.98 (s, 3H), 3.95 (s, 3H), 3.70 (s, 3H). LCMS (ESI) Rt = 1.83 minutes MS m/z 411 [M + H]$^+$ Using 3-chloro-6-(1-methyl-1H-pyrazol-4-yl)isoquinoline (Preparation 20) and 2-methoxy-4-(1-methyl-1H-imidazol-5-yl)aniline (Preparation 73) purification method A. | 0.003 |
| 22 | N-(2-chloro-4-(1,2-dimethyl-1H-imidazol-5-yl)phenyl)-6-(1-methyl-1H-pyrazol-4-yl)isoquinolin-3-amine 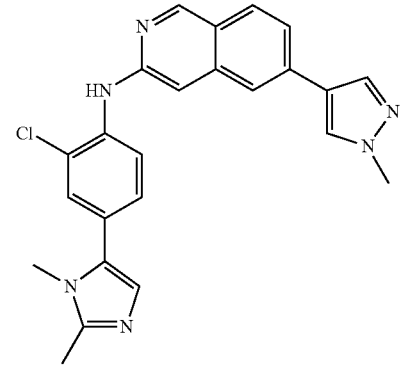 | $^1$H NMR (500 MHz, CDCl$_3$): δ 8.97 (d, J = 0.9 Hz, 1H), 7.98 (d, J = 8.5 Hz, 1H), 7.91 (d, J = 0.8 Hz, 1H), 7.86 (d, J = 8.5 Hz, 1H), 7.77 (d, J = 0.8 Hz, 2H), 7.74-7.69 (m, 1H), 7.51 (dd, J = 8.5, 1.6 Hz, 1H), 7.44 (d, J = 2.0 Hz, 1H), 7.27-7.21 (m, 1H), 7.24 (s, 1H), 7.03 (s, 1H), 6.97 (s, 1H), 4.00 (s, 3H), 3.56 (s, 3H), 2.47 (s, 3H). LCMS (ESI) Rt = 1.93 minutes MS m/z 429 [M + H]$^+$ Using 3-chloro-6-(1-methyl-1H-pyrazol-4-yl)isoquinoline (Preparation 20), 2-chloro-4-(1,2-dimethyl-1H-imidazol-5-yl)aniline (Preparation 75) and purification method A. | 0.004 |

| Example No | Name/Structure | Data | MPS1 IC50 (μM) |
|---|---|---|---|
| 23 | N-(4-(1,2-dimethyl-1H-imidazol-5-yl)-2-methoxyphenyl)-6-(1-methyl-1H-pyrazol-4-yl)isoquinolin-3-amine 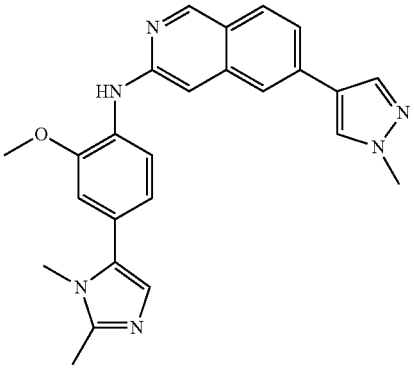 | $^1$H NMR (500 MHz, CDCl$_3$): δ 8.95 (d, J = 0.9 Hz, 1H), 7.93 (d, J = 8.2 Hz, 1H), 7.91 (d, J = 0.8 Hz, 1H), 7.84 (dt, J = 8.5, 0.8 Hz, 1H), 7.76 (d, J = 0.8 Hz, 1H), 7.70 (d, J = 1.6 Hz, 1H), 7.46 (dd, J = 8.5, 1.6 Hz, 1H), 7.26 (d, J = 1.1 Hz, 1H), 7.18 (s, 1H), 6.99 (dd, J = 8.1, 1.8 Hz, 2H), 6.92 (d, J = 1.9 Hz, 1H), 4.00 (s, 3H), 3.95 (s, 3H), 3.57 (s, 3H), 2.48 (s, 3H). LCMS (ESI) Rt = 1.87 minutes MS m/z 425 [M + H]$^+$ Using 3-chloro-6-(1-methyl-1H-pyrazol-4-yl)isoquinoline (Preparation 20) and purification method A. | 0.002 |
| 24 | (3-Methoxy-4-((6-(1-methyl-1H-pyrazol-4-yl)isoquinolin-3-yl)amino)phenyl)(3-methoxyazetidin-1-yl)methanone 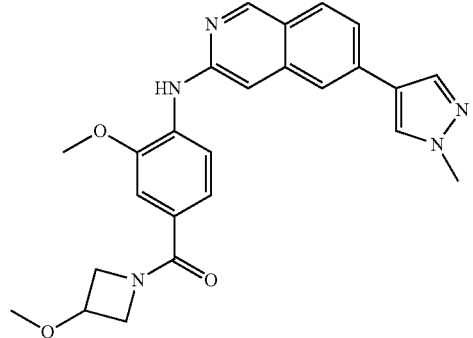 | $^1$H NMR (500 MHz, CDCl$_3$): δ 8.96 (d, J = 0.9 Hz, 1H), 7.96 (d, J = 8.3 Hz, 1H), 7.91 (d, J = 0.8 Hz, 1H), 7.88-7.82 (m, 1H), 7.77 (d, J = 0.9 Hz, 1H), 7.75-7.67 (m, 1H), 7.49 (dd, J = 8.5, 1.6 Hz, 1H), 7.36 (d, J = 1.6 Hz, 1H), 7.33 (s, 1H), 7.27 (d, J = 1.8 Hz, 1H), 7.23 (dd, J = 8.3, 1.8 Hz, 1H), 4.55-4.53 (m, broad, 2H), 4.30-4.25 (m, 2H), 4.15-4.05 (m, 1H), 4.00 (s, 3H), 3.98 (s, 3H), 3.35 (s, 3H). LCMS (ESI) Rt = 2.47 minutes MS m/z 444 [M + H]$^+$ Using 3-chloro-6-(1-methyl-1H-pyrazol-4-yl)isoquinoline (Preparation 20), (4-amino-3-methoxyphenyl)(3-methoxyazetidin-1-yl)methanone (Preparation 92) and purification method A. | 0.002 |
| 25 | (5-(3-Methoxy-4-((6-(1-(2-methoxyethyl)-1H-pyrazol-4-yl)isoquinolin-3-yl)amino)phenyl)-1-methyl-1H-imidazol-2-yl)methanol 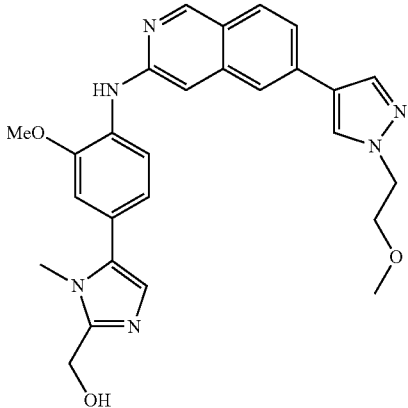 | $^1$H NMR (500 MHz, CDCl$_3$): δ 8.96 (d, J = 1.0 Hz, 1H), 8.01 (d, J = 8.2 Hz, 1H), 7.95 (d, J = 0.8 Hz, 1H), 7.90 (dd, J = 2.1, 0.8 Hz, 1H), 7.85 (d, J = 8.4 Hz, 1H), 7.74 (d, J = 0.8 Hz, 1H), 7.51 (dd, J = 8.5, 1.6 Hz, 1H), 7.25 (s, 1H), 7.22 (s, 1H), 7.07 (s, 1H), 7.01 (dd, J = 8.1, 1.9 Hz, 1H), 6.92 (d, J = 1.9 Hz, 1H), 4.88 (s, 2H), 4.38 (t, J = 5.1 Hz, 2H), 3.98 (s, 3H), 3.83 (t, J = 5.1 Hz, 2H), 3.76 (s, 3H), 3.40 (s, 3H). LCMS (ESI) Rt = 1.85 minutes MS m/z 485 [M + H]$^+$ Using 3-chloro-6-(1-(2-methoxyethyl)-1H-pyrazol-4-yl)isoquinoline (Preparation 15) and 4-(1,2-dimethyl-1H-imidazol-5-yl)-2-methoxyaniline (Preparation 76). | 0.028 |

| Example No | Name/Structure | Data | MPS1 IC50 (μM) |
|---|---|---|---|
| 26 | N-(4-(1,2-dimethyl-1H-imidazol-5-yl)-2-methoxyphenyl)-6-(5-methylpyridin-3-yl)isoquinolin-3-amine 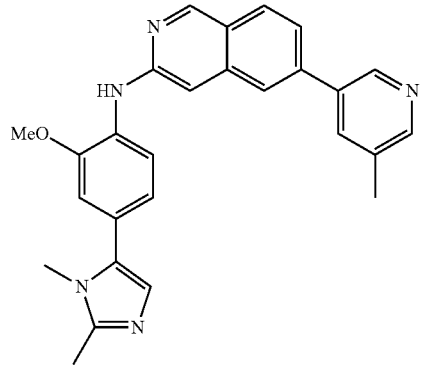 | $^1$H NMR (500 MHz, CDCl$_3$): δ 9.03 (s, 1H), 8.76 (d, J = 2.2 Hz, 1H), 8.49 (d, J = 2.0 Hz, 1H), 7.94 (dd, J = 8.4, 7.2 Hz, 2H), 7.82-7.75(m, 2H), 7.54 (dd, J = 8.5, 1.7 Hz, 1H), 7.32 (s, 1H), 7.21 (s, 1H), 7.03-6.94 (m, 2H), 6.92 (d, J = 1.9 Hz, 1H), 3.95 (s, 3H), 3.57 (s, 3H), 2.48 (s, 3H), 2.44 (s, 3H). LCMS (ESI) Rt = 1.75 minutes MS m/z 436 [M + H]$^+$ Using 3-chloro-6-(5-methylpyridin-3-yl)isoquinoline (Preparation 38) and purification method E. | 0.010 |
| 27 | N-(4-(1,2-dimethyl-1H-imidazol-5-yl)-2-methoxyphenyl)-6-(1-methyl-1H-1,2,3-triazol-5-yl)isoquinolin-3-amine 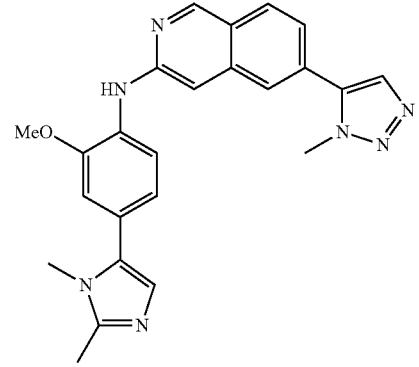 | $^1$H NMR (500 MHz, CDCl$_3$): δ 9.08 (d, J = 1.0 Hz, 1H), 7.99-7.94 (m, 2H), 7.85 (d, J = 1.0 Hz, 1H), 7.70-7.66 (m, 1H), 7.34 (dd, J = 8.4, 1.6 Hz, 1H), 7.30 (d, J = 1.0 Hz, 1H), 7.26 (s, 1H), 7.05-6.97 (m, 2H), 6.94 (d, J = 1.9 Hz, 1H), 4.17 (s, 3H), 3.97 (s, 3H), 3.59 (s, 3H), 2.49 (s, 3H). LCMS (ESI) Rt = 1.70 minutes MS m/z 426 [M + H]$^+$ Using 3-chloro-6-(1-methylpyridin-3-yl)isoquinoline (Preparation 40) and purification method E. | 0.004 |
| 28 | 6-(1-(Cyclobutylmethyl)-1H-pyrazol-4-yl)-N-(4-(1,2-dimethyl-1H-imidazol-5-yl)-2-methoxyphenyl)isoquinolin-3-amine 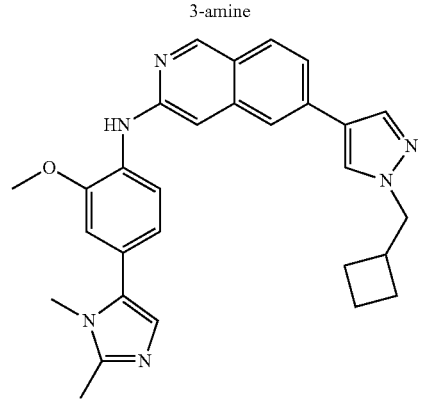 | $^1$H NMR (500 MHz, CDCl$_3$): δ 8.95 (s, 1H), 7.95 (d, J = 8.21 Hz, 1H), 7.91 (s, 1H), 7.83 (d, J = 8.50 Hz, 1H), 7.75 (s, 1H), 7.70 (s, 1H), 7.47 (dd, J = 1.60, 8.50 Hz, 1H), 7.26 (s, 1H), 7.17 (s, 1H), 7.00-6.96 (m, 2H), 6.92 (d, J = 1.81 Hz, 1H), 4.21 (d, J = 7.34 Hz, 2H), 3.96 (s, 3H), 3.59 (s, 3H), 2.95-2.85 (m, 1H), 2.51 (s, 3H), 2.20-2.10 (m, 2H), 2.02-1.80 (m, 4H). LCMS (ESI) Rt = 2.17 minutes MS m/z 479 [M + H]$^+$ HRMS (ESI) MS m/z calcd for C$_{29}$H$_{31}$N$_6$O [M + H]$^+$ 479.2554, found 479.2559 Rt = 2.80 minutes Using 3-chloro-6-(1-(cyclobutylmethyl)-1H-pyrazol-4-yl)isoquinoline (Preparation 21) and purification method A. | 0.003 |

-continued

| Example No | Name/Structure | Data | MPS1 IC50 (µM) |
|---|---|---|---|
| 29 | 1-(4-(3-((4-(1,2-Dimethyl-1H-imidazol-5-yl)-2-methoxyphenyl)amino)isoquinolin-6-yl)-1H-pyrazol-1-yl)-2-methylpropan-2-ol | $^1$H NMR (500 MHz, CDCl$_3$): δ 8.95 (s, 1H), 7.96 (s, 1H), 7.94 (d, J = 8.20 Hz, 1H), 7.86 (s, 1H), 7.83 (d, J = 8.50 Hz, 1H), 7.70 (s, 1H), 7.47 (dd, J = 1.60, 8.50 Hz, 1H), 7.24 (s, 1H), 7.17 (s, 1H), 7.00-6.94 (m, 2H), 6.90 (d, J = 1.86 Hz, 1H), 4.16 (s, 2H), 3.95 (s, 3H), 3.57 (s, 3H), 2.49 (s, 3H), 1.26 (s, 6H). LCMS (ESI) Rt = 1.82 minutes MS m/z 483 [M + H]$^+$ HRMS (ESI) MS m/z calcd for C$_{28}$H$_{31}$N$_6$O$_2$ [M + H]$^+$ 483.2503, found 483.2501. Rt = 2.49 minutes Using 1-(4-(3-chloroisoquinolin-6-yl)-1H-pyrazol-1-yl)-2-methylpropan-2-ol (Preparation 22) and purification method E. | 0.002 |
| 30 | N-(4-(1,2-Dimethyl-1H-imidazol-5-yl)-2-methoxyphenyl)-6-(1-((3-methyloxetan-3-yl)methyl)-1H-pyrazol-4-yl)isoquinolin-3-amine | $^1$H NMR (500 MHz, CDCl$_3$): δ 8.97 (s, 1H), 7.99 (d, J = 8.25 Hz, 1H), 7.94 (s, 1H), 7.86 (d, J = 8.50 Hz, 1H), 7.78 (s, 1H), 7.74 (s, 1H), 7.48 (dd, J = 1.60, 8.50 Hz, 1H), 7.27 (d, J = 1.00 Hz, 1H), 7.21 (s, 1H), 7.04 (s, 1H), 6.99 (dd, J = 1.88, 8.20 Hz, 1H), 6.91 (d, J = 1.88 Hz, 1H), 4.78 (d, J = 6.16 Hz, 2H), 4.47 (d, J = 6.04 Hz, 2H), 4.42 (s, 2H), 3.97 (s, 3H), 3.61 (s, 3H), 2.57 (s, 3H), 1.33 (s, 3H). LCMS (ESI) Rt = 1.85 minutes MS m/z 495 [M + H]$^+$ HRMS (ESI) MS m/z calcd for C$_{29}$H$_{31}$N$_6$O$_2$ [M + H]$^+$ 495.2503, found 495.2496. Rt = 2.53 minutes Using 3-chloro-6-(1-((3-methyloxetan-3-yl)methyl)-1H-pyrazol-4-yl)isoquinoline (Preparation 23). | 0.002 |
| 31 | N-(2-Methoxy-4-(1-(2-methoxyethyl)-2-methyl-1H-imidazol-5-yl)phenyl)-6-(1-(2-methoxyethyl)-1H-pyrazol-4-yl)isoquinolin-3-amine | $^1$H NMR (500 MHz, CDCl$_3$): δ 8.94 (s, 1H), 7.96-7.91 (m, 2H), 7.89 (s, 1H), 7.84-7.80 (m, 1H), 7.74 (s, 1H), 7.48 (dd, J = 1.64, 8.50 Hz, 1H), 7.27 (s, 1H), 7.18 (s, 1H), 7.03-6.97 (m, 2H), 6.96 (s, 1H), 4.36 (t, J = 5.12 Hz, 2H), 4.12 (t, J = 5.80 Hz, 2H), 3.95 (s, 3H), 3.81 (t, J = 5.12 Hz, 2H), 3.51 (t, J = 5.80 Hz, 2H), 3.38 (s, 3H), 3.28 (s, 3H), 2.52 (s, 3H). LCMS (ESI) Rt = 1.90 minutes MS m/z 513 [M + H]$^+$ HRMS (ESI) MS m/z calcd for C$_{29}$H$_{33}$N$_6$O$_3$ [M + H]$^+$ 513.2609, found 513.2603. Rt = 2.52 minutes Using 3-chloro-6-(1-(2-methoxyethyl)-1H-pyrazol-4-yl)isoquinoline (Preparation 15) and 2-methoxy-4-(1-(2-methoxyethyl)-2-methyl-1H-imidazol-5-yl)aniline (Preparation 77). | 0.002 |

| Example No | Name/Structure | Data | MPS1 IC50 (µM) |
|---|---|---|---|
| 32 | (4-(3-Methoxy-4-((6-(1-(2-methoxyethyl)-1H-pyrazol-4-yl)isoquinolin-3-yl)amino)phenyl)-1-methyl-1H-pyrazol-5-yl)methanol | $^1$H NMR (500 MHz, MeOD): δ 8.87 (s, 1H), 8.17 (s, 1H), 8.02 (s, 1H), 7.89 (d, J = 8.47 Hz, 1H), 7.83 (s, 1H), 7.77 (d, J = 8.14 Hz, 1H), 7.64 (s, 1H), 7.57 (dd, J = 1.60, 8.54 Hz, 1H), 7.25 (s, 1H), 7.19 (d, J = 1.80 Hz, 1H), 7.10 (dd, J = 1.80, 8.06 Hz, 1H), 4.76 (s, 2H), 4.37 (t, J = 5.20 Hz, 2H), 4.00 (s, 3H), 3.98 (s, 3H), 3.80 (t, J = 5.20 Hz, 2H), 3.37 (s, 3H). LCMS (ESI) Rt = 2.50 minutes MS m/z 485 [M + H]$^+$ HRMS (ESI) MS m/z calcd for $C_{27}H_{29}N_6O_3$ [M + H]$^+$ 485.2296, found 485.2361. Rt = 2.71 minutes Using 3-chloro-6-(1-(2-methoxyethyl)-1H-pyrazol-4-yl)isoquinoline (Preparation 15) and (4-(4-amino-3-methoxyphenyl)-1-methyl-1H-pyrazol-5-yl)methanol (Preparation 78) and purification method A. | 0.003 |
| 33 | N-(4-(1,2-Dimethyl-1H-imidazol-5-yl)-2-methoxyphenyl)-6-(1-(oxetan-3-yl)-1H-pyrazol-4-yl)isoquinolin-3-amine | $^1$H NMR (500 MHz, CDCl$_3$): δ 8.97 (s, 1H), 8.02 (s, 1H), 8.01 (s, 1H), 7.96 (d, J = 8.20 Hz, 1H), 7.86 (d, J = 8.50 Hz, 1H), 7.77 (s, 1H), 7.49 (dd, J = 1.60, 8.50 Hz, 1H), 7.27 (s, 1H), 7.19 (s, 1H), 7.02-6.95 (m, 2H), 6.92 (d, J = 1.84 Hz, 1H), 5.58-5.50 (m, 1H), 5.14 (d, J = 6.88 Hz, 4H), 3.96 (s, 3H), 3.59 (s, 3H), 2.52 (s, 3H). LCMS (ESI) Rt = 1.77 minutes MS m/z 467 [M + H]$^+$ HRMS (ESI) MS m/z calcd for $C_{27}H_{26}N_6NaO_2$ [M + Na]$^+$ 489.2009, found 489.1996. Rt = 2.16 minutes Using 3-chloro-6-(1-(oxetan-3-yl)-1H-pyrazol-4-yl)isoquinoline (Preparation 24) and purification method E. | 0.003 |
| 34 | (4-(3-((4-(1,2-Dimethyl-1H-imidazol-5-yl)-2-methoxyphenyl)amino)isoquinolin-6-yl)-1-methyl-1H-pyrazol-5-yl)methanol | $^1$H NMR (500 MHz, CDCl$_3$): δ 8.97 (s, 1H), 8.37 (s, 1H), 7.98 (d, J = 8.20 Hz, 1H), 7.87 (d, J = 8.44 Hz, 1H), 7.69 (s, 1H), 7.67 (s, 1H), 7.45 (dd, J = 1.58, 8.44 Hz, 1H), 7.36 (s, 1H), 7.26 (s, 1H), 7.12 (s, 1H), 6.91 (dd, J = 1.90, 8.20 Hz, 1H), 6.83 (d, J = 1.90 Hz, 1H), 4.86 (s, 2H), 4.06 (s, 3H), 3.94 (s, 3H), 3.61 (s, 3H), 2.65 (s, 3H). LCMS (ESI) Rt = 1.67 minutes MS m/z 455 [M + H]$^+$ HRMS (ESI) MS m/z calcd for $C_{26}H_{27}N_6O_2$ [M + H]$^+$ 455.2190, found 455.2198. Rt = 2.11 minutes Using 4-(3-chloroisoquinolin-6-yl)-1-methyl-1H-pyrazol-5-yl)methanol (Preparation 25) and purification method D. | 0.003 |

-continued

| Example No | Name/Structure | Data | MPS1 IC50 (µM) |
|---|---|---|---|
| 35 | 1-(4-(3-((2-Methoxy-4-(1-(2-methoxyethyl)-2-methyl-1H-imidazol-5-yl)phenyl)amino)-isoquinolin-6-yl)-1H-pyrazol-1-yl)-2-methylpropan-2-ol | $^1$H NMR (500 MHz, CDCl$_3$): δ 8.98 (s, 1H), 8.33 (s, 1H), 8.05 (d, J = 8.16 Hz, 1H), 7.99 (s, 1H), 7.91-7.84 (m, 2H), 7.75 (d, J = 1.80 Hz, 1H), 7.54 (dd, J = 1.60, 8.48 Hz, 1H), 7.47 (s, 1H), 7.22 (s, 1H), 6.99 (dd, J = 1.80, 8.16 Hz, 1H), 6.94 (d, J = 1.88 Hz, 1H), 4.22 (t, J = 5.00 Hz, 2H), 4.18 (s, 2H), 3.99 (s, 3H), 3.52 (t, J = 5.00 Hz, 2H), 3.30 (s, 3H), 2.80 (s, 3H), 1.27 (s, 6H). LCMS (ESI) Rt = 1.87 minutes MS m/z 527 [M + H]$^+$ HRMS (ESI) MS m/z calcd for C$_{30}$H$_{35}$N$_6$O$_3$ [M + H]$^+$ 527.2765, found 527.2766. Rt = 2.31 minutes Using 1-(4-(3-chloroisoquinolin-6-yl)-1H-pyrazol-1-yl)-2-methylpropan-2-ol (Preparation 22) and 2-methoxy-4-(1-(2-methoxyethyl)-2-methyl-1H-imidazol-5-yl)aniline (Preparation 77). | 0.003 |
| 36 | 1-(4-(3-((4-(5-(Hydroxymethyl)-1-methyl-1H-pyrazol-4-yl)-2-methoxyphenyl)amino)-isoquinolin-6-yl)-1H-pyrazol-1-yl)-2-methylpropan-2-ol | $^1$H NMR (500 MHz, CDCl$_3$): δ 8.82 (s, 1H), 8.19 (s, 1H), 7.93 (s, 1H), 7.86 (s, 1H), 7.80 (d, J = 8.52 Hz, 1H), 7.68-7.58 (m, 3H), 7.44 (dd, J = 1.56, 8.50 Hz, 1H), 7.16 (s, 1H), 7.04-6.98 (m, 2H), 4.83 (s, 2H), 4.16 (s, 2H), 4.04 (s, 3H), 3.92 (s, 3H), 1.25 (s, 6H). LCMS (ESI) Rt = 2.38 minutes MS m/z 499 [M + H]$^+$ HRMS (ESI) MS m/z calcd for C$_{28}$H$_{31}$N$_6$O$_3$ [M + H]$^+$ 499.2452, found 499.2527. Rt = 2.67 minutes Using 1-(4-(3-chloroisoquinolin-6-yl)-1H-pyrazol-1-yl)-2-methylpropan-2-ol (Preparation 22) and (4-(4-Amino-3-methoxyphenyl)-1-methyl-1H-pyrazol-5-yl)methanol (Preparation 78). | 0.003 |
| 37 | N-(4-(1,2-Dimethyl-1H-imidazol-5-yl)-2-methoxyphenyl)-6-(1-(oxetan-3-ylmethyl)-1H-pyrazol-4-yl)isoquinolin-3-amine | $^1$H NMR (500 MHz, CDCl$_3$): δ 8.98 (s, 1H), 8.07 (d, J = 8.22 Hz, 1H), 7.94 (s, 1H), 7.88 (d, J = 8.52 Hz, 1H), 7.80 (s, 1H), 7.73 (d, J = 1.96 Hz, 1H), 7.50 (dd, J = 1.62, 8.52 Hz, 1H), 7.41 (s, 1H), 7.28 (s, 1H), 7.22 (s, 1H), 6.99 (dd, J = 1.88, 8.30 Hz, 1H), 6.89 (d, J = 1.88 Hz, 1H), 4.91 (dd, J = 6.46, 7.60 Hz, 2H), 4.60 (dd, J = 5.80, 6.46 Hz, 2H), 4.54 (d, J = 7.60 Hz, 2H), 3.99 (s, 3H), 3.67 (s, 3H), 3.64-3.56 (m, 1H), 2.76 (s, 3H). LCMS (ESI) Rt = 1.73 minutes MS m/z 481 [M + H]$^+$ HRMS (ESI) MS m/z calcd for C$_{28}$H$_{29}$N$_6$O$_2$ [M + H]$^+$ 481.2347, found 481.2338. Rt = 2.36 minutes Using 3-chloro-6-(1-(oxetan-3-ylmethyl)-1H-pyrazol-4-yl)isoquinoline (Preparation 26) and purification method D. | 0.005 |

| Example No | Name/Structure | Data | MPS1 IC50 (μM) |
|---|---|---|---|
| 38 | Racemic 1-(4-(3-((4-(1,2-Dimethyl-1H-imidazol-5-yl)-2-methoxyphenyl)amino)isoquinolin-6-yl)-1H-pyrazol-1-yl)propan-2-ol | $^1$H NMR (500 MHz, CDCl$_3$): δ 8.94 (s, 1H), 8.00 (d, J = 8.18 Hz, 1H), 7.95 (s, 1H), 7.88 (s, 1H), 7.85 (d, J = 8.50 Hz, 1H), 7.71 (d, J = 1.75 Hz, 1H), 7.49 (dd, J = 1.64, 8.48 Hz, 1H), 7.42 (s, 1H), 7.25 (s, 1H), 7.17 (s, 1H), 6.96 (dd, J = 1.94, 8.18 Hz, 1H), 6.88 (d, J = 2.00 Hz, 1H), 4.36-4.24 (m, 2H), 4.14-4.06 (m, 1H), 3.97 (s, 3H), 3.63 (s, 3H), 2.68 (s, 3H), 1.30 (d, J = 6.30 Hz, 3H). LCMS (ESI) Rt = 1.70 minutes MS m/z 469 [M + H]$^+$ HRMS (ESI) MS m/z calcd for C$_{27}$H$_{29}$N$_6$O$_2$ [M + H]$^+$ 469.2347, found 469.2376. Rt = 2.26 minutes Using Racemic 1-(4-(3-chloroisoquinolin-6-yl)-1H-pyrazol-1-yl)propan-2-ol (Preparation 27) and purification method D. | 0.002 |
| 39 | N-(4-(1,2-Dimethyl-1H-imidazol-5-yl)-2-methoxyphenyl)-6-(1-(tetrahydro-2H-pyran-4-yl)-1H-pyrazol-4-yl)isoquinolin-3-amine | $^1$H NMR (500 MHz, CDCl$_3$): δ 8.96 (s, 1H), 8.02 (d, J = 8.16 Hz, 1H), 7.96 (s, 1H), 7.86 (m, 2H), 7.74 (s, 1H), 7.51 (dd, J = 1.78, 8.20 Hz, 1H), 7.40 (s, 1H), 7.28 (s, 1H), 7.17 (s, 1H), 6.98 (dd, J = 2.08, 8.16 Hz, 1H), 6.89 (d, J = 2.08 Hz, 1H), 4.50-4.40 (m, 1H), 4.22-4.15 (m, 2H), 3.98 (s, 3H), 3.64 (s, 3H), 3.62-3.55 (m, 2H), 2.68 (s, 3H), 2.25-2.10 (m, 4H). LCMS (ESI) Rt = 1.87 minutes MS m/z 495 [M + H]$^+$ HRMS (ESI) MS m/z calcd for C$_{29}$H$_{31}$N$_6$O$_2$ [M + H]$^+$ 495.2503, found 495.2563. Rt = 2.41 minutes Using 3-chloro-6-(1-(tetrahydro-2H-pyran-4-yl)-1H-pyrazol-4-yl)isoquinoline (Preparation 28) and purification method D. | 0.006 |
| 40 | Racemic 6-(1-((2,2-Dimethyl-1,3-dioxolan-4-yl)methyl)-1H-pyrazol-4-yl)-N-(4-(1,2-dimethyl-1H-imidazol-5-yl)-2-methoxyphenyl)isoquinolin-3-amine | $^1$H NMR (500 MHz, CDCl$_3$): δ 8.96 (s, 1H), 8.45 (s, 1H), 8.02 (d, J = 8.18 Hz, 1H), 7.92 (d, J = 18.25 Hz, 1H), 7.86 (d, J = 8.45 Hz, 1H), 7.73 (s, 1H), 7.52-7.47 (m, 1H), 7.37 (s, 1H), 7.28 (d, J = 9.08 Hz, 1H), 7.15 (s, 1H), 6.97 (dd, J = 2.00, 7.90 Hz, 1H), 6.89 (d, J = 2.00 Hz, 1H), 4.60-4.50 (m, 1H), 4.40-4.28 (m, 2H), 4.14 (dd, J = 6.20, 8.64 Hz, 1H), 3.97 (s, 3H), 3.84 (dd, J = 6.00, 8.68 Hz, 1H), 3.63 (s, 3H), 2.66 (s, 3H), 1.43 (s, 3H), 1.39 (s, 3H). LCMS (ESI) Rt = 2.22 minutes MS m/z 525 [M + H]$^+$ HRMS (ESI) MS m/z calcd for C$_{30}$H$_{33}$N$_6$O$_3$ [M + H]$^+$ 525.2609, found 525.2709. Rt = 2.48 minutes Using racemic 3-chloro-6-(1-((2,2-dimethyl-1,3-dioxolan-4-yl)methyl)-1H-pyrazol-4-yl)isoquinoline (Preparation 29) and purification method D. | 0.006 |

| Example No | Name/Structure | Data | MPS1 IC50 (μM) |
|---|---|---|---|
| 41 | 1-(4-(3-((2-Methoxy-4-(4-methyl-4H-1,2,4-triazol-3-yl)phenyl)amino)isoquinolin-6-yl)-1H-pyrazol-1-yl)-2-methylpropan-2-ol | $^1$H NMR (500 MHz, CDCl$_3$): δ 8.96 (s, 1H), 8.21 (s, 1H), 8.07 (d, J = 8.22 Hz, 1H), 7.97 (d, J = 0.82 Hz, 1H), 7.88 (s, 1H), 7.85 (d, J = 8.48 Hz, 1H), 7.74-7.68 (m, 1H), 7.49 (dd, J = 1.68, 8.48 Hz, 1H), 7.39 (d, J = 1.90 Hz, 1H), 7.36 (s, 1H), 7.25 (s, 1H), 7.20 (dd, J = 1.88, 8.32 Hz, 1H), 4.17 (s, 2H), 4.00 (s, 3H), 3.82 (s, 3H), 1.26 (s, 6H). LCMS (ESI) Rt = 2.28 minutes MS m/z 470 [M + H]$^+$ HRMS (ESI) MS m/z calcd for C$_{26}$H$_{28}$N$_7$O$_2$ [M + H]$^+$ 470.2299, found 470.2319. Rt = 2.60 minutes Using 1-(4-(3-chloroisoquinolin-6-yl)-1H-pyrazol-1-yl)-2-methylpropan-2-ol (Preparation 22) and 2-methoxy-4-(4-methyl-4H-1,2,4-triazol-3-yl)aniline (Preparation 110) and purification method D. | 0.001 |
| 42 | 1-(4-(3-((2-Chloro-4-(1,2-dimethyl-1H-imidazol-5-yl)phenyl)amino)isoquinolin-6-yl)-1H-pyrazol-1-yl)-2-methylpropan-2-ol | $^1$H NMR (500 MHz, CDCl$_3$): δ 8.99 (s, 1H), 8.06 (d, J = 8.50 Hz, 1H), 7.99 (d, J = 0.80 Hz, 1H), 7.91 (d, J = 8.43 Hz, 1H), 7.89 (s, 1H), 7.77 (d, J = 1.75 Hz, 1H), 7.57 (dd, J = 1.60, 8.52 Hz, 1H), 7.44 (d, J = 2.06 Hz, 1H), 7.32 (s, 1H), 7.28 (s, 1H), 7.26 (dd, J = 2.06, 8.50 Hz, 1H), 7.15 (s, 1H), 4.18 (s, 2H), 3.63 (s, 3H), 2.67 (s, 3H), 1.27 (s, 6H). LCMS (ESI) Rt = 2.15 minutes MS m/z 487 [M + H]$^+$ HRMS (ESI) MS m/z calcd for C$_{27}$H$_{28}$ClN$_6$O [M + H]$^+$ 487.2008, found 487.2018. Rt = 2.43 minutes Using 1-(4-(3-chloroisoquinolin-6-yl)-1H-pyrazol-1-yl)-2-methylpropan-2-ol (Preparation 22) and 2-chloro-4-(1,2-dimethyl-1H-imidazol-5-yl)aniline (Preparation 75) and purification method D. | 0.003 |
| 43 | 1-((4-(3-((4-(1,2-Dimethyl-1H-imidazol-5-yl)-2-methoxyphenyl)amino)isoquinolin-6-yl)-1H-pyrazol-1-yl)methyl)cyclobutanol | $^1$H NMR (500 MHz, CDCl$_3$): δ 8.96 (s, 1H), 8.02 (d, J = 8.16 Hz, 1H), 7.95 (d, J = 0.82 Hz, 1H), 7.92 (d, J = 0.82 Hz, 1H), 7.87 (d, J = 8.50 Hz, 1H), 7.73 (d, J = 1.76 Hz, 1H), 7.51 (dd, J = 1.64, 8.48 Hz, 1H), 7.38 (s, 1H), 7.26 (s, 1H), 7.16 (s, 1H), 6.97 (dd, J = 1.90, 8.20 Hz, 1H), 6.88 (d, J = 1.90 Hz, 1H), 4.32 (s, 2H), 3.97 (s, 3H), 3.63 (s, 3H), 2.68 (s, 3H), 2.23-2.04 (m, 4H), 1.95-1.81 (m, 1H), 1.66 (dt, J = 9.08, 11.60 Hz, 1H). LCMS (ESI) Rt = 2.17 minutes MS m/z 495 [M + H]$^+$ HRMS (ESI) MS m/z calcd for C$_{29}$H$_{31}$N$_6$O$_2$ [M + H]$^+$ 495.2503, found 495.2533. Rt = 2.38 minutes Using 1-((4-(3-chloroisoquinolin-6-yl)-1H-pyrazol-1-yl)methyl)cyclobutanol (Preparation 30) and purification method D. | 0.003 |

| Example No | Name/Structure | Data | MPS1 IC50 (µM) |
|---|---|---|---|
| 44 | N-(4-(1,2-Dimethyl-1H-imidazol-5-yl)-2-methoxyphenyl)-6-(1-(2,2,2-trifluoroethyl)-1H-pyrazol-4-yl)isoquinolin-3-amine 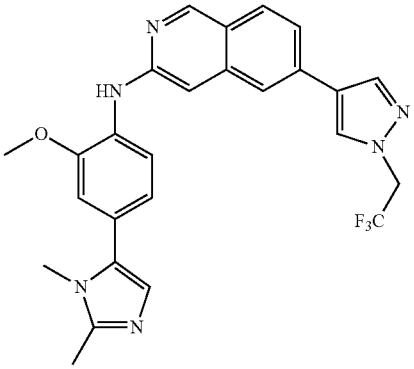 | $^1$H NMR (500 MHz, CDCl$_3$): δ 8.99 (s, 1H), 8.08-7.99 (m, 2H), 7.92 (s, 1H), 7.89 (d, J = 8.52 Hz, 1H), 7.75 (s, 1H), 7.50 (dd, J = 1.64, 8.52 Hz, 1H), 7.40 (s, 1H), 7.29 (s, 1H), 7.17 (s, 1H), 6.98 (dd, J = 1.88, 8.20 Hz, 1H), 6.90 (d, J = 2.00 Hz, 1H), 4.81 (q, J = 8.37 Hz, 2H), 3.98 (s, 3H), 3.64 (s, 3H), 2.68 (s, 3H). LCMS (ESI) Rt = 2.23 minutes MS m/z 493 [M + H]$^+$ HRMS (ESI) MS m/z calcd for C$_{26}$H$_{23}$F$_3$N$_6$NaO [M + Na]$^+$ 515.1778, found 515.1761. Rt = 2.46 minutes Using 3-chloro-6-(1-(2,2,2-trifluoroethyl)-1H-pyrazol-4-yl)isoquinoline (Preparation 31) and purification method D. | 0.004 |
| 45 | 1-(4-(3-(2-Chloro-4-morpholinophenylamino)isoquinolin-6-yl)-1H-pyrazol-1-yl)-2-methylpropan-2-ol 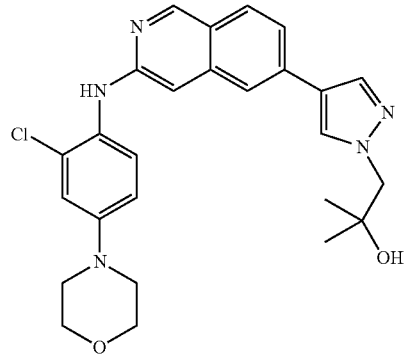 | $^1$H NMR (500 MHz, CDCl$_3$): δ 8.86 (s, 1H), 7.94 (s, 1H), 7.84-7.78 (m, 2H), 7.61 (s, 1H), 7.55 (d, J = 8.88 Hz, 1H), 7.44 (dd, J = 1.60, 8.54 Hz, 1H), 7.34 (s, 1H), 7.05 (d, J = 2.80 Hz, 1H), 6.90 (dd, J = 2.82, 8.88 Hz, 1H), 6.86 (s, 1H), 4.15 (s, 2H), 4.02-3.79 (m, 4H), 3.31-3.09 (m, 4H), 1.25 (s, 6H). LCMS (ESI) Rt = 2.62 minutes MS m/z 478 [M + H]$^+$ HRMS (ESI) MS m/z calcd for C$_{26}$H$_{29}$ClN$_5$O$_2$ [M + H]$^+$ 478.2004, found 478.2049. Rt = 2.91 minutes Using 1-(4-(3-chloroisoquinolin-6-yl)-1H-pyrazol-1-yl)-2-methylpropan-2-ol (Preparation 22) and 2-chloro-4-morpholinoaniline (Preparation 111) and purification method D. | 0.045 |
| 46 | (4-(6-(1-(2-Hydroxy-2-methylpropyl)-1H-pyrazol-4-yl)isoquinolin-3-ylamino)-3-methoxy-phenyl)(3-methoxyazetidin-1-yl)methanone 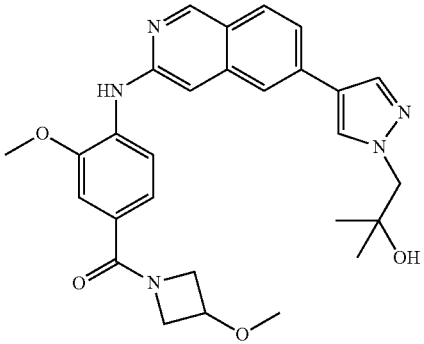 | $^1$H NMR (500 MHz, CDCl$_3$): δ 8.93 (s, 1H), 7.95 (s, 1H), 7.93 (d, J = 8.34 Hz, 1H), 7.85 (s, 1H), 7.82 (d, J = 8.34 Hz, 1H), 7.69 (d, J = 1.75 Hz, 1H), 7.47 (dd, J = 1.60, 8.46 Hz, 1H), 7.38-7.32 (m, 2H), 7.25-7.17 (m, 2H), 4.55-4.35 (m, broad, 2H), 4.30-4.24 (m, 2H), 4.15 (s, 2H), 4.14-4.05 (s, broad, 1H), 3.96 (s, 3H), 3.33 (s, 3H), 1.25 (s, 6H). LCMS (ESI) Rt = 2.60 minutes MS m/z 502 [M + H]$^+$ HRMS (ESI) MS m/z calcd for C$_{28}$H$_{32}$N$_5$O$_4$ [M + H]$^+$ 502.2449, found 502.2457. Rt = 2.82 minutes Using 1-(4-(3-chloroisoquinolin-6-yl)-1H-pyrazol-1-yl)-2-methylpropan-2-ol (Preparation 22) and (4-amino-3-methoxyphenyl)(3-methoxyazetidin-1-yl)methanone (Preparation 92) and purification method A. | 0.002 |

| Example No | Name/Structure | Data | MPS1 IC50 (μM) |
|---|---|---|---|
| 47 | 1-(4-(3-(4-(1,2-Dimethyl-1H-imidazol-5-yl)phenylamino)isoquinolin-6-yl)-1H-pyrazol-1-yl)-2-methylpropan-2-ol 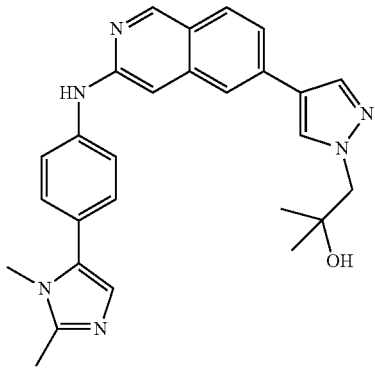 | $^1$H NMR (500 MHz, MeOD): δ 8.87 (s, 1H), 8.15 (s, 1H), 8.00 (s, 1H), 7.96-7.71 (m, 2H), 7.65-7.48 (m, 3H), 7.40-7.25 (m, 2H), 7.20 (s, 1H), 6.86 (s, 1H), 4.16 (s, 2H), 3.57 (s, 3H), 2.43 (s, 3H), 1.23 (s, 6H).<br>LCMS (ESI) Rt = 2.03 minutes MS m/z 453 [M + H]$^+$<br>HRMS (ESI) MS m/z calcd for $C_{27}H_{29}N_6O$ [M + H]$^+$ 453.2397, found 453.2406. Rt = 2.32 minutes<br>Using 1-(4-(3-chloroisoquinolin-6-yl)-1H-pyrazol-1-yl)-2-methylpropan-2-ol (Preparation 22) and 4-(1,2-dimethyl-1H-imidazol-5-yl)aniline (Preparation 80) and purification method E. | 0.006 |
| 48 | 1-(4-(3-(2-Ethoxy-4-(4-methyl-4H-1,2,4-triazol-3-yl)phenylamino)isoquinolin-6-yl)-1H-pyrazol-1-yl)-2-methylpropan-2-ol 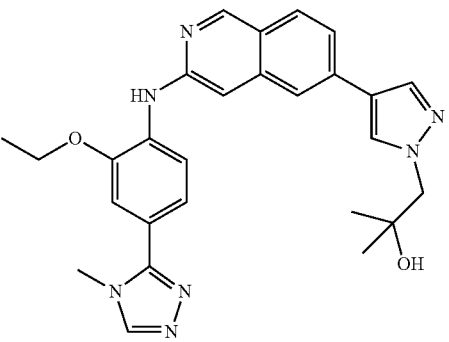 | $^1$H NMR (500 MHz, CDCl$_3$): δ 8.95 (s, 1H), 8.20 (s, 1H), 8.02 (d, J = 8.28 Hz, 1H), 7.96 (d, J = 0.72 Hz, 1H), 7.89 (s, 1H), 7.85 (d, J = 8.50 Hz, 1H), 7.72 (d, J = 1.28 Hz, 1 H), 7.49 (dd, J = 1.62, 8.50 Hz, 1H), 7.43 (s, 1H), 7.37 (d, J = 1.85 Hz, 1H), 7.27 (s, 1H), 7.20 (dd, J = 1.85, 8.22 Hz, 1H), 4.22 (q, J = 6.92 Hz, 2H), 4.17 (s, 2H), 3.82 (s, 3H), 1.52 (t, J = 6.98 Hz, 3H), 1.26 (s, 6H).<br>LCMS (ESI) Rt = 2.48 minutes MS m/z 484 [M + H]$^+$<br>HRMS (ESI) MS m/z calcd for $C_{27}H_{30}N_7O_2$ [M + H]$^+$ 484.2383, found 484.2454. Rt = 2.71 minutes<br>Using 1-(4-(3-chloroisoquinolin-6-yl)-1H-pyrazol-1-yl)-2-methylpropan-2-ol (Preparation 22) and 2-ethoxy-4-(4-methyl-4H-1,2,4-triazol-3-yl)aniline (Preparation 109). | 0.002 |
| 49 | 4-(6-(1-(2-Hydroxy-2-methylpropyl)-1H-pyrazol-4-yl)isoquinolin-3-ylamino)-3-methoxy-benzonitrile 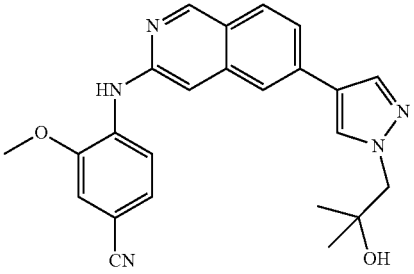 | $^1$H NMR (500 MHz, CDCl$_3$): δ 8.98 (s, 1H), 8.07 (d, J = 8.46 Hz, 1H), 8.00 (s, 1H), 7.91 (d, J = 8.64 Hz, 1H), 7.88 (s, 1H), 7.77 (s, 1H), 7.58 (dd, J = 1.62, 8.52 Hz, 1H), 7.34 (dd, J = 1.82, 8.40 Hz, 1H), 7.30 (s, 1H), 7.13 (d, J = 1.68 Hz, 1H), 4.18 (s, 2H), 4.00 (s, 3H), 1.27 (s, 6H).<br>LCMS (ESI) Rt = 2.83 minutes MS m/z 414 [M + H]$^+$<br>HRMS (ESI) MS m/z calcd for $C_{24}H_{24}N_5O_2$ [M + H]$^+$ 414.1925, found Rt = 3.01 minutes<br>Using 1-(4-(3-chloroisoquinolin-6-yl)-1H-pyrazol-1-yl)-2-methylpropan-2-ol (Preparation 22) and N-(4-cyano-2-methoxyphenyl)formamide (Preparation 71) and purification method G. | 0.011 |

| Example No | Name/Structure | Data | MPS1 IC50 (μM) |
|---|---|---|---|
| 50 | 1-(4-(3-(4-(1,2-Dimethyl-1H-imidazol-5-yl)-3-fluoro-2-methoxyphenylamino)isoquinolin-6-yl)-1H-pyrazol-1-yl)-2-methylpropan-2-ol<br>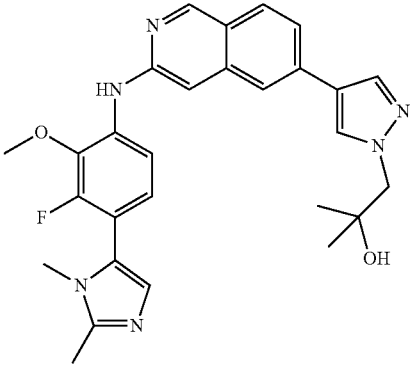 | $^1$H NMR (500 MHz, CDCl$_3$): δ 8.99 (s, 1H), 7.99 (s, 1H), 7.92-7.85 (m, 2H), 7.81 (dd, J = 1.36, 8.50 Hz, 1H), 7.76 (d, J = 1.68 Hz, 1H), 7.54 (dd, J = 1.68, 8.50 Hz, 1H), 7.28 (d, J = 1.00 Hz, 1H), 7.25 (s, 1H), 7.06-6.94 (m, 2H), 4.17 (s, 2H), 4.05 (s, 3H), 3.51 (s, 3H), 2.55 (s, 3H), 1.26 (s, 6H).<br>LCMS (ESI) Rt = 2.14 minutes MS m/z 501 [M + H]$^+$<br>HRMS (ESI) MS m/z calcd for C$_{28}$H$_{30}$FN$_6$O$_2$ [M + H]$^+$ 501.2409, found 501.2405. Rt = 2.33 minutes<br>Using 1-(4-(3-chloroisoquinolin-6-yl)-1H-pyrazol-1-yl)-2-methylpropan-2-ol (Preparation 22) and 4-(1,2-dimethyl-1H-imidazol-5-yl)-3-fluoro-2-methoxyaniline (Preparation 81) and purification method E. | 0.002 |
| 51 | 1-(4-(3-(2-Methoxy-4-(5-(methoxymethyl)-1-methyl-1H-pyrazol-4-yl)phenylamino)isoquinolin-6-yl)-1H-pyrazol-1-yl)-2-methylpropan-2-ol<br>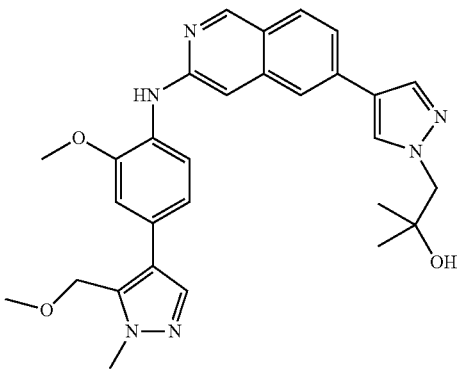 | $^1$H NMR (500 MHz, CDCl$_3$): δ 8.93 (s, 1H), 7.97 (s, 1H), 7.87-7.80 (m, 3H), 7.70 (d, J = 1.68 Hz, 1H), 7.62 (s, 1H), 7.46 (dd, J = 1.60, 8.50 Hz, 1H), 7.24 (s, 1H), 7.21 (s, 1H), 7.08-6.97 (m, 2H), 4.55 (s, 2H), 4.16 (s, 2H), 4.00 (s, 3H), 3.96 (s, 3H), 3.46 (s, 3H), 1.25 (s, 6H).<br>LCMS (ESI) Rt = 2.70 minutes MS m/z 513 [M + H]$^+$<br>HRMS (ESI) MS m/z calcd for C$_{29}$H$_{33}$N$_6$O$_3$ [M + H]$^+$ 513.2609, found 513.2605. Rt = 2.93 minutes<br>Using 1-(4-(3-chloroisoquinolin-6-yl)-1H-pyrazol-1-yl)-2-methylpropan-2-ol (Preparation 22) and 2-methoxy-4-(5-(methoxymethyl)-1-methyl-1H-pyrazol-4-yl)aniline (Preparation 82) and purification method A. | 0.004 |
| 52 | 1-(4-(3-(2-Methoxy-4-(1-methyl-1H-pyrazol-4-yl)phenylamino)isoquinolin-6-yl)-1H-pyrazol-1-yl)-2-methylpropan-2-ol<br>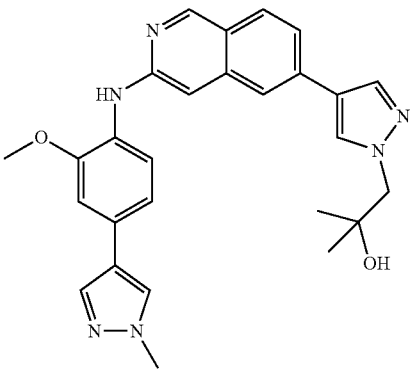 | $^1$H NMR (500 MHz, CDCl$_3$): δ 8.91 (s, 1H), 7.96 (s, 1H), 7.84 (s, 1H), 7.81 (d, J = 8.52 Hz, 1H), 7.79-7.72 (m, 2H), 7.69-7.65 (m, 1H), 7.62 (d, J = 0.82 Hz, 1H), 7.44 (dd, J = 1.60, 8.48 Hz, 1H), 7.19 (s, 1H), 7.17-7.10 (m, 2H), 7.04 (d, J = 1.80 Hz, 1H), 4.15 (s, 2H), 3.98 (s, 3H), 3.96 (s, 3H), 1.25 (s, 6H).<br>LCMS (ESI) Rt = 2.58 minutes MS m/z 469 [M + H]$^+$<br>HRMS (ESI) MS m/z calcd C$_{27}$H$_{29}$N$_6$O$_2$ [M + H]$^+$ 469.2347, found 469.2359. Rt = 2.75 minutes<br>Using 1-(4-(3-chloroisoquinolin-6-yl)-1H-pyrazol-1-yl)-2-methylpropan-2-ol (Preparation 22) and 2-methoxy-4-(1-methyl-1H-pyrazol-4-yl)aniline (Preparation 91) and purification method A. | 0.004 |

| Example No | Name/Structure | Data | MPS1 IC50 (μM) |
|---|---|---|---|
| 53 | 1-(4-(3-(4-(1,5-Dimethyl-1H-pyrazol-4-yl)-2-methoxyphenylamino)isoquinolin-6-yl)-1H-pyrazol-1-yl)-2-methylpropan-2-ol | $^1$H NMR (500 MHz, CDCl$_3$): δ 8.91 (s, 1H), 7.95 (s, 1H), 7.84 (s, 1H), 7.83-7.78 (m, 2H), 7.68 (d, J = 1.70 Hz, 1H), 7.58 (s, 1H), 7.43 (dd, J = 1.60, 8.46 Hz, 1H), 7.22 (s, 1H), 7.13 (s, 1H), 7.00 (dd, J = 1.82, 8.08 Hz, 1H), 6.94 (d, J = 1.84 Hz, 1H), 4.15 (s, 2H), 3.95 (s, 3H), 3.88 (s, 3H), 2.43 (s, 3H), 1.25 (s, 6H). LCMS (ESI) Rt = 2.73 minutes MS m/z 483 [M + H]$^+$ HRMS (ESI) MS m/z calcd C$_{28}$H$_{31}$N$_6$O$_2$ [M + H]$^+$ 483.2503, found 483.2510. Rt = 2.85 minutes Using 1-(4-(3-chloroisoquinolin-6-yl)-1H-pyrazol-1-yl)-2-methylpropan-2-ol (Preparation 22) and 4-(1,5-dimethyl-1H-pyrazol-4-yl)-2-methoxyaniline (Preparation 83) and purification method H. | 0.004 |
| 54 | 1-(4-(3-(4-Fluoro-2-methoxyphenylamino)isoquinolin-6-yl)-1H-pyrazol-1-yl)-2-methylpropan-2-ol | $^1$H NMR (500 MHz, CDCl$_3$): δ 8.89 (s, 1H), 7.95 (d, J = 0.78 Hz, 1H), 7.83 (s, 1H), 7.79 (d, J = 8.50 Hz, 1H), 7.72-7.66 (m, 1H), 7.64 (d, J = 1.78 Hz, 1H), 7.42 (dd, J = 1.64, 8.50 Hz, 1H), 7.04 (s, 1H), 6.84 (s, 1H), 6.78-6.67 (m, 2H), 4.15 (s, 2H), 3.89 (s, 3H), 1.25 (s, 6H). HRMS (ESI) MS m/z calcd C$_{23}$H$_{23}$FN$_4$NaO$_2$ [M + Na]$^+$ 429.1697, found 429.1692. Rt = 2.69 minutes Using 1-(4-(3-chloroisoquinolin-6-yl)-1H-pyrazol-1-yl)-2-methylpropan-2-ol (Preparation 22) and 4-fluoro-2-methoxyaniline and purification method G. | 0.065 |
| 55 | tert-Butyl 3-(4-(6-(1-(2-hydroxy-2-methylpropyl)-1H-pyrazol-4-yl)isoquinolin-3-ylamino)-3-methoxyphenyl)-5,6-dihydro-[1,2,4]triazolo[4,3-a]pyrazine-7(8H)-carboxylate | $^1$H NMR (500 MHz, CDCl$_3$): δ 8.95 (s, 1H), 8.06 (d, J = 8.30 Hz, 1H), 7.96 (d, J = 0.78 Hz, 1H), 7.88 (s, 1H), 7.85 (d, J = 8.58 Hz, 1H), 7.71 (d, J = 1.64 Hz, 1H), 7.49 (dd, J = 1.64, 8.58 Hz, 1H), 7.44-7.38 (m, 2H), 7.23 (s, 1H), 7.18 (dd, J = 1.86, 8.22 Hz, 1H), 4.94 (s, 2H), 4.17-4.12 (m, 2H + 2H), 4.00 (s, 3H), 3.90-3.84 (m, 2H), 1.54 (s, 9H), 1.26 (s, 6H). HRMS (ESI) MS m/z calcd for C$_{33}$H$_{39}$N$_8$O$_4$ [M + H]$^+$ 611.3089, found 611.3093. Rt = 2.94 minutes Using 1-(4-(3-chloroisoquinolin-6-yl)-1H-pyrazol-1-yl)-2-methylpropan-2-ol (Preparation 22) and tert-butyl 3-(4-amino-3-methoxyphenyl)-5,6-dihydro-[1,2,4]triazolo[4,3-a]pyrazine-7(8H)-carboxylate (Preparation 84) and purification method A. | 0.003 |

| Example No | Name/Structure | Data | MPS1 IC50 (μM) |
|---|---|---|---|
| 56 | 1-(4-(3-(6-(1,2-Dimethyl-1H-imidazol-5-yl)-2-methoxypyridin-3-ylamino)isoquinolin-6-yl)-1H-pyrazol-1-yl)-2-methylpropan-2-ol | $^1$H NMR (500 MHz, CDCl$_3$): δ 8.95 (s, 1H), 8.22 (d, J = 8.06 Hz, 1H), 7.96 (d, J = 0.78 Hz, 1H), 7.87 (s, 1H), 7.84 (d, J = 8.52 Hz, 1H), 7.69 (d, J = 1.70 Hz, 1H), 7.48 (dd, J = 1.60, 8.48 Hz, 1H), 7.22 (s, 1H), 7.15 (d, J = 8.04 Hz, 1H), 7.12 (s, 1H), 7.06 (s, 1H), 4.17 (s, 2H), 4.06 (s, 3H), 3.90 (s, 3H), 2.48 (s, 3H), 1.27 (s, 6H).<br>HRMS (ESI) MS m/z calcd for C$_{27}$H$_{30}$N$_7$O$_2$ [M + H]$^+$ 484.2455, found 484.2460. Rt = 2.45 minutes<br>Using 1-(4-(3-chloroisoquinolin-6-yl)-1H-pyrazol-1-yl)-2-methylpropan-2-ol (Preparation 22) and 6-(1,2-dimethyl-1H-imidazol-5-yl)-2-methoxypyridin-3-amine (Preparation 119) and purification method A. | 0.003 |
| 57 | 1-(4-(3-((5-(1,2-Dimethyl-1H-imidazol-5-yl)-3-methoxypyridin-2-yl)amino)isoquinolin-6-yl)-1H-pyrazol-1-yl)-2-methylpropan-2-ol | $^1$H NMR (500 MHz, CDCl$_3$): δ 8.95 (s, 1H), 8.88 (s, 1H), 8.14 (s, 1H), 8.00 (s, 1H), 7.98 (d, J = 1.84 Hz, 1H), 7.94 (d, J = 1.34 Hz, 1H), 7.91-7.82 (m, 2H), 7.55 (dd, J = 1.64, 8.44 Hz, 1H), 7.08 (s, 1H), 7.01 (d, J = 1.84 Hz, 1H), 4.17 (s, 2H), 3.99 (s, 3H), 3.61 (s, 3H), 2.59 (s, 3H), 1.26 (s, 6H).<br>HRMS (ESI) MS m/z calcd for C$_{27}$H$_{30}$N$_7$O$_2$ [M + H]$^+$ 484.2455, found 484.2440. Rt = 1.98 minutes<br>Using 1-(4-(3-chloroisoquinolin-6-yl)-1H-pyrazol-1-yl)-2-methylpropan-2-ol (Preparation 22) and 5-(1,2-dimethyl-1H-imidazol-5-yl)-3-methoxypyridin-2-amine (Preparation 120). | 0.003 |
| 58 | 1-(4-(3-((2-Chloro-4-(pyrimidin-5-yl)phenyl)amino)isoquinolin-6-yl)-1H-pyrazol-1-yl)-2-methylpropan-2-ol | $^1$H NMR (500 MHz, CDCl$_3$): δ 9.22 (s, 1H), 8.99 (s, 1H), 8.97 (s, 2H), 8.09 (d, J = 8.50 Hz, 1H), 7.99 (d, J = 0.78 Hz, 1H), 7.91 (d, J = 8.64 Hz, 1H), 7.88 (s, 1H), 7.76 (d, J = 1.74 Hz, 1H), 7.70 (d, J = 2.15 Hz, 1H), 7.57 (dd, J = 1.59, 8.53 Hz, 1H), 7.52 (dd, J = 2.20, 8.50 Hz, 1H), 7.41 (s, 1H), 7.27 (s, 1H), 4.17 (s, 2H), 1.27 (s, 6H).<br>HRMS (ESI) MS m/z calcd for C$_{26}$H$_{24}$N$_6$O [M + H]$^+$ 471.1695, found 471.1695. Rt = 3.01 minutes<br>Using 1-(4-(3-chloroisoquinolin-6-yl)-1H-pyrazol-1-yl)-2-methylpropan-2-ol (Preparation 22) and 2-chloro-4-(pyrimidine-5-yl)aniline and purification method A. | 0.005 |

-continued

| Example No | Name/Structure | Data | MPS1 IC50 (µM) |
|---|---|---|---|
| 59 | 1-(4-(3-((2-Chloro-4-(methylsulfonyl)phenyl)amino)isoquinolin-6-yl)-1H-pyrazol-1-yl)-2-methylpropan-2-ol 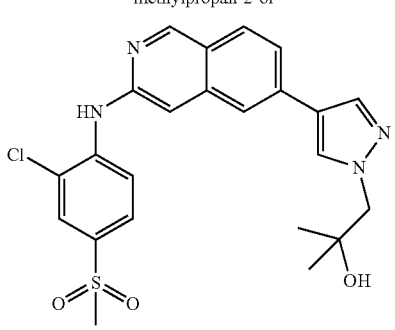 | $^1$H NMR (500 MHz, Acetone-d$_6$): δ 9.10 (s, 1H), 8.51 (d, J = 8.80 Hz, 1H), 8.50 (d, J = 8.74 Hz, 1H), 8.28 (s, 1H), 8.08-8.04 (m, 2H), 8.02 (s, 1H), 7.96 (d, J = 2.20 Hz, 1H), 7.83 (dd, J = 2.14, 8.80 Hz, 1H), 7.79 (dd, J = 1.66, 8.58 Hz, 1H), 7.57 (s, 1H), 4.21 (s, 2H), 3.17 (s, 3H), 1.21 (s, 6H). HRMS (ESI) MS m/z calcd for C$_{23}$H$_{24}$ClN$_4$O$_3$S [M + H]$^+$ 471.1252, found 471.1296. Rt = 2.78 minutes Using 1-(4-(3-chloroisoquinolin-6-yl)-1H-pyrazol-1-yl)-2-methylpropan-2-ol (Preparation 22) and 2-chloro-4-(methylsulfonyl)aniline and purification method G. | 0.004 |
| 60 | 4-((6-(1-(2-Hydroxy-2-methylpropyl)-1H-pyrazol-4-yl)isoquinolin-3-yl)amino)-3-methoxy-N,N-dimethylbenzamide 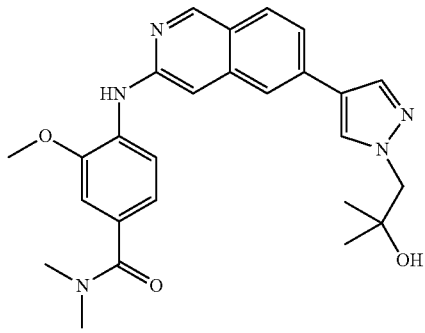 | $^1$H NMR (500 MHz, CDCl$_3$): δ 8.93 (s, 1H), 7.97 (d, J = 0.78 Hz, 1H), 7.88 (d, J = 8.02 Hz, 1H), 7.85 (s, 1H), 7.84 (d, J = 8.60 Hz, 1H), 7.72-7.68 (m, 1H), 7.48 (dd, J = 1.60, 8.50 Hz, 1H), 7.33 (s, 1H), 7.23 (t, J = 0.90 Hz, 1H), 7.12-7.05 (m, 2H), 4.16 (s, 2H), 3.96 (s, 3H), 3.13 (s, 6H), 1.25 (s, 6H). HRMS (ESI) MS m/z calcd for C$_{26}$H$_{30}$N$_5$O$_3$ [M + H]$^+$ 460.2343, found 460.2351. Rt = 2.67 minutes Using-(4-(3-chloroisoquinolin-6-yl)-1H-pyrazol-1-yl)-2-methylpropan-2-ol (Preparation 22) and 4-amino-3-methoxy-N,N-dimethylbenzamide and purification method A. | 0.002 |
| 61 | 4-((6-(1-(2-Hydroxy-2-methylpropyl)-1H-pyrazol-4-yl)isoquinolin-3-yl)amino)-N-(2-hydroxyethyl)-3-methoxybenzamide 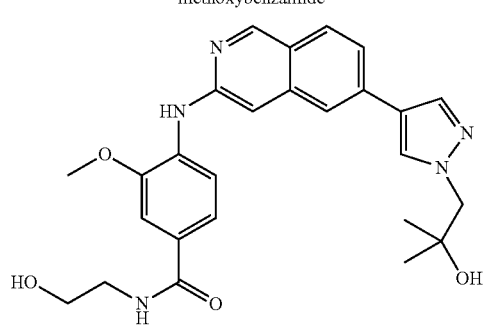 | $^1$H NMR (500 MHz, CDCl$_3$): δ 8.90 (s, 1H), 7.95 (d, J = 0.78 Hz, 1H), 7.88 (d, J = 8.32 Hz, 1H), 7.86 (d, J = 0.76 Hz, 1H), 7.81 (d, J = 8.54 Hz, 1H), 7.67 (d, J = 1.38 Hz, 1H), 7.52-7.45 (m, 2H), 7.42 (s, 1H), 7.36 (dd, J = 1.92, 8.42 Hz, 1H), 7.20 (d, J = 0.99 Hz, 1H), 6.84 (t, J = 5.68 Hz, 1H), 4.16 (s, 2H), 3.97 (s, 3H), 3.90-3.86 (m, 2H), 3.69-3.65 (m, 2H), 1.26 (s, 6H). HRMS (ESI) MS m/z calcd for C$_{26}$H$_{30}$N$_5$O$_4$ [M + H]$^+$ 476.2292, found 476.2302. Rt = 2.57 minutes Using 1-(4-(3-chloroisoquinolin-6-yl)-1H-pyrazol-1-yl)-2-methylpropan-2-ol (Preparation 22) and 4-amino-N-(2-hydroxyethyl)-3-methoxybenzamide (Preparation 93) and purification method A. | 0.002 |

| Example No | Name/Structure | Data | MPS1 IC50 (μM) |
|---|---|---|---|
| 62 | 4-((6-(1-(2-Hydroxy-2-methylpropyl)-1H-pyrazol-4-yl)isoquinolin-3-yl)amino)-3-methoxy-N-(2-methoxyethyl)benzamide | $^1$H NMR (500 MHz, CDCl$_3$): δ 8.91 (s, 1H), 7.99 (d, J = 0.74 Hz, 1H), 7.89 (s, 1H), 7.87 (d, J = 8.70 Hz, 1H), 7.82 (d, J = 8.14 Hz, 1H), 7.72 (s, 1H), 7.57-7.49 (m, 2H), 7.37 (dd, J = 2.00, 8.34 Hz, 1H), 7.27 (s, 1H), 6.58 (t, J = 5.68 Hz, 1H), 4.18 (s, 2H), 4.00 (s, 3H), 3.75-3.67 (m, 2H), 3.64-3.58 (m, 2H), 3.44 (s, 3H), 1.26 (s, 6H). HRMS (ESI) MS m/z calcd for C$_{27}$H$_{32}$N$_5$O$_4$ [M + H]$^+$ 490.2449, found 490.2446. Rt = 2.74 minutes Using 1-(4-(3-chloroisoquinolin-6-yl)-1H-pyrazol-1-yl)-2-methylpropan-2-ol (Preparation 22) and 4-amino-N-(2-hydroxyethyl)-3-methoxybenzamide (Preparation 94) and purification method A. | 0.003 |
| 63 | 1-(4-(3-((2-Methoxy-4-(2-(methoxymethyl)-1-methyl-1H-imidazol-5-yl)phenyl)amino)-isoquinolin-6-yl)-1H-pyrazol-1-yl)-2-methylpropan-2-ol | $^1$H NMR (500 MHz, CDCl$_3$): δ 8.96 (s, 1H), 7.99-7.94 (m, 2H), 7.88-7.81 (m, 2H), 7.75-7.69 (m, 1H), 7.48 (dd, J = 1.62, 8.46 Hz, 1H), 7.26 (s, 1H), 7.20 (s, 1H), 7.06 (s, 1H), 7.01 (dd, J = 1.86, 8.20 Hz, 1H), 6.93 (d, J = 1.86 Hz, 1H), 4.66 (s, 2H), 4.16 (s, 2H), 3.97 (s, 3H), 3.71 (s, 3H), 3.45 (s, 3H), 1.26 (s, 6H). HRMS (ESI) MS m/z calcd for C$_{29}$H$_{33}$N$_6$O$_3$ [M + H]$^+$ 513.2722, found 513.2724 Rt = 2.38 minutes Using 1-(4-(3-chloroisoquinolin-6-yl)-1H-pyrazol-1-yl)-2-methylpropan-2-ol (Preparation 22) and 2-methoxy-4-(2-(methoxymethyl)-1-methyl-1H-imidazol-5-yl)aniline (Preparation 85) and purification method A. | 0.001 |
| 64 | 1-(4-(3-((2-Methoxy-4-(1-methyl-1H-1,2,4-triazol-5-yl)phenyl)amino)isoquinolin-6-yl)-1H-pyrazol-1-yl)-2-methylpropan-2-ol | $^1$H NMR (500 MHz, CDCl$_3$): δ 8.96 (s, 1H), 8.08 (d, J = 8.34 Hz, 1H), 7.97 (d, J = 0.74 Hz, 1H), 7.95 (s, 1H), 7.87-7.81 (m, 2H), 7.75-7.67 (m, 1H), 7.49 (dd, J = 1.58, 8.50 Hz, 1H), 7.39 (s, 1H), 7.35 (d, J = 1.88 Hz, 1H), 7.26-7.24 (m, 2H), 4.16 (s, 2H), 4.06 (s, 3H), 4.01 (s, 3H), 1.25 (s, 6H). HRMS (ESI) MS m/z calcd for C$_{26}$H$_{27}$N$_7$NaO$_2$ [M + Na]$^+$ 492.2118, found 492.2117. Rt = 2.80 minutes Using 1-(4-(3-chloroisoquinolin-6-yl)-1H-pyrazol-1-yl)-2-methylpropan-2-ol (Preparation 22) and 2-methoxy-4-(1-methyl-1H-1,2,4-triazol-5-yl)aniline (Preparation 86) and purification method A. | 0.001 |

| Example No | Name/Structure | Data | MPS1 IC50 (μM) |
|---|---|---|---|
| 65 | (1,1-Dioxidothiomorpholino)(4-((6-(1-(2-hydroxy-2-methylpropyl)-1H-pyrazol-4-yl)isoquinolin-3-yl)amino)-3-methoxyphenyl)methanone 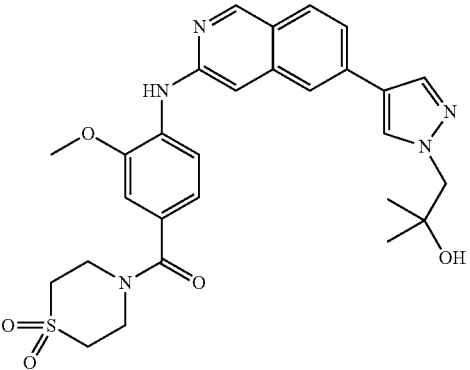 | $^1$H NMR (500 MHz, CDCl$_3$): δ 8.95 (s, 1H), 8.00-7.95 (m, 2H), 7.91-7.86 (m, 2H), 7.73 (d, J = 1.60 Hz, 1H), 7.54 (dd, J = 1.58, 8.56 Hz, 1H), 7.25 (s, 1H), 7.12-7.05 (m, 2H), 4.25-4.15 (m, 4H), 4.18 (s, 2H), 3.99 (s, 3H), 3.20-3.05 (m, 4H), 1.26 (s, 6H).<br>HRMS (ESI) MS m/z calcd for C$_{28}$H$_{32}$N$_5$O$_5$S [M + H]$^+$ 550.2119, found 550.2118. Rt = 2.50 minutes<br>Using 1-(4-(3-chloroisoquinolin-6-yl)-1H-pyrazol-1-yl)-2-methylpropan-2-ol (Preparation 22) and (4-amino-3-methoxyphenyl)(1,1-dioxidothiomorpholino)methanone (Preparation 95) and purification method A. | 0.002 |
| 66 | 4-((6-(1-(2-Hydroxy-2-methylpropyl)-1H-pyrazol-4-yl)isoquinolin-3-yl)amino)-3-methoxyphenyl)(4-methylpiperazin-1-yl)methanone 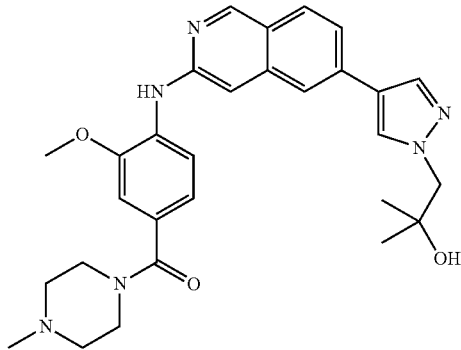 | $^1$H NMR (500 MHz, CDCl$_3$): δ 8.96 (s, 1H), 7.97 (d, J = 0.78 Hz, 1H), 7.95 (d, J = 8.12 Hz, 1H), 7.90-7.82 (m, 2H), 7.75-7.70 (m, 1H), 7.50 (dd, J = 1.64, 8.48 Hz, 1H), 7.27-7.21 (m, 2H), 7.12-7.05 (m, 2H), 4.16 (s, 2H), 3.98 (s, 3H), 3.85-3.70 (m, 4H), 2.60-2.45 (m, 4H), 2.41 (s, 3H), 1.27 (s, 6H).<br>HRMS (ESI) MS m/z calcd for C$_{29}$H$_{35}$N$_6$O$_3$ [M + H]$^+$ 515.2765, found 515.2758. Rt = 2.16 minutes<br>Using-(4-(3-chloroisoquinolin-6-yl)-1H-pyrazol-1-yl)-2-methylpropan-2-ol (Preparation 22) and (4-amino-3-methoxyphenyl)(4-methylpiperazin-1-yl)methanone (Preparation 96). | 0.002 |

| Example No | Name/Structure | Data | MPS1 IC50 (μM) |
|---|---|---|---|
| 67 | 4-((6-(1-(2-Hydroxy-2-methylpropyl)-1H-pyrazol-4-yl)isoquinolin-3-yl)amino)-3-methoxy-N-(1-methylpiperidin-4-yl)benzamide 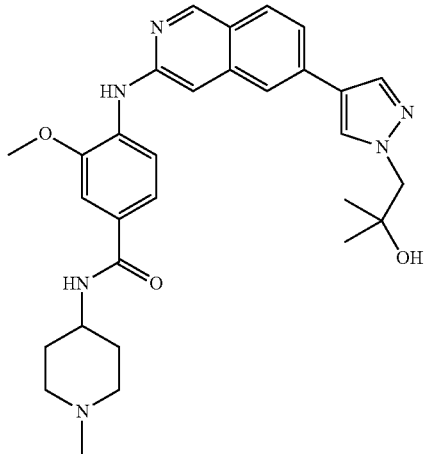 | $^1$H NMR (500 MHz, CDCl$_3$): δ 8.98 (s, 1H), 8.02-7.95 (m, 2H), 7.90-7.84 (m, 2H), 7.74 (s, 1H), 7.55-7.47 (m, 2H), 7.39-7.31 (m, 2H), 7.28 (d, J = 2.64 Hz, 1H), 4.17 (s, 2H), 4.02 (s, 3H), 3.08-2.95 (m, 1H), 2.43 (s, 3H), 2.36-2.25 (m, 2H), 2.17-1.98 (m, 4H), 1.83-1.54 (m, 2H), 1.26 (s, 6H). HRMS (ESI) MS m/z calcd for C$_{30}$H$_{37}$N$_6$O$_3$ [M + H]$^+$ 529.2922, found 529.2921. Rt = 2.35 minutes Using 1-(4-(3-chloroisoquinolin-6-yl)-1H-pyrazol-1-yl)-2-methylpropan-2-ol (Preparation 22) and 4-amino-3-methoxy-N-(1-methylpiperidin-4-yl)benzamide (Preparation 97) and purification method D. | 0.005 |
| 68 | Racemic 3-(4-(3-((4-(1,2-Dimethyl-1H-imidazol-5-yl)-2-methoxyphenyl)amino)isoquinolin-6-yl)-1H-pyrazol-1-yl)-2-methylbutan-2-ol 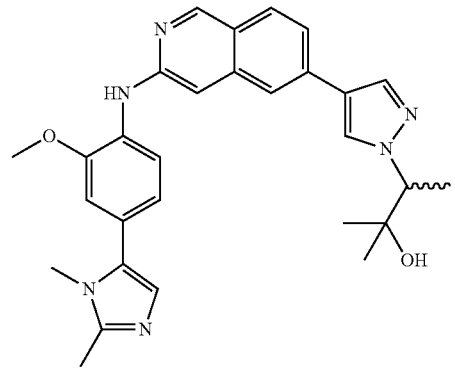 | $^1$H NMR (500 MHz, CDCl$_3$): δ 8.97 (s, 1H), 8.01-7.95 (m, 2H), 7.90-7.86 (m, 2H), 7.74 (s, 1H), 7.50 (dd, J = 1.64, 8.42 Hz, 1H), 7.27 (s, 1H), 7.23 (s, 1H), 7.05 (s, 1H), 7.00 (dd, J = 1.88, 8.18 Hz, 1H), 6.92 (d, J = 1.90 Hz, 1H), 4.25 (q, J = 6.98 Hz, 1H), 3.98 (s, 3H), 3.61 (s, 3H), 2.57 (s, 3H), 1.65 (d, J = 6.98 Hz, 3H), 1.26 (s, 6H). HRMS (ESI) MS m/z calcd for C$_{29}$H$_{33}$N$_6$O$_2$ [M + H]$^+$ 497.2660, found 497.2651. Rt = 2.45 minutes Using racemic 3-(4-(3-chloroisoquinolin-6-yl)-1H-pyrazol-1-yl)-2-methylbutan-2-ol (Preparation 32) and purification method D. | 0.006 |

| Example No | Name/Structure | Data | MPS1 IC50 (µM) |
|---|---|---|---|
| 69 | 1-(5-(4-((6-(1-(2-Hydroxy-2-methylpropyl)-1H-pyrazol-4-yl)isoquinolin-3-yl)amino)-3-methoxy-phenyl)-2-methyl-1H-imidazol-1-yl)-2-methylpropan-2-ol<br>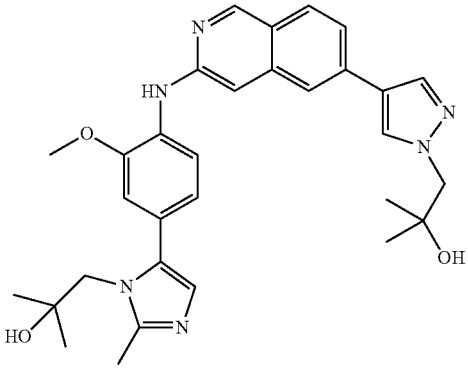 | $^1$H NMR (500 MHz, CDCl$_3$): δ 8.96 (s, 1H), 8.00-7.94 (m, 2H), 7.86 (d, J = 0.80 Hz, 1H), 7.85 (d, J = 8.58 Hz, 1H), 7.74-7.71 (m, 1H), 7.48 (dd, J = 1.62, 8.46 Hz, 1H), 7.25 (t, J = 0.88 Hz, 1H), 7.20 (s, 1H), 6.97 (dd, J = 1.84, 8.20 Hz, 1H), 6.95 (s, 1H), 6.90 (d, J = 1.80 Hz, 1H), 4.16 (s, 2H), 4.10 (s, 2H), 3.95 (s, 3H), 2.61 (s, 3H), 1.25 (s, 6H), 1.06 (s, 6H).<br>HRMS (ESI) MS m/z calcd for C$_{31}$H$_{37}$N$_6$O$_3$ [M + H]$^+$ 541.2922, found 541.3029. Rt = 2.41 minutes<br>Using 1-(4-(3-chloroisoquinolin-6-yl)-1H-pyrazol-1-yl)-2-methylpropan-2-ol (Preparation 22) and 1-(5-(4-amino-3-methoxyphenyl)-2-methyl-1H-imidazol-1-yl)-2-methyl-propan-2-ol (Preparation 87) and purification method E. | 0.002 |
| 70 | 1-(4-(3-((2-Methoxy-4-(7-methyl-5,6,7,8-tetrahydro-[1,2,4]triazolo[4,3-a]pyrazin-3-yl)-phenyl)amino)isoquinolin-6-yl)-1H-pyrazol-1-yl)-2-methylpropan-2-ol<br>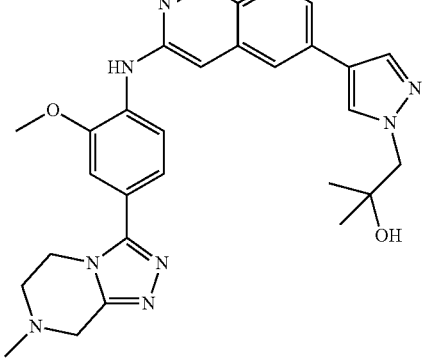 | $^1$H NMR (500 MHz, CDCl$_3$): δ 8.97 (s, 1H), 8.06 (d, J = 8.28 Hz, 1H), 7.97 (d, J = 0.76 Hz, 1H), 7.89-7.83 (m, 2H), 7.74-7.70 (m, 1H), 7.50 (dd, J = 1.62, 8.50 Hz, 1H), 7.45 (d, J = 1.84 Hz, 1H), 7.30 (s, 1H), 7.26 (s, 1H), 7.22 (dd, J = 1.84, 8.34 Hz, 1H), 4.20-4.17 (m, 2H), 4.16 (s, 2H), 4.01 (s, 3H), 3.90 (s, 2H), 2.91-2.84 (m, 2H), 2.58 (s, 3H), 1.25 (s, 6H).<br>HRMS (ESI) MS m/z calcd for C$_{29}$H$_{33}$N$_8$O$_2$ [M + H]$^+$ 525.2721, found 525.2723. Rt = 2.48 minutes<br>Using 1-(4-(3-chloroisoquinolin-6-yl)-1H-pyrazol-1-yl)-2-methylpropan-2-ol (Preparation 22) and 2-methoxy-4-(7-methyl-5,6,7,8-tetrahydro-[1,2,4]triazolo[4,3-a]pyrazin-3-yl)aniline (Preparation 88) and purification method D. | 0.002 |

| Example No | Name/Structure | Data | MPS1 IC50 (μM) |
|---|---|---|---|
| 71 | (4-((6-(1-(2-Hydroxybutyl)-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 8.96 (s, 1H), 7.98-7.93 (m, 2H), 7.87-7.82 (m, 2H), 7.73-7.69 (m, 1H), 7.49 (dd, J = 1.60, 8.50 Hz, 1H), 7.36 (d, J = 1.80 Hz, 1H), 7.34 (s, 1H), 7.26 (s, 1H), 7.23 (dd, J = 1.80, 8.28 Hz, 1H), 4.54-4.35 (m, 2H), 4.35-4.24 (m, 3H), 4.17-4.07 (m, 2H), 4.08-3.99 (m, 1H), 3.98 (s, 3H), 3.35 (s, 3H), 1.58 (qd, J = 6.20, 7.40 Hz, 2H), 1.06 (t, J = 7.40 Hz, 3H). HRMS (ESI) MS m/z calcd for $C_{28}H_{32}N_5O_4$ [M + H]$^+$ 502.2449, found 502.2499. Rt = 2.87 minutes Using racemic 1-(4-(3-chloroisoquinolin-6-yl)-1H-pyrazol-1-yl)butan-2-ol (Preparation 33) and 4-amino-3-methoxyphenyl)(3-methoxyazetidin-1-yl)methanone (Preparation 92) and purification method B. | 0.004 |
| 72 | (3-Methoxy-4-((6-(1-(2-methoxyethyl)-1H-pyrazol-4-yl)isoquinolin-3-yl)amino)phenyl)(3-methoxyazetidin-1-yl)methanone | $^1$H NMR (500 MHz, CDCl$_3$): δ 8.96 (s, 1H), 7.96 (d, J = 8.40 Hz, 1H), 7.94 (s, 1H), 7.89 (d, J = 0.80 Hz, 1H), 7.86-7.82 (m, 1H), 7.74-7.71 (m, 1H), 7.51 (dd, J = 1.60, 8.52 Hz, 1H), 7.36 (d, J = 1.82 Hz, 1H), 7.34 (s, 1H), 7.27 (s, 1H), 7.23 (dd, J = 1.82, 8.28 Hz, 1H), 4.58-4.38 (m, 2H), 4.37 (t, J = 5.12 Hz, 2H), 4.31-4.23 (m, 2H), 4.17-4.07 (m, 1H), 3.98 (s, 3H), 3.82 (t, J = 5.12 Hz, 2H), 3.39 (s, 3H), 3.35 (s, 3H). HRMS (ESI) MS m/z calcd for $C_{27}H_{30}N_5O_4$ [M + H]$^+$ 488.2292, found 488.2322. Rt = 2.89 minutes Using 3-chloro-6-(1-(2-methoxyethyl)-1H-pyrazol-4-yl)isoquinoline (Preparation 15) and (4-amino-3-methoxyphenyl)(3-methoxyazetidin-1-yl)methanone (Preparation 92) and purification method A. | 0.003 |
| 73 | Racemic (4-((6-(1-(2-Hydroxy-3-methylbutyl)-1H-pyrazol-4-yl)isoquinolin-3-yl)amino)-3-methoxy-phenyl)(3-methoxyazetidin-1-yl)methanone | $^1$H NMR (500 MHz, CDCl$_3$): δ 8.94 (s, 1H), 7.97-7.91 (m, 2H), 7.86 (d, J = 0.82 Hz, 1H), 7.83 (d, J = 8.54 Hz, 1H), 7.71-7.67 (m, 1H), 7.47 (dd, J = 1.62, 8.44 Hz, 1H), 7.36 (d, J = 1.84 Hz, 1H), 7.33 (s, 1H), 7.27-7.17 (m, 2H), 4.54-4.34 (m, 2H), 4.32 (dd, J = 2.46, 13.84 Hz, 1H), 4.30-4.25 (m, 2H), 4.14 (dd, J = 8.54, 13.84 Hz, 1H), 4.15-4.05 (m, 1H), 3.98 (s, 3H), 3.83 (ddd, J = 2.36, 5.98, 8.54 Hz, 1H), 3.35 (s, 3H), 1.87-1.73 (m, 1H), 1.07 (d, J = 5.02 Hz, 3H), 1.06 (d, J = 4.88 Hz, 3H). HRMS (ESI) MS m/z calcd for $C_{29}H_{34}N_5O_4$ [M + H]$^+$ 516.2605, found 516.2604. Rt = 2.96 minutes Using racemic 1-(4-(3-chloroisoquinolin-6-yl)-1H-pyrazol-1-yl)-3-methylbutan-2-ol (Preparation 34) and (4-amino-3-methoxyphenyl)(3-methoxyazetidin-1-yl)methanone (Preparation 92) and purification method A. | 0.004 |

| Example No | Name/Structure | Data | MPS1 IC50 (μM) |
|---|---|---|---|
| 74 | (3-Methoxy-4-((6-(1-(2-methoxy-2-methylpropyl)-1H-pyrazol-4-yl)isoquinolin-3-yl)amino)-phenyl)(3-methoxyazetidin-1-yl)methanone | $^1$H NMR (500 MHz, CDCl$_3$): δ 8.94 (s, 1H), 7.94 (d, J = 8.32 Hz, 1H), 7.89 (s, 1H), 7.88 (s, 1H), 7.84-7.81 (m, 1H), 7.73-7.70 (m, 1H), 7.50 (dd, J = 1.60, 8.52 Hz, 1H), 7.35 (d, J = 1.82 Hz, 1H), 7.33 (s, 1H), 7.25 (s, 1H), 7.22 (dd, J = 1.86, 8.34 Hz, 1H), 4.54-4.30 (m, 2H), 4.32-4.21 (m, 2H), 4.17 (s, 2H), 4.12-4.04 (m, 1H), 3.96 (s, 3H), 3.33 (s, 3H), 3.29 (s, 3H), 1.19 (s, 6H). HRMS (ESI) MS m/z calcd for C$_{29}$H$_{34}$N$_5$O$_4$ [M + H]$^+$ 516.2605, found 516.2686. Rt = 3.07 minutes Using 3-chloro-6-(1-(2-methoxy-2-methylpropyl)-1H-pyrazol-4-yl)isoquinoline (Preparation 42) and and (4-amino-3-methoxyphenyl)(3-methoxyazetidin-1-yl)methanone (Preparation 92) and purification method A. | 0.003 |
| 75 | (3-Methoxy-4-((6-(1-(3,3,3-trifluoro-2-hydroxypropyl)-1H-pyrazol-4-yl)isoquinolin-3-yl)amino)-phenyl)(3-methoxyazetidin-1-yl)methanone | $^1$H NMR (500 MHz, CDCl$_3$): δ 8.95 (s, 1H), 7.97 (d, J = 0.80 Hz, 1H), 7.93 (d, J = 8.34 Hz, 1H), 7.87 (d, J = 0.80 Hz, 1H), 7.85 (d, J = 8.50 Hz, 1H), 7.67 (s, 1H), 7.46 (dd, J = 1.60, 8.50 Hz, 1H), 7.34 (d, J = 1.80 Hz, 1H), 7.33 (s, 1H), 7.24-7.19 (m, 2H), 4.57 (dd, J = 2.50, 13.88 Hz, 1H), 4.55-4.46 (m, 2H), 4.46-4.44 (m, 1H), 4.39 (dd, J = 7.72, 13.98 Hz, 1H), 4.32-4.25 (m, 2H), 4.16-4.05 (m, 1H), 3.97 (s, 3H), 3.36 (s, 3H). HRMS (ESI) MS m/z calcd for C$_{27}$H$_{26}$F$_3$N$_5$NaO$_4$ [M + Na]$^+$ 564.1829, found 564.1822. Rt = 2.86 minutes Using racemic 3-(4-(3-chloroisoquinolin-6-yl)-1H-pyrazol-1-yl)-1,1,1-trifluoropropan-2-ol (Preparation 35) and 4-amino-3-methoxyphenyl)(3-methoxyazetidin-1-yl)methanone (Preparation 92) and purification method D. | 0.003 |
| 76 | (4-((6-(1-(3-Hydroxy-3-methylbutan-2-yl)-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 8.97 (s, 1H), 7.97 (d, J = 0.78 Hz, 1H), 7.95 (d, J = 8.34 Hz, 1H), 7.89-7.84 (m, 2H), 7.75-7.72 (m, 1H), 7.51 (dd, J = 1.60, 8.46 Hz, 1H), 7.37 (d, J = 1.82 Hz, 1H), 7.34 (s, 1H), 7.24 (dd, J = 1.82, 8.30 Hz, 1H), 4.54-4.32 (m, 2H), 4.34-4.27 (m, 2H), 4.16-4.08 (m, 1H), 3.99 (s, 3H), 3.94-3.82 (m, 1H), 3.35 (s, 3H), 1.64 (d, J = 7.00 Hz, 3H), 1.25 (s, 6H). HRMS (ESI) MS m/z calcd for C$_{29}$H$_{34}$N$_5$O$_4$ [M + H]$^+$ 516.2605, found 516.2620. Rt = 2.96 minutes Using racemic 3-(4-(3-chloroisoquinolin-6-yl)-1H-pyrazol-1-yl)-2-methylbutan-2-ol (Preparation 32) and 4-amino-3-methoxyphenyl)(3-methoxyazetidin-1-yl)methanone (Preparation 92) and purification method D. | 0.005 |

| Example No | Name/Structure | Data | MPS1 IC50 (μM) |
|---|---|---|---|
| 77 | 1-(4-(3-((2-Chloro-4-(5-methyl-1,3,4-oxadiazol-2-yl)phenyl)amino)isoquinolin-6-yl)-1H-pyrazol-1-yl)-2-methylpropan-2-ol | $^1$H NMR (500 MHz, MeOD): δ 9.01 (s, 1H), 8.22 (d, J = 0.78 Hz, 1H), 8.10 (d, J = 8.78 Hz, 1H), 8.08 (d, J = 2.04 Hz, 1H), 8.06 (d, J = 0.80 Hz, 1H), 8.00 (d, J = 8.64 Hz, 1H), 7.98 (s, 1H), 7.90 (dd, J = 2.04, 8.72 Hz, 1H), 7.74 (dd, J = 1.63, 8.56 Hz, 1H), 7.48 (s, 1H), 4.19 (s, 2H), 2.64 (s, 3H), 1.25 (s, 6H). HRMS (ESI) MS m/z calcd for $C_{25}H_{24}ClN_6O_2$ [M + H]$^+$ 475.1644, found 475.1639. Rt = 3.06 minutes Using 1-(4-(3-chloroisoquinolin-6-yl)-1H-pyrazol-1-yl)-2-methylpropan-2-ol (Preparation 22) and 2-chloro-4-(5-methyl-1,3,4-oxadiazol-2-yl)aniline (Preparation 72) and purification method G. | 0.023 |
| 78 | Racemic (4-((6-(1-(2-Hydroxy-3-methoxypropyl)-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 8.94 (s, 1H), 7.97-7.91 (m, 2H), 7.87 (d, J = 0.86 Hz, 1H), 7.82 (d, J = 8.46 Hz, 1H), 7.70-7.67 (m, 1H), 7.47 (dd, J = 1.60, 8.46 Hz, 1H), 7.35 (d, J = 1.80 Hz, 1H), 7.34 (s, 1H), 7.25-7.19 (m, 2H), 4.54-4.36 (m, 2H), 4.39-4.33 (m, 1H), 4.31-4.20 (m, 4H), 4.15-4.05 (m, 1H), 3.97 (s, 3H), 3.45-3.38 (m, 2H), 3.42 (s, 3H), 3.34 (s, 3H). HRMS (ESI) MS m/z calcd for $C_{28}H_{32}N_5O_5$ [M + H]$^+$ 518.2398, found 518.2392. Rt = 2.76 minutes Using racemic 1-(4-(3-chloroisoquinolin-6-yl)-1H-pyrazol-1-yl)-3-methoxypropan-2-ol (Preparation 36) and 4-amino-3-methoxyphenyl)(3-methoxyazetidin-1-yl)methanone (Preparation 92) and purification method A. | 0.017 |
| 79 | Racemic (4-((6-(1-(2,3-Dimethoxypropyl)-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 8.97 (s, 1H), 7.97 (d, J = 8.40 Hz, 1H), 7.95 (d, J = 0.80 Hz, 1H), 7.87 (d, J = 0.80 Hz, 1H), 7.86 (dd, J = 0.80, 8.58 Hz, 1H), 7.74 (d, J = 1.38 Hz, 1H), 7.52 (dd, J = 1.62, 8.48 Hz, 1H), 7.37 (d, J = 1.86 Hz, 1H), 7.35 (s, 1H), 7.28 (d, J = 0.94 Hz, 1H), 7.24 (dd, J = 1.84, 8.30 Hz, 1H), 4.56-4.40 (m, 2H), 4.40 (dd, J = 4.54, 14.16 Hz, 1H), 4.32 (d, J = 7.16 Hz, 1H), 4.30-4.25 (m, 2H), 4.16-4.08 (m, 1H), 3.99 (s, 3H), 3.80 (dq, J = 4.36, 7.16 Hz, 1H), 3.55 (dd, J = 4.34, 10.32 Hz, 1H), 3.43 (s, 3H), 3.44-3.38 (m, 1H) 3.40 (s, 3H), 3.35 (s, 3H). HRMS (ESI) MS m/z calcd for $C_{29}H_{34}N_5O_5$ [M + H]$^+$ 532.2554, found 532.2559. Rt = 2.94 minutes Using racemic 3-chloro-6-(1-(2,3-dimethoxypropyl)-1H-pyrazol-4-yl)isoquinoline (Preparation 43) and 4-amino-3-methoxyphenyl)(3-methoxyazetidin-1-yl)methanone (Preparation 92) and purification method A. | 0.009 |

-continued

| Example No | Name/Structure | Data | MPS1 IC50 (μM) |
|---|---|---|---|
| 80 | 4-((6-(1-(2-Hydroxy-2-methylpropyl)-1H-pyrazol-4-yl)isoquinolin-3-yl)amino)-3-methoxy-N,N-dimethylbenzenesulfonamide | $^1$H NMR (500 MHz, CDCl$_3$): δ 9.00 (s, 1H), 8.18 (d, J = 8.46 Hz, 1H), 7.99 (d, J = 0.80 Hz, 1H), 7.89 (d, J = 8.46 Hz, 1H), 7.87 (s, 1H), 7.76 (d, J = 1.75 Hz, 1H), 7.55 (dd, J = 1.60, 8.52 Hz, 1H), 7.45 (dd, J = 1.94, 8.46 Hz, 1H), 7.43 (s, 1H), 7.29-7.28 (m, 2H), 4.17 (s, 2H), 4.02 (s, 3H), 2.75 (s, 6H), 1.26 (s, 6H). HRMS (ESI) MS m/z calcd for C$_{25}$H$_{30}$N$_5$O$_4$S [M + H]$^+$ 496.2013, found 496.2015. Rt = 2.90 minutes Using:(4-(3-chloroisoquinolin-6-yl)-1H-pyrazol-1-yl)-2-methylpropan-2-ol (Preparation 22) and 4-amino-3-methoxy-N,N-dimethylbenzenesulfonamide (Preparation 104) and purification method G. | 0.003 |
| 81 | Racemic (4-((6-(1-(2,3-Dihydroxypropyl)-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 8.97 (s, 1H), 7.98-7.92 (m, 2H), 7.87 (s, 1H), 7.86 (d, J = 8.54 Hz, 1H), 7.73-7.69 (m, 1H), 7.49 (dd, J = 1.64, 8.48 Hz, 1H), 7.36 (d, J = 1.86 Hz, 1H), 7.35 (s, 1H), 7.26 (s, 1H), 7.24 (dd, J = 1.86, 8.34 Hz, 1H), 4.56-4.44 (m, 2H), 4.36 (d, J = 5.16 Hz, 2H), 4.32-4.26 (m, 2H), 4.22-4.17 (m, 1H), 4.16-4.06 (m, 1H), 3.99 (s, 3H), 3.75-3.65 (m, 2H), 3.36 (s, 3H). HRMS (ESI) MS m/z calcd for C$_{27}$H$_{30}$N$_5$O$_5$ [M + H]$^+$ 504.2241, found 504.2241. Rt = 2.49 minutes Using racemic 3-(4-(3-chloroisoquinolin-6-yl)-1H-pyrazol-1-yl)propane-1,2-diol (Preparation 39) and 4-amino-3-methoxyphenyl)(3-methoxyazetidin-1-yl)methanone (Preparation 92) and purification method D. | 0.003 |
| 82 | Racemic (4-((6-(1-(4-Hydroxytetrahydrofuran-3-yl)-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 8.92 (s, 1H), 7.95-7.90 (m, 2H), 7.86 (d, J = 0.76 Hz, 1H), 7.84-7.79 (m, 1H), 7.66-7.63 (m, 1H), 7.45 (dd, J = 1.60, 8.48 Hz, 1H), 7.33 (d, J = 1.84 Hz, 1H), 7.32 (s, 1H), 7.22 (dd, J = 1.84, 8.36 Hz, 1H), 7.19 (s, 1H), 4.84 (ddd, J = 2.16, 3.42, 5.86 Hz, 1H), 4.69 (ddd, J = 2.16, 3.15, 5.36 Hz, 1H), 4.56-4.40 (m, 2H), 4.40 (dd, J = 6.18, 10.02 Hz, 1H), 4.33-4.24 (m, 4H), 4.18-4.06 (m, 1H), 3.97 (s, 3H), 3.89 (dd, J = 3.15, 10.02 Hz, 1H), 3.35 (s, 3H). HRMS (ESI) MS m/z calcd for C$_{28}$H$_{30}$N$_5$O$_5$ [M + H]$^+$ 516.2241, found 516.2316. Rt = 2.71 minutes Using racemic 4-(4-(3-chloroisoquinolin-6-yl)-1H-pyrazol-1-yl)tetrahydrofuran-3-ol (Preparation 44) and 4-amino-3-methoxyphenyl)(3-methoxyazetidin-1-yl)methanone (Preparation 92) and purification method D. | 0.005 |

| Example No | Name/Structure | Data | MPS1 IC50 (µM) |
|---|---|---|---|
| 83 | Racemic (4-((6-(1-(2-Hydroxycyclopentyl)-1H-pyrazol-4-yl)isoquinolin-3-yl)amino)-3-methoxyphenyl)(3-methoxyazetidin-1-yl)methanone 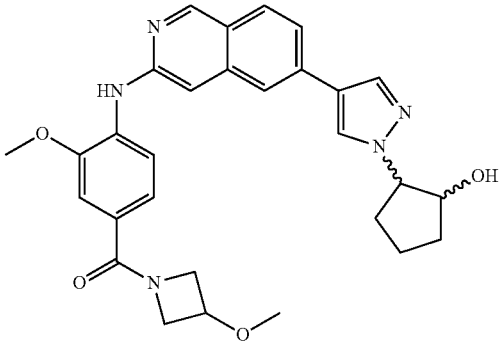 | $^1$H NMR (500 MHz, CDCl$_3$): δ 8.95 (s, 1H), 7.97-7.91 (m, 2H), 7.87-7.80 (m, 2H), 7.73-7.68 (m, 1H), 7.49 (dd, J = 1.64, 8.48 Hz, 1H), 7.36 (d, J = 1.84 Hz, 1H), 7.34 (s, 1H), 7.26 (s, 1H), 7.23 (dd, J = 1.80, 8.30 Hz, 1H), 4.56-4.35 (m, 4H), 4.32-4.24 (m, 2H), 4.16-4.06 (m, 1H), 3.99 (s, 3H), 3.36 (s, 3H), 2.47-2.34 (m, 1H), 2.29-2.10 (m, 2H), 2.03-1.91 (m, 2H), 1.85-1.75 (m, 1H). HRMS (ESI) MS m/z calcd for C$_{29}$H$_{32}$N$_5$O$_4$ M + H]$^+$ 514.2449, found 514.2545. Rt = 2.87 minutes Using racemic 2-(4-(3-chloroisoquinolin-6-yl)-1H-pyrazol-1-yl)cyclopentanol (Preparation 45) and 4-amino-3-methoxyphenyl)(3-methoxyazetidin-1-yl)methanone (Preparation 92) and purification method D. | 0.003 |
| 84 | 5-(4-((6-(1-(2-Hydroxy-2-methylpropyl)-1H-pyrazol-4-yl)isoquinolin-3-yl)amino)-3-methoxyphenyl)-1-methyl-1H-imidazole-2-carbonitrile 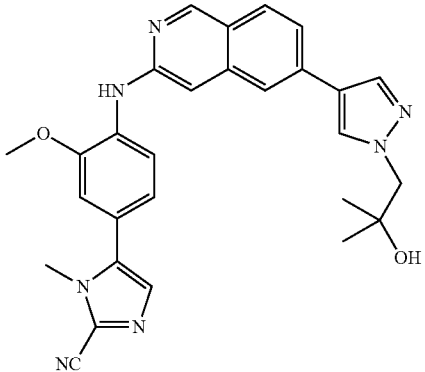 | $^1$H NMR (500 MHz, CDCl$_3$): δ 8.99 (s, 1H), 8.09 (d, J = 8.24 Hz, 1H), 7.99 (d, J = 0.78 Hz, 1H), 7.88 (d, J = 8.50 Hz, 1H), 7.86 (d, J = 0.78 Hz, 1H), 7.75 (d, J = 1.66 Hz, 1H), 7.52 (dd, J = 1.66, 8.48 Hz, 1H), 7.28 (d, J = 2.24 Hz, 2H), 7.03 (dd, J = 1.92, 8.20 Hz, 1H), 6.92 (d, J = 1.92 Hz, 1H), 4.17 (s, 2H), 4.00 (s, 3H), 3.88 (s, 3H), 1.26 (s, 6H). HRMS (ESI) MS m/z calcd for C$_{28}$H$_{28}$N$_7$O$_2$ [M + H]$^+$ 494.2299, found 494.2304. Rt = 2.83 minutes Using 1-(4-(3-chloroisoquinolin-6-yl)-1H-pyrazol-1-yl)-2-methylpropan-2-ol (Preparation 22) and 5-(4-amino-3-methoxyphenyl)-1-methyl-1H-imidazole-2-carbonitrile (Preparation 90) and purification method D. | 0.005 |
| 85 | Racemic (4-((6-(1-(2-Hydroxycyclohexyl)-1H-pyrazol-4-yl)isoquinolin-3-yl)amino)-3-methoxyphenyl)(3-methoxyazetidin-1-yl)methanone 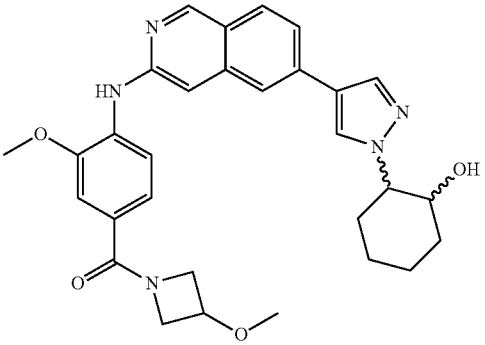 | $^1$H NMR (500 MHz, CDCl$_3$): δ 8.96 (s, 1H), 7.97 (s, 1H), 7.95 (d, J = 8.34 Hz, 1H), 7.89 (s, 1H), 7.85 (d, J = 8.52 Hz, 1H), 7.71 (d, J = 1.60 Hz, 1H), 7.49 (dd, J = 1.60, 8.50 Hz, 1H), 7.36 (d, J = 1.84 Hz, 1H), 7.35 (s, 1H), 7.26 (s, 1H), 7.24 (dd, J = 1.84, 8.34 Hz, 1H), 4.52-4.36 (m, 2H), 4.32-4.26 (m, 2H), 4.15-4.06 (m, 1H), 4.02-3.94 (m, 2H), 3.99 (s, 3H), 3.35 (s, 3H), 2.31-2.17 (m, 2H), 1.98-1.82 (m, 3H), 1.56-1.40 (m, 3H). HRMS (ESI) MS m/z calcd for C$_{30}$H$_{34}$N$_5$O$_4$ [M + H]$^+$ 528.2605, found 528.2667. Rt = 2.88 minutes Using racemic 2-(4-(3-chloroisoquinolin-6-yl)-1H-pyrazol-1-yl)cyclohexanol (Preparation 46) and 4-amino-3-methoxyphenyl)(3-methoxyazetidin-1-yl)methanone (Preparation 92) and purification method D. | 0.015 |

-continued

| Example No | Name/Structure | Data | MPS1 IC50 (μM) |
|---|---|---|---|
| 86 | (4-((6-(1-(2-Hydroxy-2-methylpropyl)-1H-pyrazol-4-yl)isoquinolin-3-yl)amino)-3-methoxy-phenyl)(3-(methoxymethyl)azetidin-1-yl)methanone | $^1$H NMR (500 MHz, CDCl$_3$): δ 8.94 (s, 1H), 7.96 (d, J = 0.78 Hz, 1H), 7.92 (d, J = 8.34 Hz, 1H), 7.85 (s, 1H), 7.83 (d, J = 8.52 Hz, 1H), 7.72-7.67 (m, 1H), 7.48 (dd, J = 1.62, 8.50 Hz, 1H), 7.37 (d, J = 1.82 Hz, 1H), 7.33 (s, 1H), 7.28-7.22 (m, 2H), 4.45-4.44 (m, 1H), 4.35-4.25 (m, 1H), 4.20-4.10 (m, 1H), 4.15 (s, 2H), 3.96-3.90 (m, 1H), 3.97 (s, 3H), 3.58 (dd, J = 2.08, 6.64 Hz, 2H), 3.40 (s, 3H), 2.99-2.87 (m, 1H), 1.25 (s, 6H). HRMS (ESI) MS m/z calcd for C$_{29}$H$_{33}$N$_5$NaO$_4$ [M + Na]$^+$ 538.2425, found 538.2393. Rt = 2.78 minutes Using 1-(4-(3-chloroisoquinolin-6-yl)-1H-pyrazol-1-yl)-2-methylpropan-2-ol (Preparation 22) and (4-amino-3-methoxyphenyl)(3-(methoxymethyl)azetidin-1-yl)methanone (Preparation 98) and purification method E. | 0.007 |
| 87 | (4-((6-(1-((1-Hydroxycyclobutyl)methyl)-1H-pyrazol-4-yl)isoquinolin-3-yl)amino)-3-methoxy-phenyl)(3-methoxyazetidin-1-yl)methanone | $^1$H NMR (500 MHz, CDCl$_3$): δ 8.98 (s, 1H), 7.98-7.94 (m, 2H), 7.90 (d, J = 0.76 Hz, 1H), 7.87 (d, J = 8.42 Hz, 1H), 7.75-7.72 (m, 1H), 7.51 (dd, J = 1.62, 8.48 Hz, 1H), 7.37 (d, J = 1.84 Hz, 1H), 7.35 (s, 1H), 7.28 (d, J = 0.96 Hz, 1H), 7.24 (dd, J = 1.84, 8.34 Hz, 1H), 4.56-4.36 (m, 2H), 4.32 (s, 2H), 4.31-4.26 (m, 2H), 4.16-4.06 (m, 1H), 3.99 (s, 3H), 3.36 (s, 3H), 2.21-2.06 (m, 4H), 1.94-1.84 (m, 1H), 1.71-1.60 (m, 1H). HRMS (ESI) MS m/z calcd for C$_{29}$H$_{32}$N$_5$O$_4$ [M + H]$^+$ 514.2449, found 514.2463. Rt = 2.87 minutes Using-((4-(3-chloroisoquinolin-6-yl)-1H-pyrazol-1-yl)methyl)cyclobutanol (Preparation 30) and 4-amino-3-methoxyphenyl)(3-methoxyazetidin-1-yl)methanone (Preparation 92) and purification method D. | 0.008 |
| 88 | 1-((4-(3-((2-Ethoxy-4-(4-methyl-4H-1,2,4-triazol-3-yl)phenyl)amino)isoquinolin-6-yl)-1H-pyrazol-1-yl)methyl)cyclobutanol | $^1$H NMR (500 MHz, CDCl$_3$): δ 8.99 (s, 1H), 8.21 (s, 1H), 8.06 (d, J = 8.28 Hz, 1H), 7.96 (d, J = 0.78 Hz, 1H), 7.91 (s, 1H), 7.88 (d, J = 8.48 Hz, 1H), 7.75 (d, J = 1.22 Hz, 1 H), 7.51 (dd, J = 1.62, 8.50 Hz, 1H), 7.39 (d, J = 1.84 Hz, 1H), 7.34 (s, 1H), 7.31 (s, 1H), 7.21 (dd, J = 1.86, 8.24 Hz, 1H), 4.32 (s, 2H), 4.24 (q, J = 6.98 Hz, 2H), 3.84 (s, 3H), 2.21-2.06 (m, 4H), 1.92-1.82 (m, 1H), 1.71-1.63 (m, 1H), 1.54 (t, J = 6.98 Hz, 3H). HRMS (ESI) MS m/z calcd for C$_{28}$H$_{30}$N$_7$O$_2$ [M + H]$^+$ 496.2455, found 496.2444. Rt = 2.74 minutes Using 1-((4-(3-chloroisoquinolin-6-yl)-1H-pyrazol-1-yl)methyl)cyclobutanol (Preparation 30) and 2-ethoxy-4-(4-methyl-4H-1,2,4-triazol-3-yl)aniline (Preparation 109) and purification method D. | 0.007 |

| Example No | Name/Structure | Data | MPS1 IC50 (μM) |
|---|---|---|---|
| 89 | 3-((4-(1,2-Dimethyl-1H-imidazol-5-yl)-2-methoxyphenyl)amino)-N,N-dimethylisoquinoline-6-carboxamideone 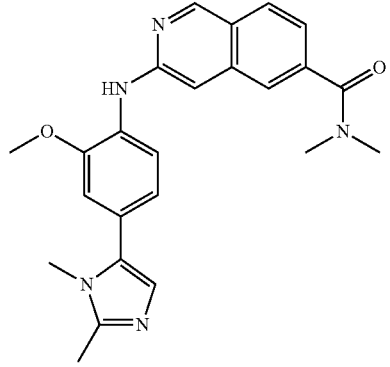 | $^1$H NMR (500 MHz, CDCl$_3$): δ 9.04 (s, 1H), 7.96 (d, J = 8.16 Hz, 1H), 7.90 (d, J = 8.34 Hz, 1H), 7.68 (d, J = 1.38 Hz, 1H), 7.34 (dd, J = 1.50, 8.36 Hz, 1H), 7.28 (s, 1H), 7.21 (s, 1H), 7.02-6.97 (m, 2H), 6.93 (d, J = 1.86 Hz, 1H), 3.97 (s, 3H), 3.59 (s, 3H), 3.18 (s, 3H), 3.04 (s, 3H), 2.51 (s, 3H). HRMS (ESI) MS m/z calcd for C$_{24}$H$_{26}$N$_5$O$_2$ [M + H]$^+$ 416.2081, found 416.2067. Rt = 2.01 minutes Using 3-chloro-N,N-dimethylisoquinoline-6-carboxamide (Preparation 53) and purification method D. | 0.472 |
| 90 | 3-((4-(1,2-Dimethyl-1H-imidazol-5-yl)-2-methoxyphenyl)amino)-N-methylisoquinoline-6-carboxamide 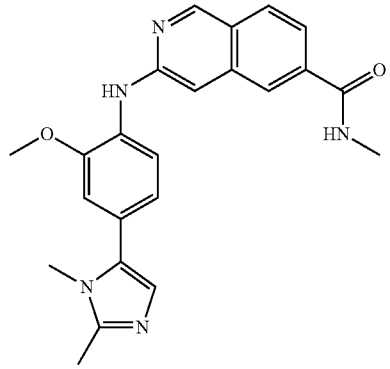 | $^1$H NMR (500 MHz, CDCl$_3$): δ 9.05 (s, 1H), 8.07 (d, J = 1.78 Hz, 1H), 7.94 (d, J = 8.18 Hz, 1H), 7.91 (d, J = 8.50 Hz, 1H), 7.64 (dd, J = 1.60, 8.50 Hz, 1H), 7.32 (s, 1H), 7.22 (s, 1H), 7.02-6.95 (m, 2H), 6.92 (d, J = 1.84 Hz, 1H), 6.44 (s, broad, 1H), 3.96 (s, 3H), 3.58 (s, 3H), 3.09 (d, J = 4.80 Hz, 3H), 2.50 (s, 3H). HRMS (ESI) MS m/z calcd for C$_{23}$H$_{24}$N$_5$O$_2$ [M + H]$^+$ 402.1925, found 402.1908. Rt = 1.97 minutes Using 3-chloro-N-methylisoquinoline-6-carboxamide (Preparation 52) and purification method D. | 0.005 |
| 91 | (3-(Difluoromethoxy)-4-(6-(1-(2-hydroxy-2-methylpropyl)-1H-pyrazol-4-yl)isoquinolin-3-ylamino)phenyl)(3-methoxyazetidin-1-yl)methanone 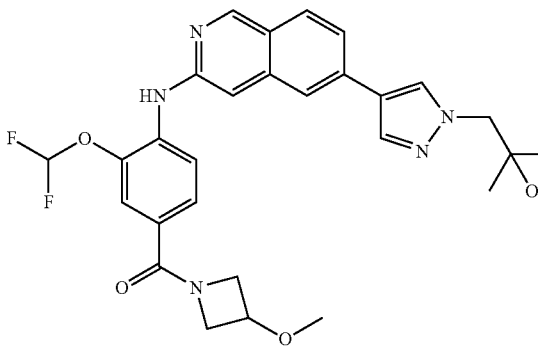 | $^1$H NMR (500 MHz, DMSO-d$_6$): δ 8.99 (s, 1H), 8.68 (s, 1H), 8.29 (s, 1H), 8.15 (d, J = 9.1 Hz, 1H), 8.08 (s, 1H), 7.95 (d, J = 8.8 Hz, 1H), 7.92 (s, 1H), 7.65 (dd, J = 8.6, 1.6 Hz, 1H), 7.5-7.48 (m, 2 H), 7.37 (s, 1H), 7.25 (t, J = 70 Hz, 1H), 4.77 (s, 1H), 4.52-4.5 (m, 1H), 4.26-4.25 (m, 3H), 4.07 (s, 2H), 3.83-3.8 (m, 1H), 3.23 (s, 3H), 1.11 (s, 6H). HRMS (ESI) MS m/z calcd for C$_{28}$H$_{30}$F$_2$N$_5$O$_4$ [M + H]$^+$ 538.226, found 538.2264 Using 1-(4-(3-chloroisoquinolin-6-yl)-1H-pyrazol-1-yl)-2-methylpropan-2-ol (Preparation 22) and (4-amino-3-(difluoromethoxy)phenyl)(3-methoxyazetidin-1-yl)methanone (Preparation 108) and purification method I. | 0.002 |

| Example No | Name/Structure | Data | MPS1 IC50 (μM) |
|---|---|---|---|
| 92 | (3-Ethoxy-4-(6-(1-(2-hydroxy-2-methylpropyl)-1H-pyrazol-4-yl)isoquinolin-3-ylamino)phenyl)(3-methoxyazetidin-1-yl)methanone 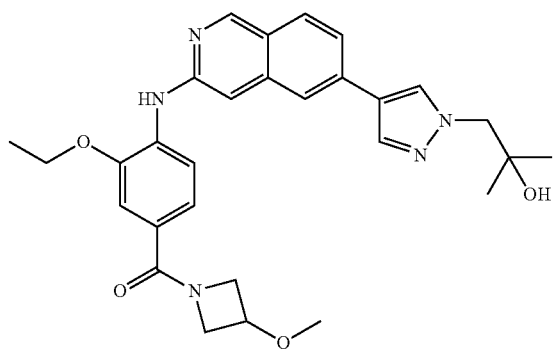 | $^1$H NMR (500 MHz, DMSO-$d_6$): δ 8.98 (s, 1H), 8.28 (s, 1H), 8.11 (s, 1H), 8.06 (s, 1H), 8.05 (d, J = 8.9 Hz, 1H), 7.93 (d, J = 8.8 Hz, 1H), 7.91 (s, 1H), 7.62 (dd, J = 8.6, 1.7 Hz, 1H), 7.36 (s, 1H), 7.24-7.23 (m, 2 H), 4.77 (s, 1H), 4.5 (br s, 1H), 4.25-4.22 (m, 2H), 4.16 (q, J = 7 Hz, 2H), 4.07 (s, 2H), 3.85 (br s, 1H), 3.23 (s, 3H), 1.42 (t, J = 7 Hz, 3H), 1.11 (s, 6H). HRMS (ESI) MS m/z calcd for $C_{29}H_{34}N_5O_4$ [M + H]$^+$ 516.2605, found 516.261 Using 1-(4-(3-chloroisoquinolin-6-yl)-1H-pyrazol-1-yl)-2-methylpropan-2-ol (Preparation 22) and (4-amino-3-ethoxyphenyl)(3-methoxyazetidin-1-yl)methanone (Preparation 107) and purification method I. | 0.002 |
| 93 | (3,3-Difluoroazetidin-1-yl)(4-(6-(1-(2-hydroxy-2-methylpropyl)-1H-pyrazol-4-yl)isoquinolin-3-ylamino)-3-methoxyphenyl)methanone 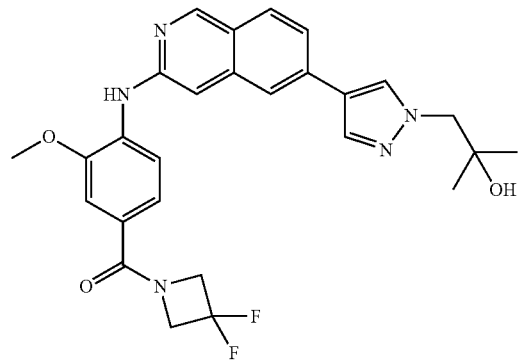 | $^1$H NMR (500 MHz, DMSO-$d_6$): δ 8.99 (s, 1H), 8.38 (s, 1H), 8.29 (s, 1H), 8.18 (d, J = 8.9 Hz, 1H), 8.07 (s, 1H), 7.94 (d, J = 8.7 Hz, 1H), 7.89 (s, 1H), 7.63 (dd, J = 8.6, 1.7 Hz, 1H), 7.39 (s, 1H), 7.31-7.29 (m, 2 H), 4.77 (s, 1H), 4.68-4.65 (m, 4H), 4.07 (s, 2H), 3.95 (s, 3H), 1.11 (s, 6H). HRMS (ESI) MS m/z calcd for $C_{27}H_{28}F_2N_5O_3$ [M + H]$^+$ 508.2155, found 508.2168 Using 1-(4-(3-chloroisoquinolin-6-yl)-1H-pyrazol-1-yl)-2-methylpropan-2-ol (Preparation 22) and (4-amino-3-methoxyphenyl)(3,3-difluoroazetidin-1-yl)methanone (Preparation 99) and purification method J. | 0.005 |
| 94 | 1-(4-(6-(1-(2-Hydroxy-2-methylpropyl)-1H-pyrazol-4-yl)isoquinolin-3-ylamino)-3-methoxybenzoyl)piperidine-4-carbonitrile 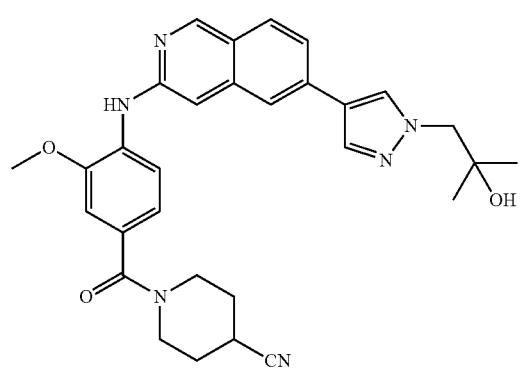 | $^1$H NMR (500 MHz, DMSO-$d_6$): δ 8.95(s, 1H), 8.28 (s, 1H), 8.18 (s, 1H), 8.06 (s, 1H), 8.03 (d, J = 8.2 Hz, 1H), 7.91 (d, J = 8.7 Hz, 1H), 7.87 (s, 1H), 7.6 (dd, J = 8.6, 1.6 Hz, 1H), 7.28 (s, 1H), 7.07 (d, J = 1.8 Hz, 1H), 6.99 (dd, J = 8.2, 1.8 Hz, 1H), 4.77 (s, 1H), 4.06 (s, 2H), 3.9 (s, 3H), 3.75 (br s, 1H), 3.38-3.36 (m, 2H), 3.16-3.15 (m, 1H), 1.92-1.9 (m, 2H), 1.76-1.75 (m, 2H), 1.11 (s, 6H). HRMS (ESI) MS m/z calcd for $C_{30}H_{33}N_6O_3$ [M + H]$^+$ 525.2609, found 525.2618 Using 1-(4-(3-chloroisoquinolin-6-yl)-1H-pyrazol-1-yl)-2-methylpropan-2-ol (Preparation 22) and 1-(4-amino-3-methoxybenzoyl)piperidine-4-carbonitrile (Preparation 101) and purification method I. | 0.002 |

| Example No | Name/Structure | Data | MPS1 IC50 (μM) |
|---|---|---|---|
| 95 | (4-(6-(1-(2-Hydroxy-2-methylpropyl)-1H-pyrazol-4-yl)isoquinolin-3-ylamino)-3-methoxyphenyl)(6-oxa-2-azaspiro[3.4]octan-2-yl)methanone | $^1$H NMR (500 MHz, DMSO-d$_6$): δ 8.98(s, 1H), 8.28 (d, J = 5 Hz, 1H), 8.11 (d, J = 8.4 Hz, 1H), 8.07 (s, 1H), 7.93 (d, J = 8.7 Hz, 1H), 7.88 (s, 1H), 7.62 (dd, J = 8.6, 1.6 Hz, 1H), 7.34 (s, 1H), 7.27 (d, J = 1.8 Hz, 1H), 7.24 (dd, J = 8.4, 1.8 Hz, 1H), 4.77 (s, 1H), 4.37 (br s, 2H), 4.07 (s, 2H), 4.02 (br s, 2H), 3.93 (s, 3H), 3.8 (br s, 2H), 3.71 (br s, 2H), 2.15 (t, J = 6.8 Hz, 2H), 1.11 (s, 6H).<br>HRMS (ESI) MS m/z calcd for C$_{30}$H$_{34}$N$_5$O$_4$ [M + H]$^+$ 528.2605, found 528.2614<br>Using 1-(4-(3-chloroisoquinolin-6-yl)-1H-pyrazol-1-yl)-2-methylpropan-2-ol (Preparation 22) and (4-amino-3-methoxyphenyl)(6-oxa-2-azaspiro[3.4]octan-2-yl)methanone (Preparation 100) and purification method I. | 0.001 |
| 96 | (4-(6-(1-(2-Hydroxy-2-methylpropyl)-1H-1,2,3-triazol-4-yl)isoquinolin-3-ylamino)-3-methoxyphenyl)(3-methoxyazetidin-1-yl)methanone | $^1$H NMR (500 MHz, CD$_3$OD): δ 8.96 (s, 1H), 8.44 (s, 1H), 8.15 (s, 1H), 8 (d, J = 8.4 Hz, 1H), 7.96 (d, J = 8.6 Hz, 1H), 7.82 (dd, J = 8.6, 1.5 Hz, 1H), 7.38 (s, 1H), 7.31 (d, J = 1.9 Hz, 1H), 7.25 (dd, J = 8.3, 1.9 Hz, 1H), 4.6 (br s, 1H), 4.44 (s, 2H), 4.31 (br s, 1H), 4.31-4.29 (m, 2H), 4.1-4 (m, 1H), 3.99 (s, 3H), 3.33 (s, 3H), 1.26 (s, 6H).<br>HRMS (ESI) MS m/z calcd for C$_{27}$H$_{31}$N$_6$O$_4$ [M + H]$^+$, 503.2401 found 503.2402<br>Using 1-(4-(3-chloroisoquinolin-6-yl)-1H-1,2,3-triazol-1-yl)-2-methylpropan-2-ol (Preparation 47) and (4-amino-3-methoxyphenyl)(3-methoxyazetidin-1-yl)methanone (Preparation 92) and purification method A. | 0.002 |
| 97 | (4-(6-(2-(2-Hydroxy-2-methylpropyl)-2H-1,2,3-triazol-4-yl)isoquinolin-3-ylamino)-3-methoxyphenyl)(3-methoxyazetidin-1-yl)methanone | $^1$H NMR (500 MHz, CD$_3$OD): δ 8.99 (s, 1H), 8.21 (s, 1H), 8.18 (s, 1H), 8.02 (d, J = 8.4 Hz, 1H), 7.98 (d, J = 8.6 Hz, 1H), 7.88 (dd, J = 8.6, 1.6 Hz, 1H), 7.42 (s, 1H), 7.33 (d, J = 1.9 Hz, 1H), 7.27 (dd, J = 8.4, 1.9 Hz, 1H), 4.6 (br s, 1H), 4.49 (s, 2H), 4.32-4.3 (m, 3H), 4.31-4.29 (m, 2H), 4.1-3.99 (m, 1H), 4 (s, 3H), 3.34 (s, 3H), 1.29 (s, 6H).<br>HRMS (ESI) MS m/z calcd for C$_{27}$H$_{31}$N$_6$O$_4$ [M + H]$^+$, 503.2401 found 503.2446<br>Using 1-(4-(3-chloroisoquinolin-6-yl)-2H-1,2,3-triazol-2-yl)-2-methylpropan-2-ol (Preparation 48) and (4-amino-3-methoxyphenyl)(3-methoxyazetidin-1-yl)methanone (Preparation 92) and purification method A. | 0.009 |

Examples 98 and 99: (R) and (S) enantiomers of 1-(4-(3-((4-(1,2-dimethyl-1H-imidazol-5-yl)-2-methoxyphenyl)amino)isoquinolin-6-yl)-1H-pyrazol-1-yl)propan-2-ol

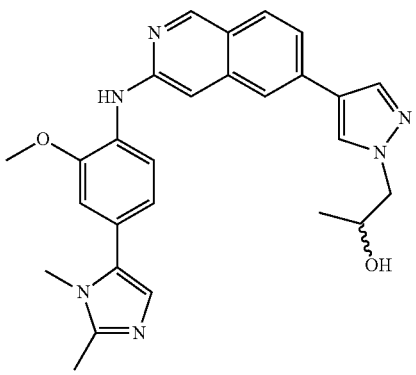 [SMILES: COc1cc(-c2cnc(C)n2C)ccc1Nc1cc2cc(-c3cnn(CC(C)O)c3)ccc2cn1]

The (R) and (S) enantiomers of 1-(4-(3-((4-(1,2-dimethyl-1H-imidazol-5-yl)-2-methoxyphenyl)amino)isoquinolin-6-yl)-1H-pyrazol-1-yl)propan-2-ol (Example 38) were separated using a Chiralpak IA column (20 uM, 250×10 mm), using a Gilson GX-281 liquid handler system combined with a Gilson 322 HPLC pump over a 40 minute isocratic elution at 80% MeCN/20% propan-2-ol (both modified with 0.1% diethylamine) at a flow rate of 5 mL/min.

Example 98

Rt=10.6 minutes ee>99% MPS1 IC50 (µM): 0.003

Example 99

Rt=16.1 minutes ee>99% MPS1 IC50 (µM): 0.005

Example 100

N-(2-Methoxy-4-(1-methyl-1H-pyrazol-4-yl)phenyl)-2-(1-methyl-1H-pyrazol-4-yl)-1,6-naphthyridin-7-amine

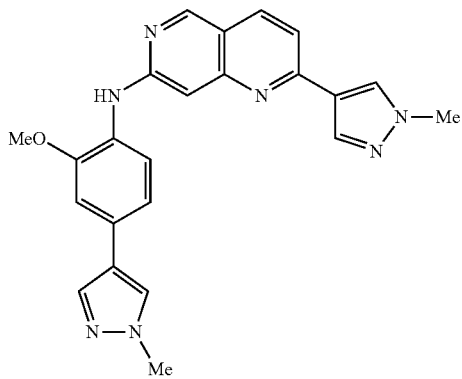 [SMILES: COc1cc(-c2cnn(C)c2)ccc1Nc1cc2nc(-c3cnn(C)c3)ccc2cn1]

Method B

To 7-Bromo-2-(1-methyl-1H-pyrazol-4-yl)-1,6-naphthyridine (Preparation 58, 25 mg 0.086 mmol) and 2-methoxy-4-(1-methyl-1H-pyrazol-4-yl)aniline (Preparation 91, 18.4 mg 0.091 mmol) was added cesium carbonate (56 mg 0.17 mmol) and Xantphos (5.0 mg 0.0086 mmol). DMA (0.95 mL) was added and the mixture degassed with nitrogen. Palladium$_2$(dba)$_3$ complex (3.94 mg 0.0044 mmol) was added and the reaction heated to 80° C. for 5 hours. The reaction was cooled and diluted with ethyl acetate (15 mL). The solution was washed with water (3×5 mL), brine, dried over sodium sulphate and concentrated in vacuo. The residue was purified by preparative TLC eluting with 10% EtOH in EtOAc followed by trituration with diethyl ether to afford the title compound (18 mg, 50%).

$^1$H NMR (500 MHz, CDCl$_3$): δ 8.87 (s, 1H), 8.15 (br s, 1H), 8.10 (s, 1H), 8.06 (d, J=8.20 Hz, 1H), 7.83 (d, J=8.20 Hz, 1H), 7.62 (d, J=0.63 Hz, 1H), 7.40 (br s, 1H), 7.40 (d, J=8.20 Hz, 1H), 7.17 (br s, 1H), 7.13 (dd, J=1.89, 8.20 Hz, 1H), 7.04 (d, J=1.89 Hz, 1H), 4.00 (s, 3H), 3.98 (s, 3H), 3.96 (s, 3H).

HRMS (ESI) MS m/z calcd for C$_{23}$H$_{22}$N$_7$O [M+H]$^+$ 412.1880. found 412.1880. Rt=2.51 minutes.

MPS1 IC50 (µM): 0.006

The following Examples were prepared according to Method B (Example 100) above using the appropriate halo-naphthyridine and aniline as described below. The crude reaction residues were purified as above or according to one of the following methods:

Method A: Trituration with EtOAc followed by diethyl ether.

Method B: Grade III basic alumina column chromatography eluting with a gradient of 0-10% EtOH in DCM.

Method C: Elution though an SCX-2 cartridge using 2M NH$_3$/MeOH followed by preparative TLC eluting with 10% EtOH in EtOAc followed by trituration with diethylether.

Method D: Preparative TLC eluting with EtOAc followed by trituration with diethyl ether.

| Example No | Name/Structure | Data | MPS1 IC50 (μM) |
|---|---|---|---|
| 101 | 1-(4-(7-(2-Methoxy-4-(1-methyl-1H-pyrazol-4-yl)phenylamino)-1,6-naphthyridin-2-yl)-1H-pyrazol-1-yl)-2-methylpropan-2-ol | $^1$H NMR (500 MHz, CDCl$_3$): δ 8.87 (s, 1H), 8.23 (br s, 1H), 8.17 (s, 1H), 8.08 (d, J = 8.51 Hz, 1H), 7.83 (d, J = 8.20 Hz, 1H), 7.77 (s, 1H), 7.62 (s, 1H), 7.41 (d, J = 8.51 Hz, 1H), 7.40 (s, 1H), 7.19 (s, 1H), 7.13 (dd, J = 1.58, 7.88 Hz, 1H), 7.04 (d, J = 1.89 Hz, 1H), 4.16 (s, 2H), 3.98 (s, 3H), 3.97 (s, 3H), 1.24 (s, 6H). HRMS (ESI) MS m/z calcd for C$_{26}$H$_{28}$N$_7$O$_2$ [M + H]$^+$ 470.2299, found 472.2287. Rt = 2.55 minutes Using 1-(4-(7-Bromo-1,6-naphthyridin-2-yl)-1H-pyrazol-1-yl)-2-methylpropan-2-ol (Preparation 59) and 2-methoxy-4-(1-methyl-1H-pyrazol-4-yl)aniline (Preparation 91) | 0.003 |
| 102 | 1-(4-(7-(4-(1,2-Dimethyl-1H-imidazol-5-yl)-2-methoxyphenylamino)-1,6-naphthyridin-2-yl)-1H-pyrazol-1-yl)-2-methylpropan-2-ol | $^1$H NMR (500 MHz, CDCl$_3$): δ 8.89 (d, J = 0.63 Hz, 1H), 8.42 (d, J = 0.63 Hz, 1H), 8.51 (s, 1H), 8.25 (d, J = 0.63, 8.51 Hz, 1H), 8.22 (d, J = 0.95 Hz, 1H), 7.89 (d, J = 8.20 Hz, 1H), 7.62 (d, J = 8.51 Hz, 1H), 7.30 (s, 1H), 7.08 (d, J = 1.89 Hz, 1H), 7.03 (dd, J = 1.89, 7.88 Hz, 1H), 6.89 (s, 1H), 4.19 (s, 2H), 3.97 (s, 3H), 3.62 (s, 3H), 2.44 (s, 3H), 1.23 (s, 6H). HRMS (ESI) MS m/z calcd for C$_{27}$H$_{30}$N$_7$O$_2$ [M + H]$^+$ 484.2455, found 484.2453. Rt = 2.07 minutes Using 1-(4-(7-Bromo-1,6-naphthyridin-2-yl)-1H-pyrazol-1-yl)-2-methylpropan-2-ol (Preparation 59) and 4-(1,2-dimethyl-1H-imidazol-5-yl)-2-methoxyaniline (Preparation 74) and purification method A. | 0.002 |
| 103 | 1-(4-(7-(2-Ethoxy-4-(4-methyl-4H-1,2,4-triazol-3-yl)phenylamino)-1,6-naphthyridin-2-yl)-1H-pyrazol-1-yl)-2-methylpropan-2-ol | $^1$H NMR (500 MHz, CDCl$_3$): δ 8.93 (d, J = 0.63 Hz, 1H), 8.24 (br s, 1H), 8.20 (s, 1H), 8.18 (s, 1H), 8.12 (dd, J = 0.63, 8.51 Hz, 1H), 8.11 (d, J = 8.20 Hz, 1H), 7.51 (s, 1H), 7.47 (d, J = 8.51 Hz, 1H), 7.40 (d, J = 1.89 Hz, 1H), 7.21 (dd, J = 1.89, 8.51 Hz, 1H), 4.24 (q, J = 7.25 Hz, 2H), 4.18 (s, 2H), 3.83 (s, 3H), 1.53 (t, J = 7.25 Hz, 3H), 1.25 (s, 6H). HRMS (ESI) MS m/z calcd for C$_{26}$H$_{29}$N$_8$O$_2$ [M + H]$^+$ 485.2408, found 485.2409. Rt = 2.42 minutes Using 1-(4-(7-Bromo-1,6-naphthyridin-2-yl)-1H-pyrazol-1-yl)-2-methylpropan-2-ol (Preparation 59) and 2-ethoxy-4-(4-methyl-4H-1,2,4-triazol-3-yl)aniline (Preparation 109) and purification method B. | 0.001 |

| Example No | Name/Structure | Data | MPS1 IC50 (μM) |
|---|---|---|---|
| 104 | (4-(2-(1-(2-Hydroxy-2-methylpropyl)-1H-pyrazol-4-yl)-1,6-naphthyridin-7-ylamino)-3-methoxyphenyl)(3-methoxyazetidin-1-yl)methanone | $^1$H NMR (500 MHz, DMSO-d$_6$): δ 8.98 (d, J = 0.63 Hz, 1H), 8.54 (s, 1H), 8.44 (d, J = 0.63 Hz, 1H), 8.30 (dd, J = 0.63, 8.51 Hz, 1H), 8.19 (s, 1H), 8.16 (d, J = 8.51 Hz, 1H), 7.68 (d, J = 8.51 HZ, 1H), 7.36 (s, 1H), 7.28 (d, J = 1.58 Hz, 1H), 7.25 (dd, J = 1.89, 8.20 Hz, 1H), 4.52 (br, 1H), 4.21-4.25 (br, 3H), 4.10 (s, 2H), 3.93 (s, 3H), 3.85 (br s, 1H), 3.24 (s, 3H), 1.11 (s, 6H). HRMS (ESI) MS m/z calcd for C$_{27}$H$_{31}$N$_6$O$_4$ [M + H]$^+$ 503.2401, found 503.2411. Rt = 2.54 minutes Using 1-(4-(7-Bromo-1,6-naphthyridin-2-yl)-1H-pyrazol-1-yl)-2-methylpropan-2-ol (Preparation 59) and (4-amino-3-methoxyphenyl)(3-methoxyazetidin-1-yl)methanone (Preparation 92) and purification method C. | 0.002 |
| 105 | 1-(4-(7-(2-Methoxy-4-(4-methyl-4H-1,2,4-triazol-3-yl)phenylamino)-1,6-naphthyridin-2-yl)-1H-pyrazol-1-yl)-2-methylpropan-2-ol | $^1$H NMR (500 MHz, CDCl$_3$): δ 8.92 (s, 1H), 8.22 (br s, 1H), 8.21 (s, 1H), 8.18 (s, 1H), 8.12 (d, J = 8.51 Hz, 1H), 8.11 (d, J = 8.83 Hz, 1H), 7.47 (d, J = 8.51 Hz, 1H), 7.47 (s, 1H), 7.45 (s, 1H), 7.43 (d, J = 1.58 Hz, 1H), 7.22 (dd, J = 1.89, 8.20 Hz, 1H), 4.18 (s, 2H), 4.01 (s, 3H), 3.84 (s, 3H), 1.25 (s, 6H). HRMS (ESI) MS m/z calcd for C$_{25}$H$_{25}$N$_8$O$_2$ [M + H]$^+$ 471.2251, found 471.2260. Rt = 2.31 minutes Using 1-(4-(7-Bromo-1,6-naphthyridin-2-yl)-1H-pyrazol-1-yl)-2-methylpropan-2-ol (Preparation 59) and 2-methoxy-4-(4-methyl-4H-1,2,4-triazol-3-yl)aniline (Preparation 110) and purification method B. | 0.001 |
| 106 | 1-((4-(7-(4-(1,2-Dimethyl-1H-imidazol-5-yl)-2-methoxyphenylamino)-1,6-naphthyridin-2-yl)-1H-pyrazol-1-yl)methyl)cyclobutanol | $^1$H NMR (500 MHz, CDCl$_3$): δ 8.90 (d, J = 0.63 Hz, 1H), 8.23 (d, J = 0.63 Hz, 1H), 8.14 (d, J = 0.63 Hz, 1H), 8.09 (dd, J = 0.63, 8.51 Hz, 1H), 7.96 (d, J = 8.20 Hz, 1H), 7.44 (d, J = 8.51 Hz, 1H), 7.43 (s, 1H), 7.27 (s, 1H), 7.00 (dd, J = 1.89, 8.20 Hz, 1H), 6.98 (s, 1H), 6.93 (d, J = 1.89 Hz, 1H), 4.32 (s, 2H), 3.95 (s, 3H), 3.58 (s, 3H), 2.48 (s, 3H), 2.06-2.17 (m, 4H), 1.82-1.91 (m, 1H), 1.59-1.70 (m, 1H). HRMS (ESI) MS m/z calcd for C$_{28}$H$_{30}$N$_7$O$_2$ [M + H]$^+$ 496.2455, found 496.2458. Rt = 2.17 minutes Using 1-((4-(7-Bromo-1,6-naphthyridin-2-yl)-1H-pyrazol-1-yl)methyl)cyclobutanol (Preparation 60) and 4-(1,2-dimethyl-1H-imidazol-5-yl)-2-methoxyaniline (Preparation 74) and purification method B. | 0.001 |

-continued

| Example No | Name/Structure | Data | MPS1 IC50 (μM) |
|---|---|---|---|
| 107 | 7-(2-Methoxy-4-(1-methyl-1H-pyrazol-4-yl)phenylamino)-N,N-dimethyl-1,6-naphthyridine-2-carboxamide 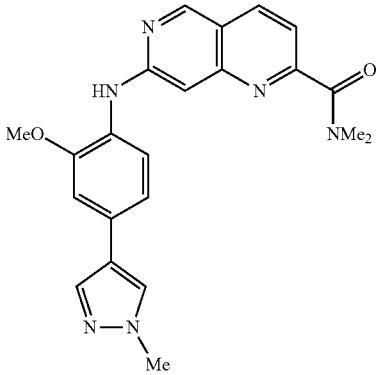 | $^1$H NMR (500 MHz, DMSO-d$_6$): δ 9.06 (d, J = 0.63 Hz, 1H), 8.46 (s, 1H), 8.40 (dd, J = 0.95, 8.51 Hz, 1H), 8.14 (s, 1H), 7.88 (d, J = 0.63 Hz, 1H), 7.72 (d, J = 8.20 Hz, 1H), 7.30 (d, J = 8.20 Hz, 1H), 7.26 (d, J = 1.89 Hz, 1H), 7.15 (dd, J = 1.89, 7.88 Hz, 1H), 7.04 (s, 1H), 3.89 (s, 3H), 3.87 (s, 3H), 3.03 (s, 3H), 2.93 (s, 3H). HRMS (ESI) MS m/z calcd for C$_{22}$H$_{23}$N$_6$O$_2$ [M + H]$^+$ 403.1877, found 403.1884. Rt = 2.52 minutes Using 7-Bromo-N,N-dimethyl-1,6-naphthyridine-2-carboxamide (Preparation 62) and 2-methoxy-4-(1-methyl-1H-pyrazol-4-yl)aniline (Preparation 91). | 0.411 |
| 108 | 7-(2-Methoxy-4-(1-methyl-1H-pyrazol-4-yl)phenylamino)-N-methyl-1,6-naphthyridine-2-carboxamide 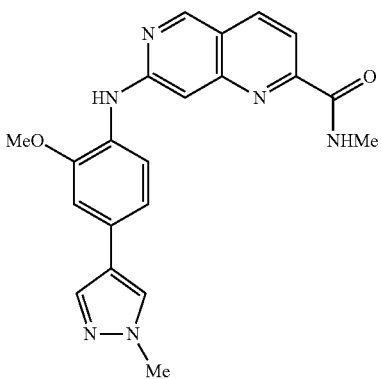 | $^1$H NMR (500 MHz, DMSO-d$_6$): δ 9.12 (s, 1H), 8.89 (br m, 1H), 8.51 (s, 1H), 8.47 (d, J = 8.51 Hz, 1H), 8.18 (s, 1H), 7.91 (s, 1H), 7.84 (d, J = 8.20 Hz, 1H), 7.59 (d, J = 8.20 Hz, 1H), 7.30 (d, J = 1.57 Hz, 1H), 7.19 (dd, J = 1.89, 8.20 Hz, 1H), 6.99 (s, 1H), 3.89 (s, 6H), 2.84 (s, 3H). HRMS (ES1) MS m/z calcd for C$_{21}$H$_{21}$N$_6$O$_2$ [M + H]$^+$ 289.1721, found 389.1716 Using 7-Bromo-N-methyl-1,6-naphthyridine-2-carboxamide (Preparation 63) and 2-methoxy-4-(1-methyl-1H-pyrazol-4-yl)aniline (Preparation 91) and purification method D. | 0.007 |

Example 109

Racemic 3-(4-(3-((4-(1,2-Dimethyl-1H-imidazol-5-yl)-2-methoxyphenyl)amino)isoquinolin-6-yl)-1H-pyrazol-1-yl)propane-1,2-diol

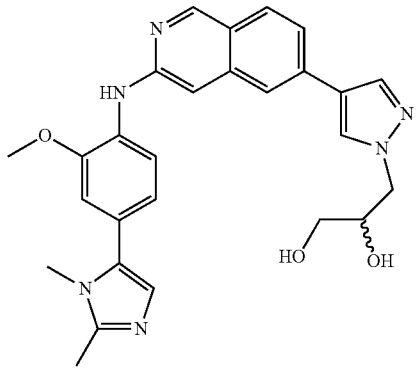 [SMILES: COc1cc(-c2cnc(C)n2C)ccc1Nc1cc2cc(-c3cnn(CC(O)CO)c3)ccc2cn1]

To a solution of 6-(1-((2,2-dimethyl-1,3-dioxolan-4-yl)methyl)-1H-pyrazol-4-yl)-N-(4-(1,2-dimethyl-1H-imidazol-5-yl)-2-methoxyphenyl)isoquinolin-3-amine (Example 40, 20 mg, 0.038 mmol) in THF (8 mL) at 0° C. was added TFA (1 mL). the reaction was stirred at room temperature for 16 hours before concentrating in vacuo. The residue was purified by elution through an SCX-2 column using 2M NH$_3$/MeOH to afford the title compound (18 mg, 97%).

$^1$H NMR (500 MHz, CDCl$_3$): δ 8.90 (s, 1H), 7.91-7.86 (m, 3H), 7.77 (d, J=8.50 Hz, 1H), 7.61 (d, J=1.60 Hz, 1H), 7.16-7.13 (m, 2H), 7.15 (d, J=4.48 Hz, 1H), 6.90 (dd, J=1.85, 8.20 Hz, 1H), 6.88 (s, 1H), 6.83 (d, J=1.85 Hz, 1H), 4.41-4.28 (m, 2H), 4.24-4.16 (m, 1H), 3.88 (s, 3H), 3.68 (qd, J=4.98, 11.40 Hz, 2H), 3.51 (s, 3H), 2.43 (s, 3H).

LCMS (ESI) Rt=1.80 minutes MS m/z 485 [M+H]$^+$
HRMS (ESI) MS m/z calcd for C$_{27}$H$_{29}$N$_6$O$_3$ [M+H]$^+$ 485.2296. found 485.2286. Rt=2.09 minutes.
MPS1 IC50 (μM): 0.003

Example 110

1-(4-(3-((2-Methoxy-4-(2-methyl-1-(piperidin-4-ylmethyl)-1H-imidazol-5-yl)phenyl)amino)-isoquinolin-6-yl)-1H-pyrazol-1-yl)-2-methylpropan-2-ol

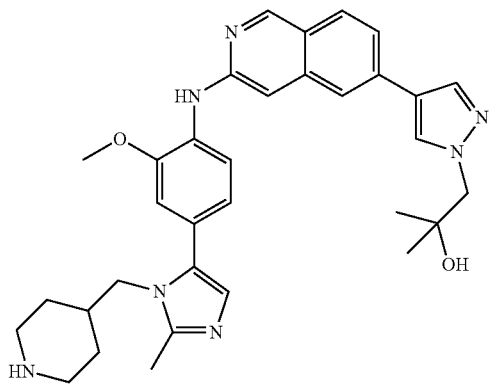 [SMILES: COc1cc(-c2cnc(C)n2CC2CCNCC2)ccc1Nc1cc2cc(-c3cnn(CC(C)(C)O)c3)ccc2cn1]

A suspension of 1-(4-(3-chloroisoquinolin-6-yl)-1H-pyrazol-1-yl)-2-methylpropan-2-ol (Preparation 22, 15 mg, 0.050 mmol), tert-butyl 4-((5-(4-amino-3-methoxyphenyl)-2-methyl-1H-imidazol-1-yl)methyl)piperidine-1-carboxylate (Preparation 79, 19.9 mg, 0.050 mmol), xantphos (17.3 mg, 0.030 mmol), Pd$_2$(dba)$_3$ (4.6 mg, 0.005 mmol) and Cs$_2$CO$_3$ (130 mg, 0.398 mmol) in toluene/DMF (3/1 mL) was stirred at 160° C. under microwave irradiation for 2 hours. The reaction mixture was filtered, diluted with NaCl solution and extracted with EtOAc. The organic solution was purified by elution through an SCX-2 column using 2M NH$_3$/MeOH followed by preparative HPLC. The residue was dissolved in DCM (6 mL) and cooled to 0° C. TFA (0.2 mL) was added and the reaction stirred at room temperature for 16 hours. The reaction was concentrated in vacuo and purified by elution through an SCX-2 column using 2M NH$_3$/MeOH followed by preparative HPLC to afford the title compound as a yellow oil (2.5 mg, 59%).

$^1$H NMR (500 MHz, MeOD): δ 8.94 (s, 1H), 8.20 (s, 1H), 8.07-8.02 (m, 2H), 7.94 (d, J=8.60 Hz, 1H), 7.90 (s, 1H), 7.65 (dd, J=1.60, 8.52 Hz, 1H), 7.36 (s, 1H), 7.10-6.99 (m, 3H), 4.19 (s, 2H), 4.14 (d, J=7.62 Hz, 2H), 4.00 (s, 3H), 3.35-3.25 (m, 2H), 2.85 (td, J=3.02, 12.88 Hz, 2H), 2.58 (s, 3H), 1.98-1.88 (m, 1H), 1.70 (d, J=13.84 Hz, 2H), 1.30-1.22 (m, 2H), 1.25 (s, 6H).

HRMS (ESI) MS m/z calcd for C$_{33}$H$_{40}$N$_7$O$_2$ (M+H)$^+$ 566.3238. found 566.3236. Rt=2.25 minutes.
MPS1 IC50 (μM): 0.005

Example 111

1-(4-(3-((2-Methoxy-4-(5,6,7,8-tetrahydroimidazo[1,2-a]pyrazin-3-yl)phenyl)amino)-isoquinolin-6-yl)-1H-pyrazol-1-yl)-2-methylpropan-2-ol

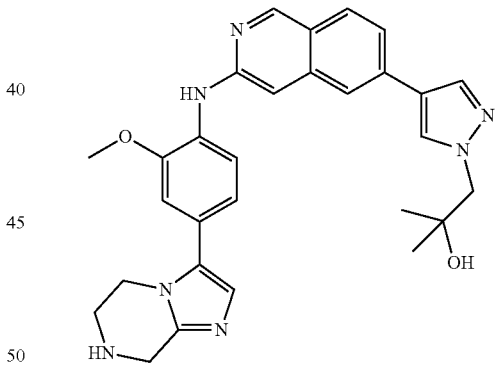

The title compound was prepared according to the method described for Example 110 using 1-(1-(4-(3-chloroisoquinolin-6-yl)-1H-pyrazol-1-yl)-2-methylpropan-2-ol (Preparation 22) and tert-butyl 3-(4-amino-3-methoxyphenyl)-5,6-dihydroimidazo[1,2-a]pyrazine-7(8H)-carboxylate (Preparation 89).

$^1$H NMR (500 MHz, CDCl$_3$) δ 8.95 (s, 1H), 7.97 (d, J=0.78 Hz, 1H), 7.92 (d, J=8.20 Hz, 1H), 7.87-7.80 (m, 2H), 7.73-7.68 (m, 1H), 7.47 (dd, J=1.62, 8.46 Hz, 1H), 7.25 (t, J=0.94 Hz, 1H), 7.16 (s, 1H), 7.07 (s, 1H), 7.01 (dd, J=1.86, 8.16 Hz, 1H), 6.94 (d, J=1.86 Hz, 1H), 4.22 (s, 2H), 4.15 (s, 2H), 3.99 (t, J=5.40 Hz, 2H), 3.96 (s, 3H), 3.27 (t, J=5.40 Hz, 2H), 1.25 (s, 6H).

HRMS (ESI) MS m/z calcd for C$_{29}$H$_{32}$N$_7$O$_2$ [M+H]$^+$ 510.2612. found 510.2617. Rt=2.23 minutes.
MPS1 IC50 (μM): 0.003

Example 112

1-(4-(3-(2-Methoxy-4-(5,6,7,8-tetrahydro-[1,2,4]triazolo[4,3-a]pyrazin-3-yl)phenylamino)-isoquinolin-6-yl)-1H-pyrazol-1-yl)-2-methylpropan-2-ol

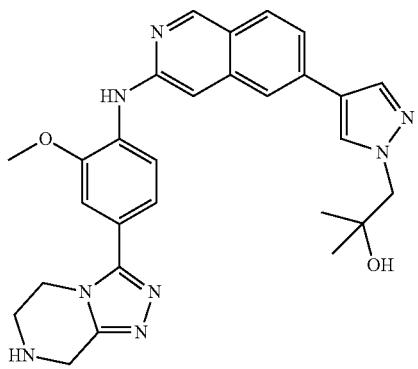 [SMILES: COc1cc(-c2nnc3n2CCNC3)ccc1Nc1cc2cc(-c3cnn(CC(C)(C)O)c3)ccc2cn1]

To a solution of tert-Butyl 3-(4-(6-(1-(2-hydroxy-2-methylpropyl)-1H-pyrazol-4-yl)isoquinolin-3-ylamino)-3-methoxyphenyl)-5,6-dihydro-[1,2,4]triazolo[4,3-a]pyrazine-7(8H)-carboxylate (Example 55, 29 mg, 0.047 mmol) in DCM (10 mL) at 0° C. was added TFA (0.35 mL). The reaction was stirred at room temperature for 16 hours before concentrating in vacuo. The residue was purified by elution through an SCX-2 column using 2M NH$_3$/MeOH to afford the title compound as a yellow solid (17.5 mg, 72%).

$^1$H NMR (500 MHz, DMSO-d$_6$): δ 8.98 (s, 1H), 8.29 (d, J=0.84 Hz, 1H), 8.27 (s, 1H), 8.17 (d, J=8.38 Hz, 1H), 8.07 (d, J=0.80 Hz, 1H), 7.94 (d, J=8.64 Hz, 1H), 7.89 (s, 1H), 7.62 (dd, J=1.64, 8.58 Hz, 1H), 7.39 (d, J=1.94 Hz, 1H), 7.34-7.28 (m, 2H), 4.24-4.06 (m, 2H+2H), 4.04 (s, 2H), 3.96 (s, 3H), 3.06 (t, J=5.46 Hz, 2H), 1.12 (s, 6H).

HRMS (ESI) MS m/z calcd for $C_{28}H_{31}N_8O_2$ [M+H]$^+$ 511.2564. found 511.2564. Rt=2.17 minutes.

MPS1 IC50 (μM): 0.002

Example 113

N-(4-(1,2-dimethyl-1H-imidazol-5-yl)-2-methoxyphenyl)-6-(1-(piperidin-4-yl)-1H-pyrazol-4-yl)isoquinolin-3-amine

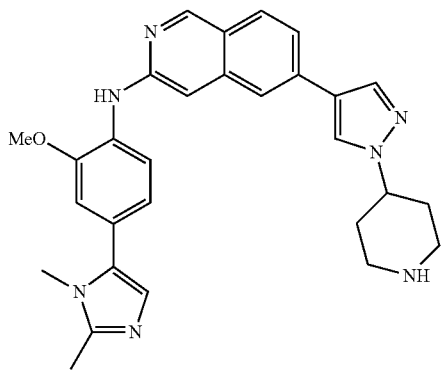 [SMILES: COc1cc(-c2cnc(C)n2C)ccc1Nc1cc2cc(-c3cnn(C4CCNCC4)c3)ccc2cn1]

To a solution of tert-butyl 4-(4-(3-((4-(1,2-dimethyl-1H-imidazol-5-yl)-2-methoxyphenyl)-amino)isoquinolin-6-yl)-1H-pyrazol-1-yl)piperidine-1-carboxylate (Example 4, 27 mg, 0.045 mmol) in DCM (6 mL) at 0° C. was added TFA (0.6 mL) and the reaction was stirred at room temperature for 4 hours. The solvents were removed in vacuo and the residue was purified by SCX-2 column eluting with 2M NH$_3$/MeOH to afford the title compound as a yellow oil (19 mg, 85%).

$^1$H NMR (500 MHz, CDCl$_3$): δ 8.95 (s, 1H), 7.90-7.95 (m, 2H), 7.85-7.82 (m, 2H), 7.71 (s, 1H), 7.52-7.43 (m, 1H), 7.26 (s, 1H), 7.16 (s, 1H), 6.99 (dd, J=8.0, 2.1 Hz, 1H), 6.97 (s, 1H), 6.92 (s, 1H), 4.35-4.25 (m, 1H), 3.96 (s, 3H), 3.57 (s, 3H), 3.36-3.21 (m, 2H), 2.85-2.75 (m, 2H), 2.48 (s, 3H), 2.30-2.16 (m, 2H), 2.05-1.88 (m, 2H).

(Agilent ToF method) Rt=1.79 minutes MS m/z 494 [M+H]$^+$

MPS1 IC50 (μM): 0.004

Example 114

N-(4-(1,2-dimethyl-1H-imidazol-5-yl)-2-methoxyphenyl)-6-(6-(methylamino)pyridin-3-yl)isoquinolin-3-amine

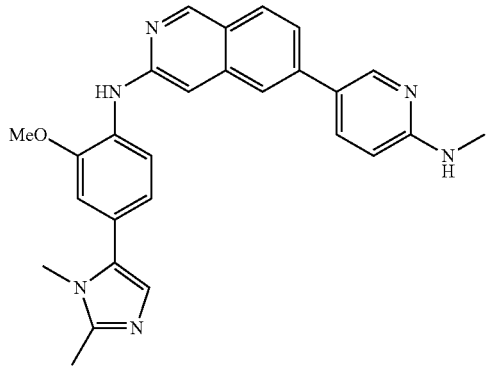 [SMILES: CNc1ccc(-c2ccc3cnc(Nc4ccc(-c5cnc(C)n5C)cc4OC)cc3c2)cn1]

To a solution of tert-butyl (5-(3-((4-(1,2-dimethyl-1H-imidazol-5-yl)-2-methoxyphenyl)-amino)isoquinolin-6-yl)pyridin-2-yl)(methyl)carbamate (Example 12, 10 mg, 0.018 mmol) in DCM (4 mL) at 0° C. was added TFA (0.6 mL). The reaction was stirred at room temperature for 16 hours. The solvents were removed in vacuo and the residue was purified by SCX-2 column eluting with 2M NH$_3$/MeOH to afford the title compound as a yellow oil (8 mg, 98%).

$^1$H NMR (500 MHz, CDCl$_3$): δ 9.00 (d, J=1.1 Hz, 1H), 8.50 (dd, J=2.5, 1.0 Hz, 1H), 8.00-7.94 (m, 1H), 7.90 (d, J=8.6 Hz, 1H), 7.83 (ddd, J=8.5, 2.4, 1.7 Hz, 1H), 7.73 (d, J=1.6 Hz, 1H), 7.53 (dt, J=8.3, 1.6 Hz, 1H), 7.31 (d, J=1.5 Hz, 1H), 7.19 (s, 1H), 7.04-6.96 (m, 2H), 6.93 (d, J=1.8 Hz, 1H), 6.54 (dd, J=8.7, 0.9 Hz, 1H), 3.97 (s, 39H), 3.59 (s, 3H), 3.02 (s, 3H), 2.50 (s, 3H).

(Agilent ToF method) Rt=1.77 minutes MS m/z 451 [M+H]$^+$

MPS1 IC50 (μM): 0.021

Example 115

N-(4-(1,2-dimethyl-1H-imidazol-5-yl)-2-methoxyphenyl)-7-(1-methyl-1H-pyrazol-4-yl)pyrido[2,3-d]pyrimidin-2-amine

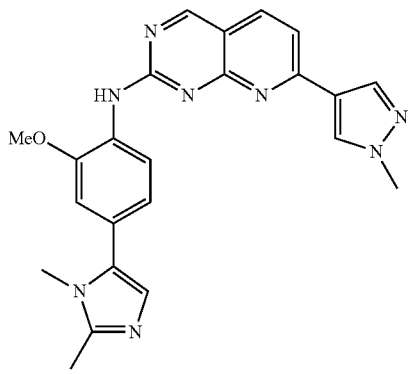 [SMILES: COc1cc(-c2cnc(C)n2C)ccc1Nc1ncc2ccc(-c3cnn(C)c3)nc2n1]

A suspension of 2-chloro-7-(1-methyl-1H-pyrazol-4-yl)pyrido[2,3-d]pyrimidine (Preparation 55, 7.5 mg, 0.03 mmol), 4-(1,2-dimethyl-1H-imidazol-5-yl)-2-methoxyaniline (Preparation 74, 10 mg, 0.05 mmol), R-(+)BINAP (2 mg, 3 umol), Pd(OAc)$_2$ (0.69 mg, 3 umol), K$_2$CO$_3$ (42 mg, 0.31 mmol) in DMF (3 mL) was stirred at 160° C. under microwave irradiation for 2 hours. The reaction mixture was filtered, diluted with NaCl solution and extracted with EtOAc. The organic layer was purified by SCX-2 column eluting with 2M NH$_3$ in MeOH and concentrated in vacuo. The residue was purified by Biotage silica gel column chromatography eluting with 0-10% MeOH in EtOAc followed by preparative HPLC to afford the title compound (4 mg, 31%):

$^1$H NMR (500 MHz, CDCl$_3$): δ 9.07 (s, 1H), 9.03-9.01 (m, 1H), 8.27 (s, 1H), 8.25 (d, J=14.0 Hz, 1H), 8.17 (d, J=0.7 Hz, 1H), 8.07 (d, J=8.3 Hz, 1H), 7.52 (d, J=8.3 Hz, 1H), 7.17-6.99 (m, 2H), 6.89 (d, J=1.8 Hz, 1H), 4.03 (s, 3H), 3.98 (s, 3H), 3.62 (s, 3H), 2.64 (s, 3H).

LCMS (ESI) Rt=1.87 minutes MS m/z 427 [M+H]$^+$
MPS1 IC50 (μM): 0.016

Example 116

1-(4-(2-((4-(1,2-Dimethyl-1H-imidazol-5-yl)-2-methoxyphenyl)amino)pyrido[2,3-d]pyrimidin-7-yl)-1H-pyrazol-1-yl)-2-methylpropan-2-ol

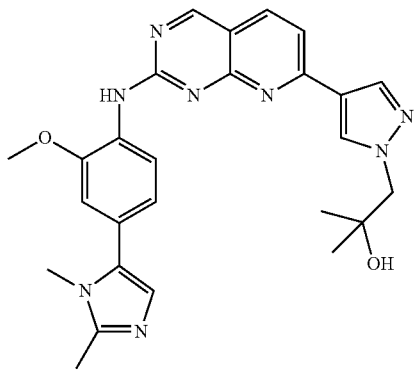 [SMILES: COc1cc(-c2cnc(C)n2C)ccc1Nc1ncc2ccc(-c3cnn(CC(C)(C)O)c3)nc2n1]

A suspension of NaH (4.3 mg), 2-methyl-1-(4-(2-(methylsulfonyl)pyrido[2,3-d]pyrimidin-7-yl)-1H-pyrazol-1-yl)propan-2-ol (Preparation 69, 15.5 mg, 0.045 mmol), N-(4-(1,2-dimethyl-1H-imidazol-5-yl)-2-methoxyphenyl)formamide (Preparation 74, 16.4 mg, 0.067 mmol) in NMP/THF (⅓ mL) was stirred at 160° C. under microwave irradiation for 2 hours. The reaction mixture was filtered, diluted with NaCl solution and extracted with EtOAc. The EtOAc portion was purified by elution through an SCX-2 column using 2M NH$_3$/MeOH to give the title compound as yellow oil (3 mg, 14%).

$^1$H NMR (500 MHz, CDCl$_3$): δ 9.09 (s, 1H), 9.03 (s, broad, 1H), 8.36 (s, 1H), 8.27-8.20 (m, 2H), 8.09 (d, J=8.24 Hz, 1H), 7.55 (d, J=8.24 Hz, 1H), 7.11 (s, 1H), 7.08 (dd, J=1.86, 8.34 Hz, 1H), 6.91 (d, J=1.86 Hz, 1H), 4.20 (s, 2H), 3.99 (s, 3H), 3.63 (s, 3H), 2.66 (s, 3H), 1.26 (s, 6H).

HRMS (ESI) MS m/z calcd for C$_{26}$H$_{29}$N$_8$O$_2$ [M+H]$^+$ 485.2408. found 485.2399.

Preparation Methods

Preparation 1: 3-Chloro-6-(1-((tetrahydro-2H-pyran-4-yl)methyl)-1H-pyrazol-4-yl)isoquinoline

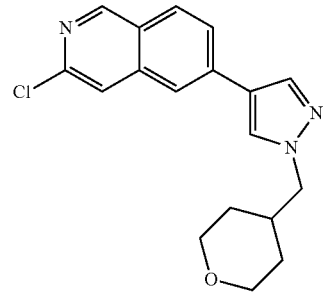 [SMILES: Clc1cc2cc(-c3cnn(CC4CCOCC4)c3)ccc2cn1]

Method C

A suspension of 6-bromo-3-chloroisoquinoline (50 mg, 0.21 mmol), 1-((tetrahydro-2H-pyran-4-yl)methyl)-4-(4,4,5,5-tetramethyl-1,3,2-dioxaborolan-2-yl)-1H-pyrazole (60 mg, 0.21 mmol), Pd(dppf)Cl$_2$.DCM (17.5 mg, 0.02 mmol), Na$_2$CO$_3$ (2M, 0.21 mL, 0.42 mmol) in DME (4 mL) was stirred at 140° C. under microwave irradiation for 60 minutes. The reaction mixture was diluted with EtOAc, dried with Na$_2$SO$_4$ and concentrated in vacuo. The residue was purified using Biotage silica gel column chromatography eluting with between 25-60% EtOAc/cyclohexane to afford the title compound (10.5 mg, 16%).

$^1$H NMR (500 MHz, CDCl$_3$): δ 9.00 (s, 1H), 8.01-7.92 (m, 2H), 7.83-7.76 (m, 2H), 7.73 (dd, J=8.6, 1.6 Hz, 1H), 7.68 (s, 1H), 4.08 (d, J=7.2 Hz, 2H), 4.06-3.96 (m, 2H), 3.40 (td, J=11.8, 2.2 Hz, 2H), 2.25 (m, 1H), 1.63-1.52 (m, 2H), 1.49-1.39 (m, 2H).

LCMS (ESI) Rt=2.49 minutes MS m/z 328 [M+H]$^+$

Preparation 2: 3-Chloro-6-cyclopropylisoquinoline

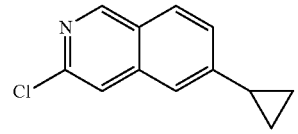 [SMILES: Clc1cc2cc(C3CC3)ccc2cn1]

Method D

A suspension of 6-bromo-3-chloroisoquinoline (50 mg, 0.21 mmol), potassium cyclopropyltrifluoroborate (40 mg, 0.27 mmol), Pd(OAc)$_2$ (3.7 mg, 0.016 mmol), Cs$_2$CO$_3$ (202 mg, 0.62 mmol) and di(1-adamantyl)-n-butylphosphine (5.54 mg, 0.015 mmol) in toluene/water (4/0.4 mL) was stirred at 100° C. under microwave irradiation for 120 minutes. The reaction mixture was filtered, concentrated in vacuo and purified using Biotage silica gel column chromatography eluting with DCM to afford the title compound (17 mg, 41%).

$^1$H NMR (500 MHz, CDCl$_3$): δ 8.97 (s, 1H), 7.85 (d, J=8.6 Hz, 1H), 7.61 (d, J=1.0 Hz, 1H), 7.46-7.38 (m, 1H), 7.33-723 (m, 1H), 2.05-2.01 (m, 1H), 1.19-1.10 (m, 2H), 0.91-0.85 (m, 2H).

LCMS (ESI) Rt=2.77 minutes MS m/z 204 [M+H]$^+$

Preparation 3:
3-Chloro-6-(pyrimidin-5-yl)isoquinoline

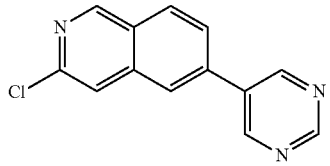 [SMILES: Clc1cc2cc(-c3cncnc3)ccc2cn1]

Method E

A suspension of 6-bromo-3-chloroisoquinoline (62 mg, 0.27 mmol), pyrimidin-5-ylboronic acid (45 mg, 0.36 mmol), Pd(PPh$_3$)$_4$ (29.5 mg, 0.026 mmol) and CsF (117 mg, 0.77 mmol) in DME/MeOH (3/1 mL) was stirred at 150° C. under microwave irradiation for 30 minutes. The reaction mixture was filtered and concentrated in vacuo. The residue was purified using Biotage silica gel column chromatography eluting with between 20-60% EtOAc in cyclohexane to afford the title compound (26 mg, 42%).

$^1$H NMR (500 MHz, CDCl$_3$): δ 9.32 (s, 1H), 9.17 (s, 1H), 9.09 (s, 2H), 8.16 (dt, J=8.5, 0.9 Hz, 1H), 7.98 (dd, J=1.8, 0.9 Hz, 1H), 7.88-7.78 (m, 2H).

LCMS (ESI) Rt=2.14 minutes MS m/z 242 [M+H]$^+$

The following Preparations were prepared according to Methods C, D or E (Preparations 1, 2 or 3) above using 6-bromo-3-chloroisoquinoline and the appropriate cross-coupling partner as described.

| Preparation No | Name/Structure | Data |
|---|---|---|
| 4 | 3-Chloro-6-(1-(cyclopropylmethyl)-1H-pyrazol-4-yl)isoquinoline | $^1$H NMR (500 MHz, CDCl$_3$): δ 8.99 (d, J = 0.9 Hz, 1H), 7.99-7.91 (m, 3H), 7.83-7.78 (m, 1H), 7.74 (dd, J = 8.5, 1.7 Hz, 1H), 7.67 (t, J = 0.9 Hz, 1H), 4.08 (d, J = 7.1 Hz, 2H), 1.37 (m, 1H), 0.79-0.68 (m, 2H), 0.51-0.43 (m, 2H). LCMS (ESI) Rt = 2.63 minutes MS m/z 284 [M + H]$^+$ Using 1-(cyclopropylmethyl)-4-(4,4,5,5-tetramethyl-1,3,2-dioxaborolan-2-yl)-1H-pyrazole (Preparation 139) and Method 12. |
| 5 | 3-Chloro-6-(1-(2,2-difluoroethyl)-1H-pyrazol-4-yl)isoquinoline | $^1$H NMR (500 MHz, CDCl$_3$): δ 9.01 (t, J = 0.9 Hz, 1H), 7.99 (d, J = 0.8 Hz, 1H), 7.96 (dt, J = 8.6, 0.8 Hz, 1H), 7.90 (d, J = 0.7 Hz, 1H), 7.81 (dq, J = 1.4, 0.7 Hz, 1H), 7.72 (dd, J = 8.5, 1.7 Hz, 1H), 7.68 (d, J = 1.0 Hz, 1H), 6.17 (tt, J = 55.3, 4.2 Hz, 1H), 4.56 (td, J = 13.6, 4.2 Hz, 2H). LCMS (ESI) Rt = 2.40 minutes MS m/z 294 [M + H]$^+$ Using 1-(2,2-difluoroethyl)-4-(4,4,5,5-tetramethyl-1,3,2-dioxaborolan-2-yl)-1H-pyrazole (Preparation 138) and Method 12. |
| 6 | tert-Butyl 4-(4-(3-chloroisoquinolin-6-yl)-1H-pyrazol-1-yl)piperidine-1-carboxylate | $^1$H NMR (500 MHz, CDCl$_3$): δ 8.99 (d, J = 0.9 Hz, 1H), 7.99-7.91 (m, 3H), 7.83-7.78 (m, 1H), 7.74 (dd, J = 8.5, 1.7 Hz, 1H), 7.67 (t, J = 0.9 Hz, 1H), 4.35-4.25 (m, 3H), 3.00-2.83 (m, 2H), 2.24-2.16 (m, 2H), 2.02-1.85 (m, 2H), 1.48 (s, 9H). LCMS (ESI) Rt = 2.83 minutes MS m/z 413 [M + H]$^+$ Using tert-butyl 4-(4-(4,4,5,5-tetramethyl-1,3,2-dioxaborolan-2-yl)-1H-pyrazol-1-yl)piperidine-1-carboxylate and Method 12 at 110° C. for 90 minutes. |

| Preparation No | Name/Structure | Data |
|---|---|---|
| 7 | 3-Chloro-6-(1,2-dimethyl-1H-imidazol-5-yl)isoquinoline | $^1$H NMR (500 MHz, CDCl$_3$): δ 9.04 (t, J = 0.9 Hz, 1H), 7.99 (dt, J = 8.5, 0.8 Hz, 1H), 7.74-7.67 (m, 2H), 7.61 (dd, J = 8.5, 1.6 Hz, 1H), 7.13 (s, 1H), 3.64 (s, 3H), 2.49 (s, 3H).<br>LCMS (ESI) Rt = 1.18 minutes MS m/z 258 [M + H]$^+$<br>Using 1,2-dimethyl-1H-imidazole and Method 13 at 150° C. for 1 hour. |
| 8 | 5-(3-Chloroisoquinolin-6-yl)oxazole | $^1$H NMR (500 MHz, CDCl$_3$): δ 9.05 (t, J = 0.9 Hz, 1H), 8.04 (s, 1H), 8.01 (dt, J = 9.4, 1.0 Hz, 2H), 7.84 (dd, J = 8.6, 1.7 Hz, 1H), 7.74 (d, J = 1.0 Hz, 1H), 7.59 (s, 1H).<br>LCMS Rt = 2.35 minutes MS m/z 231 [M + H]$^+$<br>Using oxazole and Method 13 at 150° C. for 1 hour. |
| 9 | 3-Chloro-6-(pyridin-4-yl)isoquinoline | $^1$H NMR (500 MHz, CDCl$_3$): δ 9.15 (s, 1H), 8.78 (d, J = 5.2 Hz, 2H), 8.14-8.13 (m, 1H), 7.99-8.05 (m, 1H), 7.88 (dd, J = 8.6, 1.7 Hz, 1H), 7.83 (s, 1H), 7.60-7.69 (m, 2H).<br>LCMS (ESI) RT = 1.73 minutes MS m/z 241 [M + H]$^+$<br>Using pyridin-4-yl-boronic acid and Method 12 at 120° C. |
| 10 | 5-(3-Chloroisoquinolin-6-yl)-N,N-dimethylpyridin-2-amine | $^1$H NMR (500 MHz, CDCl$_3$): δ 9.02 (t, J = 0.9 Hz, 1H), 8.56 (dd, J = 2.6, 0.8 Hz, 1H), 7.99 (dt, J = 8.5, 0.9 Hz, 1H), 7.75-7.85 (m, 3H), 7.71 (d, J = 0.9 Hz, 1H), 6.64 (dd, J = 8.9, 0.8 Hz, 1H), 3.18 (s, 6H).<br>LCMS (ESI) Rt = 1.73 minutes MS m/z 284 [M + H]$^+$<br>Using (6-(dimethylamino)-pyridin-3-yl)-boronic acid hydrate and Method 12. |
| 11 | 3-Chloro-6-(1-ethyl-1H-pyrazol-4-yl)isoquinoline | $^1$H NMR (500 MHz, CDCl$_3$): δ 8.96 (s, 1H), 7.96-7.88 (m, 2H), 7.82 (d, J = 0.8 Hz, 1H), 7.79-7.74 (m, 1H), 7.70 (dd, J = 8.5, 1.6 Hz, 1H), 7.64 (s, 1H), 4.25 (q, J = 7.3 Hz, 2H), 1.56 (t, J = 7.2 Hz, 3H).<br>LCMS (ESI) Rt = 2.48 minutes MS m/z 258 [M + H]$^+$<br>Using 1-ethyl-4-(4,4,5,5-tetramethyl-1,3,2-dioxaborolan-2-yl)-1H-pyrazole and Method 12. |
| 12 | 3-Chloro-6-(6-methylpyridin-3-yl)isoquinoline | $^1$H NMR (500 MHz, CDCl$_3$): δ 9.10 (s, 1H), 8.84 (d, J = 3.6 Hz, 1H), 8.08 (d, J = 8.4 Hz, 1H), 7.94-7.88 (m, 2H), 7.82 (dd, J = 8.6, 2.5 Hz, 1H), 7.78 (s, 1H), 7.32 (d, J = 8.6 Hz, 1H), 2.66 (s, 3H).<br>LCMS (ESI) Rt = 1.83 minutes MS m/z 255 [M + H]$^+$<br>Using 2-methyl-5-(4,4,5,5-tetramethyl-1,3,2-dioxaborolan-2-yl)pyridine and Method 12. |

| Preparation No | Name/Structure | Data |
|---|---|---|
| 13 | tert-Butyl (5-(3-chloroisoquinolin-6-yl)pyridin-2-yl)(methyl)carbamate | $^1$H NMR (500 MHz, CDCl$_3$): δ 9.10 (d, J = 0.9 Hz, 1H), 8.72 (dd, J = 2.4, 1.0 Hz, 1H), 8.07 (dt, J = 8.6, 0.8 Hz, 1H), 7.95-7.90 (m, 3H), 7.82 (dd, J = 8.5, 1.7 Hz, 1H), 7.78 (d, J = 1.0 Hz, 1H), 3.49 (s, 3H), 1.56 (s, 9H). LCMS (ESI) Rt = 2.97 minutes MS m/z 370 [M + H]$^+$ Using tert-butyl methyl(5-(4,4,5,5-tetramethyl-1,3,2-dioxaborolan-2-yl)pyridin-2-yl)carbamate and Method 12. |
| 14 | 5-(3-Chloroisoquinolin-6-yl)-2,4-dimethylthiazole | $^1$H NMR (500 MHz, CDCl$_3$): δ 9.08 (t, J = 0.9 Hz, 1H), 8.01 (dt, J = 8.5, 0.9 Hz, 1H), 7.76 (dt, J = 15.7, 1.0 Hz, 2H), 7.67 (dd, J = 8.5, 1.7 Hz, 1H), 2.75 (s, 3H), 2.56 (s, 3H). LCMS (ESI) Rt = 2.73 minutes MS m/z 275 [M + H]$^+$ Using 2,4-dimethyl-5-(4,4,5,5-tetramethyl-1,3,2-dioxaborolan-2-yl)thiazole and Method 12. |
| 15 | 3-Chloro-6-(1-(2-methoxyethyl)-1H-pyrazol-4-yl)isoquinoline | $^1$H NMR (500 MHz, CDCl$_3$): δ 9.01 (s, 1H), 7.98-7.94 (m, 2H), 7.93 (s, 1H), 7.83 (d, J = 1.6 Hz, 1H), 7.76 (dd, J = 8.6, 1.6 Hz, 1H), 7.70 (s, 1H), 4.38 (t, J = 5.1 Hz, 2H), 3.82 (t, J = 5.1 Hz, 2H), 3.40 (s, 3H). LCMS (ESI) Rt = 2.40 minutes MS m/z 288 [M + H]$^+$ Using 1-(2-methoxyethyl)-4-(4,4,5,5-tetramethyl-1,3,2-dioxaborolan-2-yl)-1H-pyrazole (Preparation 122) and Method 12. |
| 16 | 3-Chloro-6-(1-(2-isopropyl)-1H-pyrazol-4-yl)isoquinoline | $^1$H NMR (500 MHz, CDCl$_3$): δ 9.00 (t, J = 0.9 Hz, 1H), 7.95 (dd, J = 8.3, 0.9 Hz, 2H), 7.86 (d, J = 0.9 Hz, 1H), 7.82-7.79 (m, 1H), 7.74 (dd, J = 8.5, 1.7 Hz, 1H), 7.68 (d, J = 1.1 Hz, 1H), 4.59 (hept, J = 6.7 Hz, 1H), 1.59 (d, J = 6.7 Hz, 6H). LCMS (ESI) Rt = 2.58 minutes MS m/z 272 [M + H]$^+$ Using 1-isopropyl-4-(4,4,5,5-tetramethyl-1,3,2-dioxaborolan-2-yl)-1H-pyrazole and Method 12. |
| 17 | 3-Chloro-6-(pyridin-3-yl)isoquinoline | $^1$H NMR (500 MHz, CDCl$_3$); δ 9.12 (d, J = 0.9 Hz, 1H), 8.97 (dd, J = 2.5, 0.9 Hz, 1H), 8.70 (dd, J = 4.8, 1.6 Hz, 1H), 8.10 (dd, J = 8.4, 1.0 Hz, 1H), 8.01 (ddd, J = 7.9, 2.4, 1.6 Hz, 1H), 7.94 (d, J = 1.7 Hz, 1H), 7.84 (dd, J = 8.5, 1.7 Hz, 1H), 7.80 (d, J = 1.0 Hz, 1H), 7.64-7.71 (m, 1H). LCMS (ESI) Rt = 2.14 minutes MS m/z 241 [M + H]$^+$ Using pyridin-3-ylboronic acid and Method 14. |

| Preparation No | Name/Structure | Data |
|---|---|---|
| 18 | 3-Chloro-6-(1,3-dimethyl-1H-pyrazol-4-yl)isoquinoline | $^1$H NMR (500 MHz, CDCl$_3$): δ 9.03 (d, J = 0.9 Hz, 1H), 7.96 (dt, J = 8.5, 0.9 Hz, 1H), 7.71 (dt, J = 7.8, 1.0 Hz, 2H), 7.65 (dd, J = 8.5, 1.7 Hz, 1H), 7.61 (s, 1H), 3.93 (s, 3H), 2.50 (s, 3H).<br>LCMS (ESI) Rt = 2.50 minutes MS m/z 258 [M + H]$^+$<br>Using 1,3-dimethyl-4-(4,4,5,5-tetramethyl-1,3,2-dioxaborolan-2-yl)-1H-pyrazole and Method 14. |
| 19 | 3-Chloro-6-(1,5-dimethyl-1H-pyrazol-4-yl)isoquinoline | $^1$H NMR (500 MHz, CDCl$_3$): δ 9.04 (d, J = 0.9 Hz, 1H), 7.99 (dt, J = 8.6, 0.9 Hz, 1H), 7.72-7.69 (m, 2H), 7.68-7.67 (m, 1H), 7.65 (dd, J = 8.4, 1.6 Hz, 1H), 3.91 (s, 3H), 2.49 (s, 3H).<br>LCMS (ESI) Rt = 2.47 minutes MS m/z 258 [M + H]$^+$<br>Using 1,5-dimethyl-4-(4,4,5,5-tetramethyl-1,3,2-dioxaborolan-2-yl)-1H-pyrazole and Method 14. |
| 20 | 3-Chloro-6-(1-methyl-1H-pyrazol-4-yl)isoquinoline | $^1$H NMR (500 MHz, CDCl$_3$): δ 8.98 (t, J = 0.9 Hz, 1H), 7.93 (dt, J = 8.6, 0.8 Hz, 1H), 7.91 (d, J = 0.9 Hz, 1H), 7.80-7.75 (m, 2H), 7.71 (dd, J = 8.5, 1.6 Hz, 1H), 7.66 (d, J = 1.0 Hz, 1H), 4.00 (s, 3H).<br>LCMS (ESI) Rt = 2.36 minutes MS m/z 244 [M + H]$^+$<br>Using 1-methyl-4-(4,4,5,5-tetramethyl-1,3,2-dioxaborolan-2-yl)-1H-pyrazole and Method 14. |
| 21 | 3-Chloro-6-(1-(cyclobutylmethyl)-1H-pyrazol-4-yl)isoquinoline | $^1$H NMR (500 MHz, CDCl$_3$): δ 8.98 (s, 1H), 7.95-7.90 (m, 2H), 7.77 (d, J = 1.08 Hz, 1H), 7.71 (dd, J = 1.60, 8.48 Hz, 2H), 7.65 (s, 1H), 4.21 (d, J = 7.34 Hz, 2H), 2.95-2.85 (m, 1H), 2.20-2.08 (m, 2H), 2.01-1.77 (m, 4H).<br>LCMS (ESI) Rt = 2.81 minutes MS m/z 298 [M + H]$^+$<br>Using 1-(cyclobutylmethyl)-4-(4,4,5,5-tetramethyl-1,3,2-dioxaborolan-2-yl)-1H-pyrazole (Preparation 123) and Method 12. |
| 22 | 1-(4-(3-Chloroisoquinolin-6-yl)-1H-pyrazol-1-yl)-2-methylpropan-2-ol | $^1$H NMR (500 MHz, CDCl$_3$): δ 8.98 (s, 1H), 7.96 (s, 1H), 7.93 (d, J = 8.46 Hz, 1H), 7.88 (s, 1H), 7.77 (d, J = 1.60 Hz, 1H), 7.71 (dd, J = 1.60, 8.54 Hz, 1H), 7.65 (s, 1H), 4.17 (s, 2H), 1.26 (s, 6H).<br>LCMS (ESI) Rt = 2.38 minutes MS m/z 302 [M + H]$^+$<br>Using 2-methyl-1-(4-(4,4,5,5-tetramethyl-1,3,2-dioxaborolan-2-yl)-1H-pyrazol-1-yl)propan-2-ol (Preparation 124) and Method 12. |

| Preparation No | Name/Structure | Data |
|---|---|---|
| 23 | 3-Chloro-6-(1-((3-methyloxetan-3-yl)methyl)-1H-pyrazol-4-yl)isoquinoline | $^1$H NMR (500 MHz, CDCl$_3$): δ 9.00 (s, 1H), 8.00-7.58 (m, 2H), 7.80 (d, J = 4.16 Hz, 2H), 7.72 (d, J = 8.54 Hz, 1H), 7.68 (s, 1H), 4.77 (d, J = 6.04 Hz, 2H), 4.47 (d, J = 6.04 Hz, 2H), 4.43 (s, 2H), 1.33 (s, 3H).<br>LCMS (ESI) Rt = 2.44 minutes MS m/z 314 [M + H]$^+$<br>Using 1-((3-methyloxetan-3-yl)methyl)-4-(4,4,5,5-tetramethyl-1,3,2-dioxaborolan-2-yl)-1H-pyrazole (Preparation 125) and Method 12. |
| 24 | 3-Chloro-6-(1-(oxetan-3-yl)-1H-pyrazol-4-yl)isoquinoline | $^1$H NMR (500 MHz, CDCl$_3$): δ 9.04 (s, 1H), 8.16-7.90 (m, 3H), 7.85 (s, 1H), 7.80-7.62 (m, 2H), 5.62-5.48 (m, 1H), 5.14 (d, J = 5.70 Hz, 4H).<br>LCMS (ESI) Rt = 2.17 minutes MS m/z 479 [M + H]$^+$<br>Using 1-(oxetan-3-yl)-4-(4,4,5,5-tetramethyl-1,3,2-dioxaborolan-2-yl)-1H-pyrazole (Preparation 126) and Method 12. |
| 25 | (4-(3-Chloroisoquinolin-6-yl)-1-methyl-1H-pyrazol-5-yl)methanol | $^1$H NMR (500 MHz, CDCl$_3$): δ 9.04 (s, 1H), 8.00 (d, J = 8.44 Hz, 1H), 7.78 (d, J = 1.74 Hz, 1H), 7.75-7.71 (m, 2H), 7.69 (dd, J = 1.58, 8.464 Hz, 1H), 6.23 (s, 1H), 4.86 (s, 2H), 4.06 (s, 3H).<br>LCMS (ESI) Rt = 2.15 minutes MS m/z 274 [M + H]$^+$<br>Using (1-methyl-4-(4,4,5,5-tetramethyl-1,3,2-dioxaborolan-2-yl)-1H-pyrazol-5-yl)methanol (Preparation 141) and Method 12. |
| 26 | 3-Chloro-6-(1-(oxetan-3-ylmethyl)-1H-pyrazol-4-yl)isoquinoline | $^1$H NMR (500 MHz, CDCl$_3$): δ 9.00 (s, 1H), 7.96 (d, J = 8.68 Hz, 1H), 7.93 (s, 1H), 7.84-7.76 (m, 2H), 7.71 (d, J = 8.94 Hz, 1H), 7.68 (s, 1H), 4.89 (t, J = 7.08 Hz, 2H), 4.57 (t, J = 6.14 Hz, 2H), 4.53 (d, J = 7.34 Hz, 2H), 3.65-3.54 (m, 1H).<br>LCMS (ESI) Rt = 2.30 minutes MS m/z 300 [M + H]$^+$<br>Using 1-(oxetan-3-ylmethyl)-4-(4,4,5,5-tetramethyl-1,3,2-dioxaborolan-2-yl)-1H-pyrazole (Preparation 127) and Method 12. |

| Preparation No | Name/Structure | Data |
|---|---|---|
| 27 | Racemic 1-(4-(3-chloroisoquinolin-6-yl)-1H-pyrazol-1-yl)propan-2-ol | $^1$H NMR (500 MHz, CDCl$_3$): δ 8.92 (s, 1H), 7.90 (s, 1H), 7.89-7.84 (m, 2H), 7.68 (d, J = 1.60 Hz, 1H), 7.65 (dd, J = 1.54, 8.56 Hz, 1H), 7.58 (s, 1H), 4.36-4.28 (m, 1H), 4.25 (dd, J = 2.68, 13.80 Hz, 1H), 4.08 (dd, J = 7.98, 13.80 Hz, 1H), 1.29 (d, J = 6.26 Hz, 3H). LCMS (ESI) Rt = 2.23 minutes MS m/z 288 [M + H]$^+$<br>Using racemic 1-(4-(4,4,5,5-tetramethyl-1,3,2-dioxaborolan-2-yl)-1H-pyrazol-1-yl)propan-2-ol (Preparation 128) and Method 12. |
| 28 | 3-Chloro-6-(1-tetrahydro-2H-pyran-4-yl)-1H-pyrazol-4-yl)isoquinoline | $^1$H NMR (500 MHz, CDCl$_3$): δ 8.99 (s, 1H), 7.98-7.92 (m, 2H), 7.87 (d, J = 0.80 Hz, 1H), 7.81-7.79 (m, 1H), 7.73 (dd, J = 1.64, 8.56 Hz, 1H), 7.67 (s, 1H), 4.48-4.40 (m, 1H), 4.22-4.12 (m, 2H), 3.63-3.55 (m, 2H), 2.25-2.10 (m, 4H). LCMS (ESI) Rt = 2.45 minutes MS m/z 314 [M + H]$^+$<br>Using 1-(tetrahydro-2H-pyran-4-yl)-4-(4,4,5,5-tetramethyl-1,3,2-dioxaborolan-2-yl)-1H-pyrazole (Preparation 129) and Method 12. |
| 29 | Racemic 3-chloro-6-(1-((2,2-dimethyl-1,3-dioxolan-4-yl)methyl)-1H-pyrazol-4-yl)isoquinoline | $^1$H NMR (500 MHz, CDCl$_3$): δ 8.99 (s, 1H), 7.96-7.91 (m, 3H), 7.79 (d, J = 1.86 Hz, 1H), 7.72 (dd, J = 1.64, 8.58 Hz, 1H), 7.67 (d, J = 0.94 Hz, 1H), 4.53 (qd, J = 4.49, 6.02 Hz, 1H), 4.39-4.26 (m, 2H), 4.14 (dd, J = 6.34, 8.68 Hz, 1H), 3.84 (dd, J = 6.02, 8.68 Hz, 1H), 1.25 (s, 6H). LCMS (ESI) Rt = 2.69 minutes MS m/z 344 [M + H]$^+$<br>Using racemic 1-((2,2-dimethyl-1,3-dioxolan-4-yl)methyl)-4-(4,4,5,5-tetramethyl-1,3,2-dioxaborolan-2-yl)-1H-pyrazole (Preparation 130) and Method 12. |
| 30 | 1-((4-(3-Chloroisoquinolin-6-yl)-1H-pyrazol-1-yl)methyl)cyclobutanol | $^1$H NMR (500 MHz, CDCl$_3$): δ 9.00 (s, 1H), 7.99-7.91 (m, 3H), 7.80 (d, J = 1.68 Hz, 1H), 7.74 (dd, J = 1.60, 8.46 Hz, 1H), 7.68 (s, 1H), 4.33 (s, 2H), 2.22-2.08 (m, 4H), 1.93-1.83 (m, 1H), 1.74-1.61 (m, 1H). LCMS (ESI) Rt = 2.55 minutes MS m/z 314 [M + H]$^+$<br>Using 1-((2,2-dimethyl-1,3-dioxolan-4-yl)methyl)-4-(4,4,5,5-tetramethyl-1,3,2-dioxaborolan-2-yl)-1H-pyrazole (Preparation 131) and Method 12. |

| Preparation No | Name/Structure | Data |
|---|---|---|
| 31 | 3-Chloro-6-(1-(2,2,2-trifluoroethyl)-1H-pyrazol-4-yl)isoquinoline | $^1$H NMR (500 MHz, CDCl$_3$): δ 9.03 (s, 1H), 8.03 (d, J = 0.60 Hz, 1H), 7.98 (d, J = 8.52 Hz, 1H), 7.95 (s, 1H), 7.83 (d, J = 1.88 Hz, 1H), 7.73 (dd, J = 1.64, 8.52 Hz, 1H), 7.70 (s, 1H), 4.82 (q, J = 8.34 Hz, 2H). LCMS (ESI) Rt = 2.65 minutes MS m/z 312 [M + H]$^+$ Using 4-(4,4,5,5-tetramethyl-1,3,2-dioxaborolan-2-yl)-1-(2,2,2-trifluoroethyl)-1H-pyrazole (Preparation 132) and Method 12. |
| 32 | Racemic 3-(4-(3-chloroisoquinolin-6-yl)-1H-pyrazol-1-yl)-2-methylbutan-2-ol | $^1$H NMR (500 MHz, CDCl$_3$): δ 9.00 (s, 1H), 7.97 (s, 1H), 7.89 (s, 1H), 7.81 (s, 1H), 7.74 (dd, J = 1.66, 8.52 Hz, 1H), 7.68 (s, 1H), 7.46-7.42 (m, 1H), 4.17 (q, J = 6.96 Hz, 1H), 1.64 (d, J = 6.96 Hz, 3H), 1.25 (s, 6H). LCMS (ESI) Rt = 2.65 minutes MS m/z 316 [M + H]$^+$ Using 2-methyl-3-(4-(4,4,5,5-tetramethyl-1,3,2-dioxaborolan-2-yl)-1H-pyrazol-1-yl)butan-2-ol (Preparation 140) and Method 12. |
| 33 | Racemic 1-(4-(3-chloroisoquinolin-6-yl)-1H-pyrazol-1-yl)butan-2-ol | $^1$H NMR (500 MHz, CDCl$_3$): δ 8.86 (d, J = 0.78 Hz, 1H), 7.86 (d, J = 0.78 Hz, 1H), 7.84 (s, 1H), 7.81 (dd, J = 0.90, 9.12 Hz, 1H), 7.63-7.55 (m, 2H), 7.52 (d, J = 0.90 Hz, 1H), 4.29 (dd, J = 2.34, 13.54 Hz, 1H), 4.06-4.00 (m, 1H), 3.92-3.84 (m, 1H), 1.63-1.53 (m, 2H), 1.06 (t, J = 7.46 Hz, 3H). LCMS (ESI) Rt = 2.51 minutes MS m/z 302 [M + H]$^+$ Using racemic 1-(4-(4,4,5,5-tetramethyl-1,3,2-dioxaborolan-2-yl)-1H-pyrazol-1-yl)butan-2-ol (Preparation 134) and Method 12. |
| 34 | Racemic 1-(4-(3-chloroisoquinolin-6-yl)-1H-pyrazol-1-yl)-3-methylbutan-2-ol | $^1$H NMR (500 MHz, CDCl$_3$): δ 8.83 (s, 1H), 7.84 (d, J = 0.90 Hz, 1H), 7.82 (d, J = 0.96 Hz, 1H), 7.77 (dd, J = 0.90, 9.00 Hz, 1H), 7.57-7.53 (m, 2H), 7.48 (d, J = 0.96 Hz, 1H), 4.30 (dd, J = 2.42, 13.84 Hz, 1H), 4.09 (dd, J = 8.74, 13.84 Hz, 1H), 3.92 (d, J = 4.58 Hz, 1H), 3.86-3.80 (m, 1H), 1.85-1.72 (m, 1H), 1.05 (d, J = 3.30 Hz, 3H), 1.03 (d, J = 3.30 Hz, 3H). LCMS (ESI) Rt = 2.66 minutes MS m/z 316 [M + H]$^+$ Using racemic 3-methyl-1-(4-(4,4,5,5-tetramethyl-1,3,2-dioxaborolan-2-yl)-1H-pyrazol-1-yl)butan-2-ol (Preparation 135) and Method 12. |

-continued

| Preparation No | Name/Structure | Data |
|---|---|---|
| 35 | Racemic 3-(4-(3-chloroisoquinolin-6-yl)-1H-pyrazol-1-yl)-1,1,1-trifluoropropan-2-ol | $^1$H NMR (500 MHz, CDCl$_3$): δ 9.00 (s, 1H), 8.01-7.95 (m, 2H), 7.90 (d, J = 1.02 Hz, 1H), 7.80 (s, 1H), 7.75-7.69 (m, 2H), 4.58 (dd, J = 2.53, 14.06 Hz, 1H), 4.44-4.36 (m, 2H). LCMS (ESI) Rt = 2.60 minutes MS m/z 342 [M + H]$^+$ Using racemic 1,1,1-trifluoro-3-(4-(4,4,5,5-tetramethyl-1,3,2-dioxaborolan-2-yl)-1H-pyrazol-1-yl)propan-2-ol (Preparation 136) and Method 12. |
| 36 | Racemic 1-(4-(3-chloroisoquinolin-6-yl)-1H-pyrazol-1-yl)-3-methoxypropan-2-ol | $^1$H NMR (500 MHz, CDCl$_3$): δ 9.00 (s, 1H), 7.98-7.93 (m, 2H), 7.91 (d, J = 0.80 Hz, 1H), 7.79 (dd, J = 0.74, 1.44 Hz, 1H), 7.72 (dd, J = 1.64, 8.56 Hz, 1H), 7.67 (s, 1H), 4.42-4.36 (m. 1H), 4.32-4.24 (m, 2H), 3.49 (d, J = 4.45 Hz, 1H), 3.44-3.40 (m, 2H), 3.43 (s, 3H). LCMS (ESI) Rt = 2.43 minutes MS m/z 318 [M + H]$^+$ Using racemic 1-methoxy-3-(4-(4,4,5,5-tetramethyl-1,3,2-dioxaborolan-2-yl)-1H-pyrazol-1-yl)propan-2-ol (Preparation 137) and Method 12. |
| 37 | 3-Chloro-6-(1H-pyrazol-4-yl)isoquinoline | $^1$H NMR (500 MHz, MeOD): δ 9.03 (s, 1H), 8.35-8.15 (m, broad, 2H), 8.14-8.09 (m, 2H), 7.98 (dd, J = 1.80, 8.42 Hz, 1H), 7.88 (d, J = 0.82 Hz, 1H). LCMS (ESI) Rt = 2.32 minutes MS m/z 230 [M + H]$^+$ Using tert-butyl 4-(4,4,5,5-tetramethyl-1,3,2-dioxaborolan-2-yl)-1H-pyrazole-1-carboxylate and Method 12. |
| 38 | 3-chloro-6-(5-methylpyridin-3-yl)isoquinoline | $^1$H NMR (500 MHz, CDCl$_3$): δ 9.10 (s, 1H), 8.86 (s, broad, 1H), 8.63 (s, broad, 1H), 8.09 (d, J = 8.1 Hz, 1H), 7.94 (s, 1H), 7.89-7.75 (m, 2H), 7.69 (s, 1H), 2.49 (s, 3H). LCMS (ESI) Rt = 2.21 minutes MS m/z 255 [M + H]$^+$ Using (5-methylpyridin-3-yl)boronic acid and Method 12. |

Preparation 39: 3-(4-(3-Chloroisoquinolin-6-yl)-1H-pyrazol-1-yl)propane-1,2-diol

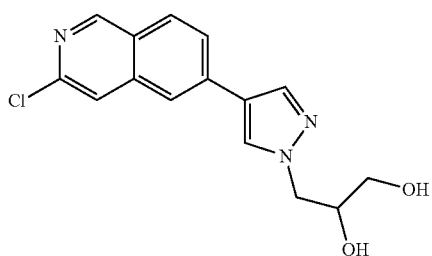 [SMILES: OCC(O)Cn1cc(-c2ccc3cnc(Cl)cc3c2)cn1]

To a solution of 3-chloro-6-(1-((2,2-dimethyl-1,3-dioxolan-4-yl)methyl)-1H-pyrazol-4-yl)isoquinoline (Preparation 29, 40 mg, 0.116 mmol) in THF (6 mL) at 0° C. was added hydrochloric acid (2.5M, 0.30 mL) and the reaction was stirred at room temperature for 16 hours. The solution was diluted with DCM, washed with saturated NaHCO$_3$ solution, dried over Na$_2$SO$_4$ and concentrated in vacuo to afford the title compound as a yellow oil that was used directly in the next step (23 mg, 65%).

$^1$H NMR (500 MHz, CDCl$_3$): δ 9.01 (s, 1H), 7.99-7.95 (m, 2H), 7.90 (d, J=0.82 Hz, 1H), 7.81-7.79 (m, 1H), 7.72 (dd, J=1.64, 8.54 Hz, 1H), 7.69 (s, 1H), 4.37 (d, J=5.62 Hz, 2H), 4.15-4.22 (m, 1H), 3.75-3.64 (m, 2H).

LCMS (ESI) Rt=2.17 minutes MS m/z 304 [M+H]$^+$

Preparation 40: 3-chloro-6-(1-methyl-1H-1,2,3-triazol-5-yl)isoquinoline

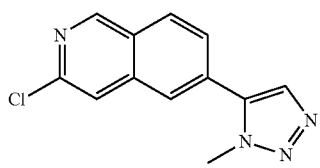 [SMILES: Cn1nncc1-c1ccc2cnc(Cl)cc2c1]

A suspension of 6-bromo-3-chloroisoquinoline (60 mg, 0.25 mmol), 1-methyl-1H-1,2,3-triazole (41 mg, 0.50 mmol), Pd(OAc)$_2$ (2.22 mg, 9.9 umol) and KOAc (49 mg, 0.50 mmol) in DMA (4 mL) was stirred at 150° C. under microwave irradiation for 60 minutes. The reaction mixture was diluted with brine and extracted with EtOAc. The combined organic layers were washed with water and dried with Na$_2$SO$_4$ and concentrated in vacuo. The residue was purified using Biotage silica gel column chromatography eluting with 40% EtOAc in cyclohexane to afford the title compound as a white solid (19 mg, 31%).

$^1$H NMR (500 MHz, CDCl$_3$): δ 0.17 (t, J=0.9 Hz, 1H), 8.15 (dt, J=8.5, 0.9 Hz, 1H), 7.94-7.85 (m, 2H), 7.82 (d, J=1.1 Hz, 1H), 7.67 (dd, J=8.5, 1.6 Hz, 1H), 4.19 (s, 3H).

LCMS (ESI) Rt=2.00 minutes MS m/z 245 [M+H]$^+$

Preparation 41: 5-(3-Chloroisoquinolin-6-yl)thiazole

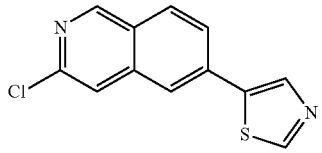 [SMILES: Clc1cc2cc(-c3cncs3)ccc2cn1]

A suspension of 6-bromo-3-chloroisoquinoline (39 mg, 0.16 mmol), 5-(tributylstannyl)-thiazole (72 mg, 0.19 mmol) and Pd(PPh$_3$)$_4$ (18.6 mg, 0.016 mmol) in DME/MeOH (3/1 mL) was stirred at 120° C. under microwave irradiation for 60 minutes. The reaction mixture was filtered and concentrated in vacuo. The residue was purified using Biotage silica gel column chromatography eluting with 25% EtOAc in cyclohexane to afford the title compound (11 mg, 28%).

$^1$H NMR (500 MHz, CDCl$_3$): δ 9.06 (d, J=0.9 Hz, 1H), 8.89 (s, 1H), 8.28 (d, J=0.6 Hz, 1H), 8.02 (dt, J=8.4, 0.8 Hz, 1H), 7.95-7.87 (m, 1H), 7.83 (dd, J=8.5, 1.7 Hz, 1H), 7.74 (d, J=1.0 Hz, 1H).

LCMS (ESI) Rt=2.42 minutes MS m/z 247 [M+H]$^+$

Preparation 42: 3-Chloro-6-(1-(2-methoxy-2-methylpropyl)-1H-pyrazol-4-yl)isoquinoline

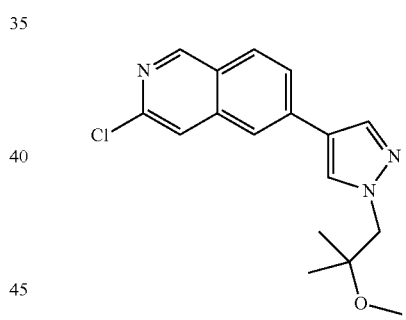

NaH (60%, 18 mg) was added to a solution of 1-(4-(3-chloroisoquinolin-6-yl)-1H-pyrazol-1-yl)-2-methylpropan-2-ol (Preparation 22, 96 mg, 0.318 mmol) in THF (6 mL). After stirring for 15 minutes, iodomethane (0.1 mL, 0.57 mmol) was added. The resulting solution was stirred at 60° C. under microwave irradiation for 60 minutes. The reaction mixture was diluted with EtOAc, filtered and purified using Biotage silica gel column chromatography eluting with 25% EtOAc/cyclohexane to give the title compound as yellow oil (57 mg, 57%).

$^1$H NMR (500 MHz, CDCl$_3$): δ 8.99 (s, 1H), 7.94 (d, J=8.68 Hz, 1H), 7.92 (d, J=0.80 Hz, 1H), 7.91 (d, J=0.80 Hz, 1H), 7.80 (d, J=1.54 Hz, 1H), 7.74 (dd, J=1.66, 8.56 Hz, 1H), 7.68-7.65 (m, 1H), 4.19 (s, 2H), 3.30 (s, 3H), 1.20 (s, 6H).

LCMS (ESI) Rt=2.79 minutes MS m/z 316 [M+H]$^+$

Preparation 43: Racemic 3-Chloro-6-(1-(2,3-dimethoxypropyl)-1H-pyrazol-4-yl)isoquinoline

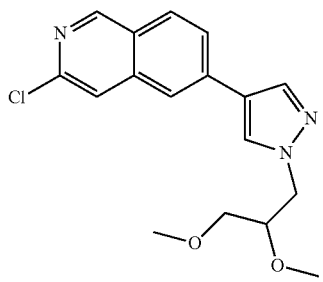 [SMILES: COCC(Cn1cc(-c2ccc3cnc(Cl)cc3c2)cn1)OC]

NaH (60%, 3.5 mg) was added to a solution of racemic 1-(4-(3-chloroisoquinolin-6-yl)-1H-pyrazol-1-yl)-3-methoxypropan-2-ol (Preparation 36, 20 mg, 0.063 mmol) in THF (4 mL). After stirring for 15 minutes, iodomethane (20 uL, 0.32 mmol) was added. The resulting solution was stirred at 60° C. under microwave irradiation for 60 minutes. The reaction mixture was extracted with EtOAc, dried over sodium sulphate and concentrated in vacuo. The residue was used in the next step without further purification.

$^1$H NMR (500 MHz, CDCl$_3$) δ 9.00 (s, 1H), 7.98-7.93 (m, 2H), 7.89 (d, J=0.82 Hz, 1H), 7.82-7.79 (m, 1H), 7.74 (dd, J=1.62, 8.54 Hz, 1H), 7.69 (s, 1H), 4.40 (dd, J=4.42, 14.16 Hz, 1H), 4.30 (dd, J=7.14, 14.16 Hz, 1H), 3.83-3.76 (m, 1H), 3.54 (dd, J=4.42, 10.32 Hz, 1H), 3.42-3.38 (m, 1H), 3.42 (s, 3H), 3.39 (s, 3H).

LCMS (ESI) Rt=2.63 minutes MS m/z 332 [M+H]$^+$

Preparation 44: 4-(4-(3-Chloroisoquinolin-6-yl)-1H-pyrazol-1-yl)tetrahydrofuran-3-ol

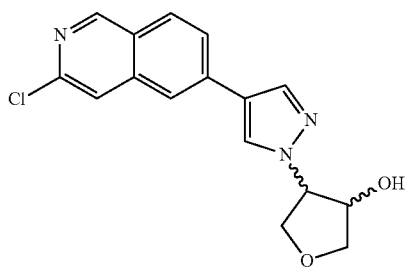 [SMILES: OC1COCC1n1cc(-c2ccc3cnc(Cl)cc3c2)cn1]

A mixture of Cs$_2$CO$_3$ (34 mg, 0.105 mmol), 3-chloro-6-(1H-pyrazol-4-yl)isoquinoline (16 mg, 0.070 mmol) and 3,6-dioxabicyclo[3.1.0]hexane (Preparation 37, 24 mg, 0.279 mmol) in DMF (3 mL) was stirred at 120° C. under microwave irradiation for 60 minutes. The reaction was cooled, concentrated in vacuo and purified using Biotage silica gel column chromatography eluting with 50-75% EtOAc/cyclohexane to give the title compound as white solid (10 mg, 46%).

$^1$H NMR (500 MHz, MeOD) δ 9.01 (s, 1H), 8.31 (d, J=0.80 Hz, 1H), 8.11 (d, J=0.80 Hz, 1H), 8.09 (d, J=8.78 Hz, 1H), 8.06 (d, J=2.02 Hz, 1H), 7.93 (dd, J=1.68, 8.62 Hz, 1H), 7.86 (s, 1H), 4.84 (ddd, J=2.32, 3.54, 6.13 Hz, 1H), 4.61 (dt, J=2.64, 5.24 Hz, 1H), 4.34 (dd, J=6.32, 9.92 Hz, 1H), 4.23 (dd, J=4.56, 9.16 Hz, 1H), 4.20 (dd, J=3.04, 9.36 Hz, 1H), 3.79 (dd, J=3.04, 9.76 Hz, 1H).

LCMS (ESI) Rt=2.38 minutes MS m/z 316 [M+H]$^+$

Preparation 45: 2-(4-(3-Chloroisoquinolin-6-yl)-1H-pyrazol-1-yl)cyclopentanol

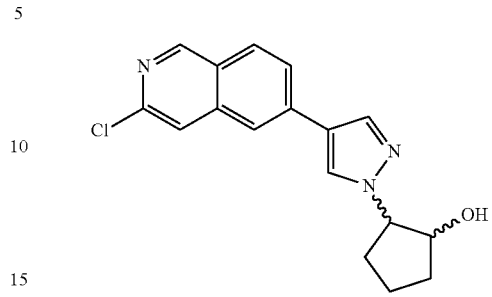

A mixture of Cs$_2$CO$_3$ (45.4 mg, 0.139 mmol), 3-chloro-6-(1H-pyrazol-4-yl)isoquinoline (16 mg, 0.070 mmol) and 6-oxabicyclo[3.1.0]hexane (Preparation 37, 23.4 mg, 0.279 mmol) in DMF (3 mL) was stirred at 120° C. under microwave irradiation for 60 minutes. The reaction was cooled, concentrated in vacuo and purified using Biotage silica gel column chromatography eluting with 50-75% EtOAc/cyclohexane to give the title compound as white solid (11 mg, 50%).

$^1$H NMR (500 MHz, CDCl$_3$) δ 8.96 (s, 1H), 7.94 (d, J=0.80 Hz, 1H), 7.92 (d, J=8.58 Hz, 1H), 7.84 (d, J=0.86 Hz, 1H), 7.73 (dd, J=0.80, 1.40 Hz, 1H), 7.69 (dd, J=1.62, 8.52 Hz, 1H), 7.64 (s, 1H), 4.50 (q, J=7.50 Hz, 1H), 4.40 (ddd, J=7.06, 8.08, 9.34 Hz, 1H), 2.42-2.34 (m, 1H), 2.26-2.12 (m, 2H), 2.01-1.90 (m, 2H), 1.85-1.75 (m, 1H).

LCMS (ESI) Rt=2.58 minutes MS mz/314 [M+H]$^+$

Preparation 46: Racemic 2-(4-(3-Chloroisoquinolin-6-yl)-1H-pyrazol-1-yl)cyclohexanol

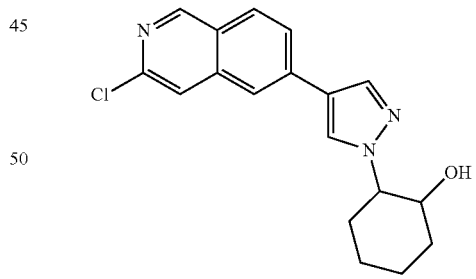

The title compound was prepared according to the method described for Preparation 45 using 3-chloro-6-(1H-pyrazol-4-yl)isoquinoline and 7-oxabicyclo[4.1.0]heptane.

$^1$H NMR (500 MHz, CDCl$_3$) δ 8.97 (s, 1H), 7.95 (d, J=0.80 Hz, 1H), 7.93 (d, J=8.56 Hz, 1H), 7.90 (d, J=0.92 Hz, 1H), 7.75 (d, J=1.46 Hz, 1H), 7.70 (dd, J=1.68, 8.56 Hz, 1H), 7.65 (s, 1H), 4.03-3.93 (m, 2H), 2.28-2.19 (m, 2H), 2.00-1.82 (m, 3H), 1.52-1.42 (m, 3H).

LCMS (ESI) Rt=2.68 minutes MS m/z 328 [M+H]$^+$

Preparations 47 and 48: 1-(4-(3-Chloroisoquinolin-6-yl)-2H-1,2,3-triazol-2-yl)-2-methylpropan-2-ol and 1-(4-(3-Chloroisoquinolin-6-yl)-1H-1,2,3-triazol-1-yl)-2-methylpropan-2-ol

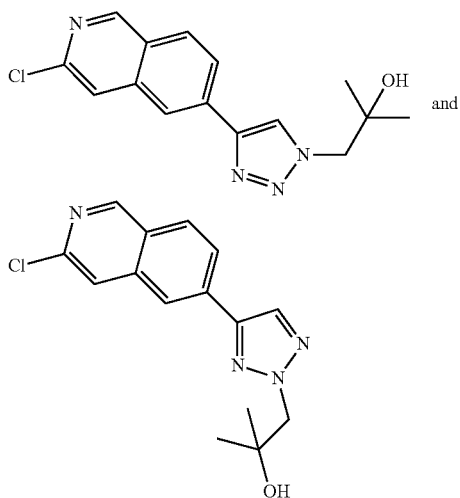

3-Chloro-6-(2H-1,2,3-triazol-4-yl)isoquinoline (Preparation 49, 90 mg, 0.39 mmol), cesium carbonate (96 mg, 0.3 mmol) and 2,2-dimethyloxirane (200 mg, 2.77 mmol) were suspended in dry DMF (2 mL). The reaction was heated to 120° C. under microwave irradiation for 1 hour. The reaction was cooled to room temperature and diluted with ethyl acetate. The organic solution was washed with water (20 mL), brine (20 mL), dried over sodium sulphate and concentrated in vacuo. The residue was purified using silica gel column chromatography eluting with 2% methanol in dichloromethane to afford two isomers:

First eluting compound: 1-(4-(3-Chloroisoquinolin-6-yl)-1H-1,2,3-triazol-1-yl)-2-methylpropan-2-ol (Preparation 48)

$^1$H NMR (500 MHz, CDCl$_3$): δ 9.09 (s, 1H), 8.18 (d, J=0.7 Hz, 1H), 8.08 (s, 1H), 8.06 (d, J=1.1 Hz, 2H), 7.77 (s, 1H), 4.55 (s, 2H), 1.29 (s, 6H).

LCMS (ESI) Rt=1.61 minutes MS m/z 303 [M+H]$^+$

Second eluting compound: 1-(4-(3-Chloroisoquinolin-6-yl)-1H-1,2,3-triazol-1-yl)-2-methylpropan-2-ol (Preparation 47)

$^1$H NMR (500 MHz, CD$_3$OD): δ 9.09 (s, 1H), 8.54 (s, 1H), 8.35 (d, J=0.5 Hz, 1H), 8.19-8.18 (m, 2H), 7.93 (s, 1H), 4.47 (s, 2H), 1.27 (s, 6H).

LCMS (ESI) Rt=1.49 minutes MS m/z 303 [M+H]$^+$

Preparation 49:
3-Chloro-6-(2H-1,2,3-triazol-4-yl)isoquinoline

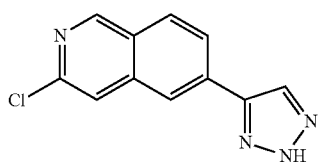 [SMILES: Clc1cc2cc(-c3cn[nH]n3)ccc2cn1]

3-chloro-6-ethynylisoquinoline (Preparation 50, 120 mg, 0.64 mmol) was dissolved in dry DMF (1 mL). Azidotrimethylsilane (1 mL, 7.5 mmol) was added and the reaction stirred at 120° C. for 2 hours. The reaction was cooled to room temperature and diluted with ethyl acetate (20 mL). The organic solution was washed with water (20 mL), brine (20 mL), dried over sodium sulphate and concentrated in vacuo. The residue was purified using silica gel column chromatography eluting with 2% 7N NH$_3$ in methanol in DCM followed by elution through an SCX-2 column using 50% methanol in chloroform followed by 50% 7N NH$_3$ in methanol in chloroform to afford the title compound as a pale brown powder (90 mg, 61%).

$^1$H NMR (500 MHz, DMSO-d$_6$): δ 9.21 (s, 1H), 8.6 (s, 1H), 8.48 (s, 1H), 8.27-8.2 (m, 2H), 8.07 (s, 1H).

LCMS (ESI) R$_t$=1.53 minutes MS m/z 231 [M+H]$^+$

Preparation 50: 3-Chloro-6-ethynylisoquinoline

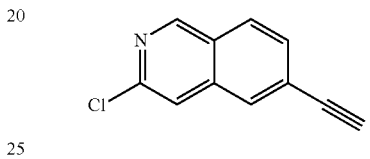

Potassium carbonate (9 mg, 0.0654 mmol) was added to a solution of 3-chloro-6-((trimethylsilyl)ethynyl)isoquinoline (Preparation 51, 170 mg, 0.654 mmol) in methanol (1 mL) and the reaction was stirred for 1 hour. Ethyl acetate (20 mL) was added and the organic solution was washed with water (20 mL), brine (20 mL), dried over sodium sulphate and concentrated in vacuo. The residue was purified by silica gel column chromatography eluting with 50% hexane in dichloromethane to afford the title compound as a white powder (110 mg, 90%).

$^1$H NMR (500 MHz, DMSO-d$_6$) δ 9.24 (s, 1H), 8.18 (d, J=8.5 Hz, 1H), 8.15 (s, 1H), 8.05 (s, 1H), 7.7 (dd, J=8.5, 1.6 Hz, 1H), 4.57 (s, 1H).

LCMS (ESI) R$_t$=1.65 minutes MS m/z 188 [M+H]$^+$

Preparation 51:
3-Chloro-6-((trimethylsilyl)ethynyl)isoquinoline

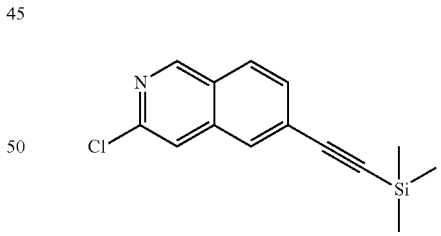

A suspension of 6-bromo-3-chloroisoquinoline (240 mg, 1 mmol), ethynyltrimethylsilane (150 mg, 1.5 mmol), triethylamine (150 mg, 1.5 mmol), copper iodide (20 mg, 0.1 mmol), triphenylphosphine (26 mg, 0.1 mmol), and palladium acetate (22.4 mg, 1 mmol) in dry DMF (1 mL) was heated at 65° C. for 30 minutes. The reaction was cooled to room temperature and diluted with ethyl acetate (20 mL). The organic solution was washed with water (20 mL), brine (20 mL), dried over sodium sulfate and concentrated in vacuo. The residue was purified by silica gel column chromatography eluting with 20% ethyl acetate in hexane to afford the title compound as a white powder (180 mg, 70%).

¹H NMR (500 MHz, DMSO-d₆): δ 9.23 (s, 1H), 8.16 (d, J=9 Hz, 1H), 8.14 (s, 1H), 8.02 (s, 1H), 7.7 (dd, J=9, 0.9 Hz, 1H), 0.27 (s, 9H).
LCMS (ESI) $R_t$=2.01 minutes MS m/z 260 [M+H]⁺

Preparation 52:
3-Chloro-N-methylisoquinoline-6-carboxamide

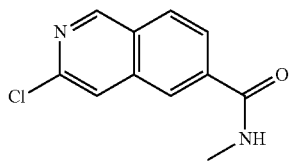

HATU (17.6 mg, 0.046 mmol) was added to a solution of 3-chloroisoquinoline-6-carboxylic acid (Preparation 54, 8 mg, 0.039 mmol), DIPEA (54 uL, 0.31 mmol) and methanamine hydrochloride (15.6 mg, 0.231 mmol) in DMF (4 mL) and the reaction was stirred for 18 hours. The reaction was partitioned between EtOAc and brine, the separated organic phase was washed with saturated NaHCO₃ solution, citric acid and brine, dried over Na₂SO₄ and concentrated in vacuo to afford the title compound as yellow oil (5.2 mg, 61%).
¹H NMR (500 MHz, MeOD) δ 9.18 (s, 1H), 8.34-8.30 (m, 1H), 8.21 (d, J=8.52 Hz, 1H), 8.03 (dd, J=1.65, 8.52 Hz, 1H), 8.00 (s, 1H), 3.00 (s, 3H).
LCMS (ESI) Rt=1.98 minutes MS m/z 221 [M+H]⁺

Preparation 53:
3-Chloro-N,N-dimethylisoquinoline-6-carboxamide

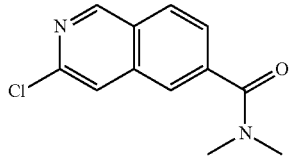 [SMILES: CN(C)C(=O)c1ccc2cnc(Cl)cc2c1]

The title compound was prepared according to the method described for Preparation 52 using 3-chloroisoquinoline-6-carboxylic acid (Preparation 54) and dimethylamine hydrochloride.
¹H NMR (500 MHz, CDCl₃) δ 9.10 (s, 1H), 8.04 (dd, J=0.86, 8.42 Hz, 1H), 7.81 (d, J=1.40 Hz, 1H), 7.76 (s, 1H), 7.63 (dd, J=1.40, 8.42 Hz, 1H), 3.19 (s, 3H), 3.01 (s, 3H).
LCMS (ESI) Rt=2.03 minutes MS m/z 235 [M+H]⁺

Preparation 54: 3-Chloroisoquinoline-6-carboxylic acid

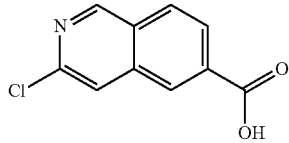 [SMILES: O=C(O)c1ccc2cnc(Cl)cc2c1]

A suspension of 6-bromo-3-chloroisoquinoline (93.5 mg, 0.386 mmol), 2-(trimethylsilyl)-ethanol (456 mg, 3.856 mmol), Pd(OAc)₂ (8.7 mg, 0.039 mmol), 1,1'-Bis(diphenylphosphino)ferrocene (45.1 mg, 0.077 mmol) and DMSO (27 uL, 0.386 mmol) in DMF (6 mL) was placed in a microwave tube (15 mL). The reaction was saturated with CO gas for 10 minutes before the tube was sealed and stirred at 120° C. under microwave irradiation for 10 hours. The reaction mixture was diluted with EtOAc and filtered. 2M NaOH (0.5 mL) was added to the filtrate and extracted with brine. The combined aqueous layers were washed with EtOAc and acidified carefully with drops of concentrated HCl to pH=3. The resulting cloudy solution was extracted with EtOAc, dried over sodium sulphate and concentrated in vacuo to afford the title compound as light brown solid (21 mg, 26%).
¹H NMR (500 MHz, DMSO) δ 13.57 (s, broad, 1H), 9.33 (s, 1H), 8.64 (d, J=1.60 Hz, 1H), 8.30-8.25 (m, 2H), 8.13 (dd, J=1.60, 8.56 Hz, 1H).
LCMS (ESI) Rt=2.28 minutes MS m/z 208 [M+H]⁺

Preparation 55: 2-Chloro-7-(1-methyl-1H-pyrazol-4-yl)pyrido[2,3-d]pyrimidine

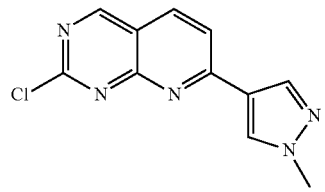 [SMILES: Cn1cc(-c2ccc3cnc(Cl)nc3n2)cn1]

7-(1-Methyl-1H-pyrazol-4-yl)-2-(methylthio)pyrido[2,3-d]pyrimidine (Preparation 56, 13 mg, 0.05 mmol), was dissolved in acetonitrile and stirred at 0° C. for 15 minutes followed by the addition of SO₂Cl₂ in DCM. After 20 minutes the solution was quenched with NaHCO₃ solution at 0° C., the organic solvents were removed in vacuo, and the solids were filtered, washed with water and dried to afford the title compound (7.5 mg, 60%).
¹H NMR (500 MHz, CDCl₃): δ 9.23 (s, 1H), 8.33 (s, 1H), 8.26 (d, J=8.4 Hz, 1H), 8.20 (s, 1H), 7.80 (d, J=8.4 Hz, 1H), 4.03 (s, 3H).
LCMS (ESI) Rt=1.82 minutes MS m/z 246 [M+H]⁺

Preparation 56: 7-(1-Methyl-1H-pyrazol-4-yl)-2-(methylthio)pyrido[2,3-d]pyrimidine

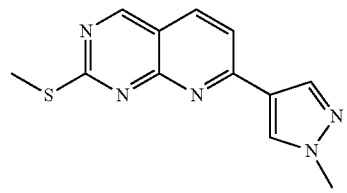 [SMILES: CSc1ncc2ccc(-c3cnn(C)c3)nc2n1]

A suspension of 7-chloro-2-(methylthio)pyrido[2,3-d]pyrimidine (Preparation 57, 31 mg, 0.146 mmol), 1-methyl-4-(4,4,5,5-tetramethyl-1,3,2-dioxaborolan-2-yl)-1H-pyrazole (43 mg, 0.21 mmol), Pd(PPh₃)₄ (17 mg, 0.015 mmol) and CsF (67 mg, 0.44 mmol), in DME/MeOH (3/1 mL) was stirred at 150° C. under microwave irradiation for 30 minutes. The reaction mixture was filtered, concentrated in vacuo onto silica gel and purified by Biotage silica gel column chromatography eluting with 80% EtOAc in cyclohexane to afford title compound as an yellow oil (13 mg, 35%).

¹H NMR (500 MHz, CDCl₃): δ 9.07 (s, 1H), 8.29 (s, 1H), 8.17 (d, J=0.8 Hz, 1H), 8.13 (d, J=8.4 Hz, 1H), 7.65 (d, J=8.4 Hz, 1H), 4.02 (s, 3H), 2.77 (s, 3H).

LCMS (ESI) Rt=2.04 minutes MS m/z 258 [M+H]⁺

Preparation 57:
7-Chloro-2-(methylthio)pyrido[2,3-d]pyrimidine

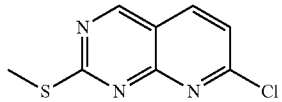

A suspension of 2-(methylthio)pyrido[2,3-d]pyrimidin-7(8H)-one (297 mg, 1.54 mmol) in POCl₃ (6 mL) was stirred under argon at 80° C. for 16 hours. The solution was cooled, and the resulting precipitate was filtered and washed with EtOAc to afford the title compound (43 mg, 13%). The filtrate was diluted with EtOAc, washed with NaHCO₃ and dried with Na₂SO₄. After removal of the solvent, a second crop was obtained (154 mg, 48%).

¹H NMR (500 MHz, DMSO-d₆): δ 9.52 (s, 1H), 8.61 (d, J=8.4 Hz, 1H), 7.74 (d, J=8.4 Hz, 1H), 2.63 (s, 3H).

LCMS (ESI) Rt=1.98 minutes MS m/z 212 [M+H]⁺

Preparation 58: 7-Bromo-2-(1-methyl-1H-pyrazol-4-yl)-1,6-naphthyridine

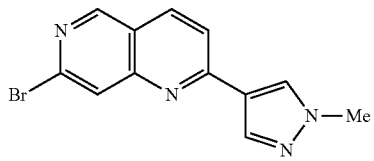 [SMILES: Cn1cc(-c2ccc3cnc(Br)cc3n2)cn1]

7-Bromo-2-chloro-1,6-naphthyridine (Preparation 61, 44.5 mg 0.183 mmole) and 1-methyl-4-(4,4,5,5-tetramethyl-1,3,2-dioxaborolan-2-yl)-1H-pyrazole (53.4 mg 0.256 mmole) were stirred in THF (1 mL) and 2M aqueous sodium carbonate solution (0.35 mL) was added. Palladium(dppf) dichloride.dichloromethane complex (4.0 mg, 0.0049 mmole) was added and the reaction heated at 60° C. for 4.5 hours under nitrogen. The reaction was diluted with ethyl acetate (15 mL) and the solution was washed with brine (7 mL). The brine was backwashed with ethyl acetate (7 mL) and the combined organic layers were dried and concentrated in vacuo. The residue was purified using preparative TLC eluting with EtOAc to afford the title compound (29 mg, 54%).

¹H NMR (500 MHz, CDCl₃): δ 8.95 (s, 1H), 8.22 (d, J=8.83 Hz, 1H), 8.18 (br s, 1H), 8.14 (s, 1H), 8.09 (br s, 1H), 7.72 (d, J=8.51 Hz, 1H), 4.03 (s, 3H).

Preparation 59: 1-(4-(7-Bromo-1,6-naphthyridin-2-yl)-1H-pyrazol-1-yl)-2-methylpropan-2-ol

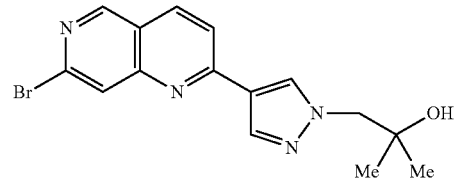 [SMILES: CC(C)(O)Cn1cc(-c2ccc3cnc(Br)cc3n2)cn1]

The title compound was prepared according to the method described for Preparation 58 using 7-Bromo-2-chloro-1,6-naphthyridine (Preparation 61) and 2-methyl-1-(4-(4,4,5,5-tetramethyl-1,3,2-dioxaborolan-2-yl)-1H-pyrazol-1-yl)propan-2-ol (Preparation 124).

¹H NMR (500 MHz, CDCl₃): δ 8.96 (s, 1H), 8.25 (s, 1H), 8.23 (d, J=8.51 Hz, 1H), 8.20 (s, 1H), 8.09 (s, 1H), 7.74 (d, J=8.83 Hz, 1H), 4.19 (s, 2H), 1.26 (s, 6H).

Preparation 60: 1-((4-(7-Bromo-1,6-naphthyridin-2-yl)-1H-pyrazol-1-yl)methyl)cyclobutanol

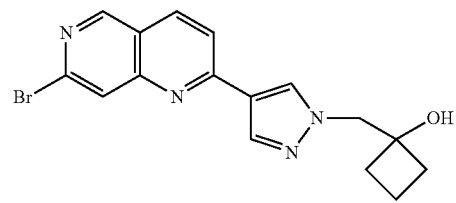 [SMILES: OC1(Cn2cc(-c3ccc4cnc(Br)cc4n3)cn2)CCC1]

The title compound was prepared according to the method described for Preparation 58 using 7-Bromo-2-chloro-1,6-naphthyridine (Preparation 61) and 1-((4-(4,4,5,5-tetramethyl-1,3,2-dioxaborolan-2-yl)-1H-pyrazol-1-yl)methyl)cyclobutanol (Preparation 131).

¹H NMR (500 MHz, CDCl₃): δ 8.96 (d, J=0.63 Hz, 1H), 8.30 (s, 1H), 8.23 (dd, J=0.95, 8.83 Hz, 1H), 8.17 (d, J=0.63 Hz, 1H), 8.10 (s, 1H), 7.74 (d, J=8.51 Hz, 1H), 4.35 (s, 2H), 2.08-2.16 (m, 4H), 1.83-1.92 (m, 1H), 1.62-1.72 (m, 1H).

Preparation 61:
7-Bromo-2-chloro-1,6-naphthyridine

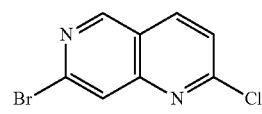 [SMILES: Clc1ccc2cnc(Br)cc2n1]

7-Bromo-1,6-naphthyridin-2(1H)-one (Preparation 67, 800 mg 3.55 mmole) was treated with phosphorus oxychloride (18 mL) and catalytic DMF (2 drops). The reaction was heated at 80° C. for 2.5 hours. The phosphorus oxychloride was evaporated and the residue was azeotroped with toluene (15 mL). The solid was partitioned between ethyl acetate (50 mL) and saturated aqueous sodium bicarbonate solution (30 mL) with ice (10 g). The aqueous layer was washed with EtOAc, the organic layers combined, washed with sodium bicarbonate solution, brine, dried over sodium sulphate and concentrated in vacuo to afford the title compound (826 mg, 95%).

¹H NMR (500 MHz, CDCl₃): δ 9.07 (d, 1H), 8.25 (dd, J=0.95, 8.83 Hz, 1H), 8.11 (t, J=0.63 Hz, 1H), 7.55 (d, J=8.51 Hz, 1H).

Preparation 62: 7-Bromo-N,N-dimethyl-1,6-naphthyridine-2-carboxamide

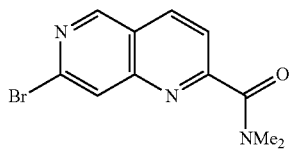

7-Bromo-1,6-naphthyridine-2-carboxylic acid (Preparation 64, 232 mg 0.92 mmole) was azeotroped with ethanol (10 mL) and then with toluene (2×12 mL). The residue was dissolved in acetone (3 mL) with triethylamine (260 uL, 1.85 mmole) and cooled in ice. Ethyl chloroformate (195 uL, 2.03 mmole) was added and the reaction stirred at 0-5° C. for 25 minutes. Dimethylamine (2M in THF, 2.2 mL, 4.4 mmole) was added and the reaction stirred at 0-5° C. for 10 minutes followed by room temperature for 50 minutes. The acetone was evaporated and the residue partitioned between ethyl acetate (25 mL) and water (8 mL). The organic layer was washed with water (8 mL), brine, dried over sodium sulphate and concentrated in vacuo. The residue was purified using preparative TLC eluting with 9:1 ethyl acetate:acetone to afford the title compound (106 mg, 41%).

¹H NMR (500 MHz, CD₃COCD₃): δ 9.27 (d, J=0.63 Hz, 1H), 8.72 (dd, J=0.63, 8.51 Hz, 1H), 8.17 (t, J=0.95 Hz, 1H), 7.85 (d, J=8.51 Hz, 1H), 3.14 (s, 3H), 3.09 (s, 3H).

Preparation 63: 7-Bromo-N-methyl-1,6-naphthyridine-2-carboxamide

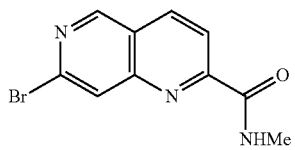 [SMILES: CNC(=O)c1ccc2cnc(Br)cc2n1]

The title compound was prepared according to the method described for Preparation 62 using methylamine and eluting with EtOAc.

¹H NMR (500 MHz, DMSO-d₆): δ 9.38 (d, J=0.63 Hz, 1H), 9.00 (br m, 1H), 8.81 (dd, J=0.95, 8.51 Hz, 1H), 8.30 (d, J=8.51 Hz, 1H), 8.20 (s, 1H), 2.89 (s, 3H).

Preparation 64: 7-Bromo-1,6-naphthyridine-2-carboxylic acid

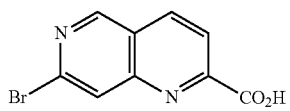 [SMILES: O=C(O)c1ccc2cnc(Br)cc2n1]

7-Bromo-2-methyl-1,6-napthyridine (Preparation 65, 206 mg, 0.92 mmol) and selenium dioxide (102.5 mg, 0.92 mmol) were heated in dioxane (3 mL) at 80° C. for 2 hours. The reaction was diluted with DCM (6 mL) and filtered through celite. The filter cake was washed with DCM (3×9 mL) and the combined filtrates concentrated in vacuo. The residue was stirred with formic acid (1 mL) and hydrogen peroxide (35% aqueous solution, 50 uL, 0.67 mmol) was added. The reaction was stirred at 0° C. for 1 hour before the reaction was quenched by the addition of palladium on charcoal (3 mg) and stirred for a further 20 minutes. The reaction was concentrated in vacuo to afford the title compound.

¹H NMR (500 MHz, DMSO-d₆): δ 9.39 (d, J=0.63 Hz, 1H), 8.81 (dd, J=0.95, 8.83 Hz, 1H), 8.35 (s, 1H), 8.26 (d, J=8.51 Hz, 1H).

Preparation 65: 7-Bromo-2-methyl-1,6-naphthyridine

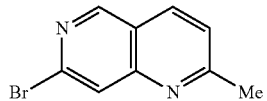

(E)-4-(4-Amino-6-bromopyridin-3-yl)but-3-en-2-one (Preparation 66, 331 mg 1.37 mmol) and sodium thiomethoxide (97.5 mg 1.39 mmol) were stirred in ethanol (2.9 mL) at 20° C. for 50 minutes. Iodomethane (86 uL, 1.38 mmole) was added and the reaction stirred for another 45 minutes. The reaction was concentrated in vacuo and diluted with ethyl acetate (30 mL) and washed with water (10 mL). The aqueous was back extracted with ethyl acetate (5 mL) and the combined organic layers were washed with brine, dried over sodium sulfate and concentrated in vacuo to afford the title compound (275 mg, 89%).

¹H NMR (500 MHz, CDCl₃): δ 9.00 (d, J=0.63 Hz, 1H), 8.17 (dd, J=0.95, 8.51 Hz, 1H), 8.09 (s, 1H), 7.44 (d, J=8.51 Hz), 2.80 (s, 3H).

Preparation 66: (E)-4-(4-Amino-6-bromopyridin-3-yl)but-3-en-2-one

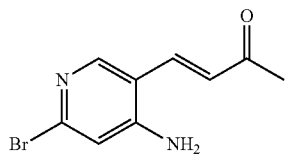

4-Amino-2-bromo-5-iodopyridine (4.49 g 15 mmol), tri-o-tolylphosphine (363 mg 1.2 mmol) and palladium acetate (135 mg 0.60 mmol) were dissolved in DMF (45 mL) and di-isopropylethylamine (3.76 mL, 21.6 mmol) and methyl vinyl ketone (2.45 mL, 30 mmol) were added. The reaction was placed under nitrogen and heated at 80° C. for 70 minutes. The reaction was cooled and concentrated in vacuo. Ethyl acetate (150 mL) was added and the solution was washed with water (80 mL). The organic layer was collected, washed with water (2×60 mL) brine, dried over sodium sulfate and concentrated in vacuo. The residue was triturated with ether (2×10 mL) to afford the title compound (2.85 g, 78%).

$^1$H NMR (500 MHz, DMSO-d$_6$): δ 8.21 (s, 1H), 7.65 (d, J=16.1 Hz, 1H), 6.82 (br s, 1H, NH$_2$), 6.77 (s, 1H), 6.68 (d, J=16.1 Hz, 1H), 2.33 (s, 3H).

Preparation 67:
7-Bromo-1,6-naphthyridin-2(1H)-one

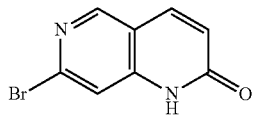

(E)-Ethyl 3-(4-amino-6-bromopyridin-3-yl)acrylate (Preparation 68, 1.20 g 4.43 mmole) and sodium methanethiolate (320 mg 4.57 mmole) in ethanol (12 mL) were heated under microwave radiation at 80° C. for 25 minutes. Iodomethane (284 uL, 648 mg, 4.56 mmole) was added to the cooled reaction and the reaction was stirred at room temperature for 45 minutes before diluting with water (6 mL). The resulting precipitate was collected, washed with water and dried under high vacuum to afford the title compound (803 mg, 80%).

$^1$H NMR (500 MHz, DMSO-d$_6$): δ 12.10 (br s, 1H), 8.65 (s, 1H), 7.99 (d, J=9.77 Hz), 7.36 (s, 1H), 6.62 (d, J=9.77 Hz, 1H).

Preparation 68: (E)-Ethyl 3-(4-amino-6-bromopyridin-3-yl)acrylate

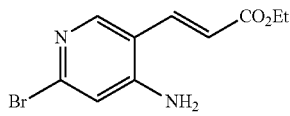

4-Amino-2-bromo-5-iodopyridine (9.0 g 30.0 mmole) was dissolved in DMF (90 mL) and ethyl acrylate (6.5 mL, 60 mmole), triethylamine (6.1 mL, 43.2 mmole), tri-o-tolylphosphine (728 mg 2.4 mmole) and palladium acetate (270 mg 1.2 mmole) were added. The reaction was placed under nitrogen and heated at 100° C. for 3 hours. The reaction was concentrated in vacuo and diluted with EtOAc (250 mL). Water (100 mL) was added and the biphasic mixture filtered through celite. The filter cake was washed with EtOAc and the organic layers collected. The combined organic layers were washed with water (2×100 mL), brine, dried over sodium sulphate and concentrated in vacuo. The residue was purified using silica gel column chromatography eluting with a gradient of 10-40% EtOAc in DCM to afford the title compound (7.29 g, 89%).

$^1$H NMR (500 MHz, DMSO-d$_6$): δ 8.23 (s, 1H), 7.73 (d, J=16.1 Hz, 1H), 6.81 (br s, 2H), 6.76 (s, 1H), 6.53 (d, J=15.8 Hz, 1H), 4.18 (q, J=7.3 Hz, 2H), 1.26 (t, J=7.1 Hz, 3H).

Preparation 69: 2-Methyl-1-(4-(2-(methylsulfonyl)pyrido[2,3-d]pyrimidin-7-yl)-1H-pyrazol-1-yl)propan-2-ol

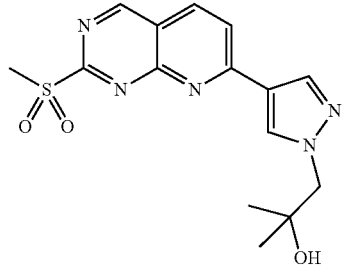 [SMILES: CC(C)(O)Cn1cc(-c2ccc3cnc(S(C)(=O)=O)nc3n2)cn1]

To a solution of 2-methyl-1-(4-(2-(methylthio)pyrido[2,3-d]pyrimidin-7-yl)-1H-pyrazol-1-yl)propan-2-ol (Preparation 70, 21 mg, 0.067 mmol) in DCM (8 mL) at 0° C. was added mCPBA (35.8 mg, 0.160 mmol). The reaction mixture was stirred for at room temperature for 16 hours. The reaction mixture was purified using Biotage silica gel column chromatography eluting with 0-4% MeOH/EtOAc to give the title compound as yellow semi-solid (15.5 mg, 67%).

$^1$H NMR (500 MHz, CDCl$_3$): δ 9.54 (s, 1H), 8.46 (s, 1H), 8.41 (d, J=8.54 Hz, 1H), 8.27 (d, J=0.70 Hz, 1H), 7.97 (d, J=8.54 Hz, 1H), 4.22 (s, 2H), 3.54 (s, 3H), 1.26 (s, 6H).
LCMS (ESI) Rt=1.53 minutes MS m/z 348 [M+H]$^+$ Preparation 70: 2-Methyl-1-(4-(2-(methylthio)pyrido[2,3-d]pyrimidin-7-yl)-1H-pyrazol-1-yl)propan-2-ol

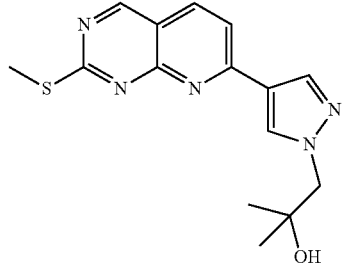 [SMILES: CSc1ncc2ccc(-c3cnn(CC(C)(C)O)c3)nc2n1]

A suspension of 7-chloro-2-(methylthio)pyrido[2,3-d]pyrimidine (Preparation 57, 50.6 mg, 0.239 mmol), 2-methyl-1-(4-(4,4,5,5-tetramethyl-1,3,2-dioxaborolan-2-yl)-1H-pyrazol-1-yl)propan-2-ol (Preparation 124, 63.6 mg, 0.239 mmol), Pd(dppf)Cl$_2$.DCM (20.2 mg, 0.024 mmol), Na$_2$CO$_3$ (2M, 0.24 mL, 0.48 mmol) in DME (4 mL) was stirred at 140° C. under microwave irradiation for 60 minutes. The reaction mixture was diluted with EtOAc and dried with Na$_2$SO$_4$, filtered and concentrated in vacuo. The residue was purified using Biotage silica gel column chromatography eluting with 25-80% EtOAc/cyclohexane to give the title compound as orange semi-solid (21 mg, 28%).

$^1$H NMR (500 MHz, CDCl$_3$): δ 9.07 (s, 1H), 8.37 (s, 1H), 8.21 (d, J=0.75 Hz, 1H), 8.15 (d, J=8.36 Hz, 1H), 7.67 (d, J=8.36 Hz, 1H), 4.17 (s, 2H), 2.75 (s, 3H), 1.24 (s, 6H).
LCMS (ESI) Rt=2.18 minutes MS m/z 316 [M+H]$^+$ Preparation 71:
N-(4-Cyano-2-methoxyphenyl)formamide

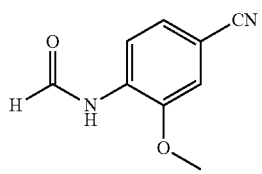

Acetic anhydride (0.65 mL, 6.7 mmol) was cooled in an ice bath and formic acid (0.38 mL, 10 mmol) was added with stirring. The ice-bath was removed and the mixture was stirred for a further 60 minutes. The reaction was re-cooled in the ice-bath and 4-amino-3-methoxybenzonitrile (0.25 g, 1.58 mmol) was added. The reaction was stirred at ice-bath temperature for 5 minutes, then at room temperature for 60 minutes. The reaction was concentrated in vacuo, azeotroped with toluene and the title compound was precipitated from ether/hexanes as a white powder (255 mg, 71.3%).

$^1$H NMR (500 MHz, DMSO-$d_6$): δ 10.07 (s, 1H), 8.39 (s, 1H), 8.37 (s, 1H), 7.52 (d, J=1.7 Hz, 1H), 7.4 (dd, J=8.4, 1.8 Hz, 1H), 3.92 (s, 3H).

LCMS (ESI) $R_t$=1.76 minutes MS m/z 177 [M+H]$^+$

Preparation 72:
2-Chloro-4-(5-methyl-1,3,4-oxadiazol-2-yl)aniline

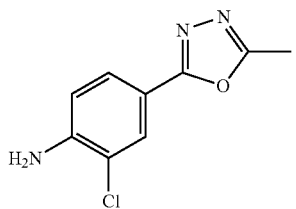

To a mixture of 4-(5-methyl-1,3,4-oxadiazol-2-yl)aniline (0.220 g, 1.26 mmol) and anhydrous DMF (1.9 mL) was added N-chlorosuccinimide (0.168 g, 1.26 mmol). The reaction mixture was heated at 40° C. for 1.5 hours under argon before being allowed to cool to room temperature and partitioned between EtOAc (90 mL) and saturated aqueous NaHCO$_3$ (15 mL). The organic layer was washed with saturated aqueous NaHCO$_3$ (15 mL), dried (Na$_2$SO$_4$) and concentrated in vacuo. The brown residue was absorbed on silica gel (1.4 g), and purified using silica gel column chromatography eluting with a gradient of 0-30% EtOAc in CH$_2$Cl$_2$ to afford the title compound as a white solid (0.130 g, 49%).

$^1$H NMR (500 MHz, DMSO-$d_6$): δ 7.72 (d, J=2.0 Hz, 1H), 7.61 (dd, J=2.0, 8.5 Hz, 1H), 6.90 (d, J=8.2 Hz, 1H), 6.14 (s, 2H), 2.53 (s, 3H).

LCMS (ESI) Rt=2.06 minutes MS m/z 210 [M$^{35}$Cl+H]$^+$

Preparation 73:
2-methoxy-4-(1-methyl-1H-imidazol-5-yl)aniline

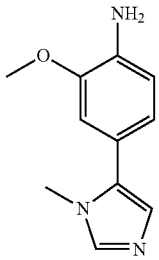

Method F

A suspension of 5-bromo-1-methyl-1H-imidazole (228 mg, 1.42 mmol), 2-methoxy-4-(4,4,5,5-tetramethyl-1,3,2-dioxaborolan-2-yl)aniline (423 mg, 1.70 mmol), Pd(PPh$_3$)$_4$ (164 mg, 0.142 mmol) and CsF (645 mg, 4.25 mmol) in DME/MeOH (9/3 mL) was stirred at 150° C. under microwave irradiation for 60 minutes. The reaction mixture was filtered and concentrated in vacuo. The residue was purified using Biotage silica gel column chromatography eluting with between 0-4% MeOH in EtOAc to afford the title compound (137 mg, 48%).

$^1$H NMR (500 MHz, CDCl$_3$): δ 7.56 (s, 1H), 7.02 (s, 1H), 6.81-6.76 (m, 3H), 3.95 (s, broad, 2H), 3.88 (s, 3H), 3.64 (s, 3H).

LCMS (ESI) Rt=0.43 minutes MS m/z 204 [M+H]$^+$

The following Preparations were prepared according to Method F (Preparation 73) above using the appropriate aniline and heterocyclic cross-coupling partner as described.

The Preparations were purified according to the method described or as described below:

Method A: Biotage silica gel column chromatography eluting with 1-5% MeOH in DCM.
Method B: Biotage silica gel column chromatography eluting with EtOAc followed by elution through an SCX-2 cartridge.
Method C: Biotage silica gel column chromatography eluting with from 30-100% EtOAc in cyclohexanes.
Method D: Biotage silica gel column chromatography eluting with EtOAc.
Method E: Elution through an SCX-2 cartridge using 2M NH$_3$/MeOH.

| Preparation No | Name/Structure | Data |
|---|---|---|
| 74 | 4-(1,2-dimethyl-1H-imidazol-5-yl)-2-methoxyaniline | $^1$H NMR (500 MHz, DMSO-$d_6$): δ 6.77 (s, 1H), 6.65-6.72 (s, 3H), 4.87 (s, 2H), 3.78 (s, 3H), 3.46 (s, 3H), 2.31 (s, 3H). LCMS (ESI) Rt = 0.49 minutes MS m/z 218 [M + H]$^+$ Using 5-bromo-1,2-dimethyl-1H-imidazole and 2-methoxy-4-(4,4,5,5-tetramethyl-1,3,2-dioxaborolan-2-yl)aniline. |

| Preparation No | Name/Structure | Data |
|---|---|---|
| 75 | 2-Chloro-4-(1,2-dimethyl-1H-imidazol-5-yl)aniline 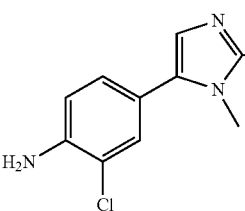 | $^1$H NMR (500 MHz, CDCl$_3$): δ 2.43 (s, 3H), 3.48 (s, 3H), 4.21 (br s, 2H), 6.81 (d, J = 8.2 Hz, 1H), 6.87 (s, 1H), 7.05 (dd, J = 8.2, 2.0 Hz, 1H), 7.24 (d, J = 2.0 Hz, 1H). LCMS (ESI) Rt = 0.96 minutes MS m/z 222 [M + H]$^+$ Using 5-bromo-1,2-dimethyl-1H-imidazole and 2-chloro-4-(4,4,5,5-tetramethyl-1,3,2-dioxaborolan-2-yl)aniline for 10 minutes at 150° C. and purification method A. |
| 76 | (5-(4-Amino-3-methoxyphenyl)-1-methyl-1H-imidazol-2-yl)methanol 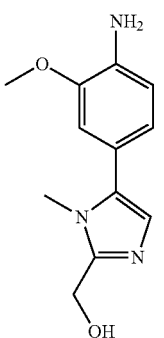 | LCMS (ESI) Rt = 0.40 minutes MS m/z 234 [M + H]$^+$ Using (5-bromo-1-methyl-1H-imidazol-2-yl)methanol and 2-methoxy-4-(4,4,5,5-tetramethyl-1,3,2-dioxaborolan-2-yl)aniline. |
| 77 | 2-Methoxy-4-(1-(2-methoxyethyl)-2-methyl-1H-imidazol-5-yl)aniline 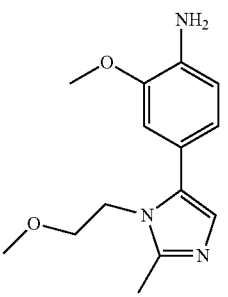 | $^1$H NMR (500 MHz, CDCl$_3$): δ 6.86 (s, 1H), 6.81 (d, J = 1.72 Hz, 1H), 6.78 (dd, J = 1.72, 7.86 Hz, 1H), 6.73 (d, J = 7.88 Hz, 1H), 4.03 (t, J = 5.92 Hz, 2H), 3.86 (s, 3H), 3.43 (t, J = 5.92 Hz, 2H), 3.23 (s, 3H), 2.48 (s, 3H). LCMS (ESI) Rt = 0.73 minutes MS m/z 262 [M + H]$^+$ Using 5-bromo-1-(2-methoxyethyl)-2-methyl-1H-imidazole (Preparation 143) and 2-methoxy-4-(4,4,5,5-tetramethyl-1,3,2-dioxaborolan-2-yl)aniline. |
| 78 | (4-(4-Amino-3-methoxyphenyl)-1-methyl-1H-pyrazol-5-yl)methanol 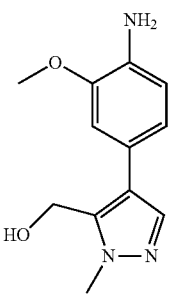 | $^1$H NMR (500 MHz, CDCl$_3$): δ 7.53 (s, 1H), 6.85 (d, J = 1.80 Hz, 1H), 6.82 (dd, J = 1.80, 7.90 Hz, 1H), 6.77 (d, J = 7.90 Hz, 1H), 4.77 (s, 2H), 4.00 (s, 3H), 3.90 (s, 3H). LCMS (ESI) Rt = 0.82 minutes MS m/z 234 [M + H]$^+$ Using (4-bromo-1-methyl-1H-pyrazol-5-yl)methanol (Preparation 149) and 2-methoxy-4-(4,4,5,5-tetramethyl-1,3,2-dioxaborolan-2-yl)aniline and purification method B. |

| Preparation No | Name/Structure | Data |
|---|---|---|
| 79 | tert-Butyl 4-((5-(4-amino-3-methoxyphenyl)-2-methyl-1H-imidazol-1-yl)methyl)piperidine-1-carboxylate | $^1$H NMR (500 MHz, CDCl$_3$): δ 6.93 (d, J = 1.33 Hz, 1H), 6.87 (s, 1H), 6.79 (d, J = 1.36 Hz, 1H), 6.75-6.73 (m, 1H), 4.08-3.88 (m, broad, 2H), 3.87 (s, 3H), 3.72 (d, J = 7.40 Hz, 2H), 2.72-2.58 (m, 2H), 2.43 (s, 3H), 1.98-1.86 (m, 1H), 1.63-1.51 (m, 2H), 1.47 (s, 9H), 1.30-1.13 (m, 2H). LCMS (ESI) Rt = 1.72 minutes MS m/z 401 [M + H]$^+$ Using tert-butyl 4-((5-bromo-2-methyl-1H-imidazol-1-yl)methyl)piperidine-1-carboxylate (Preparation 144) and 2-methoxy-4-(4,4,5,5-tetramethyl-1,3,2-dioxaborolan-2-yl)aniline. |
| 80 | 4-(1,2-Dimethyl-1H-imidazol-5-yl)aniline | $^1$H NMR (500 MHz, CDCl$_3$): δ 7.14 (d, J = 8.60 Hz, 2H), 6.89 (s, 1H), 6.75 (d, J = 8.60 Hz, 2H), 3.50 (s, 3H), 2.48 (s, 3H). LCMS (ESI) Rt = 0.53 minutes MS m/z 188 [M + H]$^+$ Using 5-bromo-1,2-dimethyl-1H-imidazole and 4-(4,4,5,5-tetramethyl-1,3,2-dioxaborolan-2-yl)aniline. |
| 81 | 4-(1,2-Dimethyl-1H-imidazol-5-yl)-3-fluoro-2-methoxyaniline | $^1$H NMR (500 MHz, CDCl$_3$): δ 6.88 (s, 1H), 6.79 (dd, J = 7.46, 8.28 Hz, 1H), 6.53 (dd, J = 1.48, 8.36 Hz, 1H), 3.93 (d, J = 1.38 Hz, 3H), 3.41 (d, J = 1.70 Hz, 3H), 2.44 (s, 3H). LCMS (ESI) Rt = 1.07 minutes MS m/z 236 [M + H]$^+$ Using 5-bromo-1,2-dimethyl-1H-imidazole and 3-fluoro-2-methoxy-4-(4,4,5,5-tetramethyl-1,3,2-dioxaborolan-2-yl)aniline (Preparation 102). |
| 82 | 2-Methoxy-4-(5-(methoxymethyl)-1-methyl-1H-pyrazol-4-yl)aniline | $^1$H NMR (500 MHz, CDCl$_3$): δ 7.53 (s, 1H), 6.85 (d, J = 1.74 Hz, 1H), 6.81 (dd, J = 1.78, 7.86 Hz, 1H), 6.76 (d, J = 7.86 Hz, 1H), 4.48 (s, 2H), 3.95 (s, 3H), 3.89 (s, 3H), 3.40 (s, 3H). LCMS (ESI) Rt = 1.37 minutes MS m/z 248 [M + H]$^+$ Using 4-bromo-5-(methoxymethyl)-1-methyl-1H-pyrazole (Preparation 150) and 2-methoxy-4-(4,4,5,5-tetramethyl-1,3,2-dioxaborolan-2-yl)aniline and purification method C. |

-continued

| Preparation No | Name/Structure | Data |
|---|---|---|
| 83 | 4-(1,5-Dimethyl-1H-pyrazol-4-yl)-2-methoxyaniline 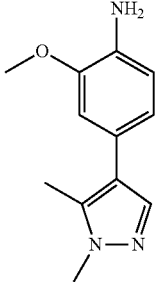 | $^1$H NMR (500 MHz, CDCl$_3$): δ 7.51 (s, 1H), 6.86 (d, J = 8.46 Hz, 1H), 6.82-6.77 (m, 2H), 3.90 (s, 3H), 3.85 (s, 3H), 2.37 (s, 3H). LCMS (ESI) Rt = 1.37 minutes MS m/z 218 [M + H]$^+$ Using 4-bromo-2-methoxyaniline and 1,5-dimethyl-4-(4,4,5,5-tetramethyl-1,3,2-dioxaborolan-2-yl)-1H-pyrazole and purification method C. |
| 84 | tert-Butyl 3-(4-amino-3-methoxyphenyl)-5,6-dihydro-[1,2,4]triazolo[4,3-a]pyrazine-7(8H)-carboxylate 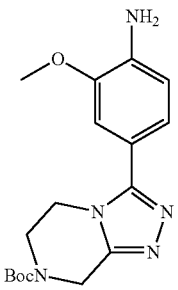 | $^1$H NMR (500 MHz, CDCl$_3$): δ 7.29 (s, 1H), 7.00 (dd, J = 1.84, 8.02 Hz, 1H), 6.77 (d, J = 8.02 Hz, 1H), 4.91 (s, 2H), 4.14-4.07 (m, 2H), 3.93 (s, 3H), 3.87-3.76 (m, 2H), 1.52 (s, 9H). LCMS (ESI) Rt = 2.07 minutes MS m/z 346 [M + H]$^+$ Using tert-butyl 3-bromo-5,6-dihydro-[1,2,4]triazolo[4,3-a]pyrazine-7(8H)-carboxylate and 2-methoxy-4-(4,4,5,5-tetramethyl-1,3,2-dioxaborolan-2-yl)aniline at 140° C. |
| 85 | 2-Methoxy-4-(2-(methoxymethyl)-1-methyl-1H-imidazol-5-yl)aniline 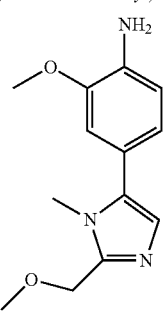 | $^1$H NMR (500 MHz, CDCl$_3$): δ 6.97 (s, 1H), 6.81-6.75 (m, 3H), 4.61 (s, 2H), 3.88 (s, 3H), 3.63 (s, 3H), 3.41 (s, 3H). LCMS (ESI) Rt = 0.90 minutes MS m/z 248 [M + H]$^+$ Using 5-bromo-2-(methoxymethyl)-1-methyl-1H-imidazole (Preparation 151) and 2-methoxy-4-(4,4,5,5-tetramethyl-1,3,2-dioxaborolan-2-yl)aniline. |
| 86 | 2-Methoxy-4-(2-(methoxymethyl)-1-methyl-1H-imidazol-5-yl)aniline 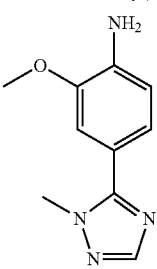 | $^1$H NMR (500 MHz, CDCl$_3$): δ 7.88 (s, 1H), 7.18 (d, J = 1.86 Hz, 1H), 7.04 (dd, J = 1.86, 8.02 Hz, 1H), 6.76 (d, J = 8.02 Hz, 1H), 3.98 (s, 3H), 3.90 (s, 3H). LCMS (ESI) Rt = 1.25 minutes MS m/z 205 [M + H]$^+$ Using 5-bromo-1-methyl-1H-1,2,4-triazole and 2-methoxy-4-(4,4,5,5-tetramethyl-1,3,2-dioxaborolan-2-yl)aniline and purification method D. |

| Preparation No | Name/Structure | Data |
|---|---|---|
| 87 | 1-(5-(4-Amino-3-methoxyphenyl)-2-methyl-1H-imidazol-1-yl)-2-methylpropan-2-ol 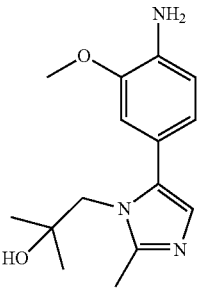 | $^1$H NMR (500 MHz, CDCl$_3$): δ 6.78 (s, 1H), 6.76-6.70 (m, 3H), 4.00 (s, 2H), 3.86 (s, 3H), 2.52 (s, 3H), 1.00 (s, 6H). LCMS (ESI) Rt = 0.78 minutes MS m/z 276 [M + H]$^+$ Using 1-(5-bromo-2-methyl-1H-imidazol-1-yl)-2-methylpropan-2-ol (Preparation 145) and 2-methoxy-4-(4,4,5,5-tetramethyl-1,3,2-dioxaborolan-2-yl)aniline. |
| 88 | 2-Methoxy-4-(7-methyl-5,6,7,8-tetrahydro-[1,2,4]triazolo[4,3-a]pyrazine-3-yl)aniline 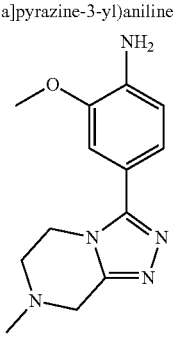 | $^1$H NMR (500 MHz, CDCl$_3$): δ 7.02 (dd, J = 1.80, 8.00 Hz, 1H), 6.82-6.78 (m, 1H), 6.78-6.75 (m, 1H), 4.13-4.08 (m, 2H), 3.86 (s, 3H), 3.81 (s, 2H), 2.85-2.82 (m, 2H), 2.55 (s, 3H). Using 3-bromo-7-methyl-5,6,7,8-tetrahydro-[1,2,4]triazolo[4,3-a]pyrazine (Preparation 153) and 2-methoxy-4-(4,4,5,5-tetramethyl-1,3,2-dioxaborolan-2-yl)aniline and purification method E. |
| 89 | tert-Butyl 3-(4-amino-3-methoxyphenyl)-5,6-dihydro-imidazo[1,2-a]pyrazine-7(8H)-carboxylate 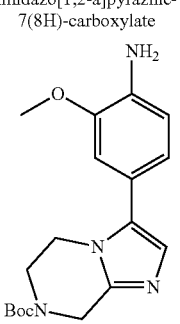 | $^1$H NMR (500 MHz, CDCl$_3$): δ 7.03 (s, 1H), 6.80-6.72 (m, 3H), 4.79 (s, 2H), 3.98-3.94 (m, 2H), 3.88 (s, 3H), 3.84-3.80 (m, 2H), 1.51 (s, 9H). LCMS (ESI) Rt = 1.63 minutes MS m/z 345 [M + H]$^+$ Using tert-butyl 3-bromo-5,6-dihydroimidazo[1,2-a]pyrazine-7(8H)-carboxylate and 2-methoxy-4-(4,4,5,5-tetramethyl-1,3,2-dioxaborolan-2-yl)aniline and purification method D. |
| 90 | 5-(4-Amino-3-methoxyphenyl)-1-methyl-1H-imidazole-2-carbonitrile 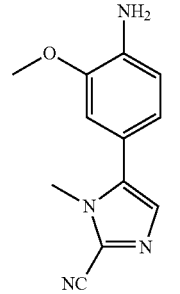 | $^1$H NMR (500 MHz, CDCl$_3$): δ 7.16 (s, 1H), 6.81 (d, J = 1.68 Hz, 1H), 6.79 (s, 1H), 6.77 (d, J = 1.68 Hz, 1H), 3.90 (s, 3H), 3.80 (s, 3H). LCMS (ESI) Rt = 1.67 minutes MS m/z 229 [M + H]$^+$ Using 5-bromo-1-methyl-1H-imidazole-2-carbonitrile (Preparation 121) and 2-methoxy-4-(4,4,5,5-tetramethyl-1,3,2-dioxaborolan-2-yl)aniline and method C. |

| Preparation No | Name/Structure | Data |
|---|---|---|
| 91 | 2-methoxy-4-(1-methyl-1H-pyrazol-4-yl)aniline<br>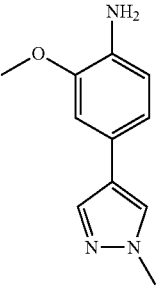 | $^1$H NMR (500 MHz, CDCl$_3$): δ 7.70 (s, 1H), 7.52 (s, 1H), 6.92 (dd, J = 7.9, 1.8 Hz, 1H), 6.90 (d, J = 1.8 Hz, 1H), 6.73 (d, J = 7.9 Hz, 1H), 3.94 (s, 3H), 3.91 (s, 3H), 3.80 (s, broad, 2H).<br>LCMS (ESI) Rt = 0.95 minutes MS m/z 204 [M + H]$^+$<br>Using 4-bromo-2-methoxyaniline and 1-methyl-4-(4,4,5,5-tetramethyl-1,3,2-dioxaborolan-2-yl)-1H-pyrazole and purification method A. |

Preparation 92: (4-amino-3-methoxyphenyl)(3-methoxyazetidin-1-yl)methanone

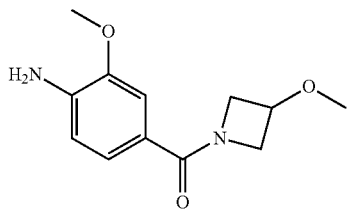 [SMILES: COc1cc(C(=O)N2CC(OC)C2)ccc1N]

Method G

HATU (2.70 g, 7.10 mmol) was added to a solution of 4-amino-3-methoxybenzoic acid (880 mg, 5.26 mmol), 3-methoxyazetidine hydrochloride (0.971 g, 7.86 mmol) and DIPEA (2.85 mL, 16.32 mmol) in THF (15 mL) at room temperature. THF was removed under reduced pressure, and the residue partitioned between EtOAc and saturated aqueous NaHCO$_3$. The aqueous layer was extracted with EtOAc and the combined organic layers were washed with brine, dried and concentrated. The residue was purified by silica gel column chromatography eluting with 0 to 100% EtOAc in cyclohexane followed by a second chromatography eluting with 0 to 4% MeOH in DCM to afford the title compound (728 mg, 59%).

$^1$H NMR (500 MHz, CDCl$_3$): δ 7.24 (d, J=1.7 Hz, 1H), 7.06 (dd, J=8.1, 1.8 Hz, 1H), 6.66 (d, J=8.0 Hz, 1H), 4.42 (br s, 2H), 4.31-3.99 (m,5H), 3.91 (s, 3H), 3.34 (s, 3H).

The following Preparations were prepared according to Method G (Preparation 92) using 4-amino-3-methoxybenzoic acid and the appropriate amine as described below. The Preparations were purified according to the method described or as described below:

Method A: Biotage silica gel column chromatography eluting with between 0-4% MeOH in EtOAc.

Method B: Elution through an SCX-2 cartridge using 2M NH$_3$/MeOH.

| Preparation No | Name/Structure | Data |
|---|---|---|
| 93 | 4-Amino-N-(2-hydroxyethyl)-3-methoxybenzamide<br>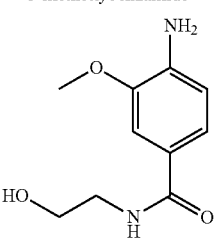 | $^1$H NMR (500 MHz, CDCl$_3$): δ 7.37 (d, J = 1.92 Hz, 1H), 7.18 (dd, J = 1.92, 8.10 Hz, 1H), 6.67 (d, J = 8.10 Hz, 1H), 3.91 (s, 3H), 3.86-3.80 (m, 2H), 3.64-3.60 (m, 2H).<br>LCMS (ESI) Rt = 0.71 minutes MS m/z 211 [M + H]$^+$<br>Using 2-aminoethanol in DMF and purification method A. |

-continued

| Preparation No | Name/Structure | Data |
|---|---|---|
| 94 | 4-Amino-3-methoxy-N-(2-methoxyethyl)benzamide 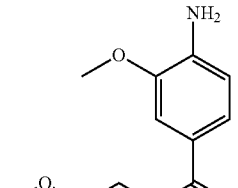 | ¹H NMR (500 MHz, CDCl₃): δ 7.36 (d, J = 1.88 Hz, 1H), 7.16 (dd, J = 1.88, 8.06 Hz, 1H), 6.68 (d, J = 8.06 Hz, 1H), 3.89 (s, 3H), 3.65-3.60 (m, 2H), 3.56-3.51 (m, 2H), 3.38 (s, 3H).<br>LCMS (ESI) Rt = 1.20 minutes MS m/z 225 [M + H]<br>Using 2-methoxyethanamine in DMF and purification method A. |
| 95 | (4-Amino-3-methoxyphenyl)(1,1-dioxidothiomorpholino)methanone 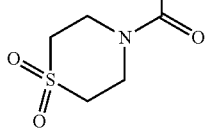 | ¹H NMR (500 MHz, MeOD): δ 6.95 (s, 1H), 6.89 (d, J = 7.88 Hz, 1H), 6.74 (d, J = 7.88 Hz, 1H), 4.14-4.05 (m, 1H), 3.94-3.85 (m, 2H), 3.89 (s, 3H), 3.79-3.68 (m, 1H), 3.28-3.16 (m, 2H), 3.15-3.08 (m, 2H).<br>LCMS (ESI) Rt = 0.90 minutes MS m/z 285 [M + H]⁺<br>Using thiomorpholine 1,1-dioxide in DMF and purification method B. |
| 96 | (4-Amino-3-methoxyphenyl)(4-methylpiperazin-1-yl)methanone | ¹H NMR (500 MHz, MeOD): δ 6.94 (dd, J = 1.78, 8.62 Hz, 1H), 6.88 (ddd, J = 1.78, 8.00, 8.62 Hz, 1H), 6.73 (dd, J = 0.87, 8.00 Hz, 1H), 3.87 (s, 3H), 3.72-3.60 (m, 4H), 3.08 (s, 3H), 2.50-2.42 (m, 4H).<br>LCMS (ESI) Rt = 0.43 minutes MS m/z 250 [M + H]⁺<br>Using 1-methylpiperazine in DMF and purification method B. |
| 97 | 4-Amino-3-methoxy-N-(1-methyl-piperidin-4-yl)benzamide 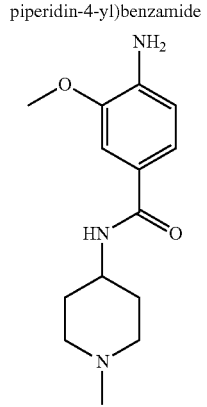 | ¹H NMR (500 MHz, MeOD): δ 7.36 (d, J = 1.90 Hz, 1H), 7.33 (dd, J = 1.90, 8.16 Hz, 1H), 6.72 (d, J = 8.16 Hz, 1H), 3.91 (s, 3H), 3.08-2.95 (m, 1H), 2.98-2.90 (m, 2H), 2.32 (s, 3H), 2.25-2.14 (m, 2H), 1.98-1.91 (m, 2H), 1.75-1.63 (m, 2H).<br>LCMS (ESI) Rt = 0.63 minutes MS m/z 264 [M + H]⁺<br>Using 1-methylpiperidin-4-amine in DMF and purification method B. |

| Preparation No | Name/Structure | Data |
|---|---|---|
| 98 | (4-Amino-3-methoxyphenyl)(3-(methoxymethyl)azetidin-1-yl)methanone 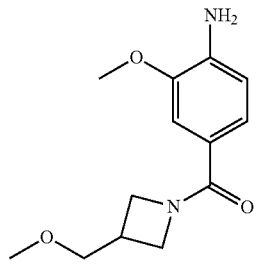 | $^1$H NMR (500 MHz, CDCl$_3$): δ 7.25 (d, J = 1.76 Hz, 1H), 7.07 (dd, J = 1.76, 8.06 Hz, 1H), 6.64 (d, J = 8.06 Hz, 1H), 4.45-4.20 (m, 2H), 4.15-4.05 (m, 2H), 3.95-3.87 (m, 1H), 3.89 (s, 3H), 3.56 (d, J = 6.62 Hz, 2H), 3.38 (s, 3H). LCMS (ESI) Rt = 1.58 minutes MS m/z 251 [M + H]$^+$ Using 3-(methoxymethyl)azetidine 4-methylbenzenesulfonate salt and purification method A. |
| 99 | (4-Amino-3-methoxyphenyl)(3,3-difluoroazetidin-1-yl)methanone 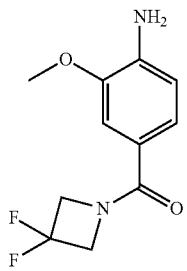 | $^1$H NMR (500 MHz, DMSO-d$_6$): δ 7.09 (s, 1H), 7.08 (d, J = 9.3 Hz, 1H), 6.61 (d, J = 8.3 Hz, 1H), 5.44 (s, 2H), 4.57 (br s, 4H), 3.8 (s, 3H). LCMS (ESI) Rt = 1.65 minutes MS m/z 243 [M + H]$^+$ Using 3,3-difluoroazetidine hydrochloride and triethylamine in DCM with purification method A. |
| 100 | (4-Amino-3-methoxyphenyl)(6-oxa-2-azaspiro[3.4]octan-2-yl)methanone 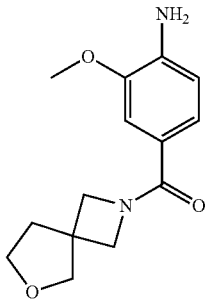 | $^1$H NMR (500 MHz, CDCl$_3$): δ 7.23 (d, J = 1.8 Hz, 1H), 7.04 (dd, J = 8.1, 1.9 Hz, 1H), 6.62 (d, J = 8.1 Hz, 1H), 4.23 (br s, 4H), 3.89 (s, 2H), 3.87 (s, 3H), 3.83 (t, J = 6.9 Hz, 2H), 2.16 (t, J = 6.9 Hz, 2H). LCMS (ESI) Rt = 1.33 minutes MS m/z 263 [M + H]$^+$ Using 6-oxa-2-azaspiro[3.4]octane oxalate and triethylamine in DCM with purification method A. |
| 101 | 1-(4-Amino-3-methoxybenzoyl)piperidine-4-carbonitrile 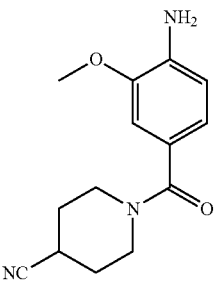 | $^1$H NMR (500 MHz, DMSO-d$_6$): δ 6.84 (d, J = 1.8 Hz, 1H), 6.79 (dd, J = 8, 1.8 Hz, 1H), 6.6 (d, J = 8 Hz, 1H), 5.15 (s, 2H), 3.77 (s, 3H), 3.74-3.76 (m, 2H), 3.34-3.32 (m, 2H), 3.12-3.11 (m, 1H), 1.88-1.85 (m, 2H), 1.72-1.7 (m, 2H). LCMS (ESI) Rt = 1.27 minutes MS m/z 260 [M + H]$^+$ Using piperidine-4-carbonitrile and triethylamine in DCM with purification method A. |

Preparation 102: 3-Fluoro-2-methoxy-4-(4,4,5,5-tetramethyl-1,3,2-dioxaborolan-2-yl)aniline

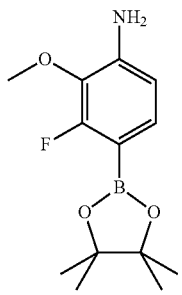

A mixture of 4-bromo-3-fluoro-2-methoxyaniline (Preparation 103, 527 mg, 2.40 mmol), KOAc (705 mg, 7.19 mmol), Pd(dppf)C$_2$∩DCM (101 mg, 0.12 mmol) and bis(pinacolato)diboron (669 mg, 2.63 mmol) in dioxane (10 mL) was stirred at 100° C. under microwave irradiation for 8 hours. The reaction mixture was filtered, diluted with NaCl solution and extracted with EtOAc. The organic layer was collected and concentrated in vacuo. The residue was purified using Biotage silica gel column chromatography eluting with 15% EtOAc in cyclohexanes to give the title compound as white solid (291 mg, 46%).

$^1$H NMR (500 MHz, CDCl$_3$): δ 7.26 (dd, J=5.98, 8.06 Hz, 1H), 6.51 (dd, J=0.92, 8.12 Hz, 1H), 3.93 (d, J=1.42 Hz, 3H), 1.36 (s, 12H).

LCMS (ESI) Rt=2.43 minutes MS m/z 268 [M+H]$^+$

Preparation 103: 4-Bromo-3-fluoro-2-methoxyaniline

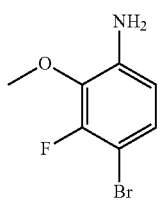

To a solution of 2-methoxy-3-fluoroaniline (2.18 g, 15.46 mmol) in AcOH (10 mL) was added a solution of bromine (1.98 g, 12.37 mmol) in AcOH (2 mL) dropwise. The reaction mixture was stirred at room temperature for 30 minutes. The resulting solid was filtered and washed with acetic acid to give the title and a di-bromo-compound as the HBr salt. The solid (2.53 g) was dissolved in water, basified by addition of KOH, and extracted with EtOAc. The organic layer was dried with Na$_2$SO$_4$ and concentrated in vacuo. The residue was purified by Biotage silica gel column chromatography eluting with 15% EtOAc in cyclohexanes to give the title compound as white solid (1.24 g, 36%).

$^1$H NMR (500 MHz, CDCl$_3$): δ 7.08-6.97 (m, 1H), 6.51-6.41 (m, 1H), 3.95 (s, 3H).

LCMS (ESI) Rt=2.43 minutes MS m/z 220 [M$^{79}$Br+H]$^+$

Preparation 104: 4-Amino-3-methoxy-N,N-dimethylbenzenesulfonamide

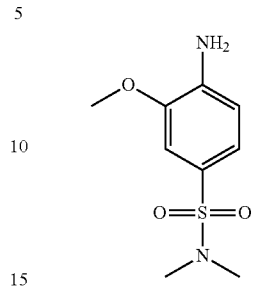

4-(1,3-Dioxoisoindolin-2-yl)-3-methoxy-N,N-dimethylbenzenesulfonamide (Preparation 105, 50 mg, 0.139 mmol) was suspended in MeOH (6 mL) and hydrazine hydrate (1 mL) was added. The resulting solution was stirred at room temperature for 2 hours before concentrating in vacuo. The residue was purified using Biotage silica gel column chromatography eluting with 50% EtOAc in cyclohexane to give the title compound as white solid (11 mg, 34%).

$^1$H NMR (500 MHz, CDCl$_3$): δ 7.26 (dd, J=1.92, 8.24 Hz, 1H), 7.16 (d, J=1.92 Hz, 1H), 6.76 (d, J=8.24 Hz, 1H), 4.30 (s, broad, 2H), 3.92 (s, 3H), 2.69 (s, 6H).

LCMS (ESI) Rt=1.60 minutes MS m/z 231 [M+H]$^+$

Preparation 105: 4-(1,3-Dioxoisoindolin-2-yl)-3-methoxy-N,N-dimethylbenzenesulfonamide

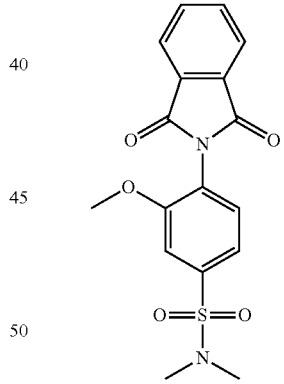

A suspension of 4-(1,3-dioxoisoindolin-2-yl)-3-hydroxy-N,N-dimethylbenzenesulfonamide (Preparation 106, 83 mg, 0.240 mmol), K$_2$CO$_3$ (50 mg, 0.359 mmol) and iodomethane (0.1 mL, 1.60 mmol) in EtOH (4 mL) was stirred at 100° C. under microwave irradiation for 60 minutes. When cooled, the resulting crystals (50 mg, 58%) obtained were filtered, washed with EtOH and dried to afford the title compound.

$^1$H NMR (500 MHz, DMSO-d$_6$): δ 8.08-7.98 (m, 2H), 7.98-7.91 (m, 2H), 7.71 (d, J=8.10 Hz, 1H), 7.51 (dd, J=1.86, 8.10 Hz, 1H), 7.45 (d, J=1.86 Hz, 1H), 3.34 (s, 3H), 2.74 (s, 6H).

LCMS (ESI) Rt=2.27 minutes MS m/z 361 [M+H]$^+$

Preparation 106: 4-(1,3-Dioxoisoindolin-2-yl)-3-hydroxy-N,N-dimethylbenzenesulfonamide

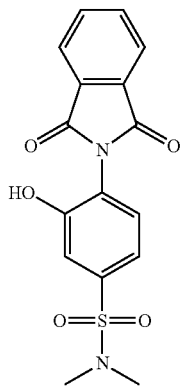

A suspension of 4-amino-3-hydroxy-N,N-dimethylbenzenesulfonamide (120 mg, 0.555 mmol) and phthalic anhydride (82 mg, 0.555 mmol) in AcOH (3 mL) was stirred at 120° C. under microwave irradiation for 60 minutes. The reaction was cooled and diluted with water to afford a suspension. The precipitate was filtered, washed with water and dried under high vacuum to afford the title compound as a pink solid (142 mg, 74%).

$^1$H NMR (500 MHz, DMSO-d$_6$): δ 10.72 (s, 1H), 7.99 (dd, J=2.92, 5.58 Hz, 2H), 7.94-7.92 (dd, J=2.92, 5.58 Hz, 2H), 7.59 (d, J=8.10 Hz, 1H), 7.33 (d, J=1.98 Hz, 1H), 7.31 (dd, J=1.98, 8.10 Hz, 1H), 2.70 (s, 6H).

LCMS (ESI) Rt=2.17 minutes MS m/z 347 [M+H]$^+$

Preparation 107: (4-Amino-3-ethoxyphenyl)(3-methoxyazetidin-1-yl)methanone

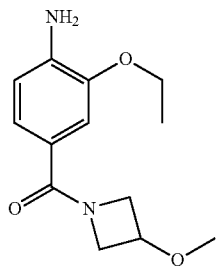

A solution of (3-ethoxy-4-nitrophenyl)(3-methoxyazetidin-1-yl)methanone (Preparation 113, 230 mg, 0.821 mmol) in ethyl acetate (10 mL) was stirred with 10% palladium on charcoal under an atmosphere of hydrogen gas for 1 hour. The reaction mixture was filtered through a pad of celite, the filtrate collected and concentrated in vacuo to afford the title compound as a white solid (202 mg, 98%).

$^1$H NMR (500 MHz, DMSO-d$_6$): δ 7.03 (d, J=1.7 Hz, 1H), 7.01 (dd, J=8, 1.8 Hz, 1H), 6.6 (d, J=8 Hz, 1H), 5.3 (br s, 2H), 4.4 (br s, 1H), 4.19-4.17 (m, 2H), 4.01 (q, J=7 Hz, 2H), 3.85 (br s, 2H), 3.21 (s, 3H), 1.34 (t, J=7 Hz, 3H).

LCMS (ESI) R$_t$=1.59 minutes MS m/z 251 [M+H]$^+$

Preparation 108: (4-Amino-3-(difluoromethoxy)phenyl)(3-methoxyazetidin-1-yl)methanone

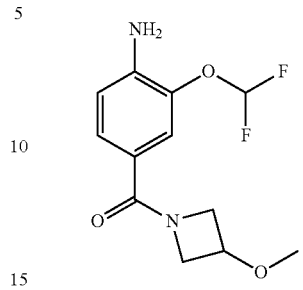

The title compound was prepared according to the method described for Preparation 107 using (3-(difluoromethoxy)-4-nitrophenyl)(3-methoxyazetidin-1-yl)methanone (Preparation 114).

$^1$H NMR (500 MHz, DMSO-d$_6$): δ 7.28 (m, 2H), 7.08 (t, J=74.3 Hz, 1H), 6.73 (d, J=8.3 Hz, 1H), 5.7 (br s, 2H), 4.43 (br s, 1H), 4.22-4.2 (m, 2H), 4.14 (br s, 1H), 3.8 (br s, 1H), 3.21 (s, 3H).

LCMS (ESI) R$_t$=1.65 minutes MS m/z 273 [M+H]$^+$

Preparation 109: 2-Ethoxy-4-(4-methyl-4H-1,2,4-triazol-3-yl)aniline

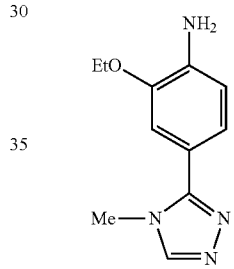

The title compound was prepared according to the method described for Preparation 107 using 3-(3-Ethoxy-4-nitrophenyl)-4-methyl-4H-1,2,4-triazole (Preparation 116) in EtOAc and EtOH (1:8 v:v).

$^1$H NMR (500 MHz, DMSO-d$_6$): δ 8.44 (s, 1H), 7.11 (d, J=1.89 Hz, 1H), 7.04 (dd, J=1.89, 7.88 Hz, 1H), 6.73 d, J=7.88 Hz, 1H), 5.12 (s, 2H), 4.06 (q, J=6.94 Hz, 2H), 3.69 (s, 3H), 1.36 (t, J=6.94 Hz, 3H).

Preparation 110: 2-Methoxy-4-(4-methyl-4H-1,2,4-triazol-3-yl)aniline

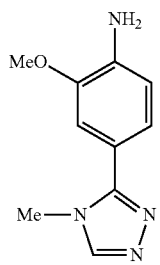 [SMILES: COc1cc(-c2nncn2C)ccc1N]

The title compound was prepared according to the methods described for Preparations, 107, 116, 117 and 118 using 3-methoxy-4-nitrobenzoic acid.

¹H NMR (500 MHz, DMSO-d₆): δ 8.45 (s, 1H), 7.12 (d, J=1.89 Hz, 1H), 7.05 (dd, J=1.89, 8.20 Hz, 1H), 6.73 (d, J=8.20 Hz, 1H), 5.21 (br s, 2H), 3.82 (s, 3H), 3.70 (s, 3H).

Preparation 111: 2-chloro-4-morpholinoaniline

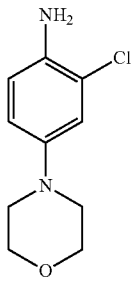

A solution of 4-(3-chloro-4-nitrophenyl)morpholine (Preparation 112, 450 mg, 1.854 mmol) in EtOH/EtOAc (1:1, 30 mL) was passed through a 10% Pd/C cartridge using an H-cube (atmospheric H₂, room temperature, 1 mL/min). The reaction mixture was concentrated in vacuo. The residue was purified by reverse phase column chromatography eluting with 0-20% MeCN in water to afford the title compound (150 mg, 38%).

¹H NMR (500 MHz, MeOD): δ 6.90 (dd, J=2.5, 0.5 Hz, 1H), 6.83-6.79 (m, 2H), 3.82-3.80 (m, 4H), 3.00-2.98 (m, 4H).

LCMS (ESI) Rt=1.13 minutes MS m/z 213 [M+H]⁺

Preparation 112:
4-(3-chloro-4-nitrophenyl)morpholine

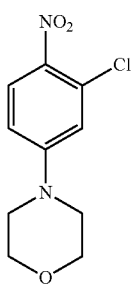

To a solution of 2-chloro-4-fluoro-1-nitrobenzene (500 mg, 2.85 mmol) in MeCN (10 mL) was added morpholine (0.62 mL, 7.12 mmol) and potassium carbonate (394 mg, 2.85 mmol). The reaction mixture was heated at 70° C. for 18 hours. The reaction mixture was concentrated in vacuo. The residue was dissolved in DCM (30 mL) and washed with water (2×30 mL), dried (MgSO₄) and concentrated in vacuo. The residue was purified by silica gel column chromatography eluting with 0-50% EtOAc in cyclohexane to afford the title compound (473 mg, 68%).

¹H NMR (500 MHz, CDCl₃): δ 8.05 (d, J=9.5 Hz, 1H), 6.89 (d, J=2.5 Hz, 1H), 6.77 (dd, J=9.5, 2.5 Hz, 1H), 3.88-3.87 (m, 4H), 3.37-3.35 (m, 4H).

LCMS (ESI) Rt=2.31 minutes MS m/z 243 [M+H]⁺

Preparation 113: (3-Ethoxy-4-nitrophenyl)(3-methoxyazetidin-1-yl)methanone

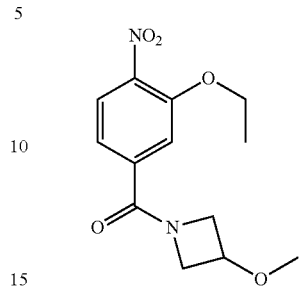

A mixture of (3-hydroxy-4-nitrophenyl)(3-methoxyazetidin-1-yl)methanone (Preparation 115, 250 mg, 1.007 mmol), iodoethane (185 mg, 1.208 mmol) and potassium carbonate (278 mg, 2.014 mmol) in DMF (10 mL) was stirred at room temperature for 2 hours. The reaction was filtered and the filtrate diluted with ethyl acetate (60 mL). The organic phase was washed with water (20 mL×2), brine (20 mL) and dried over sodium sulphate. The solvent was concentrated in vacuo and the residue purified by silica gel column chromatography eluting with 20% hexane in ethyl acetate to afford the title compound as a yellow powder (230 mg, 84%).

¹H NMR (500 MHz, CDCl₃): δ 7.79 (d, J=8.2 Hz, 1H), 7.38 (d, J=1.5 Hz, 1H), 7.14 (dd, J=8.2, 1.5 Hz, 1H), 4.38-4.36 (m, 2H), 4.28-4.25 (m, 1H), 4.22 (q, J=7 Hz, 2H), 4.13-4.12 (m, 2H), 3.32 (s, 3H), 1.47 (t, J=7 Hz, 3H).

LCMS (ESI) R$_t$=2.10 minutes MS m/z 281 [M+H]⁺

Preparation 114: (3-(Difluoromethoxy)-4-nitrophenyl)(3-methoxyazetidin-1-yl)methanone

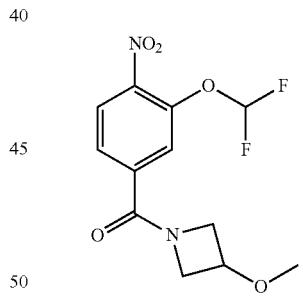

(3-Hydroxy-4-nitrophenyl)(3-methoxyazetidin-1-yl)methanone (Preparation 115, 300 mg, 1.19 mmol) and methyl 2-chloro-2,2-difluoroacetate (258 mg, 1.78 mmol) were dissolved in dry DMF (2 mL). Potassium carbonate (328 mg, 2.38 mmol) was added and the reaction was heated to 120° C. under microwave irradiation for 1 hour. The reaction was cooled to room temperature and diluted with ethyl acetate (20 mL). The organic solution was washed with water (20 mL), brine (20 mL), dried over sodium sulphate and concentrated in vacuo. The residue was purified by silica gel column chromatography eluting with a gradient of 20% hexanes in ethyl acetate to 100% ethyl acetate to afford the title compound as a yellow oil (250 mg, 67.3%).

¹H NMR (500 MHz, CDCl₃): δ 7.95 (d, J=8.4 Hz, 1H), 7.65 (d, J=1.2 Hz, 1H), 7.61 (dd, J=8.3, 1.7 Hz, 1H), 6.67 (t,

J=72.4 Hz, 1H), 4.42-4.4 (m, 2H), 4.31-4.29 (m, 1H), 4.16-4.14 (m, 2H), 3.33 (s, 3H).

LCMS (ESI) $R_t$=2.03 minutes MS m/z 303 [M+H]$^+$

Preparation 115: (3-Hydroxy-4-nitrophenyl)(3-methoxyazetidin-1-yl)methanone

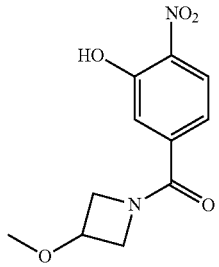

HATU (2.1 g, 5.5 mmol) was added to a solution of 3-hydroxy-4-nitrobenzoic acid (915 mg, 5 mmol), triethylamine (1.1 g, 11 mmol)) and 3-methoxyazetidine hydrochloride (740 mg, 5.5 mmol) in dichloromethane (10 mL). The reaction mixture was stirred at room temperature for 30 minutes. The reaction was partitioned between EtOAc (30 mL) and water (30 mL). The organic phase was collected, washed with water, brine, dried over Na$_2$SO$_4$ and concentrated in vacuo. The residue was purified by silica gel column chromatography eluting with a gradient of 100% ethyl acetate to 3% methanol in ethyl acetate to afford the title compound as a pale yellow solid (830 mg, 66%).

$^1$H NMR (500 MHz, DMSO-d$_6$): δ 11.3 (br s, 1H), 7.88 (d, J=8.5 Hz, 1H), 7.33 (d, J=1.7 Hz, 1H), 7.17 (dd, J=8.4 1.7 Hz, 1H), 4.42-4.40 (m, 1H), 4.26-4.21 (m, 2H), 4.11-4.09 (m, 1H), 3.86-3.82 (m, 1H), 3.22 (s, 3H).

LCMS (ESI) $R_t$=1.81 minutes MS m/z 253 [M+H]$^+$

Preparation 116: 3-(3-Ethoxy-4-nitrophenyl)-4-methyl-4H-1,2,4-triazole

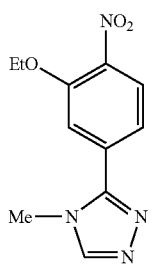 [SMILES: CCOc1cc(-c2nncn2C)ccc1[N+](=O)[O-]]

5-(3-Ethoxy-4-nitrophenyl)-4-methyl-4H-1,2,4-triazole-3-thiol (Preparation 117, 1.16 g 4.14 mmole) was stirred with dichloromethane (11.8 mL) and the suspension cooled in ice. A solution of 35% hydrogen peroxide (0.91 mL, 12.2 mmole) in acetic acid (6 mL) was added dropwise and the reaction was stirred at room temperature for 70 minutes. Dichloromethane (50 mL) was added followed by 2M aqueous sodium hydroxide (48 mL) to pH=7. The layers were separated, the aqueous extracted with more dichloromethane, the organic layers combined, dried over sodium sulphate and concentrated in vacuo. The residue was purified by silica gel column chromatography eluting with 5-10% EtOH in DCM to afford the title compound (607 mg, 60%).

$^1$H NMR (500 MHz, DMSO-d$_6$): δ 8.66 (s, 1H), 8.03 (d, J=8.51 Hz, 1H), 7.65 (d, J=1.58 Hz, 1H), 7.47 (dd, J=1.58, 8.51 Hz, 1H), 4.31 (q, J=7.25 Hz, 2H), 3.81 (s, 3H), 1.36 (t, J=6.94 Hz, 3H).

Preparation 117: 5-(3-Ethoxy-4-nitrophenyl)-4-methyl-4H-1,2,4-triazole-3-thiol

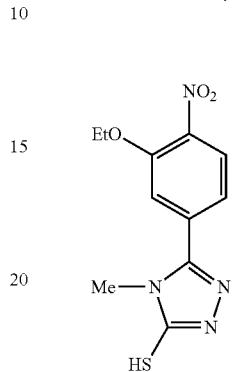

3-Ethoxy-4-nitrobenzohydrazide (Preparation 118, 1287 mg 5.72 mmole) was stirred in THF (26 mL) and a solution of methyl isothiocyanate (422 mg 5.78 mmole) in THF (5 mL) was added. Triethylamine (102 uL, 0.71 mmole) was added and the reaction was stirred at 20° C. for 22 hours. The solvent was evaporated and replaced with 1M sodium hydroxide solution (85 mL) and the reaction was stirred at 45° C. for 2.5 hours. The reaction was filtered through Celite and the filtrate extracted with ether (2×45 mL). The aqueous was acidified using conc. hydrochloric acid and extracted with ethyl acetate (2×50 mL). The combined ethyl acetate extracts were washed with water and with brine, dried over sodium sulfate and concentrated in vacuo to afford the title compound (1.16 g, 72%).

$^1$H NMR (500 MHz, DMSO-d$_6$): δ 14.11 (br s, 1H), 8.03 (d, J=8.51 Hz, 1H), 7.66 (d, J=1.58 Hz, 1H), 7.44 (dd, J=1.89, 8.51 Hz, 1H), 4.29 (q, J=6.94 Hz, 2H), 3.56 (s, 3H), 1.35 (t, J=6.94 Hz, 3H).

Preparation 118: 3-Ethoxy-4-nitrobenzohydrazide

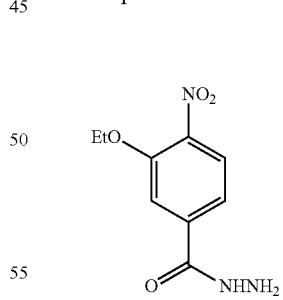

3-Ethoxy-4-nitrobenzoic acid (PCT Int Appl. 2008003958, 1.06 g 5.02 mmole) was stirred with dry THF (10 mL) and triethylamine (0.86 mL, 6.1 mmol) and the solution was cooled in an ice bath. Ethyl chloroformate (0.56 mL, 5.85 mmol) was added dropwise and the reaction was stirred in the ice bath for 15 minutes. Hydrazine hydrate (1.27 mL, 26 mmol) was added in one portion and the reaction stirred in the ice bath for 5 minutes and then at 20° C. for 1 hour. The reaction was concentrated in vacuo, partitioned between EtOAc (100 mL) and saturated aqueous sodium bicarbonate (15 mL). The organic layer was collected, washed with brine, dried over sodium sulfate and concentrated in vacuo to afford the title compound (1.07 g, 95%).

¹H NMR (500 MHz, DMSO-d₆): δ 10.05 (br s, 1H, NH), 7.92 (d, J=8.20 Hz, 1H), 7.69 (d, J=1.89 Hz, 1H), 7.51 (dd, J=1.58, 8.51 Hz, 1H), 4.70 (br s, 2H, NH₂), 4.27 (q, J=6.94 Hz, 2H), 1.35 (t, J=6.94 Hz, 3H).

Preparation 119: 6-(1,2-Dimethyl-1H-imidazol-5-yl)-2-methoxypyridin-3-amine

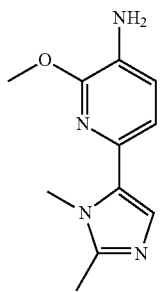 [SMILES: COc1nc(-c2cnc(C)n2C)ccc1N]

A suspension of 6-bromo-2-methoxypyridin-3-amine (96 mg, 0.473 mmol), 1,2-dimethyl-1H-imidazole (91 mg, 0.946 mmol), Pd(OAc)₂ (4.3 mg, 0.019 mmol), KOAc (93 mg, 0.95 mmol) in DMA (3 mL) was stirred at 150° C. under microwave irradiation for 8 hours. The reaction mixture was filtered, diluted with NaCl solution and extracted with EtOAc. The organic layer was purified by eluting through an SCX-2 column using 2M NH₃/MeOH followed by Biotage silica gel column chromatography eluting with 0-4% MeOH/EtOAc to give the title compound as pink solid (17 mg, 16%).

¹H NMR (500 MHz, CDCl₃): δ 7.11 (s, 1H), 6.98 (d, J=7.74 Hz, 1H), 6.91 (d, J=7.74 Hz, 1H), 4.00 (s, 3H), 3.85 (s, 3H), 2.45 (s, 3H).

LCMS (ESI) Rt=1.10 minutes MS m/z 219 [M+H]⁺

Preparation 120: 5-(1,2-Dimethyl-1H-imidazol-5-yl)-3-methoxypyridin-2-amine

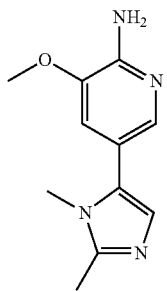 [SMILES: COc1cc(-c2cnc(C)n2C)cnc1N]

A suspension of 5-bromo-3-methoxypyridin-2-amine (55.5 mg, 0.273 mmol), 1,2-dimethyl-1H-imidazole (52.6 mg, 0.547 mmol), Pd(OAc)₂ (2.5 mg, 0.011 mmol), KOAc (53.7 mg, 0.55 mmol) in DMA (3 mL) was stirred at 150° C. under microwave irradiation for 8 hours. The reaction mixture was filtered, diluted with NaCl solution and extracted with EtOAc. The organic layer was purified by eluting through an SCX-2 column using 2M NH₃/MeOH followed by Biotage silica gel column chromatography eluting with 0-12% MeOH/EtOAc to give the title compound as yellow waxy solid (9 mg, 15%).

¹H NMR (500 MHz, CDCl₃): δ 7.67 (d, J=1.78 Hz, 1H), 6.92 (s, 1H), 6.88 (d, J=1.78 Hz, 1H), 4.83 (s, 2H), 3.88 (s, 3H), 3.50 (s, 3H), 2.46 (s, 3H).

LCMS (ESI) Rt=0.42 minutes MS m/z 219 [M+H]⁺

Preparation 121
5-Bromo-1-methyl-1H-imidazole-2-carbonitrile

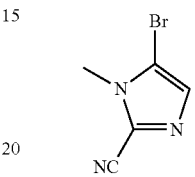

(E)-5-Bromo-1-methyl-1H-imidazole-2-carbaldehyde oxime (Preparation 155, 38 mg, 0.186 mmol) and TEA (39 uL, 0.279 mmol) was stirred in THF (6 mL) and cooled at 0° C., TFAA (28 uL, 0.205 mmol) was added. Then the mixture was stirred at 60° C. under microwave irradiation for 3 hours. The reaction was purified directly by Biotage silica gel column chromatography eluting with 20% EtOAc in cyclohexanes to give the title compound as yellow solid (15 mg, 43%).

¹H NMR (500 MHz, CDCl₃): δ 7.20 (s, 1H), 3.82 (s, 3H).
LCMS (ESI) Rt=1.60 minutes MS m/z 186 [M⁷⁹Br+H]⁺

Preparation 122: 1-(2-Methoxyethyl)-4-(4,4,5,5-tetramethyl-1,3,2-dioxaborolan-2-yl)-1H-pyrazole

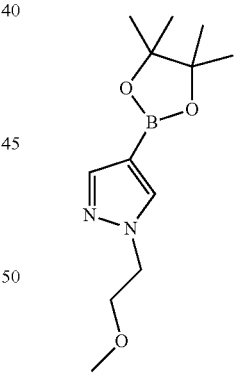

Method H

NaH (60%, 83 mg) was added to a solution of 4-(4,4,5,5-tetramethyl-1,3,2-dioxaborolan-2-yl)-1H-pyrazole (204 mg, 1.05 mmol) in DMF (4 mL). After stirring for 15 minutes, 1-bromo-2-methoxyethane (175 mg, 1.26 mmol) in DMF (1 mL) was added. The resulting solution was stirred at 80° C. under microwave irradiation for 60 minutes. The reaction mixture was diluted with brine and extracted with EtOAc. The combined organic layers were washed with water, dried with Na₂SO₄, and concentrated in vacuo to afford the title compound as a yellow oil that was used directly in the next step (148 mg, 56%).

¹H NMR (500 MHz, CDCl₃): δ 7.80 (d, J=0.7 Hz, 1H), 7.77 (d, J=0.7 Hz, 1H), 4.31 (t, J=5.3 Hz, 2H), 3.76 (t, J=5.3 Hz, 2H), 3.33 (s, 3H), 1.32 (s, 12H).
LCMS (ESI) Rt=2.17 minutes MS m/z 253 [M+H]⁺

The following Preparations were prepared according to Method H (Preparation 122) using 4-(4,4,5,5-tetramethyl-1,3,2-dioxaborolan-2-yl)-1H-pyrazole and the appropriate alkyl electrophile.

| Preparation No | Name/Structure | Data |
|---|---|---|
| 123 | 1-(Cyclobutylmethyl)-4-(4,4,5,5-tetramethyl-1,3,2-dioxaborolan-2-yl)-1H-pyrazole | ¹H NMR (500 MHz, CDCl₃): δ 7.78 (d, J = 0.70 Hz, 1H), 7.66 (d, J = 0.70 Hz, 1H), 4.15 (d, J = 7.34 Hz, 2H), 2.85-2.75 (m, 1H), 2.12-2.04 (m, 2H), 1.96-1.74 (m, 4H), 1.32 (s, 12H). LCMS (ESI) Rt = 2.67 minutes MS m/z 263 [M + H]⁺ Using (bromomethyl)-cyclobutane. |
| 124 | 2-Methyl-1-(4-(4,4,5,5-tetramethyl-1,3,2-dioxaborolan-2-yl)-1H-pyrazol-1-yl)propan-2-ol | ¹H NMR (500 MHz, CDCl₃): δ 7.81 (d, J = 0.70 Hz, 1H), 7.70 (d, J = 0.70 Hz, 1H), 4.07 (s, 2H), 1.31 (s, 12H), 1.15 (s, 6H). LCMS (ESI) Rt = 2.67 minutes MS m/z 263 [M + H]⁺ Using 2,2-dimethyloxirane at 120° C. |
| 125 | 1-((3-Methyloxetan-3-yl)methyl)-4-(4,4,5,5-tetramethyl-1,3,2-dioxaborolan-2-yl)-1H-pyrazole | ¹H NMR (500 MHz, CDCl₃): δ 7.79 (d, J = 0.70 Hz, 1H), 7.67 (d, J = 0.70 Hz, 1H), 4.72 (d, J = 6.10 Hz, 2H), 4.40 (d, J = 6.10 Hz, 2H), 4.35 (s, 2H), 1.33 (s, 12H), 1.24 (s, 3H). LCMS (ESI) Rt = 2.23 minutes MS m/z 279 [M + H]⁺ Using 3-(iodomethyl)-3-methyloxetane. |

-continued

| Preparation No | Name/Structure | Data |
|---|---|---|
| 126 | 1-(Oxetan-3-yl)-4-(4,4,5,5-tetramethyl-1,3,2-dioxaborolan-2-yl)-1H-pyrazole 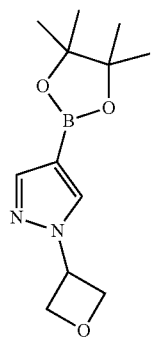 | $^1$H NMR (500 MHz, CDCl$_3$): δ 7.92 (d, J = 0.68 Hz, 1H), 7.88 (d, J = 0.68 Hz, 1H), 5.06 (d, J = 6.92 Hz, 4H), 4.78-4.62 (m, 1H), 1.34 (s, 12H). LCMS (ESI) Rt = 2.05 minutes MS m/z 251 [M + H]$^+$ Using oxetan-3-yl 4-methylbenzenesulfonate at 160° C. in NMP. |
| 127 | 1-(Oxetan-3-ylmethyl)-4-(4,4,5,5-tetramethyl-1,3,2-dioxaborolan-2-yl)-1H-pyrazole 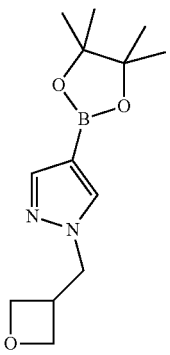 | $^1$H NMR (500 MHz, CDCl$_3$): δ 7.79 (d, J = 0.70 Hz, 1H), 7.67 (d, J = 0.70 Hz, 1H), 4.83 (dd, J = 6.46, 7.67 Hz, 2H), 4.51 (t, J = 6.14 Hz, 2H), 4.46 (d, J = 7.48 Hz, 2H), 3.58-3.48 (m, 1H), 1.33 (s, 12H). LCMS (ESI) Rt = 2.12 minutes MS m/z 265 [M + H]$^+$ Using oxetan-3-ylmethyl 4-methylbenzene sulfonate at 90° C. |
| 128 | Racemic 1-(4-(4,4,5,5-tetramethyl-1,3,2-dioxaborolan-2-yl)-1H-pyrazol-1-yl)propan-2-ol 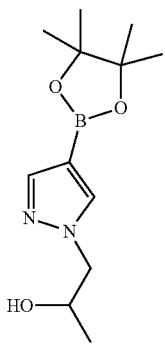 | $^1$H NMR (500 MHz, CDCl$_3$): δ 7.81 (d, J = 0.70 Hz, 1H), 7.72 (d, J = 0.70 Hz, 1H), 4.21-4.17 (m, 2H), 4.03 (dd, J = 8.16, 14.14 Hz, 1H), 1.32 (s, 12H), 1.21 (d, J = 6.24 Hz, 3H). LCMS (ESI) Rt = 2.03 minutes MS m/z 253 [M + H]$^+$ Using racemic 2-methyloxirane and cesium carbonate at 120° C. |

| Preparation No | Name/Structure | Data |
|---|---|---|
| 129 | 1-(Tetrahydro-2H-pyran-4-yl)-4-(4,4,5,5-tetramethyl-1,3,2-dioxaborolan-2-yl)-1H-pyrazole 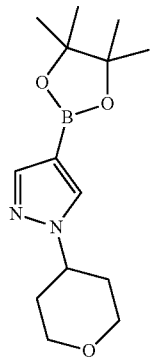 | $^1$H NMR (500 MHz, CDCl$_3$): δ 7.81 (d, J = 0.70 Hz, 1H), 7.77 (d, J = 0.70 Hz, 1H), 4.41-4.33 (m, 1H), 4.15-4.06 (m, 2H), 3.52-3.50 (m, 2H), 2.16-1.98 (m, 4H), 1.33 (s, 12H).<br>LCMS (ESI) Rt = 2.25 minutes MS m/z 379 [M + H]$^+$<br>Using tetrahydro-2H-pyran-4-yl methanesulfonate at 160° C. |
| 130 | Racemic 1-((2,2-dimethyl-1,3-dioxolan-4-yl)methyl)-4-(4,4,5,5-tetramethyl-1,3,2-dioxaborolan-2-yl)-1H-pyrazole 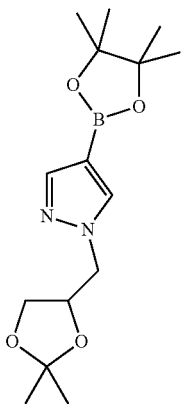 | $^1$H NMR (500 MHz, CDCl$_3$): δ 7.80 (s, 1H), 7.78 (s, 1H), 4.50-4.45 (m, 1H), 4.26 (d, J = 5.90 Hz, 2H), 4.07 (dd, J = 6.28, 8.68 Hz, 1H), 3.79 (dd, J = 5.90, 8.68 Hz, 1H), 1.35 (s, 6H), 1.32 (d, J = 1.76 Hz, 12H).<br>LCMS (ESI) Rt = 2.32 minutes MS m/z 309 [M + H]$^+$<br>Using racemic (2,2-dimethyl-1,3-dioxolan-4-yl)methyl 4-methylbenzenesulfonate at 140° C. |
| 131 | 1-((4-(4,4,5,5-Tetramethyl-1,3,2-dioxaborolan-2-yl)-1H-pyrazol-1-yl)methyl)cyclobutanol 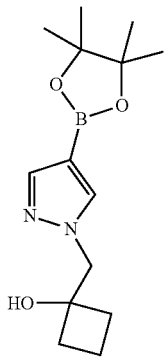 | $^1$H NMR (500 MHz, CDCl$_3$): δ 7.80 (d, J = 0.68 Hz, 1H), 7.77 (d, J = 0.68 Hz, 1H), 4.24 (s, 2H), 2.14-2.06 (m, 2H), 2.02-1.96 (m, 2H), 1.85-1.77 (m, 1H), 1.62-1.52 (m, 1H), 1.33 (s, 12H).<br>LCMS (ESI) Rt = 2.38 minutes MS m/z 279 [M + H]$^+$<br>Using 1-oxaspiro[2.3]hexane and cesium carbonate at 120° C. |

| Preparation No | Name/Structure | Data |
|---|---|---|
| 132 | 4-(4,4,5,5-Tetramethyl-1,3,2-dioxaborolan-2-yl)-1-(2,2,2-trifluoroethyl)-1H-pyrazole 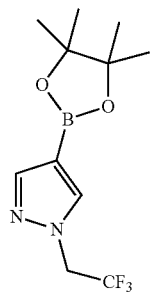 | $^1$H NMR (500 MHz, CDCl$_3$): δ 7.86 (d, J = 0.64 Hz, 1H), 7.82 (d, J = 0.64 Hz, 1H), 4.73 (q, J = 8.38 Hz, 2H), 1.34 (s, 12H). LCMS (ESI) Rt = 2.53 minutes MS m/z 277 [M + H]$^+$<br>Using 2,2,2-trifluoroethyl trifluoromethanesulfonate at 120° C. |
| 133 | 3-(4-(4,4,5,5-Tetramethyl-1,3,2-dioxaborolan-2-yl)-1H-pyrazol-1-yl)butan-2-one 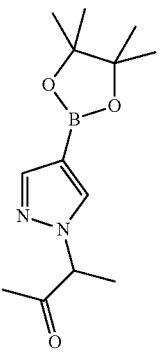 | $^1$H NMR (500 MHz, CDCl$_3$): δ 7.86 (d, J = 0.62 Hz, 1H), 7.80 (d, J = 0.62 Hz, 1H), 4.97 (q, J = 7.28 Hz, 1H), 1.99 (s, 3H), 1.70 (d, J = 7.30 Hz, 3H), 1.34 (s, 12H). LCMS (ESI) Rt = 2.32 minutes MS m/z 265 [M + H]$^+$<br>Using 3-bromobutan-2-one at 120° C. |
| 134 | Racemic 1-(4-(4,4,5,5-tetramethyl-1,3,2-dioxaborolan-2-yl)-1H-pyrazol-1-yl)butan-2-ol 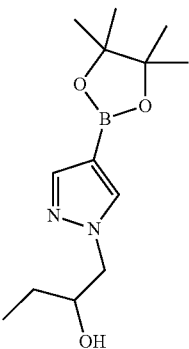 | $^1$H NMR (500 MHz, CDCl$_3$): δ 7.81 (d, J = 0.68 Hz, 1H), 7.72 (d, J = 0.68 Hz, 1H), 4.22 (dd, J = 2.64, 13.72 Hz, 1H), 4.04 (dd, J = 7.46, 13.72 Hz, 1H), 3.97-3.85 (m, 1H), 3.46 (d, J = 4.24 Hz, 1H), 1.53-1.44 (m, 2H), 1.32 (s, 12H), 1.00 (t, J = 7.46 Hz, 3H). LCMS (ESI) Rt = 2.28 minutes MS m/z 267 [M + H]$^+$<br>Using racemic 2-ethyloxirane and cesium carbonate at 120° C. |

| Preparation No | Name/Structure | Data |
|---|---|---|
| 135 | Racemic 3-methyl-1-(4-(4,4,5,5-tetramethyl-1,3,2-dioxaborolan-2-yl)-1H-pyrazol-1-yl)butan-2-ol 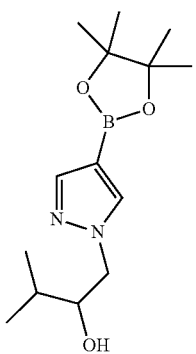 | $^1$H NMR (500 MHz, CDCl$_3$): δ 7.81 (d, J = 0.78 Hz, 1H), 7.73 (d, J = 0.78 Hz, 1H), 4.24 (dd, J = 2.46, 13.78 Hz, 1H), 4.08 (dd, J = 8.20, 13.78 Hz, 1H), 3.75-3.68 (m, 1H), 3.41 (d, J = 4.06 Hz, 1H), 1.75-1.65 (m, 1H), 1.33 (s, 12H), 1.01 (d, J = 6.80 Hz, 3H), 0.99 (d, J = 6.80 Hz, 3H). LCMS (ESI) Rt = 2.45 minutes MS m/z 281 [M + H]$^+$ Using racemic 2-isopropyloxirane and cesium carbonate at 120° C. |
| 136 | Racemic 1,1,1-Trifluoro-3-(4-(4,4,5,5-tetramethyl-1,3,2-dioxaborolan-2-yl)-1H-pyrazol-1-yl)propan-2-ol 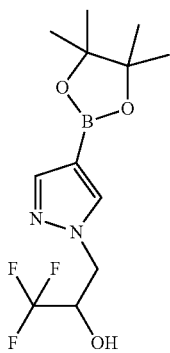 | $^1$H NMR (500 MHz, CDCl$_3$): δ 7.86 (d, J = 0.60 Hz, 1H), 7.75 (d, J = 0.60 Hz, 1H), 4.56-4.53 (m, 1H), 4.48-4.45 (m, 2H), 1.33 (d, J = 1.16 Hz, 12H). LCMS (ESI) Rt = 2.40 minutes MS m/z 307 [M + H]$^+$ Using racemic 2-(trifluoromethyl)oxirane at 120° C. |
| 137 | Racemic 1-Methoxy-3-(4-(4,4,5,5-tetramethyl-1,3,2-dioxaborolan-2-yl)-1H-pyrazol-1-yl)propan-2-ol 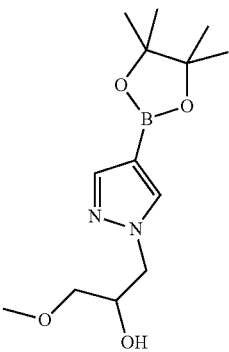 | $^1$H NMR (500 MHz, CDCl$_3$): δ 7.80 (d, J = 0.68 Hz, 1H), 7.74 (d, J = 0.68 Hz, 1H), 4.30 (dd, J = 3.52, 13.62 Hz, 1H), 4.20 (dd, J = 6.62, 13.62 Hz, 1H), 4.17-4.13 (m, 1H), 3.58 (d, J = 4.68 Hz, 1H), 3.37 (s, 3H), 3.36 (dd, J = 5.44, 9.66 Hz, 1H), 3.30 (dd, J = 5.44, 9.66 Hz, 1H), 1.32 (s, 12H). LCMS (ESI) Rt = 2.12 minutes MS m/z 283 [M + H]$^+$ Using racemic 2-(methoxymethyl)oxirane at 120° C. |

| Preparation No | Name/Structure | Data |
|---|---|---|
| 138 | 1-(2,2-difluoroethyl)-4-(4,4,5,5-tetramethyl-1,3,2-dioxaborolan-2-yl)-1H-pyrazole | $^1$H NMR (500 MHz, CDCl$_3$): δ 7.84 (d, J = 0.7 Hz, 1H), 7.77 (d, J = 0.7 Hz, 1H), 6.25-5.93 (m, 1H), 4.57-4.39 (m, 2H), 1.33 (s, 12H).<br>LCMS (ESI) Rt = 2.64 minutes MS m/z 259 [M + H]$^+$<br>Using 1,1-difluoro-2-iodoethane |
| 139 | 1-(cyclopropylmethyl)-4-(4,4,5,5-tetramethyl-1,3,2-dioxaborolan-2-yl)-1H-pyrazole | $^1$H NMR (500 MHz, CDCl$_3$): δ 7.82 (d, J = 0.7 Hz, 1H), 7.80 (d, J = 0.7 Hz, 1H), 4.00 (d, J = 7.1 Hz, 2H), 1.33 (s, 12H), 1.27 (m, 1H), 0.68-0.63 (m, 2H), 0.40-0.35 (m, 2H).<br>LCMS (ESI) Rt = 2.58 minutes MS m/z 249 [M + H]$^+$<br>Using (bromomethyl)-cyclopropane. |

Preparation 140: 2-Methyl-3-(4-(4,4,5,5-tetramethyl-1,3,2-dioxaborolan-2-yl)-1H-pyrazol-1-yl)butan-2-ol

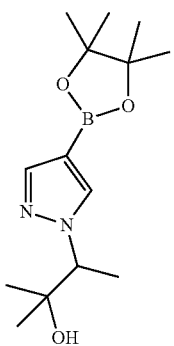 [SMILES: CC(n1cc(B2OC(C)(C)C(C)(C)O2)cn1)C(C)(C)O]

To a solution of 3-(4-(4,4,5,5-tetramethyl-1,3,2-dioxaborolan-2-yl)-1H-pyrazol-1-yl)butan-2-one (Preparation 133, in THF (6 mL) at 0° C. was added MeMgBr (3M, 0.24 mL, 0.71 mmol). After stirring for 3 hours, another portion of MeMgBr was added. The solution was stirred at room temperature for 16 hours. The reaction was diluted with brine and extracted with EtOAc. The combined organic layers were washed with water, dried over Na$_2$SO$_4$ and concentrated in vacuo to afford the title compound as a yellow oil (99 mg, 70%).

$^1$H NMR (500 MHz, CDCl$_3$): δ 7.83 (d, J=0.68 Hz, 1H), 7.74 (d, J=0.68 Hz, 1H), 4.18 (q, J=7.24 Hz, 1H), 1.56 (d, J=6.98 Hz, 3H), 1.34 (s, 12H), 1.26 (s, 6H).

LCMS (ESI) Rt=2.45 minutes MS m/z 281 [M+H]$^+$

Preparation 141: (1-Methyl-4-(4,4,5,5-tetramethyl-1,3,2-dioxaborolan-2-yl)-1H-pyrazol-5-yl)methanol

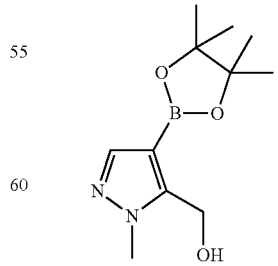

To a solution of 1-methyl-4-(4,4,5,5-tetramethyl-1,3,2-dioxaborolan-2-yl)-1H-pyrazole-5-carbaldehyde (Preparation 142, 80 mg, 0.339 mmol) in MeOH (4 mL) at room temperature was added NaBH₄ (25.6 mg, 0.678 mmol). The resulting solution was stirred at room temperature for 2 hours before concentrating in vacuo. EtOAc (10 mL) and water (0.5 mL) were added to the residue and the mixture was dried over Na₂SO₄ and concentrated in vacuo to afford the title compound as a white solid (26 mg, 32%).

$^1$H NMR (500 MHz, CDCl₃): δ 7.72 (s, 1H), 4.78 (s, 2H), 3.90 (s, 3H), 1.34 (s, 12H).

LCMS (ESI) Rt=2.02 minutes MS m/z 239 [M+H]⁺

Preparation 142: 1-Methyl-4-(4,4,5,5-tetramethyl-1,3,2-dioxaborolan-2-yl)-1H-pyrazole-5-carbaldehyde

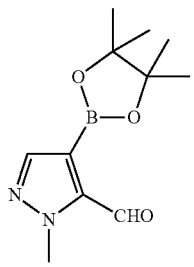 [SMILES: Cn1ncc(B2OC(C)(C)C(C)(C)O2)c1C=O]

A mixture of 4-bromo-1-methyl-1H-pyrazole-5-carbaldehyde (150 mg, 0.794 mmol), KOAc (234 mg, 2.38 mmol), Pd(dppf)Cl₂.DCM (33.6 mg, 0.040 mmol) and bis(pinacolato)diboron (222 mg, 0.873 mmol) in dioxane (4 mL) was stirred at 100° C. under microwave irradiation for 1 hour. The reaction mixture was diluted with EtOAc. The mixture was filtered and purified using Biotage silica gel column chromatography eluting with 20% EtOAc/cyclohexanes to give the title compound (96 mg, 51%).

$^1$H NMR (500 MHz, CDCl₃): δ 10.28 (s, 1H), 7.79 (s, 1H), 4.20 (s, 3H), 1.34 (s, 12H).

LCMS (ESI) Rt=2.55 minutes MS m/z 237 [M+H]⁺

Preparation 143:
5-Bromo-1-(2-methoxyethyl)-2-methyl-1H-imidazole

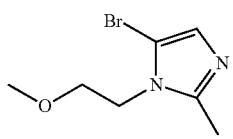

To a solution of 1-(2-methoxyethyl)-2-methyl-1H-imidazole (Preparation 146, 604 mg, 4.31 mmol) in THF (8 mL), K₂CO₃ (119 mg, 0.86 mmol) was added and followed by N-Bromosuccinimide (652 mg, 3.66 mmol). The suspension was stirred at room temperature for 16 hours, diluted with brine and extracted with EtOAc. The organic layer was collected and concentrated in vacuo to afford the title compound as a yellow oil (219 mg, 26%) that was used directly in the next reaction.

$^1$H NMR (500 MHz, CDCl₃): δ 6.91 (s, 1H), 4.06 (t, J=5.60 Hz, 2H), 3.59 (t, J=5.60 Hz, 2H), 3.31 (s, 3H), 2.45 (s, 3H).

Preparation 144: tert-Butyl 4-((5-bromo-2-methyl-1H-imidazol-1-yl)methyl)piperidine-1-carboxylate

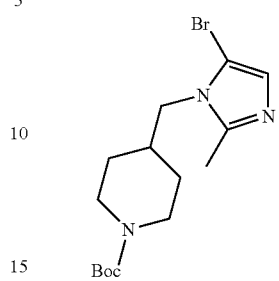

The title compound was prepared according to the method described for Preparation 143 using tert-butyl 4-((2-methyl-1H-imidazol-1-yl)methyl)piperidine-1-carboxylate (Preparation 147). The residue was purified using Biotage silica gel column chromatography eluting with 60-100% EtOAc/cyclohexanes.

$^1$H NMR (500 MHz, CDCl₃): δ 6.92 (s, 1H), 4.26-4.05 (m, 2H), 3.76 (d, J=7.46 Hz, 2H), 2.72-2.58 (m, 2H), 2.43 (s, 3H), 1.98-1.86 (m, 1H), 1.63-1.51 (m, 2H), 1.47 (s, 9H), 1.30-1.13 (m, 2H).

LCMS (ESI) Rt=1.67 minutes MS m/z 358 [M$^{79}$Br+H]⁺

Preparation 145: 1-(5-Bromo-2-methyl-1H-imidazol-1-yl)-2-methylpropan-2-ol

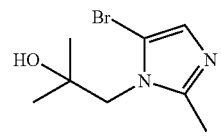

The title compound was prepared according to the method described for Preparation 143 using 2-methyl-1-(2-methyl-1H-imidazol-1-yl)propan-2-ol (Preparation 148). The residue was purified using Biotage silica gel column chromatography eluting with 0-4% MeOH in EtOAc.

$^1$H NMR (500 MHz, CDCl₃): δ 6.78 (s, 1H), 3.88 (s, 2H), 3.41 (s, broad, 1H), 2.47 (s, 3H), 1.32 (s, 6H).

LCMS (ESI) Rt=0.65 minutes MS m/z 233 [M$^{79}$Br+H]⁺

Preparation 146:
1-(2-Methoxyethyl)-2-methyl-1H-imidazole

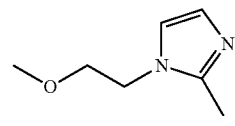

NaH (60%, 620 mg) was added to a solution of 2-methyl-1H-imidazole (1.06 g, 12.95 mmol) in DMF (8 mL). After stirring for 15 minutes, 1-bromo-2-methoxyethane (2.16 g, 15.54 mmol) in DMF (1 mL) was added. The resulting solution was stirred at 80° C. under microwave irradiation for 60 minutes. Water (1 mL) was added and all solvents were removed by high vacuum. EtOAc was added to the residue, stirred for 15 minutes, filtered and concentrated in vacuo to afford the title compound as a colourless oil (604 mg, 33%) that was used directly in the next step:

$^1$H NMR (500 MHz, CDCl$_3$): δ 6.93 (d, J=1.36 Hz, 1H), 6.89 (d, J=1.36 Hz, 1H), 4.02 (t, J=5.44 Hz, 2H), 3.62 (t, J=5.44 Hz, 2H), 3.34 (s, 3H), 2.41 (s, 3H).

Preparation 147: tert-Butyl 4-((2-methyl-1H-imidazol-1-yl)methyl)piperidine-1-carboxylate

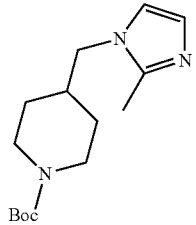 [SMILES: Cc1nccn1CC1CCN(C(=O)OC(C)(C)C)CC1]

The title compound was prepared according to the method described for Preparation 146 using 2-methyl-1H-imidazole and tert-butyl 4-((tosyloxy)methyl)piperidine-1-carboxylate.

$^1$H NMR (500 MHz, CDCl$_3$): δ 6.95 (d, J=1.38 Hz, 1H), 6.80 (d, J=1.38 Hz, 1H), 4.05-4.02 (m, 2H), 3.73 (d, J=7.34 Hz, 2H), 2.70-2.60 (m, 2H), 2.42 (s, 3H), 1.86-1.78 (m, 1H), 1.62-1.54 (m, 2H), 1.46 (s, 9H), 1.24-1.10 (m, 2H).

LCMS (ESI) Rt=1.44 minutes MS m/z 280 [M+H]$^+$

Preparation 148: 2-Methyl-1-(2-methyl-1H-imidazol-1-yl)propan-2-ol

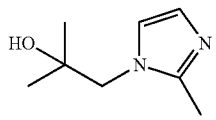

The title compound was prepared according to the method described for Preparation 146 using 2-methyl-1H-imidazole and 2,2-dimethyloxirane.

$^1$H NMR (500 MHz, CDCl$_3$): δ 6.91 (d, J=1.38 Hz, 1H), 6.83 (d, J=1.38 Hz, 1H), 3.80 (s, 2H), 2.38 (s, 3H), 1.26 (s, 6H).

Preparation 149: (4-Bromo-1-methyl-1H-pyrazol-5-yl)methanol

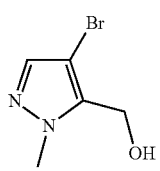

To a solution of 4-bromo-1-methyl-1H-pyrazole-5-carbaldehyde (677 mg, 3.58 mmol) in MeOH (8 mL) at 0° C., NaBH$_4$ (136 mg, 0.86 mmol) was added. The solution was stirred at room temperature for 2 hours. The reaction was concentrated in vacuo and diluted with water. The solution was extracted with EtOAc, the organic layer collected, dried over sodium sulphate and concentrated in vacuo to afford the title compound as a white solid (614 mg, 90%).

$^1$H NMR (500 MHz, CDCl$_3$): δ 7.43 (s, 1H), 4.72 (s, 2H), 3.97 (s, 3H), 2.09 (s, 1H).

LCMS (ESI) Rt=1.29 minutes MS m/z 191 [M$^{79}$Br+H]$^+$

Preparation 150: 4-Bromo-5-(methoxymethyl)-1-methyl-1H-pyrazole

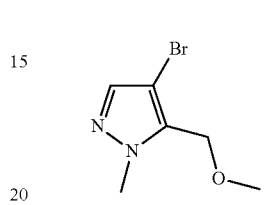

NaH (60%, 58 mg) was added to a solution of (4-bromo-1-methyl-1H-pyrazol-5-yl)methanol (Preparation 149, 97 mg, 1.03 mmol) in THF/DMF (8/4 mL). After stirring for 15 minutes, iodomethane (439 mg, 3.09 mmol) in THF (1 mL) was added. The resulting solution was stirred at room temperature for 16 hours. The reaction mixture was diluted with brine and extracted with EtOAc. The combined organic layers were washed with water, dried over sodium sulphate and concentrated in vacuo to afford the title compound (142 mg, 67%).

$^1$H NMR (500 MHz, CDCl$_3$): δ 7.42 (s, 1H), 4.49 (s, 2H), 3.91 (s, 3H), 3.34 (s, 3H).

LCMS (ESI) Rt=2.13 minutes MS m/z 205 [M$^{79}$Br+H]$^+$

Preparation 151: 5-Bromo-2-(methoxymethyl)-1-methyl-1H-imidazole

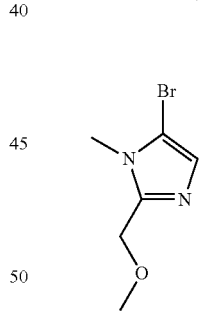

NaH (60%, 30 mg) was added to a solution of (5-bromo-1-methyl-1H-imidazol-2-yl)methanol (120 mg, 0.63 mmol) in THF (4 mL). After stirring for 15 minutes, iodomethane (35 uL, 0.57 mmol) was added. The resulting solution was stirred at 60° C. under microwave irradiation for 60 minutes. The reaction mixture was diluted with EtOAc, filtered and concentrated in vacuo. The residue was purified using Biotage silica gel column chromatography eluting with EtOAc to give the title compound as light brown oil (32 mg, 25%).

$^1$H NMR (500 MHz, CDCl$_3$): δ 6.96 (s, 1H), 4.52 (s, 2H), 3.63 (s, 3H), 3.33 (s, 3H).

LCMS (ESI) Rt=0.74 minutes MS m/z 205 [M$^{79}$Br+H]$^+$

Preparation 152: 1-Oxaspiro[2.3]hexane

To a solution of methylenecyclobutane (724 mg, 10.63 mmol) in DCM (40 mL) was added dropwise a solution of mCPBA in DCM (20 mL) at room temperature and the reaction was stirred for 16 hours. The reaction was washed with $Na_2SO_3$ solution (40 mL), $Na_2CO_3$ solution (40 mL), water (40 mL), dried over sodium sulfate and concentrated in vacuo at a temperature below 30° C. to afford the title compound as a colourless liquid (112 mg, 13%) that was used in the next step without further purification:

$^1$H NMR (500 MHz, $CDCl_3$): δ 2.73 (s, 2H), 2.61-2.46 (m, 2H), 2.36-2.24 (m, 2H), 1.95-1.76 (m, 2H).

Preparation 153: 3-Bromo-7-methyl-5,6,7,8-tetrahydro-[1,2,4]triazolo[4,3-a]pyrazine

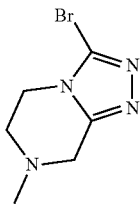

A suspension of 3-bromo-5,6,7,8-tetrahydro-[1,2,4]triazolo[4,3-a]pyrazine (Preparation 154, 29 mg, 0.143 mmol), $K_2CO_3$ (23.7 mg, 0.171 mmol), dimethyl sulfate (14 uL, 0.143 mmol in THF (3 mL) was stirred at 80° C. under microwave irradiation for 60 minutes. The reaction mixture was filtered and purified by elution through an SCX-2 column using 2M $NH_3$/MeOH to give the title compound as yellow oil (16.5 mg, 53%).

$^1$H NMR (500 MHz, $CDCl_3$): δ 3.91 (dd, J=5.10, 6.08 Hz, 2H), 3.76 (s, 2H), 2.88 (dd, J=5.10, 6.08 Hz, 2H), 2.53 (s, 3H).

LCMS (ESI) Rt=0.47 minutes MS m/z 217 $[M^{79}Br+H]^+$

Preparation 154: 3-bromo-5,6,7,8-tetrahydro-[1,2,4]triazolo[4,3-a]pyrazine

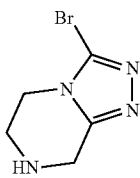

To a solution of tert-butyl 3-bromo-5,6-dihydro-[1,2,4]triazolo[4,3-a]pyrazine-7(8H)-carboxylate (52 mg, 0.172 mmol) in DCM (6 mL) at 0° C. was added TFA (0.26 mL). The reaction was stirred at room temperature for 16 hours before concentrating in vacuo. The residue was purified by elution through an SCX-2 column using 2M $NH_3$/MeOH to give the title compound as yellow solid (29 mg, 83%).

$^1$H NMR (500 MHz, MeOD): δ 4.10 (s, 1H), 3.93 (t, J=5.63 Hz, 2H), 3.25 (t, J=5.63 Hz, 2H).

LCMS (ESI) Rt=0.40 minutes MS m/z 203 $[M^{79}Br+H]^+$

Preparation 155: (E)-5-Bromo-1-methyl-1H-imidazole-2-carbaldehyde oxime

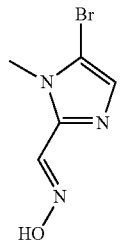

A mixture of $K_2CO_3$ (360 mg, 2.61 mmol), 5-bromo-1-methyl-1H-imidazole-2-carbaldehyde (98.5 mg, 0.521 mmol) and hydroxylamine hydrochloride (109 mg, 1.563 mmol) in EtOH (4 mL) was stirred at 120° C. under microwave irradiation for 60 minutes. The resulting suspension was filtered, washing through with EtOAc and MeOH. The filtrate was concentrated in vacuo to afford the title compound as a white solid (100 mg, 94%).

$^1$H NMR (500 MHz, $CDCl_3$): δ 8.17 (s, 1H), 7.14 (s, 1H), 3.86 (s, 3H).

The invention claimed is:

1. A method of treating a proliferative disorder in a patient in need of such treatment, wherein said proliferative disorder is selected from lung, colon, breast, ovarian, prostate, liver, pancreas, brain, and skin cancer, said method comprising administering to said patient a therapeutically effective amount of a compound having the structural formula II shown below:

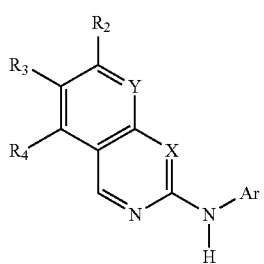

II wherein:
X is CH or N;
Y is N or C—H;
$R_2$ is (1-6C)alkyl, (1-8C)heteroalkyl, aryl, aryl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, (3-8C)cycloalkyl(1-2C)alkyl, $OR_{13}$, C(O)$R_{13}$, C(O)O$R_{13}$, OC(O)$R_{13}$, C(O)N($R_{14}$)$R_{13}$, S(O)$_x$$R_{13}$ (where x is 0, 1 or 2), or $SO_2N(R_{14})R_{13}$;

and wherein $R_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, S(O)$_x$CH$_3$ (where x is 0, 1 or 2), methylamino or dimethylamino, aryl, aryl(1-2C)alkyl, heteroaryl, heteroaryl(1-2C)alkyl, heterocyclyl, heterocyclyl(1-2C)alkyl, (3-8C)cycloalkyl, and (3-8C)cycloalkyl(1-2C)alkyl;

and wherein any (1-4C)alkyl, (1-4C)alkoxy, aryl, heteroaryl, heterocyclyl, or (3-8C)cycloalkyl moiety present within a substituent group on R$_2$ is optionally further substituted by fluoro, chloro, trifluoromethyl, trifluoromethoxy, cyano, nitro, hydroxy, amino, carboxy, carbamoyl, sulphamoyl, (1-4C)alkyl, NR$_c$R$_d$, OR$_c$, C(O)R$_c$, C(O)OR$_c$, OC(O)R$_c$, N(R$_d$)OR$_c$, C(O)N(R$_d$)R$_c$, N(R$_d$)C(O)R$_c$, S(O)$_y$R$_c$ (where y is 0, 1 or 2), SO$_2$N(R$_d$)R$_c$, or N(R$_d$)SO$_2$R$_c$, wherein R$_c$ and R$_d$ are each independently H or (1-4C)alkyl;

R$_3$ is hydrogen, (1-4C)alkyl, (3-6C)cycloalkyl, halo, CF$_3$, CN or (1-4C)alkoxy;

R$_4$ is hydrogen, (1-3C)alkyl, fluoro, chloro or CF$_3$;

Ar has the formula:

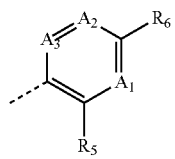

wherein:
(i) all of A$_1$, A$_2$ and A$_3$ are CH; or
(ii) A$_3$ is CH and A$_1$ or A$_2$ are N or CH;

R$_5$ is hydrogen, cyano, (1-3C)alkyl, (1-3C)fluoroalkyl, (1-3C)alkoxy, (1-3C)fluoroalkoxy, halo, (1-3C)alkanoyl, C(O)NR$_{15}$R$_{16}$ or S(O)$_2$NR$_{15}$R$_{16}$, and wherein R$_{15}$ and R$_{16}$ are each independently H or (1-3C)alkyl, and wherein any alkyl or alkoxy moieties present within a R$_5$ substituent group are optionally further substituted by hydroxy or methoxy;

R$_6$ is halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or R$_6$ is a group of the formula:

-L$^1$-L$^2$-R$_{17}$ wherein
L$^1$ is absent or a linker group of the formula —[CR$_{18}$R$_{19}$]$_n$— in which n is an integer selected from 1, 2, 3 and 4, and R$_{18}$ and R$_{19}$ are each independently hydrogen or (1-2C)alkyl;

L$^2$ is absent or is O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{21}$)SO$_2$, wherein R$_{20}$ and R$_{21}$ are each independently hydrogen or (1-2C)alkyl; and R$_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, or heterocyclyl-(1-4C)alkyl, and wherein R$_{17}$ is optionally further substituted by one or more substituent groups independently selected from oxo, halo, cyano, nitro, hydroxy, NR$_{22}$R$_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, CONR$_{22}$R$_{23}$, and SO$_2$NR$_{22}$R$_{23}$; wherein R$_{22}$ and R$_{23}$ are each independently hydrogen, (1-4C)alkyl, (3-6C)cycloalkyl or (3-6C)cycloalkyl(1-2C)alkyl; or R$_{22}$ and R$_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently hydrogen, (1-3C)alkyl, (3-6C)cycloalkyl, or (3-6C)cycloalkyl(1-2C)alkyl);

or R$_{17}$ is a group having the formula:

-L$^3$-L$^4$-R$_{24}$ wherein
L$^3$ is absent or a linker group of the formula —[CR$_{25}$R$_{26}$]$_n$— in which n is an integer selected from 1, 2, 3 and 4, and R$_{25}$ and R$_{26}$ are each independently hydrogen or (1-2C)alkyl;

L$^4$ is absent or is O, S, SO, SO$_2$, N(R$_{27}$), C(O), C(O)O, OC(O), CH(OR$_{27}$), C(O)N(R$_{27}$), N(R$_{27}$)C(O), N(R$_{27}$)C(O)N(R$_{28}$), S(O)$_2$N(R$_{27}$), or N(R$_{28}$)SO$_2$, wherein R$_{27}$ and R$_{28}$ are each independently hydrogen or (1-2C)alkyl; and R$_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, or heterocyclyl-(1-4C)alkyl;

R$_{13}$ is hydrogen, (1-6C)alkyl, (1-6C)alkoxy, (3-6C)cycloalkyl, (3-6C)cycloalkyl-(1-2C)alkyl, aryl, aryl-(1-2C)alkyl, heteroaryl, or heteroaryl-(1-2C)alkyl, and wherein R$_{13}$ is optionally further substituted by one or more substituents selected from hydroxy, fluoro, chloro, cyano, CF$_3$, OCF$_3$ (1-2C)alkyl and (1-2C)alkoxy;

R$_{14}$ is hydrogen, (1-6C)alkyl, (3-6C)cycloalkyl, or (3-6C)cycloalkyl-(1-2C)alkyl, and wherein R$_{14}$ is optionally further substituted by one or more substituents selected from hydroxy, fluoro, chloro, cyano, CF$_3$, OCF$_3$, (1-2C)alkyl and (1-2C)alkoxy;

subject to the proviso that:
X can only be N when Y is N; and
when X and Y are both N, R$_3$ is H or fluoro;

or a pharmaceutically acceptable salt or solvate thereof.

2. The method of claim 1, wherein said compound has one of the structures IIa, IIb or IIc shown below:

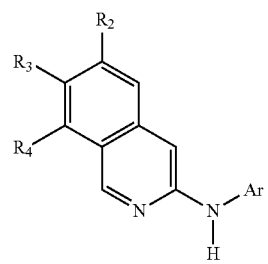

IIa

-continued

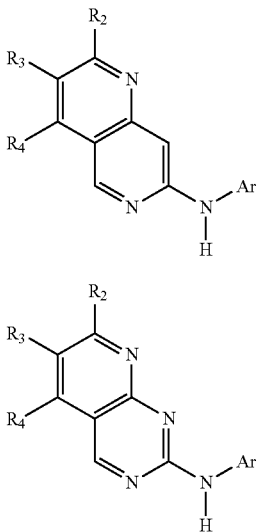

and wherein Ar, $R_2$, $R_3$ and $R_4$ are as defined in claim 1.

3. The method of claim 1, wherein $R_2$ is (1-6C)alkyl, phenyl, phenyl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, (3-8C)cycloalkyl(1-2C)alkyl, $OR_{13}$, $C(O)R_{13}$, $C(O)OR_{13}$, $OC(O)R_{13}$, $C(O)N(R_{14})R_{13}$, $S(O)_xR_{13}$ (where x is 0, 1 or 2), or $SO_2N(R_{14})R_{13}$;

and wherein $R_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_xCH_3$ (where x is 0, 1 or 2), methylamino, dimethylamino, phenyl, phenyl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, and (3-8C)cycloalkyl(1-2C)alkyl, and wherein any (1-4C)alkyl, (1-4C)alkoxy, phenyl, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently H or (1-4C)alkyl.

4. The method of claim 1, wherein $R_2$ is (1-6C)alkyl, a 5 or 6 membered heteroaryl, a 3 to 6 membered heterocyclyl, a 3 to 6 membered heterocyclyl(1-2C)alkyl, (3-8C)cycloalkyl, $C(O)N(R_{14})R_{13}$, $S(O)_xR_{13}$ (where x is 0, 1 or 2), or $SO_2N(R_{14})R_{13}$;

and wherein $R_2$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, 5 or 6 membered heteroaryl, a 3 to 6 membered heterocyclyl, a 3 to 6 membered heterocyclyl(1-2C)alkyl, (3-6C)cycloalkyl, or (3-8C)cycloalkyl(1-2C)alkyl, and wherein any (1-4C)alkyl, (1-4C)alkoxy, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently H or (1-4C)alkyl.

5. The method of claim 1, wherein $R_3$ is hydrogen, (1-2C)alkyl or (3-6C)cycloalkyl.

6. The method of claim 1, wherein $R_3$ is hydrogen.

7. The method of claim 1, wherein $R_4$ is hydrogen, (1-2C)alkyl, fluoro, chloro or $CF_3$.

8. The method of claim 1, wherein $R_4$ is hydrogen.

9. The method of claim 1, wherein $R_5$ is hydrogen, (1-3C)alkyl, (1-3C)alkoxy, (1-3C)fluoroalkoxy or halo, and wherein any alkyl or alkoxy moieties present within a $R_5$ substituent group are optionally further substituted by methoxy.

10. The method of claim 1, wherein $R_5$ is $OCH_3$ or Cl.

11. The method of claim 1, wherein $R_6$ is halo, trifluoromethyl, trifluoromethoxy, cyano, hydroxy, amino, carboxy, carbamoyl, sulphamoyl, or a group of the formula:

$-L^1-L^2-R_{17}$ wherein $L^1$ is absent or a linker group of the formula $-[CR_{18}R_{19}]_n-$ in which n is 1 or 2, and $R_{18}$ and $R_{19}$ are each independently hydrogen or methyl;

$L^2$ is absent or is O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently hydrogen or (1-2C)alkyl; and $R_{17}$ is (1-6C)alkyl, aryl, (3-6C)cycloalkyl, heteroaryl, or heterocyclyl, and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2(1-2C)$alkyl or $NR_eR_f$ (where $R_e$ and $R_f$ are each independently hydrogen, (1-3C)alkyl, (3-6C)cycloalkyl, or (3-6C)cycloalkyl(1-2C)alkyl);

or $R_{17}$ is a group having the formula:

$-L^3-L^4-R_{24}$ wherein $L^3$ is absent or a linker group of the formula $-[CR_{25}R_{26}]_n-$ in which n is an integer selected from 1 and 2, and $R_{25}$ and $R_{26}$ are each hydrogen;

L⁴ is absent or is O, S, SO, SO₂, N(R₂₇), C(O), C(O)O, OC(O), C(O)N(R₂₇), N(R₂₇)C(O), S(O)₂N(R₂₇) or N(R₂₈)SO₂, wherein R₂₇ and R₂₈ are each independently hydrogen or (1-2C)alkyl; and R₂₄ is (1-6C)alkyl, phenyl, phenyl-(1-2C)alkyl, (3-6C)cycloalkyl, (3-6C)cycloalkyl-(1-4C)alkyl, 5 or 6-membered heteroaryl, 5 or 6-membered heteroaryl-(1-2C)alkyl, 4 to 6-membered heterocyclyl, or 4 to 6-membered heterocyclyl-(1-2C)alkyl.

12. The method of claim 1, wherein R₆ is halo, trifluoromethyl, trifluoromethoxy, cyano, hydroxy, amino, carboxy, carbamoyl, sulphamoyl, or a group of the formula:

-L¹-L²-R₁₇ wherein

L¹ is absent or a linker group of the formula —[CR₁₈R₁₉]ₙ— in which n is 1 or 2, and R₁₈ and R₁₉ are each independently hydrogen or methyl;

L² is absent or is O, S, SO, SO₂, N(R₂₀), C(O), C(O)O, OC(O), CH(OR₂₀), C(O)N(R₂₀), N(R₂₀)C(O), N(R₂₀)C(O)N(R₂₁), S(O)₂N(R₂₀), or N(R₂₀)SO₂, wherein R₂₀ and R₂₁ are each independently hydrogen or (1-2C)alkyl; and R₁₇ is (1-6C)alkyl, aryl, (3-6C)cycloalkyl, heteroaryl, or heterocyclyl, and wherein R₁₇ is optionally further substituted by one or more substituent groups independently selected from oxo, halo, cyano, nitro, hydroxy, NR₂₂R₂₃, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR₂₂R₂₃, and SO₂NR₂₂R₂₃; wherein R₂₂ and R₂₃ are each independently hydrogen, (1-4C)alkyl, (3-6C)cycloalkyl or (3-6C)cycloalkyl(1-2C)alkyl; or R₂₂ and R₂₃ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, CF₃, OCF₃, (1-2C)alkyl, (1-2C)alkoxy, SO₂(1-2C)alkyl or NRₑR_f (where Rₑ and R_f are each independently hydrogen, (1-3C)alkyl, (3-6C)cycloalkyl, or (3-6C)cycloalkyl(1-2C)alkyl).

13. The method of claim 1, wherein R₁₃ is hydrogen, (1-6C)alkyl, (3-6C)cycloalkyl, (3-6C)cycloalkyl-(1-2C)alkyl, 3 to 6 membered heterocyclyl, or 3 to 6 membered heterocyclyl-(1-2C)alkyl, and wherein R₁₃ is optionally further substituted by one or more substituents selected from hydroxy, fluoro, chloro, cyano, CF₃, OCF₃, methyl and methoxy.

14. The method of claim 1, wherein R₁₄ is hydrogen or (1-4C)alkyl.

15. The method of claim 1, wherein said compound is selected from any one of the following:

(3-methoxy-4-((6-(1-methyl-1H-pyrazol-4-yl)isoquinolin-3-yl)amino)phenyl)(3-methoxyazetidin-1-yl)methanone;

N-(4-(1,2-dimethyl-1H-imidazol-5-yl)-2-methoxyphenyl)-6-(1-methyl-1H-pyrazol-4-yl)isoquinolin-3-amine;

N-(2-chloro-4-(1,2-dimethyl-1H-imidazol-5-yl)phenyl)-6-(1-methyl-1H-pyrazol-4-yl)isoquinolin-3-amine;

N-(2-methoxy-4-(1-methyl-1H-imidazol-5-yl)phenyl)-6-(1-methyl-1H-pyrazol-4-yl)isoquinolin-3-amine;

N-(4-(1,2-dimethyl-1H-imidazol-5-yl)-2-methoxyphenyl)-6-(1,5-dimethyl-1H-pyrazol-4-yl)isoquinolin-3-amine;

N-(4-(1,2-dimethyl-1H-imidazol-5-yl)-2-methoxyphenyl)-6-(1,3-dimethyl-1H-pyrazol-4-yl)isoquinolin-3-amine;

6-cyclopropyl-N-(4-(1,2-dimethyl-1H-imidazol-5-yl)-2-methoxyphenyl)isoquinolin-3-amine;

N-(4-(1,2-dimethyl-1H-imidazol-5-yl)-2-methoxyphenyl)-6-(pyrimidin-5-yl)isoquinolin-3-amine;

N-(4-(1,2-dimethyl-1H-imidazol-5-yl)-2-methoxyphenyl)-6-(pyridin-3-yl)isoquinolin-3-amine;

N-(4-(1,2-dimethyl-1H-imidazol-5-yl)-2-methoxyphenyl)-7-(1-methyl-1H-pyrazol-4-yl)pyrido[2,3-d]pyrimidin-2-amine;

N-(4-(1,2-dimethyl-1H-imidazol-5-yl)-2-methoxyphenyl)-6-(1-isopropyl-1H-pyrazol-4-yl)isoquinolin-3-amine;

N-(4-(1,2-dimethyl-1H-imidazol-5-yl)-2-methoxyphenyl)-6-(1-(2-methoxyethyl)-1H-pyrazol-4-yl)isoquinolin-3-amine;

N-(4-(1,2-dimethyl-1H-imidazol-5-yl)-2-methoxyphenyl)-6-(2,4-dimethylthiazol-5-yl)isoquinolin-3-amine;

tert-butyl (5-(3-((4-(1,2-dimethyl-1H-imidazol-5-yl)-2-methoxyphenyl)amino)isoquinolin-6-yl)pyridin-2-yl)(methyl)carbamate;

N-(4-(1,2-dimethyl-1H-imidazol-5-yl)-2-methoxyphenyl)-6-(6-(methylamino)pyridin-3-yl)isoquinolin-3-amine;

N-(4-(1,2-dimethyl-1H-imidazol-5-yl)-2-methoxyphenyl)-6-(6-methylpyridin-3-yl)isoquinolin-3-amine;

N-(4-(1,2-dimethyl-1H-imidazol-5-yl)-2-methoxyphenyl)-6-(1-ethyl-1H-pyrazol-4-yl)isoquinolin-3-amine;

N-(4-(1,2-dimethyl-1H-imidazol-5-yl)-2-methoxyphenyl)-6-(thiazol-5-yl)isoquinolin-3-amine;

N-(4-(1,2-dimethyl-1H-imidazol-5-yl)-2-methoxyphenyl)-6-(6-(dimethylamino)pyridin-3-yl)isoquinolin-3-amine;

N-(4-(1,2-dimethyl-1H-imidazol-5-yl)-2-methoxyphenyl)-6-(pyridin-4-yl)isoquinolin-3-amine;

N-(4-(1,2-dimethyl-1H-imidazol-5-yl)-2-methoxyphenyl)-6-(oxazol-5-yl)isoquinolin-3-amine;

6-(1,2-dimethyl-1H-imidazol-5-yl)-N-(4-(1,2-dimethyl-1H-imidazol-5-yl)-2-methoxyphenyl)isoquinolin-3-amine;

tert-butyl 4-(4-(3-((4-(1,2-dimethyl-1H-imidazol-5-yl)-2-methoxyphenyl)amino)isoquinolin-6-yl)-1H-pyrazol-1-yl)piperidine-1-carboxylate;

N-(4-(1,2-dimethyl-1H-imidazol-5-yl)-2-methoxyphenyl)-6-(1-(piperidin-4-yl)-1H-pyrazol-4-yl)isoquinolin-3-amine;

6-(1-(2,2-difluoroethyl)-1H-pyrazol-4-yl)-N-(4-(1,2-dimethyl-1H-imidazol-5-yl)-2-methoxyphenyl)isoquinolin-3-amine;

6-(1-(cyclopropylmethyl)-1H-pyrazol-4-yl)-N-(4-(1,2-dimethyl-1H-imidazol-5-yl)-2-methoxyphenyl)isoquinolin-3-amine;

N-(4-(1,2-dimethyl-1H-imidazol-5-yl)-2-methoxyphenyl)-6-(1-((tetrahydro-2H-pyran-4-yl)methyl)-1H-pyrazol-4-yl)isoquinolin-3-amine;

N-(4-(1,2-dimethyl-1H-imidazol-5-yl)-2-methoxyphenyl)-6-(1-methyl-1H-1,2,3-triazol-5-yl)isoquinolin-3-amine;

N-(4-(1,2-dimethyl-1H-imidazol-5-yl)-2-methoxyphenyl)-6-(5-methylpyridin-3-yl)isoquinolin-3-amine;

(5-(3-methoxy-4-((6-(1-(2-methoxyethyl)-1H-pyrazol-4-yl)isoquinolin-3-yl)amino)phenyl)-1-methyl-1H-imidazol-2-yl)methanol;

6-(1-(cyclobutylmethyl)-1H-pyrazol-4-yl)-N-(4-(1,2-dimethyl-1H-imidazol-5-yl)-2-methoxyphenyl)isoquinolin-3-amine;

1-(4-(3-((4-(1,2-dimethyl-1H-imidazol-5-yl)-2-methoxyphenyl)amino)isoquinolin-6-yl)-1H-pyrazol-1-yl)-2-methylpropan-2-ol;

N-(4-(1,2-dimethyl-1H-imidazol-5-yl)-2-methoxyphenyl)-6-(1-((3-methyloxetan-3-yl)methyl)-1H-pyrazol-4-yl)isoquinolin-3-amine;

N-(2-methoxy-4-(1-(2-methoxyethyl)-2-methyl-1H-imidazol-5-yl)phenyl)-6-(1-(2-methoxyethyl)-1H-pyrazol-4-yl)isoquinolin-3-amine;

(4-(3-methoxy-4-((6-(1-(2-methoxyethyl)-1H-pyrazol-4-yl)isoquinolin-3-yl)amino)phenyl)-1-methyl-1H-pyrazol-5-yl)methanol;

N-(4-(1,2-dimethyl-1H-imidazol-5-yl)-2-methoxyphenyl)-6-(1-(oxetan-3-yl)-1H-pyrazol-4-yl)isoquinolin-3-amine;

(4-(3-((4-(1,2-dimethyl-1H-imidazol-5-yl)-2-methoxyphenyl)amino)isoquinolin-6-yl)-1-methyl-1H-pyrazol-5-yl)methanol;

1-(4-(3-((2-methoxy-4-(1-(2-methoxyethyl)-2-methyl-1H-imidazol-5-yl)phenyl)amino)isoquinolin-6-yl)-1H-pyrazol-1-yl)-2-methylpropan-2-ol;

1-(4-(3-((4-(5-(hydroxymethyl)-1-methyl-1H-pyrazol-4-yl)-2-methoxyphenyl)amino)isoquinolin-6-yl)-1H-pyrazol-1-yl)-2-methylpropan-2-ol;

N-(4-(1,2-dimethyl-1H-imidazol-5-yl)-2-methoxyphenyl)-6-(1-(oxetan-3-ylmethyl)-1H-pyrazol-4-yl)isoquinolin-3-amine;

1-(4-(3-((4-(1,2-dimethyl-1H-imidazol-5-yl)-2-methoxyphenyl)amino)isoquinolin-6-yl)-1H-pyrazol-1-yl)propan-2-ol;

N-(4-(1,2-dimethyl-1H-imidazol-5-yl)-2-methoxyphenyl)-6-(1-(tetrahydro-2H-pyran-4-yl)-1H-pyrazol-4-yl)isoquinolin-3-amine;

6-(1-((2,2-dimethyl-1,3-dioxolan-4-yl)methyl)-1H-pyrazol-4-yl)-N-(4-(1,2-dimethyl-1H-imidazol-5-yl)-2-methoxyphenyl)isoquinolin-3-amine;

3-(4-(3-((4-(1,2-dimethyl-1H-imidazol-5-yl)-2-methoxyphenyl)amino)isoquinolin-6-yl)-1H-pyrazol-1-yl)propane-1,2-diol;

1-(4-(3-((2-methoxy-4-(2-methyl-1-(piperidin-4-ylmethyl)-1H-imidazol-5-yl)phenyl)amino)isoquinolin-6-yl)-1H-pyrazol-1-yl)-2-methylpropan-2-ol;

1-(4-(3-((2-methoxy-4-(4-methyl-4H-1,2,4-triazol-3-yl)phenyl)amino)isoquinolin-6-yl)-1H-pyrazol-1-yl)-2-methylpropan-2-ol;

1-(4-(3-((2-chloro-4-(1,2-dimethyl-1H-imidazol-5-yl)phenyl)amino)isoquinolin-6-yl)-1H-pyrazol-1-yl)-2-methylpropan-2-ol;

1-((4-(3-((4-(1,2-dimethyl-1H-imidazol-5-yl)-2-methoxyphenyl)amino)isoquinolin-6-yl)-1H-pyrazol-1-yl)methyl)cyclobutanol;

N-(4-(1,2-dimethyl-1H-imidazol-5-yl)-2-methoxyphenyl)-6-(1-(2,2,2-trifluoroethyl)-1H-pyrazol-4-yl)isoquinolin-3-amine;

1-(4-(2-((4-(1,2-dimethyl-1H-imidazol-5-yl)-2-methoxyphenyl)amino)pyrido[2,3-d]pyrimidin-7-yl)-1H-pyrazol-1-yl)-2-methylpropan-2-ol;

1-(4-(3-((2-chloro-4-morpholinophenyl)amino)isoquinolin-6-yl)-1H-pyrazol-1-yl)-2-methylpropan-2-ol;

1-(4-(3-((2-methoxy-4-morpholinophenyl)amino)isoquinolin-6-yl)-1H-pyrazol-1-yl)-2-methylpropan-2-ol;

1-(4-(3-((2-methoxy-6-morpholinopyridin-3-yl)amino)isoquinolin-6-yl)-1H-pyrazol-1-yl)-2-methylpropan-2-ol;

(4-((6-(1-(2-hydroxy-2-methylpropyl)-1H-pyrazol-4-yl)isoquinolin-3-yl)amino)-3-methoxyphenyl)(3-methoxyazetidin-1-yl)methanone;

1-(4-(3-((4-(1,2-dimethyl-1H-imidazol-5-yl)phenyl)amino)isoquinolin-6-yl)-1H-pyrazol-1-yl)-2-methylpropan-2-ol;

1-(4-(3-((2-ethoxy-4-(4-methyl-4H-1,2,4-triazol-3-yl)phenyl)amino)isoquinolin-6-yl)-1H-pyrazol-1-yl)-2-methylpropan-2-ol;

4-((6-(1-(2-hydroxy-2-methylpropyl)-1H-pyrazol-4-yl)isoquinolin-3-yl)amino)-3-methoxybenzonitrile;

1-(4-(3-((4-(1,2-dimethyl-1H-imidazol-5-yl)-3-fluoro-2-methoxyphenyl)amino)isoquinolin-6-yl)-1H-pyrazol-1-yl)-2-methylpropan-2-ol;

(S)-1-(4-(3-((4-(1,2-dimethyl-1H-imidazol-5-yl)-2-methoxyphenyl)amino)isoquinolin-6-yl)-1H-pyrazol-1-yl)propan-2-ol;

(R)-1-(4-(3-((4-(1,2-dimethyl-1H-imidazol-5-yl)-2-methoxyphenyl)amino)isoquinolin-6-yl)-1H-pyrazol-1-yl)propan-2-ol;

1-(4-(3-((2-methoxy-4-(5-(methoxymethyl)-1-methyl-1H-pyrazol-4-yl)phenyl)amino)isoquinolin-6-yl)-1H-pyrazol-1-yl)-2-methylpropan-2-ol;

1-(4-(3-((2-methoxy-4-(1-methyl-1H-pyrazol-4-yl)phenyl)amino)isoquinolin-6-yl)-1H-pyrazol-1-yl)-2-methylpropan-2-ol;

1-(4-(3-((4-(1,5-dimethyl-1H-pyrazol-4-yl)-2-methoxyphenyl)amino)isoquinolin-6-yl)-1H-pyrazol-1-yl)-2-methylpropan-2-ol;

1-(4-(3-((4-fluoro-2-methoxyphenyl)amino)isoquinolin-6-yl)-1H-pyrazol-1-yl)-2-methylpropan-2-ol;

tert-butyl 3-(4-((6-(1-(2-hydroxy-2-methylpropyl)-1H-pyrazol-4-yl)isoquinolin-3-yl)amino)-3-methoxyphenyl)-5,6-dihydro-[1,2,4]triazolo[4,3-a]pyrazine-7(8H)-carboxylate;

1-(4-(3-((2-methoxy-4-(5,6,7,8-tetrahydro-[1,2,4]triazolo[4,3-a]pyrazin-3-yl)phenyl)amino)isoquinolin-6-yl)-1H-pyrazol-1-yl)-2-methylpropan-2-ol;

1-(4-(3-((6-(1,2-dimethyl-1H-imidazol-5-yl)-2-methoxypyridin-3-yl)amino)isoquinolin-6-yl)-1H-pyrazol-1-yl)-2-methylpropan-2-ol;

1-(4-(3-((5-(1,2-dimethyl-1H-imidazol-5-yl)-3-methoxypyridin-2-yl)amino)isoquinolin-6-yl)-1H-pyrazol-1-yl)-2-methylpropan-2-ol;

1-(4-(3-((2-chloro-4-(pyrimidin-5-yl)phenyl)amino)isoquinolin-6-yl)-1H-pyrazol-1-yl)-2-methylpropan-2-ol;

1-(4-(3-((2-chloro-4-(methyl sulfonyl)phenyl)amino)isoquinolin-6-yl)-1H-pyrazol-1-yl)-2-methylpropan-2-ol;

4-((6-(1-(2-hydroxy-2-methylpropyl)-1H-pyrazol-4-yl)isoquinolin-3-yl)amino)-3-methoxy-N,N-dimethylbenzamide;

4-((6-(1-(2-hydroxy-2-methylpropyl)-1H-pyrazol-4-yl)isoquinolin-3-yl)amino)-N-(2-hydroxyethyl)-3-methoxybenzamide;

4-((6-(1-(2-hydroxy-2-methylpropyl)-1H-pyrazol-4-yl)isoquinolin-3-yl)amino)-3-methoxy-N-(2-methoxyethyl)benzamide;

1-(4-(3-((2-methoxy-4-(2-(methoxymethyl)-1-methyl-1H-imidazol-5-yl)phenyl)amino)isoquinolin-6-yl)-1H-pyrazol-1-yl)-2-methylpropan-2-ol;

1-(4-(3-((2-methoxy-4-(1-methyl-1H-1,2,4-triazol-5-yl)phenyl)amino)isoquinolin-6-yl)-1H-pyrazol-1-yl)-2-methylpropan-2-ol;

(1,1-dioxidothiomorpholino)(4-((6-(1-(2-hydroxy-2-methylpropyl)-1H-pyrazol-4-yl)isoquinolin-3-yl)amino)-3-methoxyphenyl)methanone;

N-(2-methoxy-4-(1-methyl-1H-pyrazol-4-yl)phenyl)-2-(1-methyl-1H-pyrazol-4-yl)-1,6-naphthyridin-7-amine;

1-(4-(7-((2-methoxy-4-(1-methyl-1H-pyrazol-4-yl)phenyl)amino)-1,6-naphthyridin-2-yl)-1H-pyrazol-1-yl)-2-methylpropan-2-ol;

1-(4-(7-((4-(1,2-dimethyl-1H-imidazol-5-yl)-2-methoxyphenyl)amino)-1,6-naphthyridin-2-yl)-1H-pyrazol-1-yl)-2-methylpropan-2-ol;

(4-((6-(1-(2-hydroxy-2-methylpropyl)-1H-pyrazol-4-yl)isoquinolin-3-yl)amino)-3-methoxyphenyl)(4-methylpiperazin-1-yl)methanone;

4-((6-(1-(2-hydroxy-2-methylpropyl)-1H-pyrazol-4-yl)isoquinolin-3-yl)amino)-3-methoxy-N-(1-methylpiperidin-4-yl)benzamide;

3-(4-(3-((4-(1,2-dimethyl-1H-imidazol-5-yl)-2-methoxyphenyl)amino)isoquinolin-6-yl)-1H-pyrazol-1-yl)-2-methylbutan-2-ol;

1-(5-(4-((6-(1-(2-hydroxy-2-methylpropyl)-1H-pyrazol-4-yl)isoquinolin-3-yl)amino)-3-methoxyphenyl)-2-methyl-1H-imidazol-1-yl)-2-methylpropan-2-ol;

1-(4-(3-((2-methoxy-4-(7-methyl-5,6,7,8-tetrahydro-[1,2,4]triazolo[4,3-a]pyrazin-3-yl)phenyl)amino)isoquinolin-6-yl)-1H-pyrazol-1-yl)-2-methylpropan-2-ol;

(4-((6-(1-(2-hydroxybutyl)-1H-pyrazol-4-yl)isoquinolin-3-yl)amino)-3-methoxyphenyl)(3-methoxyazetidin-1-yl)methanone;

(3-methoxy-4-((6-(1-(2-methoxyethyl)-1H-pyrazol-4-yl)isoquinolin-3-yl)amino)phenyl)(3-methoxyazetidin-1-yl)methanone;

(4-((6-(1-(2-hydroxy-3-methylbutyl)-1H-pyrazol-4-yl)isoquinolin-3-yl)amino)-3-methoxyphenyl)(3-methoxyazetidin-1-yl)methanone;

1-(4-(3-((2-methoxy-4-(5,6,7,8-tetrahydroimidazo[1,2-a]pyrazin-3-yl)phenyl)amino)isoquinolin-6-yl)-1H-pyrazol-1-yl)-2-methylpropan-2-ol;

(3-methoxy-4-((6-(1-(2-methoxy-2-methylpropyl)-1H-pyrazol-4-yl)isoquinolin-3-yl)amino)phenyl)(3-methoxyazetidin-1-yl)methanone;

(3-methoxy-4-((6-(1-(3,3,3-trifluoro-2-hydroxypropyl)-1H-pyrazol-4-yl)isoquinolin-3-yl)amino)phenyl)(3-methoxyazetidin-1-yl)methanone;

(4-((6-(1-(3-hydroxy-3-methylbutan-2-yl)-1H-pyrazol-4-yl)isoquinolin-3-yl)amino)-3-methoxyphenyl)(3-methoxyazetidin-1-yl)methanone;

1-(4-(7-((2-ethoxy-4-(4-methyl-4H-1,2,4-triazol-3-yl)phenyl)amino)-1,6-naphthyridin-2-yl)-1H-pyrazol-1-yl)-2-methylpropan-2-ol;

(4-((2-(1-(2-hydroxy-2-methylpropyl)-1H-pyrazol-4-yl)-1,6-naphthyridin-7-yl)amino)-3-methoxyphenyl)(3-methoxyazetidin-1-yl)methanone;

1-(4-(7-((2-methoxy-4-(4-methyl-4H-1,2,4-triazol-3-yl)phenyl)amino)-1,6-naphthyridin-2-yl)-1H-pyrazol-1-yl)-2-methylpropan-2-ol;

1-(4-(7-((4-(1,2-dimethyl-1H-imidazol-5-yl)-2-methoxyphenyl)amino)-1,6-naphthyridin-2-yl)-1H-pyrazol-1-yl)methyl)cyclobutanol;

(3-(difluoromethoxy)-4-((6-(1-(2-hydroxy-2-methylpropyl)-1H-pyrazol-4-yl)isoquinolin-3-yl)amino)phenyl)(3-methoxyazetidin-1-yl)methanone;

(3-ethoxy-4-((6-(1-(2-hydroxy-2-methylpropyl)-1H-pyrazol-4-yl)isoquinolin-3-yl)amino)phenyl)(3-methoxyazetidin-1-yl)methanone;

(3,3-difluoroazetidin-1-yl)(4-((6-(1-(2-hydroxy-2-methylpropyl)-1H-pyrazol-4-yl)isoquinolin-3-yl)amino)-3-methoxyphenyl)methanone;

1-(4-((6-(1-(2-hydroxy-2-methylpropyl)-1H-pyrazol-4-yl)isoquinolin-3-yl)amino)-3-methoxybenzoyl)piperidine-4-carbonitrile;

(4-((6-(1-(2-hydroxy-2-methylpropyl)-1H-pyrazol-4-yl)isoquinolin-3-yl)amino)-3-methoxyphenyl)(6-oxa-2-azaspiro[3.4]octan-2-yl)methanone;

1-(4-(3-((2-chloro-4-(5-methyl-1,3,4-oxadiazol-2-yl)phenyl)amino)isoquinolin-6-yl)-1H-pyrazol-1-yl)-2-methylpropan-2-ol;

(4-((6-(1-(2-hydroxy-3-methoxypropyl)-1H-pyrazol-4-yl)isoquinolin-3-yl)amino)-3-methoxyphenyl)(3-methoxyazetidin-1-yl)methanone;

(4-((6-(1-(2,3-dimethoxypropyl)-1H-pyrazol-4-yl)isoquinolin-3-yl)amino)-3-methoxyphenyl)(3-methoxyazetidin-1-yl)methanone;

4-((6-(1-(2-hydroxy-2-methylpropyl)-1H-pyrazol-4-yl)isoquinolin-3-yl)amino)-3-methoxy-N,N-dimethylbenzenesulfonamide;

(4-((6-(1-(2,3-dihydroxypropyl)-1H-pyrazol-4-yl)isoquinolin-3-yl)amino)-3-methoxyphenyl)(3-methoxyazetidin-1-yl)methanone;

(4-((6-(1-(4-hydroxytetrahydrofuran-3-yl)-1H-pyrazol-4-yl)isoquinolin-3-yl)amino)-3-methoxyphenyl)(3-methoxyazetidin-1-yl)methanone;

(4-((6-(1-(2-hydroxycyclopentyl)-1H-pyrazol-4-yl)isoquinolin-3-yl)amino)-3-methoxyphenyl)(3-methoxyazetidin-1-yl)methanone;

5-(4-((6-(1-(2-hydroxy-2-methylpropyl)-1H-pyrazol-4-yl)isoquinolin-3-yl)amino)-3-methoxyphenyl)-1-methyl-1H-imidazole-2-carbonitrile;

(4-((6-(1-(2-hydroxycyclohexyl)-1H-pyrazol-4-yl)isoquinolin-3-yl)amino)-3-methoxyphenyl)(3-methoxyazetidin-1-yl)methanone;

(4-((6-(1-(2-hydroxy-2-methylpropyl)-1H-pyrazol-4-yl)isoquinolin-3-yl)amino)-3-methoxyphenyl)(3-(methoxymethyl)azetidin-1-yl)methanone;

(4-((6-(1-((1-hydroxycyclobutyl)methyl)-1H-pyrazol-4-yl)isoquinolin-3-yl)amino)-3-methoxyphenyl)(3-methoxyazetidin-1-yl)methanone;

1-((4-(3-((2-ethoxy-4-(4-methyl-4H-1,2,4-triazol-3-yl)phenyl)amino)isoquinolin-6-yl)-1H-pyrazol-1-yl)methyl)cyclobutanol;

7-((2-methoxy-4-(1-methyl-1H-pyrazol-4-yl)phenyl)amino)-N,N-dimethyl-1,6-naphthyridine-2-carboxamide;

7-((2-methoxy-4-(1-methyl-1H-pyrazol-4-yl)phenyl)amino)-N-methyl-1,6-naphthyridine-2-carboxamide;

3-((4-(1,2-dimethyl-1H-imidazol-5-yl)-2-methoxyphenyl)amino)-N,N-dimethylisoquinoline-6-carboxamide; and 3-((4-(1,2-dimethyl-1H-imidazol-5-yl)-2-methoxyphenyl)amino)-N-methylisoquinoline-6-carboxamide;

or a pharmaceutically acceptable salt or solvate thereof.

* * * * *